(12) United States Patent
Ogamino et al.

(10) Patent No.: US 8,921,576 B2
(45) Date of Patent: Dec. 30, 2014

(54) SPIROINDOLINE COMPOUND, AND MEDICINAL AGENT COMPRISING SAME

(71) Applicant: Kowa Company, Ltd., Aichi (JP)

(72) Inventors: Takahisa Ogamino, Tokyo (JP); Yukiyoshi Yamazaki, Tokyo (JP); Shin Tanikawa, Tokyo (JP); Ayumu Okuda, Tokyo (JP); Tomoaki Fukuda, Tokyo (JP); Okihisa Tokuda, Tokyo (JP); Yoshiharu Miyake, Tokyo (JP); Shinsuke Itoh, Tokyo (JP); Hiroyuki Ishiwata, Tokyo (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 14/351,914

(22) PCT Filed: Oct. 18, 2012

(86) PCT No.: PCT/JP2012/006660
§ 371 (c)(1),
(2), (4) Date: Apr. 15, 2014

(87) PCT Pub. No.: WO2013/057944
PCT Pub. Date: Apr. 25, 2013

(65) Prior Publication Data
US 2014/0309207 A1    Oct. 16, 2014

(30) Foreign Application Priority Data
Oct. 19, 2011 (JP) .................................. 2011-229978

(51) Int. Cl.
*C07D 487/10* (2006.01)
*C07D 519/00* (2006.01)

(52) U.S. Cl.
CPC ............ *C07D 487/10* (2013.01); *C07D 519/00* (2013.01)
USPC ........ 548/409; 548/147; 548/110; 548/357.5; 544/70; 544/230; 546/14; 546/15; 514/63; 514/235.2; 514/252.06; 514/254.01; 514/278; 514/371; 514/380; 514/404; 514/409

(58) Field of Classification Search
USPC ................................................. 548/409, 147
See application file for complete search history.

(56) References Cited

U.S. PATENT DOCUMENTS

2008/0306102 A1    12/2008 Nakashima et al.

FOREIGN PATENT DOCUMENTS

| JP | 01-180884 | 7/1989 |
|---|---|---|
| JP | 2007-536252 | 12/2007 |
| JP | 2009-526043 | 7/2009 |
| JP | 2010-501578 | 1/2010 |
| JP | 2010-503675 | 2/2010 |
| JP | 2010-504351 | 2/2010 |
| WO | 2005/061512 | 7/2005 |
| WO | 2005/110992 | 11/2005 |
| WO | 2006/090261 | 8/2006 |
| WO | 2007/091947 | 8/2007 |
| WO | 2008/024497 | 2/2008 |
| WO | 2008/033456 | 3/2008 |
| WO | 2008/033460 | 3/2008 |
| WO | 2008/036755 | 3/2008 |
| WO | 2008/142859 | 11/2008 |
| WO | 2009/089454 | 7/2009 |
| WO | 2009/158011 | 12/2009 |
| WO | 2010/036998 | 4/2010 |
| WO | 2010/141817 | 12/2010 |
| WO | 2011/008312 | 1/2011 |

OTHER PUBLICATIONS

Ahren, et al, "Inhibition of Dipeptidyl Peptidase-4 Reduces Glycemia, Sustains Insulin Levels, and Reduces Glucagon Levels in Type 2 Diabetes," The Journal of Clinical Endocrinology and Metabolism, 89(5): 2078-2084, May 2004.

Fujimoto et al., "Administration of D-Glucosamine Into the Third Cerebroventricle Induced Feeding Accompanied by Hyperglycemia in Rats," Life Sciences, vol. 37, pp. 2475-2482, Oct. 14, 1985.

(Continued)

*Primary Examiner* — Laura L. Stockton
(74) *Attorney, Agent, or Firm* — Occhiuti & Rohlicek LLP

(57) ABSTRACT

The present invention provides a novel compound represented by a general formula (1) as shown below, which has a glucokinase-activating action in the liver and pancreatic β-cells and which is useful as an agent for preventing and/or treating diseases caused by hyperglycemia, such as diabetes. A spiroindoline compound represented by the general formula (1), or a salt thereof, or a solvate of the compound or the salt:

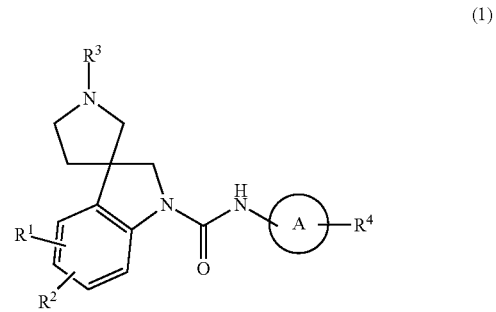

(1)

[wherein ring A represents a nitrogen-containing 5-10 membered heteroaryl group;
$R^1$ and $R^2$, which are the same or different, each represent a hydrogen atom, a halogen atom, a halo $C_{1-6}$ alkyl group, a $C_{6-10}$ aryl group, a cyano group, a $C_{1-6}$ alkyl group optionally having a substituent, a $C_{2-6}$ alkenyl group optionally having a substituent, etc.; $R^3$ represents a hydrogen atom, a $C_{1-6}$ alkyl group optionally having a substituent, etc.; and $R^4$ represents a hydrogen atom, a halogen atom, a $C_{1-6}$ alkyl group optionally having a substituent, etc.]

9 Claims, 1 Drawing Sheet

(56) References Cited

OTHER PUBLICATIONS

Glaser et al., "Familial Hyperinsulinism Caused by an Activating Glucokinase Mutation," The New England Journal of Medicine, 338(4), 226-230, Jan. 1998.
Hershenson et al., "Synthesis of β-Spiro[pyrrolidinoindolines], Their Binding to the Glycine Receptor, and in Vivo Biological Activity," Journal of Medicinal Chemistry, 1977, vol. 20, No. 11, 1448-1451.
Kang et al., "Glucokinase Is a Critical Regulator of Ventromedial Hypothalamic Neuronal Glucosensing," Diabetes, vol. 55, Feb. 2006, 412-420.
Nielsen et al., "Pharmacology of Exenatide (Synthetic Exendin-4): A Potential Therapeutic for Improved Glycemic Control of Type 2 Diabetes," Regulatory Peptides, 117 (2004) 77-88.
Sturgess et al., "The Sulphonylurea Receptor May be an ATP-Sensitive Potassium Channel," The Lancet, 326(8453), 474-475 (1985).
Vionnet et al., "Nonsense Mutation in the Glucokinase Gene Causes Early-Onset Non-Insulin-Dependent Diabetes Mellitus," Nature, vol. 356, Apr. 23, 1992, 721-722.

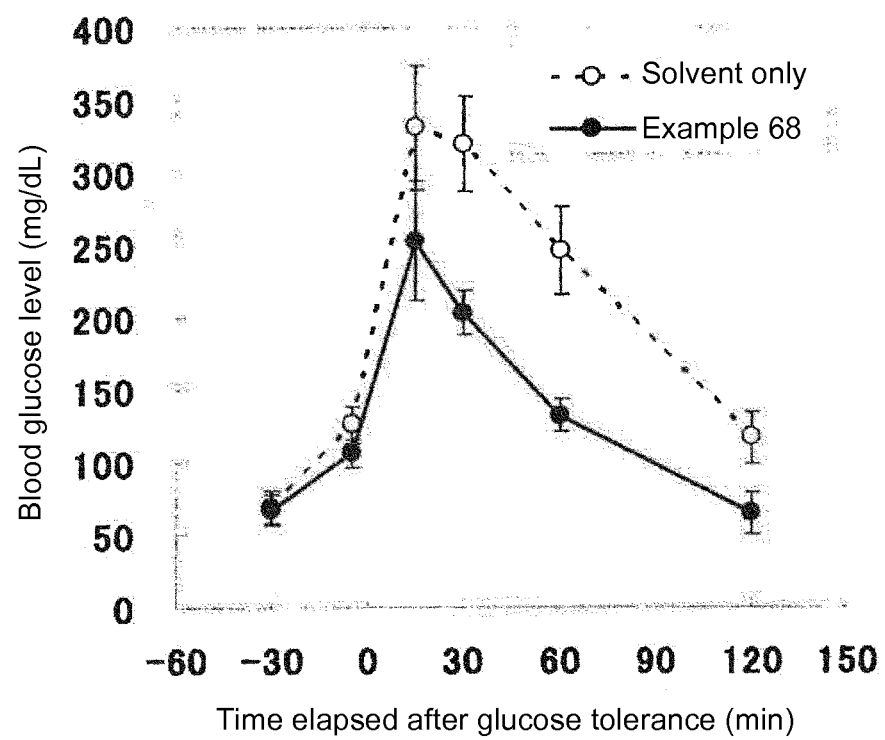

SPIROINDOLINE COMPOUND, AND MEDICINAL AGENT COMPRISING SAME

CROSS REFERENCE TO RELATED APPLICATIONS

This application is a National Stage of International Application No. PCT/JP2012/006660 filed on Oct. 18, 2012, which claims priority to Japanese Application No. 2011-229978 filed on Oct. 19, 2011.

TECHNICAL FIELD

The present invention relates to a novel compound having a glucokinase-activating action. In addition, the present invention also relates to a pharmaceutical composition for treating or preventing diabetes and the like, which comprises a glucokinase-activating compound as an active ingredient.

BACKGROUND ART

According to Outline of Results from 2007 National Health and Nutrition Survey published by the Ministry of Health, Labour and Welfare, it is estimated that there are approximately 8.9 million people who are "strongly suspected of having diabetes" and approximately 13.2 million people who are "likely to have diabetes" in Japan. That is to say, it is predicted that a total of approximately 22.1 million Japanese people are affected with or are likely to have diabetes. Diabetes is defined as a state of chronic hyperglycemia caused by impaired insulin action. Insulin is secreted from pancreatic β-cells and acts on organs on which insulin acts, such as liver or skeletal muscle. As a result of such insulin action, glucose uptake and suppression of gluconeogenesis are induced in the liver, and glucose uptake is induced in the skeletal muscle. However, if reduction in insulin secretion and/or insulin resistance are provoked by a certain reason, impaired insulin action occurs, and the normoglycemic state changes to a hyperglycemic state, thereby resulting in the onset of diabetes. There is a fear that diabetes may increase the risk of developing diabetic nephropathy, retinopathy, nervous disorder, and great vessel disorder, and that it may further lead to a significant reduction in quality of life (QOL), such as the necessity of dialysis, blindness, quadruple amputation, arteriosclerotic disease and stroke.

For the treatment of diabetes, kinesitherapy, dietetic therapy, and drug therapy are carried out. Examples of agents used in drug therapy include agents for promoting insulin secretion from pancreatic β-cells, agents for improving insulin resistance, agents for suppressing glucose absorption, and agents for promoting the use of glucose. Among these agents, since insulin secretagogues are expected to increase blood insulin level and lower blood glucose level, they are anticipated to suppress hyperglycemia and improve diabetes. A sulfonyl urea preparation (SU drug), a short acting insulin secretagogue, a DPPIV inhibitor (see non-patent document 1), a GLP-1 analog (see non-patent document 2) and the like have been practically used in the clinical setting of treating diabetes. However, the SU drug, which has been most frequently used in Japan and stimulates pancreatic β-cells and promotes endogenous insulin secretion (see non-patent document 3), may cause hypoglycemia as a side effect. Thus, attention should be paid when this drug is used, in particular, for elder people, people with deterioration of renal function, and in the case of an irregular dietary habit. In addition, with regard to the SU drug, side effects such as an increase in body weight have also been reported. Moreover, the SU drug has been known to cause primary failure in which no effects are found from an initial administration, or secondary failure in which clinical effects disappear during the administration period.

Glucokinase (hereinafter also abbreviated as "GK") belongs to a hexokinase family and has an alias "hexokinase IV." Hexokinase is an enzyme that catalyzes conversion of glucose to glucose-6-phosphate at an initial stage of the glycolysis system in a cell. In the case of three hexokinases other than GK, enzymatic activity becomes saturated at a glucose level of 1 mmol/L or less. On the other hand, GK has low affinity for glucose and shows a Km value close to a physiological blood glucose level (8 to 15 mmol/L). GK is mainly expressed in liver and pancreatic β-cells. In recent years, it has been elucidated that GK is also present in brain. The sequences of N-terminal 15 amino acids are different between GK in the liver and GK in pancreatic β-cells, depending on a difference in splicing. However, they have identical enzymatic properties, and intracellular glucose metabolism via GK is accelerated in response to a change in blood glucose levels from a normal blood glucose level (around 5 mM) to postprandial hyperglycemia (10 to 15 mmol/L).

Through the ages, a hypothesis had been proposed that GK functions as a glucose sensor in the liver and pancreatic β-cells. Recent study results have demonstrated that GK actually plays an important role for the maintenance of systemic glucose homeostasis, so that the hypothesis could be proved. For example, glucokinase gene deficient mice had significant hyperglycemic symptoms and died shortly after birth. In addition, in heterozygous GK knockout mice, glucose tolerance was deteriorated and glucose-stimulated insulin secretion was impaired. On the other hand, in normal mice in which GK was excessively expressed, the lowering of a blood glucose level, an increase in hepatic glycogen content, and the like were observed, and such phenomena were observed also in mice in which diabetes was artificially developed.

Furthermore, recent studies have revealed that GK functions as a glucose sensor and plays an important role for the maintenance of glucose homeostasis even in humans. An abnormality in the GK gene was found in a family line of maturity-onset diabetes of the young referred to as "MODY2," and the correlation between the symptoms of this disease and GK activity was clarified (non-patent document 4). Meanwhile, a family line having mutagenesis for increasing GK activity was also found. In such a family line, fasting hypoglycemic symptoms attended with an increase in the plasma insulin level were also observed (non-patent document 5). From these reports, it is considered that GK functions as a glucose sensor in mammals including humans and plays an important role for regulation of blood glucose. Accordingly, it is considered that a substance having a GK-activating action is useful as an agent for glucose metabolism-related diseases including type II diabetes as a typical example. In particular, such a GK-activating substance can be expected to simultaneously have a glucose uptake-promoting action and a glucose production-suppressing action on the liver, and also an insulin secretion-promoting action on pancreatic β-cells. As such, it is anticipated that a GK-activating substance could provide strong therapeutic effects, which existing agents could not achieve. In recent years, it became clear that pancreatic β-cell-type GK is focally expressed in the ventromedial hypothalamus (VMH) of rat brain. It has previously been known that neurons that respond to glucose level are present in VMH. When glucose is administered into the cerebral ventricle of a rat, food intake is decreased. In contrast, when glucosamine as a glucose analog is administered into the cerebral ventricle of a rat to inhibit glucose metabolism, food intake is accelerated (non-patent document 6). As a result of an electrophysiological experiment, it has been known that glucose-responsive neurons are activated, responding to a change in physiological glucose levels (5 to 20 mM). It became clear that, during such activation, glucokinase functions as a glucose sensor, as with peripheral tissues (non-patent document 7). Therefore, a substance that activates glucokinase not only in the liver and pancreatic β-cells but also in VMH can be expected to act to correct obesity, which is a problem for many patients with type II diabetes, as well as acting to lower blood glucose level.

Based on the above descriptions, a substance having a GK-activating action is useful as an agent for treating and preventing diabetes, or as an agent for treating and preventing a chronic complication of diabetes, such as retinopathy, nephropathy, neuropathy, ischemic heart disease, or arteriosclerosis.

A glucokinase-activating agent is anticipated as a new type of diabetes-treating agent having two actions, namely, an insulin secretion-enhancing action in pancreatic β-cells and a glucose use-accelerating action in liver.

With regard to the compounds of the present invention having a spiroindoline skeleton, therapeutic agents for Alzheimer's disease (patent document 1 and patent document 2), a therapeutic agent for inflammatory disease (patent document 3), anticancer agents (patent document 4 and patent document 5), a diabetes-treating agent based on a 11β-HSD1 inhibitory activity (patent document 6), an insecticide (patent document 7), an antianxiety agent (non-patent document 8) and the like have been reported. However, all of these compounds are different from the compound of the present invention in terms of a substituent on a spiroindoline ring.

PRIOR ART DOCUMENTS

Patent Documents

Patent Document 1: WO2011/008312
Patent Document 2: WO2010/036998
Patent Document 3: WO2009/158011
Patent Document 4: WO2009/089454
Patent Document 5: WO2006/090261
Patent Document 6: WO2008/024497
Patent Document 7: WO2005/061512

Non-Patent Documents

Non-patent Document 1: J. Clin. Endocrinol. Metab., 89(5), 2078-2084 (2004)
Non-patent Document 2: Regul. Pept., 117(2), 77-88 (2004)
Non-patent Document 3: The Lancet, 326(8453), 474-475 (1985)
Non-patent Document 4: Nature, 356(6371), 721-2 (1992)
Non-patent Document 5: N. Engl. J. Med., 338(4), 226-30 (1998)
Non-patent Document 6: Life Sci., 37(26), 2475-82 (1985)
Non-patent Document 7: Diabetes. 2006 February; 55(2): 412-20.
Non-patent Document 8: J. Med. Chem., 20(11), 1448-51 (1977)

SUMMARY OF THE INVENTION

Object to be Solved by the Invention

It is an object of the present invention to discover a compound having a GK-activating action, and particularly to provide an agent for treating and preventing diabetes and abnormal glucose tolerance.

Means to Solve the Object

Under such circumstances, the present inventors have conducted intensive studies regarding a compound having a GK-activating action. As a result, the inventors have found that a compound having a spiroindoline skeleton represented by a general formula (1) as shown below had an excellent glucokinase-activating action in an in vitro GK-activity measurement test, and also in an oral glucose tolerance test after completion of a single administration of a test compound in normal mice, as described in Examples later, thereby completing the present invention. The compound of the present invention having a spiroindoline skeleton is useful as an active ingredient of a pharmaceutical preparation for treating and/or preventing a disease selected from the group consisting of diabetes, abnormal glucose tolerance, gestational diabetes, a chronic complication of diabetes (including diabetic peripheral neuropathy, diabetic nephropathy, diabetic retinopathy, diabetic arteriosclerosis), and metabolic syndrome.

Specifically, the present invention relates to the following inventions.

[1] A spiroindoline compound represented by the following general formula (1), or a salt thereof, or a solvate of the compound or the salt:

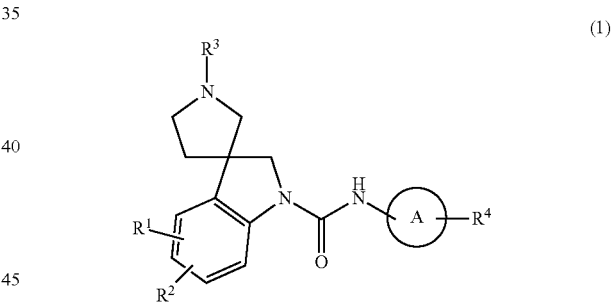

(1)

[wherein ring A represents a nitrogen-containing 5-10 membered unsaturated heterocyclic group,
$R^1$ and $R^2$, which are the same or different, each represent a hydrogen atom, a halogen atom, a halo $C_{1-6}$ alkyl group, a $C_{6-10}$ aryl group, a cyano group, a $C_{1-6}$ alkyl group optionally having a substituent, a $C_{2-6}$ alkenyl group optionally having a substituent, —O—$R^5$, —S(O)$_l$—$R^6$, or —CO—$R^{12}$,
wherein $R^5$ represents a $C_{1-6}$ alkyl group optionally having a substituent, a halo $C_{1-6}$ alkyl group, or a $C_{6-10}$ aryl group optionally having a substituent,
$R^6$ represents a $C_{1-6}$ alkyl group, a $C_{3-8}$ cycloalkyl group, a mono-$C_{1-6}$ alkylamino group optionally having a substituent, a di-$C_{1-6}$ alkylamino group optionally having a substituent, a mono-$C_{3-8}$ cycloalkylamino group, or a nitrogen-containing 3-7 membered saturated heterocyclic group optionally having a substituent,
l represents an integer of 0 to 2, and
$R^{12}$ represents a hydroxyl group, a $C_{1-6}$ alkyl group, a mono-$C_{1-6}$ alkylamino group optionally having a substituent, or a di-$C_{1-6}$ alkylamino group optionally having a substituent, R³ represents a hydrogen atom, a C₁₋₆ alkyl group optionally having a substituent, —CO—R⁷, —S(O)ₘ—R⁸, —CS—R¹³, or a group represented by the following formula (2):

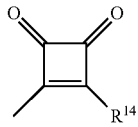
(2)

wherein

R⁷ represents a hydrogen atom, a C₁₋₆ alkyl group optionally having a substituent, a halo C₁₋₆ alkyl group, a C₃₋₈ cycloalkyl group, a C₁₋₆ alkoxy group, a C₆₋₁₀ aryl group, an amino group, a mono-C₁₋₆ alkylamino group optionally having a substituent, a di-C₁₋₆ alkylamino group, a carboxyl group, a C₁₋₆ alkoxycarbonyl group, a mono-C₁₋₆ alkylaminocarbonyl group, a di-C₁₋₆ alkylaminocarbonyl group, a carbamoyl group, a C₁₋₆ alkylcarbonyl group, a mono-C₃₋₈ cycloalkylamino group optionally having a substituent, a C₁₋₆ alkoxyamino group, or a hydroxyamino group, R⁸ represents a C₁₋₆ alkyl group or a mono-C₁₋₆ alkylamino group, m represents an integer of 0 to 2, R¹³ represents a mono-C₁₋₆ alkylamino group, and R¹⁴ represents a C₁₋₆ alkoxy group or a mono-C₁₋₆ alkylamino group, and R⁴ represents a hydrogen atom, a halogen atom, a cyano group, a C₁₋₆ alkyl group optionally having a substituent, —O—R⁹, —S(O)ₙ—R¹⁰, or —CO—R¹¹, wherein R⁹ represents a C₁₋₆ alkyl group, a C₆₋₁₀ aryl group optionally having a substituent, or a nitrogen-containing 5-10 membered unsaturated heterocyclic group optionally having a substituent, R¹⁰ represents a C₁₋₆ alkyl group optionally having a substituent, n represents an integer of 0 to 2, and R¹¹ represents a hydroxyl group, a C₁₋₆ alkoxy group, an amino group, a mono-C₁₋₆ alkylamino group, a di-C₁₋₆ alkylamino group, or a nitrogen-containing 3-7 membered saturated heterocyclic group].

[2] The compound according to [1] above, or a salt thereof, or a solvate of the compound or the salt, wherein the nitrogen-containing 5-10 membered unsaturated heterocyclic group as ring A is any one of the following formulae (3) to (12):

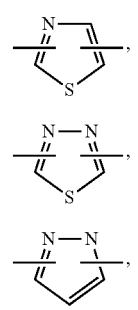
(3)
(4)
(5)

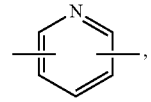
(6)

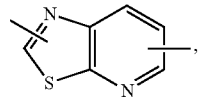
(7)

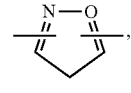
(8)

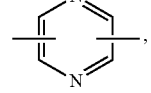
(9)

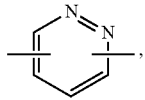
(10)

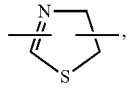
(11)

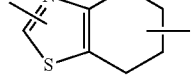
(12)

[3] A pharmaceutical composition comprising the compound according to [1] or [2] above, or a salt thereof, or a solvate of the compound or the salt, and a pharmaceutically acceptable carrier.

[4] A glucokinase-activating agent comprising, as an active ingredient, the compound according to [1] or [2] above, or a salt thereof, or a solvate of the compound or the salt.

[5] A hypoglycemic agent comprising, as an active ingredient, the compound according to [1] or [2] above, or a salt thereof, or a solvate of the compound or the salt.

[6] An agent for preventing and/or treating diabetes, abnormal glucose tolerance, gestational diabetes, a chronic complication of diabetes (including diabetic peripheral neuropathy, diabetic nephropathy, diabetic retinopathy, and diabetic arteriosclerosis), and metabolic syndrome, wherein the agent comprises, as an active ingredient, the compound according to [1] or [2] above, or a salt thereof, or a solvate of the compound or the salt.

[7] A method for activating glucokinase, which comprises administering an effective amount of the compound according to [1] or [2] above, or a salt thereof, or a solvate of the compound or the salt.

[8] A method for lowering blood glucose level, which comprises administering an effective amount of the compound according to [1] or [2] above, or a salt thereof, or a solvate of the compound or the salt.

[9] A method for preventing and/or treating diabetes, abnormal glucose tolerance, gestational diabetes, a chronic complication of diabetes (including diabetic peripheral neuropathy, diabetic nephropathy, diabetic retinopathy, and diabetic arteriosclerosis), and metabolic syndrome, wherein the method comprises administering an effective amount of the compound according to [1] or [2] above, or a salt thereof, or a solvate of the compound or the salt.

[10] The compound according to [1] or [2] above, or a salt thereof, or a solvate of the compound or the salt, which is used for activation of glucokinase.

[11] The compound according to [1] or [2] above, or a salt thereof, or a solvate of the compound or the salt, which is used for lowering blood glucose level.

[12] The compound according to [1] or [2] above, or a salt thereof, or a solvate of the compound or the salt, which is used for preventing and/or treating diabetes, abnormal glucose tolerance, gestational diabetes, a chronic complication of diabetes (including diabetic peripheral neuropathy, diabetic nephropathy, diabetic retinopathy, and diabetic arteriosclerosis), and metabolic syndrome.

[13] Use of the compound according to [1] or [2] above, or a salt thereof, or a solvate of the compound or the salt for production of a glucokinase-activating agent.

[14] Use of the compound according to [1] or [2] above, or a salt thereof, or a solvate of the compound or the salt for production of a hypoglycemic agent.

[15] Use of the compound according to [1] or [2] above, or a salt thereof, or a solvate of the compound or the salt for production of an agent for preventing and/or treating diabetes, abnormal glucose tolerance, gestational diabetes, a chronic complication of diabetes (including diabetic peripheral neuropathy, diabetic nephropathy, diabetic retinopathy, and diabetic arteriosclerosis), and metabolic syndrome.

Effect of the Invention

The spiroindoline compound of the present invention has an excellent GK-activating action, and it is useful as a pharmaceutical preparation for preventing and/or treating a disease selected from the group consisting of diabetes, abnormal glucose tolerance, gestational diabetes, a chronic complication of diabetes (including diabetic peripheral neuropathy, diabetic nephropathy, diabetic retinopathy, and diabetic arteriosclerosis), and metabolic syndrome, in hematherms (which are preferably mammals including humans). Preferred diseases include diabetes and abnormal glucose tolerance. The present spiroindoline compound can be preferably used as a pharmaceutical preparation for treating the aforementioned diseases.

BRIEF DESCRIPTION OF DRAWINGS

FIG. 1 is a view showing the results of an oral sugar tolerance test that was carried out after completion of a single administration of the compound of Example 68, in which the 30 mg/kg compound was orally administered to normal mice, and 30 minutes later, 2 g/kg glucose was orally administered thereto, followed by confirmation of a hypoglycemic action of the compound.

MODE OF CARRYING OUT THE INVENTION

In the present description, examples of the "halogen atom" include a fluorine atom, a chlorine atom, a bromine atom, and an iodine atom.

In the present description, the term "$C_{1-6}$ alkyl group" is used to mean a linear or branched alkyl group containing 1 to 6 carbon atoms. Examples of the $C_{1-6}$ alkyl group include a methyl group, an ethyl group, an n-propyl group, an isopropyl group, an n-butyl group, an isobutyl group, a sec-butyl group, a t-butyl group, an n-pentyl group, an isopentyl group, a neopentyl group, and an n-hexyl group.

In the present description, the term "$C_{2-6}$ alkenyl group" is used to mean a linear or branched alkenyl group containing 2 to 6 carbon atoms. Examples of the $C_{2-6}$ alkenyl group include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

In the present description, the term "halo $C_{1-6}$ alkyl group" is used to mean a $C_{1-6}$ alkyl group, in which one to the greatest possible number of halogen atoms are substituted. Examples of the halo $C_{1-6}$ alkyl group include a bromomethyl group, a chloromethyl group, an iodomethyl group, a trifluoromethyl group, a tribromomethyl group, a trichloromethyl group, a 2,2,2-trifluoroethyl group, and a 1,1,2,2,2-pentafluoroethyl group.

In the present description, an example of the "$C_{3-8}$ cycloalkyl group" is a monocyclic cycloalkyl group containing 3 to 8, and preferably 3 to 6 carbon atoms. Examples of such a cycloalkyl group include a cyclopropyl group, a cyclobutyl group, a cyclopentyl group, a cyclohexyl group, a cycloheptyl group, and a cyclooctyl group.

In the present description, examples of the "$C_{1-6}$ alkoxy group" include a methoxy group, an ethoxy group, an n-propoxy group, an isopropoxy group, an n-butoxy group, an isobutoxy group, a sec-butoxy group, a t-butoxy group, an n-pentoxy group, an isopentoxy group, a neopentoxy group, an n-hexyloxy group, and an isohexyloxy group.

In the present invention, the term "$C_{1-6}$ alkoxyamino group" is used to mean a group in which one of the above described $C_{1-6}$ alkoxy group binds to a nitrogen atom. Examples of the $C_{1-6}$ alkoxyamino group include a methoxyamino group, an ethoxyamino group, an n-propoxyamino group, an isopropoxyamino group, an n-butoxyamino group, an isobutoxyamino group, a sec-butoxyamino group, a t-butoxyamino group, an n-pentoxyamino group, an isopentoxyamino group, a neopentoxyamino group, an n-hexyloxyamino group, and an isohexyloxyamino group.

In the present description, the term "mono-$C_{1-6}$ alkylamino group" is used to mean a group in which one of the above described alkyl group binds to a nitrogen atom. Examples of the mono-$C_{1-16}$ alkylamino group include a methylamino group, an ethylamino group, a propylamino group, an isopropylamino group, a butylamino group, a sec-butylamino group, a t-butylamino group, an n-pentylamino group, an isopentylamino group, a neopentylamino group, an n-hexylamino group, and an isohexylamino group.

In the present description, the term "di-$C_{1-6}$ alkylamino group" is used to mean a group in which two of the above described alkyl groups, which are the same or different, bind to a nitrogen atom. Examples of the di-$C_{1-6}$ alkylamino group include a dimethylamino group, a methylethylamino group, a diethylamino group, a methylpropylamino group, an ethylpropylamino group, a dipropylamino group, a diisopropylamino group, and a dibutylamino group.

In the present description, the term "mono-$C_{3-8}$ cycloalkylamino group" is used to mean a group in which one of the above described $C_{3-8}$ cycloalkyl group binds to a nitrogen atom. Examples of the mono-$C_{3-8}$ cycloalkylamino group include a cyclopropylamino group, a cyclobutylamino group, a cyclopentylamino group, a cyclohexylamino group, a cycloheptylamino group, and a cyclooctylamino group.

In the present description, examples of the "$C_{6-10}$ aryl group" include a phenyl group, a naphthyl group, and an azulenyl group.

In the present description, the term "nitrogen-containing 5-10 membered unsaturated heterocyclic group" is used to mean a 5-10 membered, monocyclic, polycyclic or condensed cyclic, unsaturated heterocyclic group, which contains at least one nitrogen atom and further optionally contains at least one of an oxygen atom and a sulfur atom.

Herein, the unsaturated heterocyclic group means a heterocyclic group having one or more unsaturated bonds, which includes a heteroaryl group.

Examples of the "nitrogen-containing 5-10 membered unsaturated heterocyclic group" include an oxazolyl group, an isoxazolyl group, a thiazolyl group, an isothiazolyl group, an imidazolyl group, a pyrazolyl group, an oxadiazolyl group, a thiadiazolyl group, a triazolyl group, a tetrazolyl group, a pyridyl group, a pyrimidyl group, a pyrazinyl group, a pyridazinyl group, an indazolyl group, a benzimidazolyl group, a benzoxazolyl group, a benzisoxazolyl group, a benzothiazolyl group, a benzisothiazolyl group, a benzoxadiazolyl group, a benzothiadiazolyl group, a benzotriazolyl group, a quinolyl group, an isoquinolyl group, a cinnolinyl group, a quinazolinyl group, a quinoxalinyl group, a phthalazinyl group, a naphthylidinyl group, a purinyl group, a pteridinyl group, a furopyridyl group, a thienopyridyl group, a pyrrolopyridyl group, an oxazolopyridyl group, a thiazolopyridyl group, an imidazopyridyl group, a dihydrooxazolyl group, a dihydroimidazolyl group, a dihydropyrazolyl group, a dihydrothiazolyl group, and a dihydropyrazinyl group.

In the present description, the term "nitrogen-containing 3-7 membered saturated heterocyclic group" is used to mean a 3 to 7 membered monocyclic saturated heterocyclic group containing at least one nitrogen atom and further optionally containing at least one of an oxygen atom and a sulfur atom. Examples of the nitrogen-containing 3-7 membered saturated heterocyclic group include an aziridinyl group, an azetidinyl group, a pyrrolidinyl group, a piperidinyl group, an azepanyl group, a morpholinyl group, a thiomorpholinyl group, a piperazinyl group, and a homopiperazinyl group.

In the present description, the term "$C_{1-6}$ alkylcarbonyl group" is used to mean a group to which the above described $C_{1-6}$ alkyl group binds via a carbonyl group (C=O). Examples of the $C_{1-6}$ alkylcarbonyl group include an acetyl group, an n-propionyl group, an isopropionyl group, an n-butyloyl group, an isobutyloyl group, a sec-butyloyl group, a t-butyloyl group, an n-pentanoyl group, an isopentanoyl group, a neopentanoyl group, and an n-hexanoyl group.

In the present description, the term "$C_{1-6}$ alkoxycarbonyl group" is used to mean a group to which the above described $C_{1-6}$ alkoxy group binds via a carbonyl group (C=O). Examples of the $C_{1-6}$ alkoxycarbonyl group include a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a t-butoxycarbonyl group, an n-pentoxycarbonyl group, an isopentoxycarbonyl group, a neopentoxycarbonyl group, an n-hexyloxycarbonyl group, and an isohexyloxycarbonyl group.

In the present description, the term "mono-$C_{1-6}$ alkylaminocarbonyl group" is used to mean a group to which the above described mono-$C_{1-6}$ alkylamino group binds via a carbonyl group (C=O). Examples of the mono-$C_{1-6}$ alkylaminocarbonyl group include a methylaminocarbonyl group, an ethylaminocarbonyl group, a propylaminocarbonyl group, an isopropylaminocarbonyl group, a butylaminocarbonyl group, a sec-butylaminocarbonyl group, a t-butylaminocarbonyl group, an n-pentylaminocarbonyl group, an isopentylaminocarbonyl group, a neopentylaminocarbonyl group, an n-hexylaminocarbonyl group, and an isohexylaminocarbonyl group.

In the present description, the term "di-$C_{1-6}$ alkylaminocarbonyl group" is used to mean a group to which the above described di-$C_{1-6}$ alkylamino group binds via a carbonyl group (C=O). Examples of the di-$C_{1-6}$ alkylaminocarbonyl group include a dimethylaminocarbonyl group, a methylethylaminocarbonyl group, a diethylaminocarbonyl group, a methylpropylaminocarbonyl group, an ethylpropylaminocarbonyl group, a dipropylaminocarbonyl group, a diisopropylaminocarbonyl group, and a dibutylaminocarbonyl group.

In the present description, examples of the "substituent" used in the $C_{1-6}$ alkyl group optionally having a substituent, the $C_{2-6}$ alkenyl group optionally having a substituent, the mono-$C_{1-6}$ alkylamino group optionally having a substituent, the di-$C_{1-6}$ alkylamino group optionally having a substituent, the mono-$C_{3-8}$ cycloalkylamino group optionally having a substituent, the $C_{6-10}$ aryl group optionally having a substituent, the nitrogen-containing 3-7 membered saturated heterocyclic group optionally having a substituent, or the nitrogen-containing 5-10 membered unsaturated heterocyclic group optionally having a substituent, include a halogen atom, a $C_{1-6}$ alkyl group, a $C_{3-8}$ cycloalkyl group, a halo $C_{1-6}$ alkyl group, a $C_{1-6}$ alkoxy group, a $C_{1-6}$ acyloxy group, a 3-7 membered heterocyclic group, a 3-7 membered heterocyclic oxy group, a mono-$C_{1-6}$ alkylamino group, a di-$C_{1-6}$ alkylamino group, a mono-$C_{3-8}$ cycloalkylamino group, a $C_{1-6}$ acylamino group, a $C_{6-10}$ aryl group, a 5-10 membered heterocyclic group, a 3-7 membered heterocyclic carbonyl group, a $C_{1-6}$ alkoxycarbonyl group, a mono-$C_{1-6}$ alkylaminocarbonyl group, a di-$C_{1-6}$ alkylaminocarbonyl group, a mono-$C_{1-6}$ alkoxyaminocarbonyl group, a hydroxyaminocarbonyl group, a hydroxyazetidinylcarbonyl group, an amino group, a carboxyl group, a cyano group, a carbamoyl group, a sulfamoyl group, a $C_{1-6}$ alkylsulfonyl group, a $C_{1-6}$ alkylsulfonylamino group, a $C_{3-8}$ cycloalkylsulfonyl group, a $C_{3-8}$ cycloalkylsulfonylamino group, a tetrahydropyranyloxy group, a hydroxyl group, a nitro group, a 1-acetylazetidin-3-ylmethyl group, a $C_{3-8}$ cycloalkylcarbonylamino group, and a $C_{1-6}$ alkoxycarbonylamino group. These groups further optionally have a substituent.

In the general formula (1), preferred examples of the nitrogen-containing 5-10 membered unsaturated heterocyclic group as ring A include groups represented by the following formulae:

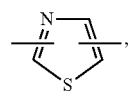

(3)

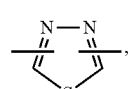

(4)

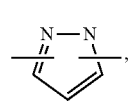

(5)

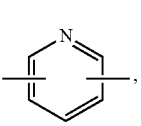

(6)

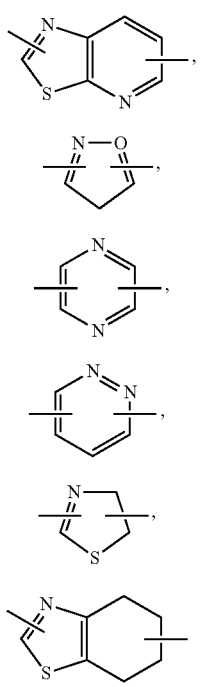

In the general formula (1), preferred examples of the halogen atoms as $R^1$ and $R^2$ include a fluorine atom, a chlorine atom, and a bromine atom.

In the general formula (1), preferred examples of the halo $C_{1-6}$ alkyl groups as $R^1$ and $R^2$ include trifluoromethyl groups.

In the general formula (1), preferred examples of the $C_{6-10}$ aryl groups as $R^1$ and $R^2$ include phenyl groups.

In the general formula (1), preferred examples of the $C_{1-6}$ alkyl groups each optionally having a substituent, as $R^1$ and $R^2$, include $C_{1-4}$ alkyl groups (a methyl group, an ethyl group, an n-propyl group, and an n-butyl group) each optionally having, as a substituent, a hydroxyl group, a carboxyl group, a 3-7 membered heterocyclic carbonyl group (an azetidinylcarbonyl group), a $C_{1-6}$ alkylsulfonyl group (a methylsulfonyl group), a $C_{3-8}$ cycloalkyl group optionally having a substituent (an (azetidine-1-carbonyl)cyclobutyl group), or the like.

In the general formula (1), preferred examples of the $C_{2-6}$ alkenyl groups each optionally having a substituent, as $R^1$ and $R^2$, include $C_{2-4}$ alkenyl groups (a vinyl group, an allyl group, a 1-propenyl group, an isopropenyl group, a 1-butenyl group, a 2-butenyl group, and a 2-methylallyl group) each optionally having, as a substituent, a $C_{1-6}$ alkoxycarbonyl group (an ethoxycarbonyl group), a 3-7 membered heterocyclic carbonyl group (an azetidinylcarbonyl group), or the like.

In the general formula (1), preferred examples of the $C_{1-6}$ alkyl group optionally having a substituent as $R^5$ include a methyl group, an ethyl group, and an isopropyl group, each optionally having a phenyl group as a substituent.

In the general formula (1), a preferred example of the halo $C_{1-6}$ alkyl group as $R^5$ is a trifluoromethyl group.

In the general formula (1), a preferred example of the $C_{6-10}$ aryl group optionally having a substituent as $R^5$ is a phenyl group optionally having, as a substituent, a halogen atom (a fluorine atom etc.), a $C_{1-6}$ alkyl group (a methyl group etc.), a halo $C_{1-6}$ alkyl group (a trifluoromethyl group etc.), a $C_{1-6}$ alkoxy group (a methoxy group etc.), or a $C_{1-6}$ alkylsulfonyl group (a methylsulfonyl group etc.).

In the general formula (1), the $C_{1-6}$ alkyl group as $R^6$ is preferably a $C_{1-4}$ alkyl group, and more preferably a methyl group.

In the general formula (1), the $C_{3-8}$ cycloalkyl group as $R^6$ is preferably a $C_{3-6}$ cycloalkyl group, and more preferably a cyclopentyl group.

In the general formula (1), the mono-$C_{1-6}$ alkylamino group optionally having a substituent as $R^6$ is preferably a $C_{1-4}$ alkylamino group, and more preferably a methylamino group.

In the general formula (1), preferred examples of the alkyl portion of the mono-$C_{1-6}$ alkylamino group optionally having a substituent as $R^6$ include $C_{1-4}$ alkyl groups (a methyl group, an ethyl group, and a propyl group) each optionally having, as a substituent, a $C_{1-6}$ alkoxy group (a methoxy group etc.), a $C_{3-8}$ cycloalkyl group (a cyclohexyl group etc.), a di-$C_{1-6}$ alkylamino group (a dimethylamino group etc.), a phenyl group, a substituted phenyl group (a methoxyphenyl group, a fluorophenyl group, a methoxyphenyl group, etc.), a 5-10 membered heterocyclic group (a furyl group, a thienyl group, a pyridinyl group, etc.), or the like.

In the general formula (1), preferred examples of the alkyl portion of the di-$C_{1-6}$ alkylamino group optionally having a substituent as $R^6$ include $C_{1-4}$ alkyl groups (a methyl group, an ethyl group, and a propyl group) each optionally having a substituent such as a $C_{1-6}$ alkoxy group (a methoxy group etc.), a $C_{3-8}$ cycloalkyl group (a cyclopropyl group etc.), a di-$C_{1-6}$ alkylamino group (a dimethylamino group etc.), a $C_{6-10}$ aryl group (a phenyl group etc.), a $C_{1-6}$ alkoxycarbonyl group (a t-butoxycarbonyl group etc.), a hydroxyl group, or a carboxyl group.

In the general formula (1), the mono-$C_{3-8}$ cycloalkylamino group as $R^6$ is preferably a mono-$C_{3-6}$ cycloalkylamino group, and more preferably a cyclopentylamino group.

In the general formula (1), preferred examples of the nitrogen-containing 3-7 membered saturated heterocyclic group optionally having a substituent as $R^6$ include a pyrrolidinyl group, a piperidinyl group, and a piperazinyl group, each optionally having a $C_{1-6}$ alkyl group (a methyl group etc.) or the like as a substituent.

In the general formula (1), 1 is preferably 2.

In the general formula (1), the $C_{1-6}$ alkyl group as $R^{12}$ is preferably a $C_{1-4}$ alkyl group, and more preferably a methyl group.

In the general formula (1), preferred examples of the $C_{1-6}$ alkyl group optionally having a substituent as $R^3$ include $C_{1-4}$ alkyl groups (methyl groups) each optionally having, as a substituent, a carbamoyl group, a mono-$C_{1-6}$ alkylaminocarbonyl group (a methylaminocarbonyl group), a $C_{1-6}$ alkoxycarbonyl group (a methoxycarbonyl group, a t-butoxycarbonyl group, etc.), a carboxyl group, or the like.

In the general formula (1), preferred examples of the $C_{1-6}$ alkyl group optionally having a substituent as $R^7$ include $C_{1-4}$ alkyl groups (a methyl group, an ethyl group, a propyl group, an isopropyl group, a butyl group, etc.) each optionally having, as a substituent(s), one or two of a hydroxyl group, a $C_{1-6}$ alkoxy group (a methoxy group etc.), a $C_{2-7}$ alkanoyloxy group (an acetoxy group etc.), a cyano group, an amino group, a mono-$C_{1-6}$ alkylamino group (a methylamino group etc.), a di-$C_{1-6}$ alkylamino group (a dimethylamino group etc.), a $C_{2-7}$ alkanoylamino group (an acetylamino group etc.), a $C_{1-6}$ alkoxycarbonylamino group (a t-butoxycarbonyloxy group etc.), and the like.

In the general formula (1), the halo $C_{1-6}$ alkyl group as $R^7$ is preferably a halo $C_{1-4}$ alkyl group, and more preferably a trifluoromethyl group.

In the general formula (1), preferred examples of the $C_{3-8}$ cycloalkyl group as $R^7$ include a cyclopropyl group, a cyclobutyl group, a cyclopentyl group, and a cyclohexyl group.

In the general formula (1), the $C_{1-6}$ alkoxy group as $R^7$ is preferably a $C_{1-4}$ alkoxy group, and more preferably a methoxy group or a t-butoxy group.

In the general formula (1), the $C_{6-10}$ aryl group as $R^7$ is preferably a phenyl group.

In the general formula (1), preferred examples of the mono-$C_{1-6}$ alkylamino group optionally having a substituent as $R^7$ include mono-$C_{1-4}$ alkylamino groups (a methylamino group, an ethylamino group, an n-propylamino group, and an n-butylamino group) each optionally having, as a substituent, a hydroxyl group, a $C_{1-6}$ alkylaminocarbonyl group (a methylaminocarbonyl group), a $C_{1-6}$ alkoxycarbonyl group (an ethoxycarbonyl group), a carboxyl group, a 3-7 membered heterocyclic carbonyl group (an azetidinylcarbonyl group), a $C_{1-6}$ alkylsulfonyl group (a methylsulfonyl group), or the like.

In the general formula (1), the di-$C_{1-6}$ alkylamino group as $R^7$ is preferably a di-$C_{1-4}$ alkylamino group, and more preferably a dimethylamino group.

In the general formula (1), the $C_{1-6}$ alkoxycarbonyl group as $R^7$ is preferably a $C_{1-4}$ alkoxycarbonyl group, and more preferably an ethoxycarbonyl group.

In the general formula (1), the mono-$C_{1-6}$ alkylaminocarbonyl group as $R^7$ is preferably a mono-$C_{1-4}$ alkylaminocarbonyl group, and more preferably a methylaminocarbonyl group.

In the general formula (1), the $C_{1-6}$ alkylcarbonyl group as $R^7$ is preferably a $C_{1-4}$ alkylcarbonyl group, and more preferably a methylcarbonyl group.

In the general formula (1), the mono-$C_{3-8}$ cycloalkylamino group optionally having a substituent as $R^7$ is preferably a mono-$C_{3-6}$ cycloalkylamino group optionally having, as a substituent, a $C_{1-6}$ alkoxycarbonyl group (an ethoxycarbonyl group), a carboxyl group, a $C_{1-6}$ alkylaminocarbonyl group (a methylaminocarbonyl group) or the like, and more preferably a cyclopropylamino group.

In the general formula (1), the $C_{1-6}$ alkoxyamino group as $R^7$ is preferably a $C_{1-4}$ alkoxyamino group, and more preferably a methoxyamino group.

In the general formula (1), the $C_{1-6}$ alkyl group as $R^8$ is preferably a $C_{1-4}$ alkyl group, and more preferably a methyl group or an ethyl group.

In the general formula (1), the mono-$C_{1-6}$ alkylamino group as $R^8$ is preferably a mono-$C_{1-4}$ alkylamino group, and more preferably a methylamino group.

In the general formula (1), m is preferably 2.

In the general formula (1), the mono-$C_{1-6}$ alkylamino group as $R^{13}$ is preferably a mono-$C_{1-4}$ alkylamino group, and more preferably a methylamino group.

In the general formula (1), the $C_{1-6}$ alkoxy group as $R^{14}$ is preferably a $C_{1-4}$ alkoxy group, and more preferably an ethoxy group.

In the general formula (1), the mono-$C_{1-6}$ alkylamino group as $R^{14}$ is preferably a mono-$C_{1-4}$ alkylamino group, and more preferably a methylamino group.

In the general formula (1), preferred examples of the $C_{1-6}$ alkyl group optionally having a substituent as $R^4$ include $C_{1-4}$ alkyl groups (a methyl group, an ethyl group, a propyl group, an isopropyl group, a butyl group, etc.) each optionally having, as a substituent, a halogen atom (a fluorine atom etc.), a hydroxyl group, a $C_{1-6}$ alkoxycarbonyl group (a methoxycarbonyl group, an ethoxycarbonyl group, etc.), a $C_{2-7}$ alkanoyloxy group (an acetyloxy group etc.), an amino group, a di-$C_{1-6}$ alkylamino group (a dimethylamino group, a diethylamino group, etc.), a carboxyl group, a carbamoyl group, a di-$C_{1-6}$ alkylaminocarbonyl group (a dimethylaminocarbonyl group etc.), or a 3-7 membered heterocyclic carbonyl group (an azetidinylcarbonyl group, a pyrrolidinylcarbonyl group, a piperidinylcarbonyl group, a morpholinylcarbonyl group, etc.).

In the general formula (1), the $C_{1-6}$ alkyl group as $R^9$ is preferably a $C_{1-4}$ alkyl group, and more preferably a methyl group or an ethyl group.

In the general formula (1), preferred examples of the $C_{6-10}$ aryl group optionally having a substituent as $R^9$ include phenyl groups each optionally having, as a substituent, a halogen atom (a fluorine atom etc.), a carboxyl group, a $C_{1-6}$ alkoxycarbonyl group (a methoxycarbonyl group etc.), a carbamoyl group, or the like.

In the general formula (1), preferred examples of the nitrogen-containing 5-10 membered heteroaryl group optionally having a substituent as $R^9$ include pyridinyl groups each optionally having, as a substituent, a carboxyl group, a $C_{1-6}$ alkoxycarbonyl group (a methoxycarbonyl group etc.), or the like.

In the general formula (1), preferred examples of the $C_{1-6}$ alkyl group optionally having a substituent as $R^{10}$ include $C_{1-6}$ alkyl groups (a methyl group, an ethyl group, a propyl group, an isopropyl group, an isobutyl group, an s-butyl group, a neopentyl group, etc.) each optionally having, as a substituent, a hydroxyl group, a $C_{1-6}$ alkoxy group (a methoxy group etc.), a tetrahydropyranyloxy group, an amino group, a di-$C_{1-6}$ alkylamino group (a dimethylamino group etc.), a $C_{2-7}$ alkanoylamino group (an acetylamino group etc.), a $C_{1-6}$ alkylsulfonyl group (a methylsulfonyl group etc.), a $C_{3-8}$ cycloalkylsulfonylamino group (a cyclopropylsulfonylamino group etc.), a carboxyl group, a $C_{1-6}$ alkoxycarbonyl group (a methoxycarbonyl group, an ethoxycarbonyl group, a t-butoxycarbonyl group, etc.), a carbamoyl group, a hydroxyaminocarbonyl group, a mono-$C_{1-6}$ alkoxyaminocarbonyl group (a methoxyaminocarbonyl group etc.), a mono-$C_{1-6}$ alkylaminocarbonyl group (a methylaminocarbonyl group etc.), a di-$C_{1-6}$ alkylaminocarbonyl group (a dimethylaminocarbonyl group etc.), or a 3-7 membered heterocyclic carbonyl group (an azetidinylcarbonyl group, a morpholinylcarbonyl group, etc.). These substituents further optionally have a substituent.

In the general formula (1), n is preferably 0 or 2.

In the general formula (1), the $C_{1-6}$ alkoxy group as $R^{11}$ is preferably a $C_{1-4}$ alkoxy group, and more preferably a methoxy group or an ethoxy group.

In the general formula (1), the di-$C_{1-6}$ alkylamino group as $R^{11}$ is preferably a di-$C_{1-4}$ alkylamino group, and more preferably a dimethylamino group.

In the general formula (1), the nitrogen-containing 3-7 membered saturated heterocyclic group as $R^{11}$ is preferably an azetidinyl group, a pyrrolidinyl group, a piperidinyl group, or a morpholinyl group.

More preferred examples of the spiroindoline compound represented by the general formula (1) include compounds selected from the following group.

t-Butyl 5-bromo-1-((5-chlorothiazol-2-yl)carbamoyl)spiro[indoline-3,3'-pyrrolidine]-1'-carboxylate (Example 1), 5-bromo-N-(5-chlorothiazol-2-yl)spiro[indoline-3,3'-pyrrolidine]-1-carboxamide (Example 2), 1'-acetyl-5-bromo-N-(5-chlorothiazol-2-yl)spiro[indoline-3,3'-pyrrolidine]-1-carboxamide (Example 3), 5-bromo-N-(5-chlorothiazol-2-yl)-1'-propionyl spiro[indoline-3,3'-pyrrolidine]-1-carboxamide (Example 4), 5-bromo-1'-butyryl-N-(5-chlorothiazol-2-yl)spiro[indoline-3,3'-pyrrolidine]-1-carboxamide (Example 5), 5-bromo-N-(5-chlorothiazol-2-yl)-1'-pentanoyl spiro[indoline-3,3'-pyrrolidine]-1-carboxamide (Example 6),
5-bromo-N-(5-chlorothiazol-2-yl)-1'-isobutyryl spiro[indoline-3,3'-pyrrolidine]-1-carboxamide (Example 7),
5-bromo-N-(5-chlorothiazol-2-yl)-1'-(cyclopropanecarbonyl)spiro[indoline-3,3'-pyrrolidine]-1-carboxamide (Example 8),
5-bromo-N-(5-chlorothiazol-2-yl)-1'-(cyclobutanecarbonyl)spiro[indoline-3,3'-pyrrolidine]-1-carboxamide (Example 9),
5-bromo-N-(5-chlorothiazol-2-yl)-1'-(cyclopentanecarbonyl)spiro[indoline-3,3'-pyrrolidine]-1-carboxamide (Example 10),
5-bromo-N-(5-chlorothiazol-2-yl)-1'-(cyclohexanecarbonyl)spiro[indoline-3,3'-pyrrolidine]-1-carboxamide (Example 11),
1'-benzoyl-5-bromo-N-(5-chlorothiazol-2-yl)spiro[indoline-3,3'-pyrrolidine]-1-carboxamide (Example 12),
methyl 5-bromo-1-((5-chlorothiazol-2-yl)carbamoyl)spiro[indoline-3,3'-pyrrolidine]-1'-carboxylate (Example 13),
5-bromo-N-(5-chlorothiazol-2-yl)-1'-(2,2,2-trifluoroacetyl)spiro[indoline-3,3'-pyrrolidine]-1-carboxamide (Example 14),
5-bromo-N1-(5-chlorothiazol-2-yl)-N1',N1'-dimethyl spiro[indoline-3,3'-pyrrolidine]-1,1'-dicarboxamide (Example 15),
5-bromo-N1-(5-chlorothiazol-2-yl)spiro[indoline-3,3'-pyrrolidine]-1,1'-dicarboxamide (Example 16),
5-bromo-N-(5-chlorothiazol-2-yl)-1'-(2-hydroxyacetyl)spiro[indoline-3,3'-pyrrolidine]-1-carboxamide (Example 17),
5-bromo-N-(5-chlorothiazol-2-yl)-1'-(2-methoxyacetyl)spiro[indoline-3,3'-pyrrolidine]-1-carboxamide (Example 18),
t-butyl (2-(5-bromo-1-((5-chlorothiazol-2-yl)carbamoyl)spiro[indoline-3,3'-pyrrolidin]-1'-yl)-2-oxoethyl)carbamate (Example 19),
1'-(2-aminoacetyl)-5-bromo-N-(5-chlorothiazol-2-yl)spiro[indoline-3,3'-pyrrolidine]-1-carboxamide (Example 20),
5-bromo-N-(5-chlorothiazol-2-yl)-1'-(methylsulfonyl)spiro[indoline-3,3'-pyrrolidine]-1-carboxamide (Example 21),
5-bromo-N-(5-chlorothiazol-2-yl)-1'-(ethylsulfonyl)spiro[indoline-3,3'-pyrrolidine]-1-carboxamide (Example 22),
5-bromo-N-(5-chlorothiazol-2-yl)-1'-formyl spiro[indoline-3,3'-pyrrolidine]-1-carboxamide (Example 23),
5-bromo-N-(5-chlorothiazol-2-yl)-1'-methyl spiro[indoline-3,3'-pyrrolidine]-1-carboxamide (Example 24),
1'-acetyl-5-bromo-N-(thiazol-2-yl)spiro[indoline-3,3'-pyrrolidine]-1-carboxamide (Example 25),
1'-acetyl-5-bromo-N-(5-fluorothiazol-2-yl)spiro[indoline-3,3'-pyrrolidine]-1-carboxamide (Example 26),
1'-acetyl-5-bromo-N-(5-methoxythiazolo[5,4-b]pyridin-2-yl)spiro[indoline-3,3'-pyrrolidine]-1-carboxamide (Example 27),
ethyl 2-((2-(1'-acetyl-5-bromospiro[indoline-3,3'-pyrrolidin]-1-ylcarboxamido)thiazol-5-yl)thio)acetate (Example 28),
2-((2-(1'-acetyl-5-bromospiro[indoline-3,3'-pyrrolidin]-1-ylcarboxamido)thiazol-5-yl)thio)acetic acid (Example 29),
1'-acetyl-5-bromo-N-(1-methyl-1H-pyrazol-3-yl)spiro[indoline-3,3'-pyrrolidine]-1-carboxamide (Example 30),
1'-acetyl-5-bromo-N-(1H-pyrazol-3-yl)spiro[indoline-3,3'-pyrrolidine]-1-carboxamide (Example 31),
1'-acetyl-5-bromo-N-(pyridin-2-yl)spiro[indoline-3,3'-pyrrolidine]-1-carboxamide (Example 32),
1'-acetyl-5-bromo-N-(5-chloropyridin-2-yl)spiro[indoline-3,3'-pyrrolidine]-1-carboxamide (Example 33),
6-(1'-acetyl-5-bromospiro[indoline-3,3'-pyrrolidin]-1-ylcarboxamido)nicotinic acid (Example 34),
methyl 5-bromo-1-(thiazol-2-ylcarbamoyl)spiro[indoline-3,3'-pyrrolidine]-1'-carboxylate (Example 35),
methyl 5-bromo-1-((5-fluorothiazol-2-yl)carbamoyl)spiro[indoline-3,3'-pyrrolidine]-1'-carboxylate (Example 36),
methyl 5-bromo-1-((5-((2-ethoxy-2-oxoethyl)thio)thiazol-2-yl)carbamoyl)spiro[indoline-3,3'-pyrrolidine]-1'-carboxylate (Example 37),
2-((2-(5-bromo-1'-(methoxycarbonyl)spiro[indoline-3,3'-pyrrolidin]-1-ylcarboxamido)thiazol-5-yl)thio)acetic acid (Example 38),
1'-acetyl-5-chloro-N-(5-chlorothiazol-2-yl)spiro[indoline-3,3'-pyrrolidine]-1-carboxamide (Example 39),
5-chloro-N-(5-chlorothiazol-2-yl)-1'-formyl spiro[indoline-3,3'-pyrrolidine]-1-carboxamide (Example 40),
methyl 5-chloro-1-((5-chlorothiazol-2-yl)carbamoyl)spiro[indoline-3,3'-pyrrolidine]-1'-carboxylate (Example 41),
5-chloro-N-(5-chlorothiazol-2-yl)-1'-(methylsulfonyl)spiro[indoline-3,3'-pyrrolidine]-1-carboxamide (Example 42),
ethyl 2-(5-chloro-1-((5-chlorothiazol-2-yl)carbamoyl)spiro[indoline-3,3'-pyrrolidin]-1'-yl)-2-oxoacetate (Example 43),
2-(5-chloro-1-((5-chlorothiazol-2-yl)carbamoyl)spiro[indoline-3,3'-pyrrolidin]-1'-yl)-2-oxoacetic acid (Example 44),
1'-(2-amino-2-oxoacetyl)-5-chloro-N-(5-chlorothiazol-2-yl)spiro[indoline-3,3'-pyrrolidine]-1-carboxamide (Example 45),
5-chloro-N-(5-chlorothiazol-2-yl)-1'-(2-(methylamino)-2-oxoacetyl)spiro[indoline-3,3'-pyrrolidine]-1-carboxamide (Example 46),
1'-(2-aminoacetyl)-5-chloro-N-(5-chlorothiazol-2-yl)spiro[indoline-3,3'-pyrrolidine]-1-carboxamide (Example 47),
5-chloro-N-(5-chlorothiazol-2-yl)-1'-(2-(methylamino)acetyl)spiro[indoline-3,3'-pyrrolidine]-1-carboxamide (Example 48),
5-chloro-N-(5-chlorothiazol-2-yl)-1'-(2-(dimethylamino)acetyl)spiro[indoline-3,3'-pyrrolidine]-1-carboxamide (Example 49),
1'-(2-acetamideacetyl)-5-chloro-N-(5-chlorothiazol-2-yl)spiro[indoline-3,3'-pyrrolidine]-1-carboxamide (Example 50),
1'-(2-aminopropanoyl)-5-chloro-N-(5-chlorothiazol-2-yl)spiro[indoline-3,3'-pyrrolidine]-1-carboxamide (Example 51),
(R)-2-(5-chloro-1-((5-chlorothiazol-2-yl)carbamoyl)spiro[indoline-3,3'-pyrrolidin]-1'-yl)-2-oxoethyl acetate (Example 52),
(R)-5-chloro-N-(5-chlorothiazol-2-yl)-1'-(2-hydroxyacetyl)spiro[indoline-3,3'-pyrrolidine]-1-carboxamide (Example 53),
(R)-5-chloro-N-(5-chlorothiazol-2-yl)-1'-(2-methoxyacetyl)spiro[indoline-3,3'-pyrrolidine]-1-carboxamide (Example 54),
(2R)-1-(5-chloro-1-((5-chlorothiazol-2-yl)carbamoyl)spiro[indoline-3,3'-pyrrolidin]-1'-yl)-1-oxopropan-2-yl acetate (Example 55),
5-chloro-N-(5-chlorothiazol-2-yl)-1'-((R)-2-hydroxypropanoyl)spiro[indoline-3,3'-pyrrolidine]-1-carboxamide (Example 56),
t-butyl 2-(5-chloro-1-((5-chlorothiazol-2-yl)carbamoyl)spiro[indoline-3,3'-pyrrolidin]-1'-yl)acetate (Example 57), methyl 2-(5-chloro-1-((5-chlorothiazol-2-yl)carbamoyl)spiro[indoline-3,3'-pyrrolidin]-1'-yl)acetate (Example 58), 2-(5-chloro-1-((5-chlorothiazol-2-yl)carbamoyl)spiro[indoline-3,3'-pyrrolidin]-1'-yl)acetic acid (Example 59), 1'-(2-amino-2-oxoethyl)-5-chloro-N-(5-chlorothiazol-2-yl)spiro[indoline-3,3'-pyrrolidine]-1-carboxamide (Example 60), 5-chloro-N-(5-chlorothiazol-2-yl)-1'-(2-(methylamino)-2-oxoethyl)spiro[indoline-3,3'-pyrrolidine]-1-carboxamide (Example 61), 5-chloro-N-(5-chlorothiazol-2-yl)-1'-(2-cyanoacetyl)spiro[indoline-3,3'-pyrrolidine]-1-carboxamide (Example 62), 1'-acetyl-N-(5-chlorothiazol-2-yl)-5-methoxyspiro[indoline-3,3'-pyrrolidine]-1-carboxamide (Example 63), 1'-acetyl-5-methoxy-N-(5-methoxythiazolo[5,4-b]pyridin-2-yl)spiro[indoline-3,3'-pyrrolidine]-1-carboxamide (Example 64), 1'-acetyl-N-(5-chlorothiazol-2-yl)-5-fluorospiro[indoline-3,3'-pyrrolidine]-1-carboxamide (Example 65), 1'-acetyl-5-fluoro-N-(5-methoxythiazolo[5,4-b]pyridin-2-yl)spiro[indoline-3,3'-pyrrolidine]-1-carboxamide (Example 66), 1'-acetyl-5-chloro-N-(5-methoxythiazolo[5,4-b]pyridin-2-yl)spiro[indoline-3,3'-pyrrolidine]-1-carboxamide (Example 67), 1'-acetyl-5-chloro-N-(5-fluorothiazol-2-yl)spiro[indoline-3,3'-pyrrolidine]-1-carboxamide (Example 68), 5-chloro-N-(5-fluorothiazol-2-yl)-1'-formyl spiro[indoline-3,3'-pyrrolidine]-1-carboxamide (Example 69), 5-chloro-N-(5-fluorothiazol-2-yl)-1'-(methylsulfonyl)spiro[indoline-3,3'-pyrrolidine]-1-carboxamide (Example 70), methyl 5-chloro-1-((5-fluorothiazol-2-yl)carbamoyl)spiro[indoline-3,3'-pyrrolidine]-1'-carboxylate (Example 71), methyl 5-chloro-1-((4-methylthiazol-2-yl)carbamoyl)spiro[indoline-3,3'-pyrrolidine]-1'-carboxylate (Example 72), methyl 5-chloro-1-((5-methylthiazol-2-yl)carbamoyl)spiro[indoline-3,3'-pyrrolidine]-1'-carboxylate (Example 73), (R)-1'-acetyl-5-chloro-N-(5-methylthiazol-2-yl)spiro[indoline-3,3'-pyrrolidine]-1-carboxamide (Example 74), N-(5-chlorothiazol-2-yl)-5-fluoro-1'-formyl spiro[indoline-3,3'-pyrrolidine]-1-carboxamide (Example 75), 5-fluoro-N-(5-fluorothiazol-2-yl)-1'-formyl spiro[indoline-3,3'-pyrrolidine]-1-carboxamide (Example 76), 1'-acetyl-5-fluoro-N-(5-fluorothiazol-2-yl)spiro[indoline-3,3'-pyrrolidine]-1-carboxamide (Example 77), N-(5-chlorothiazol-2-yl)-5-fluoro-1'-(methylsulfonyl)spiro[indoline-3,3'-pyrrolidine]-1-carboxamide (Example 78), 5-fluoro-N-(5-fluorothiazol-2-yl)-1'-(methylsulfonyl)spiro[indoline-3,3'-pyrrolidine]-1-carboxamide (Example 79), methyl 1-((5-chlorothiazol-2-yl)carbamoyl)-5-fluorospiro[indoline-3,3'-pyrrolidine]-1'-carboxylate (Example 80), methyl 5-fluoro-1-((5-fluorothiazol-2-yl)carbamoyl)spiro[indoline-3,3'-pyrrolidine]-1'-carboxylate (Example 81), ethyl 2-(5-chloro-1'-(methoxycarbonyl spiro[indoline-3,3'-pyrrolidin]-1-ylcarboxamido)thiazole-4-carboxylate (Example 82), 2-(5-chloro-1'-(methoxycarbonyl)spiro[indoline-3,3'-pyrrolidin]-1-ylcarboxamido)thiazole-4-carboxylic acid (Example 83), methyl 1-((4-carbamoylthiazol-2-yl)carbamoyl)-5-chlorospiro[indoline-3,3'-pyrrolidine]-1'-carboxylate (Example 84), methyl 5-chloro-1-((4-(dimethylcarbamoyl)thiazol-2-yl)carbamoyl)spiro[indoline-3,3'-pyrrolidine]-1'-carboxylate (Example 85), methyl 5-chloro-1-((4-(pyrrolidine-1-carbonyl)thiazol-2-yl)carbamoyl)spiro[indoline-3,3'-pyrrolidine]-1'-carboxylate (Example 86), methyl 5-chloro-1-((4-(piperidine-1-carbonyl)thiazol-2-yl)carbamoyl)spiro[indoline-3,3'-pyrrolidine]-1'-carboxylate (Example 87), methyl 5-chloro-1-((4-(morpholine-4-carbonyl)thiazol-2-yl)carbamoyl)spiro[indoline-3,3'-pyrrolidine]-1'-carboxylate (Example 88), methyl 5-chloro-1-((4-(hydroxymethyl)thiazol-2-yl)carbamoyl)spiro[indoline-3,3'-pyrrolidine]-1'-carboxylate (Example 89), methyl 5-chloro-1-((4-((dimethylamino)methyl)thiazol-2-yl)carbamoyl)spiro[indoline-3,3'-pyrrolidine]-1'-carboxylate (Example 90), methyl 5-chloro-1-((4-(piperidin-1-ylmethyl)thiazol-2-yl)carbamoyl)spiro[indoline-3,3'-pyrrolidine]-1'-carboxylate (Example 91), 1'-acetyl-5-chloro-N-(4-(2-hydroxypropan-2-yl)thiazol-2-yl)spiro[indoline-3,3'-pyrrolidine]-1-carboxamide (Example 92), methyl 5-chloro-1-((4-(2-methoxy-2-oxoethyl)thiazol-2-yl)carbamoyl)spiro[indoline-3,3'-pyrrolidine]-1'-carboxylate (Example 93), 2-(2-(5-chloro-1'-(methoxycarbonyl)spiro[indoline-3,3'-pyrrolidin]-1-ylcarboxamido)thiazol-4-yl)acetic acid (Example 94), methyl 1-((4-(2-amino-2-oxoethyl)thiazol-2-yl)carbamoyl)-5-chlorospiro[indoline-3,3'-pyrrolidine]-1'-carboxylate (Example 95), methyl 5-chloro-1-((4-(2-(dimethylamino)-2-oxoethyl)thiazol-2-yl)carbamoyl)spiro[indoline-3,3'-pyrrolidine]-1'-carboxylate (Example 96), methyl 1-((4-(2-(azetidin-1-yl)-2-oxoethyl)thiazol-2-yl)carbamoyl)-5-chloro-spiro[indoline-3,3'-pyrrolidine]-1'-carboxylate (Example 97), methyl 5-chloro-1-((4-(2-oxo-2-(pyrrolidin-1-yl)ethyl)thiazol-2-yl)carbamoyl)spiro[indoline-3,3'-pyrrolidine]-1'-carboxylate (Example 98), methyl 5-chloro-1-((4-(2-oxo-2-(piperidin-1-yl)ethyl)thiazol-2-yl)carbamoyl)spiro[indoline-3,3'-pyrrolidine]-1'-carboxylate (Example 99), methyl 5-chloro-1-((4-(2-morpholino-2-oxoethyl)thiazol-2-yl)carbamoyl)spiro[indoline-3,3'-pyrrolidine]-1'-carboxylate (Example 100), methyl 5-chloro-1-((4-(2-hydroxyethyl)thiazol-2-yl)carbamoyl)spiro[indoline-3,3'-pyrrolidine]-1'-carboxylate (Example 101), 1-(2-(5-chloro-1'-(methoxycarbonyl)spiro[indoline-3,3'-pyrrolidin]-1-ylcarboxamido)thiazol-4-yl)ethane-1,2-diyl diacetate (Example 102), methyl 5-chloro-1-((4-(1,2-dihydroxyethyl)thiazol-2-yl)carbamoyl)spiro[indoline-3,3'-pyrrolidine]-1'-carboxylate (Example 103), methyl 5-chloro-1-((4-(3-ethoxy-3-oxopropyl)thiazol-2-yl)carbamoyl)spiro[indoline-3,3'-pyrrolidine]-1'-carboxylate (Example 104), 3-(2-(5-chloro-1'-(methoxycarbonyl)spiro[indoline-3,3'-pyrrolidin]-1-ylcarboxamido)thiazol-4-yl)propionic acid (Example 105), methyl 1-((4-((3-amino-3-oxopropyl)thio)thiazol-2-yl)carbamoyl)-5-chlorospiro[indoline-3,3'-pyrrolidine]-1'-carboxylate (Example 106), methyl 5-chloro-1-((4-(3-(dimethylamino)-3-oxopropyl)thiazol-2-yl)carbamoyl)spiro[indoline-3,3'-pyrrolidine]-1'-carboxylate (Example 107), methyl 1-((4-butylthiazol-2-yl)carbamoyl)-5-chlorospiro[indoline-3,3'-pyrrolidine]-1'-carboxylate (Example 108), ethyl 2-(5-chloro-1'-(methoxycarbonyl)spiro[indoline-3,3'-pyrrolidin]-1-ylcarboxamido)thiazole-5-carboxylate (Example 109), 2-(5-chloro-1'-(methoxycarbonyl)spiro[indoline-3,3'-pyrrolidin]-1-ylcarboxamido)thiazole-5-carboxylic acid (Example 110), methyl 1-((5-carbamoylthiazol-2-yl)carbamoyl)-5-chlorospiro[indoline-3,3'-pyrrolidine]-1'-carboxylate (Example 111), methyl 5-chloro-1-((5-(dimethylcarbamoyl)thiazol-2-yl)carbamoyl)spiro[indoline-3,3'-pyrrolidine]-1'-carboxylate (Example 112), methyl 1-((5-(azetidine-1-carbonyl)thiazol-2-yl)carbamoyl)-5-chlorospiro[indoline-3,3'-pyrrolidine]-1'-carboxylate (Example 113), methyl 5-chloro-1-((5-(pyrrolidine-1-carbonyl)thiazol-2-yl)carbamoyl)spiro[indoline-3,3'-pyrrolidine]-1'-carboxylate (Example 114), methyl 5-chloro-1-((5-(piperidine-1-carbonyl)thiazol-2-yl)carbamoyl)spiro[indoline-3,3'-pyrrolidine]-1'-carboxylate (Example 115), methyl 5-chloro-1-((5-(morpholine-4-carbonyl)thiazol-2-yl)carbamoyl)spiro[indoline-3,3'-pyrrolidine]-1'-carboxylate (Example 116), methyl 5-chloro-1-((5-(2-hydroxypropan-2-yl)thiazol-2-yl)carbamoyl)spiro[indoline-3,3'-pyrrolidine]-1'-carboxylate (Example 117), methyl 5-chloro-1-((5-(1,1,1,3,3,3-hexafluoro-2-hydroxypropan-2-yl)thiazol-2-yl)carbamoyl)spiro[indoline-3,3'-pyrrolidine]-1'-carboxylate (Example 118), methyl 5-chloro-1-((5-((diethylamino)methyl)thiazol-2-yl)carbamoyl)spiro[indoline-3,3'-pyrrolidine]-1'-carboxylate (Example 119), methyl 5-chloro-1-((5-(2-hydroxyethyl)thiazol-2-yl)carbamoyl)spiro[indoline-3,3'-pyrrolidine]-1'-carboxylate (Example 120), methyl 5-chloro-1-((5-(3-ethoxy-3-oxopropyl)thiazol-2-yl)carbamoyl)spiro[indoline-3,3'-pyrrolidine]-1'-carboxylate (Example 121), 3-(2-(5-chloro-1'-(methoxycarbonyl)spiro[indoline-3,3'-pyrrolidin]-1-ylcarboxamido)thiazol-5-yl)propionic acid (Example 122), methyl 1-((5-(3-amino-3-oxopropyl)thiazol-2-yl)carbamoyl)-5-chlorospiro[indoline-3,3'-pyrrolidine]-1'-carboxylate (Example 123), methyl 5-chloro-1-((5-(4-methoxy-4-oxobutyl)thiazol-2-yl)carbamoyl)spiro[indoline-3,3'-pyrrolidine]-1'-carboxylate (Example 124), 4-(2-(5-chloro-1'-(methoxycarbonyl)spiro[indoline-3,3'-pyrrolidin]-1-ylcarboxamido)thiazol-5-yl)butyric acid (Example 125), methyl 5-chloro-1-((5-(4-(dimethylamino)-4-oxobutyl)thiazol-2-yl)carbamoyl)spiro[indoline-3,3'-pyrrolidine]-1'-carboxylate (Example 126), methyl 5-chloro-1-((5-(methylthio)thiazol-2-yl)carbamoyl)spiro[indoline-3,3'-pyrrolidine]-1'-carboxylate (Example 127), methyl 5-chloro-1-((5-(methylsulfonyl)thiazol-2-yl)carbamoyl)spiro[indoline-3,3'-pyrrolidine]-1'-carboxylate (Example 128), methyl 5-chloro-1-((5-((2-methoxy-2-oxoethyl)thio)thiazol-2-yl)carbamoyl)spiro[indoline-3,3'-pyrrolidine]-1'-carboxylate (Example 129), 2-((2-(5-chloro-1'-(methoxycarbonyl)spiro[indoline-3,3'-pyrrolidin]-1-ylcarboxamido)thiazol-5-yl)thio)acetic acid (Example 130), methyl 5-chloro-1-((5-((2-(dimethylamino)-2-oxoethyl)thio)thiazol-2-yl)carbamoyl)spiro[indoline-3,3'-pyrrolidine]-1'-carboxylate (Example 131), methyl 1-((5-((2-amino-2-oxoethyl)thio)thiazol-2-yl)carbamoyl)-5-chlorospiro[indoline-3,3'-pyrrolidine]-1'-carboxylate (Example 132), methyl 5-chloro-1-((5-((2-(methylamino)-2-oxoethyl)thio)thiazol-2-yl)carbamoyl)spiro[indoline-3,3'-pyrrolidine]-1'-carboxylate (Example 133), methyl 1-((5-((2-(azetidin-1-yl)-2-oxoethyl)thio)thiazol-2-yl)carbamoyl)-5-chlorospiro[indoline-3,3'-pyrrolidine]-1'-carboxylate (Example 134), methyl 5-chloro-1-((5-((2-morpholino-2-oxoethyl)thio)thiazol-2-yl)carbamoyl)spiro[indoline-3,3'-pyrrolidine]-1'-carboxylate (Example 135), methyl 5-chloro-1-((5-((2-((tetrahydro-2H-pyran-2-yl)oxy)ethyl)thio)thiazol-2-yl)carbamoyl)spiro[indoline-3,3'-pyrrolidine]-1'-carboxylate (Example 136), methyl 5-chloro-1-((5-((2-hydroxyethyl)thio)thiazol-2-yl)carbamoyl)spiro[indoline-3,3'-pyrrolidine]-1'-carboxylate (Example 137), methyl 5-chloro-1-((5-((2-methoxyethyl)thio)thiazol-2-yl)carbamoyl)spiro[indoline-3,3'-pyrrolidine]-1'-carboxylate (Example 138), methyl 5-chloro-1-((5-((1-ethoxy-1-oxopropan-2-yl)thio)thiazol-2-yl)carbamoyl)spiro[indoline-3,3'-pyrrolidine]-1'-carboxylate (Example 139), 2-((2-(5-chloro-1'-(methoxycarbonyl)spiro[indoline-3,3'-pyrrolidin]-1-ylcarboxamido)thiazol-5-yl)thio)propionic acid (Example 140), methyl 5-chloro-1-((5-((1-hydroxypropan-2-yl)thio)thiazol-2-yl)carbamoyl)spiro[indoline-3,3'-pyrrolidine]-1'-carboxylate (Example 141), methyl 5-chloro-1-((5-((1-ethoxy-2-methyl-1-oxopropan-2-yl)thio)thiazol-2-yl)carbamoyl)spiro[indoline-3,3'-pyrrolidine]-1'-carboxylate (Example 142), 2-((2-(5-chloro-1'-(methoxycarbonyl)spiro[indoline-3,3'-pyrrolidin]-1-ylcarboxamido)thiazol-5-yl)thio)-2-methyl propionic acid (Example 143), methyl 5-chloro-1-((5-((1-hydroxy-2-methylpropan-2-yl)thio)thiazol-2-yl)carbamoyl)spiro[indoline-3,3'-pyrrolidine]-1'-carboxylate (Example 144), methyl 5-chloro-1-((5-((1-ethoxy-1-oxobutan-2-yl)thio)thiazol-2-yl)carbamoyl)spiro[indoline-3,3'-pyrrolidine]-1'-carboxylate (Example 145), 2-((2-(5-chloro-1'-(methoxycarbonyl)spiro[indoline-3,3'-pyrrolidin]-1-ylcarboxamido)thiazol-5-yl)thio)butyric acid (Example 146), methyl 5-chloro-1-((5-((1-(dimethylamino)-1-oxobutan-2-yl)thio)thiazol-2-yl)carbamoyl)spiro[indoline-3,3'-pyrrolidine]-1'-carboxylate (Example 147), methyl 5-chloro-1-((5-((1-hydroxybutan-2-yl)thio)thiazol-2-yl)carbamoyl)spiro[indoline-3,3'-pyrrolidine]-1'-carboxylate (Example 148), methyl 5-chloro-1-((5-((3-ethoxy-3-oxopropyl)thio)thiazol-2-yl)carbamoyl)spiro[indoline-3,3'-pyrrolidine]-1'-carboxylate (Example 149), 3-((2-(5-chloro-1'-(methoxycarbonyl)spiro[indoline-3,3'-pyrrolidin]-1-ylcarboxamido)thiazol-5-yl)thio)propionic acid (Example 150), methyl 5-chloro-1-((5-((3-(methylamino)-3-oxopropyl)thio)thiazol-2-yl)carbamoyl)spiro[indoline-3,3'-pyrrolidine]-1'-carboxylate (Example 151), methyl 5-chloro-1-((5-((3-(dimethylamino)-3-oxopropyl)thio)thiazol-2-yl)carbamoyl)spiro[indoline-3,3'-pyrrolidine]-1'-carboxylate (Example 152),
methyl 1-((5-((3-(azetidin-1-yl)-3-oxopropyl)thio)thiazol-2-yl)carbamoyl)-5-chlorospiro[indoline-3,3'-pyrrolidine]-1'-carboxylate (Example 153),
methyl 5-chloro-1-((5-((3-morpholino-3-oxopropyl)thio)thiazol-2-yl)carbamoyl)spiro[indoline-3,3'-pyrrolidine]-1'-carboxylate (Example 154),
methyl 1-((5-((3-amino-3-oxopropyl)thio)thiazol-2-yl)carbamoyl)-5-chlorospiro[indoline-3,3'-pyrrolidine]-1'-carboxylate (Example 155),
methyl 5-chloro-1-((5-((3-ethoxy-2,2-dimethyl-3-oxopropyl)thio)thiazol-2-yl)carbamoyl)spiro[indoline-3,3'-pyrrolidine]-1'-carboxylate (Example 156),
3-((2-(5-chloro-1'-(methoxycarbonyl)spiro[indoline-3,3'-pyrrolidin]-1-ylcarboxamido)thiazol-5-yl)thio)-2,2-dimethyl propionic acid (Example 157),
methyl 5-chloro-1-((5-((3-hydroxy-2,2-dimethylpropyl)thio)thiazol-2-yl)carbamoyl)spiro[indoline-3,3'-pyrrolidine]-1'-carboxylate (Example 158),
methyl 5-chloro-1-((5-((4-ethoxy-4-oxobutyl)thio)thiazol-2-yl)carbamoyl)spiro[indoline-3,3'-pyrrolidine]-1'-carboxylate (Example 159),
4-((2-(5-chloro-1'-(methoxycarbonyl)spiro[indoline-3,3'-pyrrolidin]-1-ylcarboxamido)thiazol-5-yl)thio)butyric acid (Example 160),
methyl 5-chloro-1-((5-((3-hydroxypropyl)thio)thiazol-2-yl)carbamoyl)spiro[indoline-3,3'-pyrrolidine]-1'-carboxylate (Example 161),
methyl 5-chloro-1-((5-((3-methoxypropyl)thio)thiazol-2-yl)carbamoyl)spiro[indoline-3,3'-pyrrolidine]-1'-carboxylate (Example 162),
methyl 1-((5-((4-amino-4-oxobutyl)thio)thiazol-2-yl)carbamoyl)-5-chlorospiro[indoline-3,3'-pyrrolidine]-1'-carboxylate (Example 163),
methyl 5-chloro-1-((5-((4-(methylamino)-4-oxobutyl)thio)thiazol-2-yl)carbamoyl)spiro[indoline-3,3'-pyrrolidine]-1'-carboxylate (Example 164),
methyl 5-chloro-1-((5-((4-(dimethylamino)-4-oxobutyl)thio)thiazol-2-yl)carbamoyl)spiro[indoline-3,3'-pyrrolidine]-1'-carboxylate (Example 165),
methyl 5-chloro-1-((5-((4-morpholino-4-oxobutyl)thio)thiazol-2-yl)carbamoyl)spiro[indoline-3,3'-pyrrolidine]-1'-carboxylate (Example 166),
methyl 1-((5-((4-(azetidin-1-yl)-4-oxobutyl)thio)thiazol-2-yl)carbamoyl)-5-chlorospiro[indoline-3,3'-pyrrolidine]-1'-carboxylate (Example 167),
methyl 5-chloro-1-((5-((4-(methoxyamino)-4-oxobutyl)thio)thiazol-2-yl)carbamoyl)spiro[indoline-3,3'-pyrrolidine]-1'-carboxylate (Example 168),
methyl 5-chloro-1-((5-((4-(hydroxyamino)-4-oxobutyl)thio)thiazol-2-yl)carbamoyl)spiro[indoline-3,3'-pyrrolidine]-1'-carboxylate (Example 169),
methyl 5-chloro-1-((5-((4-(3-hydroxyazetidin-1-yl)-4-oxobutyl)thio)thiazol-2-yl)carbamoyl)spiro[indoline-3,3'-pyrrolidine]-1'-carboxylate (Example 170),
ethyl 4-((2-(1'-acetyl-5-chlorospiro[indoline-3,3'-pyrrolidin]-1-ylcarboxamido)thiazol-5-yl)thio)butanoate (Example 171),
4-((2-(1'-acetyl-5-chlorospiro[indoline-3,3'-pyrrolidin]-1-ylcarboxamido)thiazol-5-yl)thio)butyric acid (Example 172),
1'-acetyl-5-chloro-N-(5-((4-(methylamino)-4-oxobutyl)thio)thiazol-2-yl)spiro[indoline-3,3'-pyrrolidine]-1-carboxamide (Example 173),
methyl 1-((5-((2-aminoethyl)thio)thiazol-2-yl)carbamoyl)-5-chlorospiro[indoline-3,3'-pyrrolidine]-1'-carboxylate (Example 174),
methyl 1-((5-((2-acetamidoethyl)thio)thiazol-2-yl)carbamoyl)-5-chlorospiro[indoline-3,3'-pyrrolidine]-1'-carboxylate (Example 175),
methyl 1-((5-((3-aminopropyl)thio)thiazol-2-yl)carbamoyl)-5-chlorospiro[indoline-3,3'-pyrrolidine]-1'-carboxylate (Example 176),
methyl 1-((5-((3-acetamidopropyl)thio)thiazol-2-yl)carbamoyl)-5-chlorospiro[indoline-3,3'-pyrrolidine]-1'-carboxylate (Example 177),
methyl 5-chloro-1-((5-((3-(methylsulfonamido)propyl)thio)thiazol-2-yl)carbamoyl)spiro[indoline-3,3'-pyrrolidine]-1'-carboxylate (Example 178),
methyl 5-chloro-1-((5-((3-(cyclopropanesulfonamido)propyl)thio)thiazol-2-yl)carbamoyl)spiro[indoline-3,3'-pyrrolidine]-1'-carboxylate (Example 179),
methyl 5-chloro-1-((5-((3-(dimethylamino)propyl)thio)thiazol-2-yl)carbamoyl)spiro[indoline-3,3'-pyrrolidine]-1'-carboxylate (Example 180),
methyl 5-chloro-1-((5-methoxythiazol-2-yl)carbamoyl)spiro[indoline-3,3'-pyrrolidine]-1'-carboxylate (Example 181),
1'-acetyl-5-chloro-N-(5-methoxythiazol-2-yl)spiro[indoline-3,3'-pyrrolidine]-1-carboxamide (Example 182),
1'-acetyl-5-chloro-N-(5-ethoxythiazol-2-yl)spiro[indoline-3,3'-pyrrolidine]-1-carboxamide (Example 183),
methyl 5-chloro-1-((5-(3-(methoxycarbonyl)phenoxy)thiazol-2-yl)carbamoyl)spiro[indoline-3,3'-pyrrolidine]-1'-carboxylate (Example 184),
3-((2-(5-chloro-1'-(methoxycarbonyl)spiro[indoline-3,3'-pyrrolidin]-1-ylcarboxamido)thiazol-5-yl)oxy)benzoic acid (Example 185),
methyl 1-((5-(3-carbamoylphenoxy)thiazol-2-yl)carbamoyl)-5-chlorospiro[indoline-3,3'-pyrrolidine]-1'-carboxylate (Example 186),
methyl 3-((2-(1'-acetyl-5-chlorospiro[indoline-3,3'-pyrrolidin]-1-ylcarboxamido)thiazol-5-yl)oxy)benzoate (Example 187),
3-((2-(1'-acetyl-5-chlorospiro[indoline-3,3'-pyrrolidin]-1-ylcarboxamido)thiazol-5-yl)oxy)benzoic acid (Example 188),
methyl 4-((2-(1'-acetyl-5-chlorospiro[indoline-3,3'-pyrrolidin]-1-ylcarboxamido)thiazol-5-yl)oxy)benzoate (Example 189),
4-((2-(1'-acetyl-5-chlorospiro[indoline-3,3'-pyrrolidin]-1-ylcarboxamido)thiazol-5-yl)oxy)benzoic acid (Example 190),
methyl 4-((2-(1'-acetyl-5-chlorospiro[indoline-3,3'-pyrrolidin]-1-ylcarboxamido)thiazol-5-yl)oxy)-2-fluorobenzoate (Example 191),
4-((2-(1'-acetyl-5-chlorospiro[indoline-3,3'-pyrrolidin]-1-ylcarboxamido)thiazol-5-yl)oxy)-2-fluorobenzoic acid (Example 192),
methyl 5-((2-(1'-acetyl-5-chlorospiro[indoline-3,3'-pyrrolidin]-1-ylcarboxamido)thiazol-5-yl)oxy)nicotinate (Example 193),
5-((2-(1'-acetyl-5-chlorospiro[indoline-3,3'-pyrrolidin]-1-ylcarboxamido)thiazol-5-yl)oxy)nicotinic acid (Example 194),
methyl 1-((5-chlorothiazol-2-yl)carbamoyl)-5-cyanospiro[indoline-3,3'-pyrrolidine]-1'-carboxylate (Example 195),
1'-acetyl-N-(5-chlorothiazol-2-yl)-5-cyanospiro[indoline-3,3'-pyrrolidine]-1-carboxamide (Example 196), 1'-acetyl-N-(5-chlorothiazol-2-yl)-5-(trifluoromethoxy) spiro[indoline-3,3'-pyrrolidine]-1-carboxamide (Example 197), 1'-acetyl-N-(5-chlorothiazol-2-yl)-5-(4-fluorophenoxy) spiro[indoline-3,3'-pyrrolidine]-1-carboxamide (Example 198), 1'-acetyl-N-(5-chlorothiazol-2-yl)-5-phenoxyspiro[indoline-3,3'-pyrrolidine]-1-carboxamide (Example 199), 1'-acetyl-N-(5-methoxythiazolo[5,4-b]pyridin-2-yl)-5-phenoxyspiro[indoline-3,3'-pyrrolidine]-1-carboxamide (Example 200), 1'-acetyl-N-(5-chlorothiazol-2-yl)-5-(3-fluorophenoxy) spiro[indoline-3,3'-pyrrolidine]-1-carboxamide (Example 201), 1'-acetyl-5-(3-fluorophenoxy)-N-(5-methoxythiazolo[5,4-b] pyridin-2-yl)spiro[indolin-3,3'-pyrrolidine]-1-carboxamide (Example 202), 1'-acetyl-N-(5-chlorothiazol-2-yl)-5-(o-tolyloxy)spiro[indoline-3,3'-pyrrolidine]-1-carboxamide (Example 203), 1'-acetyl-N-(5-methoxythiazolo[5,4-b]pyridin-2-yl)-5-(o-tolyloxy)spiro[indoline-3,3'-pyrrolidine]-1-carboxamide (Example 204), 1'-acetyl-N-(5-chlorothiazol-2-yl)-5-(m-tolyloxy)spiro[indoline-3,3'-pyrrolidine]-1-carboxamide (Example 205), 1'-acetyl-N-(5-methoxythiazolo[5,4-b]pyridin-2-yl)-5-(m-tolyloxy)spiro[indoline-3,3'-pyrrolidine]-1-carboxamide (Example 206), 1'-acetyl-N-(5-chlorothiazol-2-yl)-5-(p-tolyloxy)spiro[indoline-3,3'-pyrrolidine]-1-carboxamide (Example 207), 1'-acetyl-N-(5-methoxythiazolo[5,4-b]pyridin-2-yl)-5-(p-tolyloxy)spiro[indoline-3,3'-pyrrolidine]-1-carboxamide (Example 208), 1'-acetyl-N-(5-chlorothiazol-2-yl)-5-(2-(trifluoromethyl) phenoxy)spiro[indoline-3,3'-pyrrolidine]-1-carboxamide (Example 209), 1'-acetyl-N-(5-chlorothiazol-2-yl)-5-(3-(trifluoromethyl) phenoxy)spiro[indoline-3,3'-pyrrolidine]-1-carboxamide (Example 210), 1'-acetyl-N-(5-methoxythiazolo[5,4-b]pyridin-2-yl)-5-(3-(trifluoromethyl)phenoxy)spiro[indoline-3,3'-pyrrolidine]-1-carboxamide (Example 211), 1'-acetyl-N-(5-chlorothiazol-2-yl)-5-(4-(trifluoromethyl) phenoxy)spiro[indoline-3,3'-pyrrolidine]-1-carboxamide (Example 212), 1'-acetyl-N-(5-methoxythiazolo[5,4-b]pyridin-2-yl)-5-(4-(trifluoromethyl)phenoxy)spiro[indoline-3,3'-pyrrolidine]-1-carboxamide (Example 213), 1'-acetyl-N-(5-chlorothiazol-2-yl)-5-(2-methoxyphenoxy) spiro[indoline-3,3'-pyrrolidine]-1-carboxamide (Example 214), 1'-acetyl-N-(5-chlorothiazol-2-yl)-5-(3-methoxyphenoxy) spiro[indoline-3,3'-pyrrolidine]-1-carboxamide (Example 215), 1'-acetyl-5-(3-methoxyphenoxy)-N-(5-methoxythiazolo[5, 4-b]pyridin-2-yl)spiro[indoline-3,3'-pyrrolidine]-1-carboxamide (Example 216), 1'-acetyl-N-(5-chlorothiazol-2-yl)-5-(4-methoxyphenoxy) spiro[indoline-3,3'-pyrrolidine]-1-carboxamide (Example 217), 1'-acetyl-5-(4-methoxyphenoxy)-N-(5-methoxythiazolo[5, 4-b]pyridin-2-yl)spiro[indoline-3,3'-pyrrolidine]-1-carboxamide (Example 218), 1'-acetyl-N-(5-chlorothiazol-2-yl)-5-(2-(methylsulfonyl) phenoxy)spiro[indoline-3,3'-pyrrolidine]-1-carboxamide (Example 219), 1'-acetyl-N-(5-chlorothiazol-2-yl)-5-(3-(methylsulfonyl) phenoxy)spiro[indoline-3,3'-pyrrolidine]-1-carboxamide (Example 220), 1'-acetyl-N-(5-methoxythiazolo[5,4-b]pyridin-2-yl)-5-(3-(methylsulfonyl)phenoxy)spiro[indoline-3,3'-pyrrolidine]-1-carboxamide (Example 221), 1'-acetyl-N-(5-chlorothiazol-2-yl)-5-(4-(methylsulfonyl) phenoxy)spiro[indoline-3,3'-pyrrolidine]-1-carboxamide (Example 222), 1'-acetyl-N-(5-methoxythiazolo[5,4-b]pyridin-2-yl)-5-(4-(methylsulfonyl)phenoxy)spiro[indoline-3,3'-pyrrolidine]-1-carboxamide (Example 223), 1'-acetyl-N-(5-chlorothiazol-2-yl)-5-ethoxyspiro[indoline-3,3'-pyrrolidine]-1-carboxamide (Example 224), 1'-acetyl-5-ethoxy-N-(5-methoxythiazolo[5,4-b]pyridin-2-yl)spiro[indoline-3,3'-pyrrolidine]-1-carboxamide (Example 225), methyl 1-((5-chlorothiazol-2-yl)carbamoyl)-5-(2,2,2-trifluoroethoxy)spiro[indoline-3,3'-pyrrolidine]-1'-carboxylate (Example 226), 1'-acetyl-N-(5-chlorothiazol-2-yl)-5-isopropoxyspiro[indoline-3,3'-pyrrolidine]-1-carboxamide (Example 227), 1'-acetyl-5-isopropoxy-N-(5-methoxythiazolo[5,4-b]pyridin-2-yl)spiro[indoline-3,3'-pyrrolidine]-1-carboxamide (Example 228), 1'-acetyl-5-benzyloxy-N-(5-chlorothiazol-2-yl)spiro[indoline-3,3'-pyrrolidine]-1-carboxamide (Example 229), 1'-acetyl-5-benzyloxy-N-(5-methoxythiazolo[5,4-b]pyridin-2-yl)spiro[indoline-3,3'-pyrrolidine]-1-carboxamide (Example 230), 1'-acetyl-N-(5-chlorothiazol-2-yl)-5-(1-phenylethoxy)spiro [indoline-3,3'-pyrrolidin]-1-yl carboxamide (Example 231), 1'-acetyl-N-(5-chlorothiazol-2-yl)-5-phenetoxy spiro[indoline-3,3'-pyrrolidine]-1-carboxamide (Example 232), 1'-acetyl-N-(5-methoxythiazolo[5,4-b]pyridin-2-yl)-5-phenetoxy spiro[indoline-3,3'-pyrrolidine]-1-carboxamide (Example 233), 1'-acetyl-N-(5-chlorothiazol-2-yl)-5-((1-phenylpropan-2-yl) oxy)spiro[indoline-3,3'-pyrrolidine]-1-carboxamide (Example 234), 1'-acetyl-N-(5-methoxythiazolo[5,4-b]pyridin-2-yl)-5-((1-phenylpropan-2-yl)oxy)spiro[indoline-3,3'-pyrrolidine]-1-carboxamide (Example 235), 1'-acetyl-N-(5-chlorothiazol-2-yl)-5-((4-methylpiperazin-1-yl)sulfonyl)spiro[indoline-3,3'-pyrrolidine]-1-carboxamide (Example 236), 1'-acetyl-5-((4-methylpiperazin-1-yl)sulfonyl)-N-(thiazol-2-yl)spiro[indoline-3,3'-pyrrolidine]-1-carboxamide (Example 237), 1'-acetyl-N-(5-fluorothiazol-2-yl)-5-((4-methylpiperazin-1-yl)sulfonyl)spiro[indoline-3,3'-pyrrolidine]-1-carboxamide (Example 238), ethyl 2-((2-(1'-acetyl-5-((4-methylpiperazin-1-yl)sulfonyl) spiro[indoline-3,3'-pyrrolidin]-1-ylcarboxamido)thiazol-5-yl)thio)acetate (Example 239), 2-((2-(1'-acetyl-5-((4-methylpiperazin-1-yl)sulfonyl)spiro [indoline-3,3'-pyrrolidin]-1-ylcarboxamido)thiazol-5-yl) thio)acetic acid (Example 240), 1'-acetyl-N-(1-methyl-1H-pyrazol-3-yl)-5-((4-methylpiperazin-1-yl)sulfonyl)spiro[indoline-3,3'-pyrrolidine]-1-carboxamide (Example 241), 1'-acetyl-5-((4-methylpiperazin-1-yl)sulfonyl)-N-(pyridin-2-yl)spiro[indoline-3,3'-pyrrolidine]-1-carboxamide (Example 242), methyl 6-(1'-acetyl-5-((4-methylpiperazin-1-yl)sulfonyl)spiro[indoline-3,3'-pyrrolidin]-1-carboxamido)nicotinate (Example 243), 1'-acetyl-N-(5-methoxythiazolo[5,4-b]pyridin-2-yl)-5-((4-methylpiperazin-1-yl)sulfonyl)spiro[indoline-3,3'-pyrrolidine]-1-carboxamide (Example 244), 1'-acetyl-N-(5-chlorothiazol-2-yl)-5-(N,N-diethylsulfamoyl)spiro[indoline-3,3'-pyrrolidine]-1-carboxamide (Example 245), 1'-acetyl-N-(5-chlorothiazol-2-yl)-5-(N-cyclopentylsulfamoyl)spiro[indoline-3,3'-pyrrolidine]-1-carboxamide (Example 246), 1'-acetyl-N-(5-chlorothiazol-2-yl)-5-(N-(2-methoxyethyl)sulfamoyl)spiro[indoline-3,3'-pyrrolidine]-1-carboxamide (Example 247), 1'-acetyl-N-(5-chlorothiazol-2-yl)-5-(N-(3-methoxypropyl)sulfamoyl)spiro[indoline-3,3'-pyrrolidine]-1-carboxamide (Example 248), 1'-acetyl-N-(5-chlorothiazol-2-yl)-5-(pyrrolidin-1-ylsulfonyl)spiro[indoline-3,3'-pyrrolidine]-1-carboxamide (Example 249), 1'-acetyl-N-(5-chlorothiazol-2-yl)-5-(piperidin-1-ylsulfonyl)spiro[indoline-3,3'-pyrrolidine]-1-carboxamide (Example 250), 1'-acetyl-5-(N-benzylsulfamoyl)-N-(5-chlorothiazol-2-yl)spiro[indoline-3,3'-pyrrolidine]-1-carboxamide (Example 251), 1'-acetyl-5-(N-benzylsulfamoyl)-N-(5-methoxythiazolo[5,4-b]pyridin-2-yl)spiro[indoline-3,3'-pyrrolidine]-1-carboxamide (Example 252), 1'-acetyl-N-(5-chlorothiazol-2-yl)-5-(N-(2-(dimethylamino)ethyl)sulfamoyl)spiro[indoline-3,3'-pyrrolidine]-1-carboxamide (Example 253), 1'-acetyl-N-(5-chlorothiazol-2-yl)-5-(N-(cyclohexylmethyl)sulfamoyl)spiro[indoline-3,3'-pyrrolidine]-1-carboxamide (Example 254), 1'-acetyl-N-(5-chlorothiazol-2-yl)-5-(N,N-dipropylsulfamoyl)spiro[indoline-3,3'-pyrrolidine]-1-carboxamide (Example 255), 1'-acetyl-N-(5-chlorothiazol-2-yl)-5-(N-(pyridin-2-ylmethyl)sulfamoyl)spiro[indoline-3,3'-pyrrolidine]-1-carboxamide (Example 256), 1'-acetyl-N-(5-methoxythiazolo[5,4-b]pyridin-2-yl)-5-(N-(pyridin-2-ylmethyl)sulfamoyl)spiro[indoline-3,3'-pyrrolidine]-1-carboxamide (Example 257), 1'-acetyl-N-(5-chlorothiazol-2-yl)-5-(N-(pyridin-3-ylmethyl)sulfamoyl)spiro[indoline-3,3'-pyrrolidine]-1-carboxamide (Example 258), 1'-acetyl-N-(5-methoxythiazolo[5,4-b]pyridin-2-yl)-5-(N-(pyridin-3-ylmethyl)sulfamoyl)spiro[indoline-3,3'-pyrrolidine]-1-carboxamide (Example 259), 1'-acetyl-N-(5-chlorothiazol-2-yl)-5-(N-(pyridin-4-ylmethyl)sulfamoyl)spiro[indoline-3,3'-pyrrolidine]-1-carboxamide (Example 260), 1'-acetyl-N-(5-methoxythiazolo[5,4-b]pyridin-2-yl)-5-(N-(pyridin-4-ylmethyl)sulfamoyl)spiro[indoline-3,3'-pyrrolidine]-1-carboxamide (Example 261), 1'-acetyl-N-(5-chlorothiazol-2-yl)-5-(N-(2-methoxybenzyl)sulfamoyl)spiro[indoline-3,3'-pyrrolidine]-1-carboxamide (Example 262), 1'-acetyl-5-(N-(2-methoxybenzyl)sulfamoyl)-N-(5-methoxythiazolo[5,4-b]pyridin-2-yl)spiro[indoline-3,3'-pyrrolidine]-1-carboxamide (Example 263), 1'-acetyl-N-(5-chlorothiazol-2-yl)-5-(N-(3-methoxybenzyl)sulfamoyl)spiro[indoline-3,3'-pyrrolidine]-1-carboxamide (Example 264), 1'-acetyl-5-(N-(3-methoxybenzyl)sulfamoyl)-N-(5-methoxythiazolo[5,4-b]pyridin-2-yl)spiro[indoline-3,3'-pyrrolidine]-1-carboxamide (Example 265), 1'-acetyl-N-(5-chlorothiazol-2-yl)-5-(N-(4-methoxybenzyl)sulfamoyl)spiro[indoline-3,3'-pyrrolidine]-1-carboxamide (Example 266), 1'-acetyl-5-(N-(4-methoxybenzyl)sulfamoyl)-N-(5-methoxythiazolo[5,4-b]pyridin-2-yl)spiro[indoline-3,3'-pyrrolidine]-1-carboxamide (Example 267), 1'-acetyl-N-(5-chlorothiazol-2-yl)-5-(N-(2-fluorobenzyl)sulfamoyl)spiro[indoline-3,3'-pyrrolidine]-1-carboxamide (Example 268), 1'-acetyl-5-(N-(2-fluorobenzyl)sulfamoyl)-N-(5-methoxythiazolo[5,4-b]pyridin-2-yl)spiro[indoline-3,3'-pyrrolidine]-1-carboxamide (Example 269), 1'-acetyl-N-(5-chlorothiazol-2-yl)-5-(N-(furan-2-ylmethyl)sulfamoyl)spiro[indoline-3,3'-pyrrolidine]-1-carboxamide (Example 270), 1'-acetyl-N-(furan-2-ylmethyl)sulfamoyl)-N-(5-methoxythiazolo[5,4-b]pyridin-2-yl)spiro[indoline-3,3'-pyrrolidine]-1-carboxamide (Example 271), 1'-acetyl-N-(5-chlorothiazol-2-yl)-5-(N-(thiophen-2-ylmethyl)sulfamoyl)spiro[indoline-3,3'-pyrrolidine]-1-carboxamide (Example 272), 1'-acetyl-N-(5-methoxythiazolo[5,4-b]pyridin-2-yl)-5-(N-(thiophen-2-ylmethyl)sulfamoyl)spiro[indoline-3,3'-pyrrolidine]-1-carboxamide (Example 273), 1'-acetyl-N-(5-chlorothiazol-2-yl)-5-(N-(2-methoxyethyl)-N-methylsulfamoyl)spiro[indoline-3,3'-pyrrolidine]-1-carboxamide (Example 274), 1'-acetyl-5-(N-(2-methoxyethyl)-N-methylsulfamoyl)-N-(5-methoxythiazolo[5,4-b]pyridin-2-yl)spiro[indoline-3,3'-pyrrolidine]-1-carboxamide (Example 275), 1'-acetyl-5-(N-benzyl-N-methylsulfamoyl)-N-(5-chlorothiazol-2-yl)spiro[indoline-3,3'-pyrrolidine]-1-carboxamide (Example 276), 1'-acetyl-5-(N-benzyl-N-methylsulfamoyl)-N-(5-methoxythiazolo[5,4-b]pyridin-2-yl)spiro[indoline-3,3'-pyrrolidine]-1-carboxamide (Example 277), 1'-acetyl-5-(N-benzyl-N-methylsulfamoyl)-N-(5-fluorothiazol-2-yl)spiro[indoline-3,3'-pyrrolidine]-1-carboxamide (Example 278), ethyl 2-((2-(1'-acetyl-5-(N-benzyl-N-methylsulfamoyl)spiro[indoline-3,3'-pyrrolidin]-1-ylcarboxamido)thiazol-5-yl)thio)acetate (Example 279), 2-((2-(1'-acetyl-5-(N-benzyl-N-methylsulfamoyl)spiro[indoline-3,3'-pyrrolidin]-1-ylcarboxamido)thiazol-5-yl)thio)acetic acid (Example 280), 1'-acetyl-5-(N-benzyl-N-methylsulfamoyl)-N-(1-methyl-1H-pyrazol-3-yl)spiro[indoline-3,3'-pyrrolidine]-1-carboxamide (Example 281), 1'-acetyl-5-(N-benzyl-N-methylsulfamoyl)-N-(5-methyl-1,3,4-thiadiazol-2-yl)spiro[indoline-3,3'-pyrrolidine]-1-carboxamide (Example 282), methyl 6-(1'-acetyl-5-(N-benzyl-N-methylsulfamoyl)spiro[indoline-3,3'-pyrrolidin]-1-ylcarboxamido)nicotinate (Example 283), 1'-acetyl-N-(5-chlorothiazol-2-yl)-5-(N-phenethylsulfamoyl)spiro[indoline-3,3'-pyrrolidine]-1-carboxamide (Example 284), 1'-acetyl-N-(5-methoxythiazolo[5,4-b]pyridin-2-yl)-5-(N-phenethylsulfamoyl)spiro[indoline-3,3'-pyrrolidine]-1-carboxamide (Example 285), t-butyl 3-(1'-acetyl-N-benzyl-((5-methoxythiazolo[5,4-b]pyridin-2-yl)carbamoyl)spiro[indoline-3,3'-pyrrolidin]-5-ylsulfonamido)propanoate (Example 286), 3-(1'-acetyl-N-benzyl-1-((5-methoxythiazolo[5,4-b]pyridin-2-yl)carbamoyl)spiro[indoline-3,3'-pyrrolidin]-5-ylsulfonamido)propanoic acid (Example 287), 1'-acetyl-5-(N-benzyl-N-(2-methoxyethyl)sulfamoyl)-N-(5-methoxythiazolo[5,4-b]pyridin-2-yl)spiro[indoline-3,3'-pyrrolidine]-1-carboxamide (Example 288), 1'-acetyl-5-(N-benzyl-N-(3-methoxypropyl)sulfamoyl)-N-(5-methoxythiazolo[5,4-b]pyridin-2-yl)spiro[indoline-3,3'-pyrrolidine]-1-carboxamide (Example 289), t-butyl 3-(1'-acetyl-N-(2-methoxyethyl)-1-((5-methoxythiazolo[5,4-b]pyridin-2-yl)carbamoyl)spiro[indoline-3,3'-pyrrolidin]-5-ylsulfonamido)propanoate (Example 290), 3-(1'-acetyl-N-(2-methoxyethyl)-1-((5-methoxythiazolo[5,4-b]pyridin-2-yl)carbamoyl)spiro[indoline-3,3'-pyrrolidin]-5-ylsulfonamido)propanoic acid (Example 291), t-butyl 3-(1'-acetyl-N-(3-methoxypropyl)-1-((5-methoxythiazolo[5,4-b]pyridin-2-yl)carbamoyl)spiro[indoline-3,3'-pyrrolidin]-5-ylsulfonamido)propanoate (Example 292), 3-(1'-acetyl-N-(3-methoxypropyl)-1-((5-methoxythiazolo[5,4-b]pyridin-2-yl)carbamoyl)spiro[indoline-3,3'-pyrrolidin]-5-ylsulfonamido)propanoic acid (Example 293), t-butyl 4-(1'-acetyl-N-benzyl-1-((5-methoxythiazolo[5,4-b]pyridin-2-yl)carbamoyl)spiro[indoline-3,3'-pyrrolidin]-5-ylsulfonamido)butanoate (Example 294), 4-(1'-acetyl-N-benzyl-1-((5-methoxythiazolo[5,4-b]pyridin-2-yl)carbamoyl)spiro[indoline-3,3'-pyrrolidin]-5-ylsulfonamido)butyric acid (Example 295), t-butyl 3-(1'-acetyl-N-(cyclopropylmethyl)-1-((5-methoxythiazolo[5,4-b]pyridin-2-yl)carbamoyl)spiro[indoline-3,3'-pyrrolidin]-5-ylsulfonamido)propanoate (Example 296), 3-(1'-acetyl-N-(cyclopropylmethyl)-1-((5-methoxythiazolo[5,4-b]pyridin-2-yl)carbamoyl)spiro[indoline-3,3'-pyrrolidin]-5-ylsulfonamido)propanoic acid (Example 297), 1'-acetyl-5-(N-benzyl-N-(2-(dimethylamino)ethyl)sulfamoyl)-N-(5-methoxythiazolo[5,4-b]pyridin-2-yl)carbamoyl)spiro[indoline-3,3'-pyrrolidine]-1-carboxamide (Example 298), 1'-acetyl-5-(N-(cyclopropylmethyl)-N-(2-(dimethylamino)ethyl)sulfamoyl)-N-(5-methoxythiazolo[5,4-b]pyridin-2-yl)spiro[indoline-3,3'-pyrrolidine]-1-carboxamide (Example 299), 1'-acetyl-5-(N-(cyclopropylmethyl)-N-(2-methoxyethyl)sulfamoyl)-N-(5-methoxythiazolo[5,4-b]pyridin-2-yl)spiro[indoline-3,3'-pyrrolidine]-1-carboxamide (Example 300), 1'-acetyl-5-(N-(cyclopropylmethyl)-N-(3-methoxypropyl)sulfamoyl)-N-(5-methoxythiazolo[5,4-b]pyridin-2-yl)spiro[indoline-3,3'-pyrrolidine]-1-carboxamide (Example 301), 1'-acetyl-5-(N-(cyclopropylmethyl)-N-(2-hydroxyethyl)sulfamoyl)-N-(5-methoxythiazolo[5,4-b]pyridin-2-yl)spiro[indoline-3,3'-pyrrolidine]-1-carboxamide (Example 302), 1'-acetyl-5-(N-benzyl-N-(2-hydroxyethyl)sulfamoyl)-N-(5-methoxythiazolo[5,4-b]pyridin-2-yl)spiro[indoline-3,3'-pyrrolidine]-1-carboxamide (Example 303), 3-(1'-acetyl-N-(2-hydroxyethyl)-1-((5-methoxythiazolo[5,4-b]pyridin-2-yl)carbamoyl)spiro[indoline-3,3'-pyrrolidin]-5-ylsulfonamido)propanoic acid (Example 304), t-butyl 3-(1'-acetyl-N-(2-(dimethylamino)ethyl)-1-((5-methoxythiazolo[5,4-b]pyridin-2-yl)carbamoyl)spiro[indoline-3,3'-pyrrolidin]-5-ylsulfonamido)propanoate (Example 305), methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate (Example 306), 3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propanoic acid (Example 307), 5-(N-benzyl-N-(2-(dimethylamino)ethyl)sulfamoyl)-N-(5-fluorothiazol-2-yl)-1'-formyl spiro[indoline-3,3'-pyrrolidine]-1-carboxamide (Example 308), 5-(N-benzyl-N-(2-hydroxyethyl)sulfamoyl)-N-(5-fluorothiazol-2-yl)-1'-formyl spiro[indoline-3,3'-pyrrolidine]-1-carboxamide (Example 309), 1'-acetyl-N-(5-chlorothiazol-2-yl)-5-(cyclopentylsulfonyl)spiro[indoline-3,3'-pyrrolidine]-1-carboxamide (Example 310), 1'-acetyl-N-(5-chlorothiazol-2-yl)-5-(methylsulfonyl)spiro[indoline-3,3'-pyrrolidine]-1-carboxamide (Example 311), (S)-methyl 5,6-dichloro-1-((5-chlorothiazol-2-yl)carbamoyl)spiro[indoline-3,3'-pyrrolidine]-1'-carboxylate (Example 312), (S)-1'-acetyl-5-bromo-N-(thiazol-2-yl)spiro[indoline-3,3'-pyrrolidine]-1-carboxamide (Example 326), (R)-1'-acetyl-5-bromo-N-(5-fluorothiazol-2-yl)spiro[indoline-3,3'-pyrrolidine]-1-carboxamide (Example 327), (S)-1'-acetyl-5-bromo-N-(5-fluorothiazol-2-yl)spiro[indoline-3,3'-pyrrolidine]-1-carboxamide (Example 328), (R)-methyl 5-bromo-1-(thiazol-2-ylcarbamoyl)spiro[indoline-3,3'-pyrrolidine]-1'-carboxylate (Example 329), (S)-methyl 5-bromo-1-(thiazol-2-ylcarbamoyl)spiro[indoline-3,3'-pyrrolidine]-1'-carboxylate (Example 330), (R)-methyl 5-bromo-1-((5-fluorothiazol-2-yl)carbamoyl)spiro[indoline-3,3'-pyrrolidine]-1'-carboxylate (Example 331), (S)-methyl 5-bromo-1-((5-fluorothiazol-2-yl)carbamoyl)spiro[indoline-3,3'-pyrrolidine]-1'-carboxylate (Example 332), (R)-methyl 5-bromo-1-((5-((2-ethoxy-2-oxoethyl)thio)thiazol-2-yl)carbamoyl)spiro[indoline-3,3'-pyrrolidine]-1'-carboxylate (Example 333), (S)-methyl 5-bromo-1-((5-((2-ethoxy-2-oxoethyl)thio)thiazol-2-yl)carbamoyl)spiro[indoline-3,3'-pyrrolidine]-1'-carboxylate (Example 334), (R)-2-((2-(5-bromo-1'-(methoxycarbonyl)spiro[indoline-3,3'-pyrrolidin]-1-ylcarboxamido)thiazol-5-yl)thio)acetic acid (Example 335), (S)-2-((2-(5-bromo-1'-(methoxycarbonyl)spiro[indoline-3,3'-pyrrolidin]-1-ylcarboxamido)thiazol-5-yl)thio)acetic acid (Example 336), (R)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate (Example 337), (S)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate (Example 338), (R)-3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propionic acid (Example 339), (S)-3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propionic acid (Example 340), (R)-4-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)butyric acid (Example 341), (S)-4-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)butyric acid (Example 342), (R)-methyl 5-(N-benzyl-N-(2-methoxyethyl)sulfamoyl)-1-((5-methoxythiazolo[5,4-b]pyridin-2-yl)carbamoyl)spiro[indoline-3,3'-pyrrolidine]-1'-carboxylate (Example 343), (S)-methyl 5-(N-benzyl-N-(2-methoxyethyl)sulfamoyl)-1-((5-methoxythiazolo[5,4-b]pyridin-2-yl)carbamoyl)spiro[indoline-3,3'-pyrrolidine]-1'-carboxylate (Example 344), (R)-methyl 5-(N-benzyl-N-(2-hydroxyethyl)sulfamoyl)-1-((5-methoxythiazolo[5,4-b]pyridin-2-yl)carbamoyl)spiro[indoline-3,3'-pyrrolidine]-1'-carboxylate (Example 345), (S)-methyl 5-(N-benzyl-N-(2-hydroxyethyl)sulfamoyl)-1-((5-methoxythiazolo[5,4-b]pyridin-2-yl)carbamoyl)spiro[indoline-3,3'-pyrrolidine]-1'-carboxylate (Example 346), (R)-methyl 5-(N-benzyl-N-(2-(dimethylamino)ethyl)sulfamoyl)-1-((5-methoxythiazolo[5,4-b]pyridin-2-yl)carbamoyl)spiro[indoline-3,3'-pyrrolidine]-1'-carboxylate (Example 347), (S)-methyl 5-(N-benzyl-N-(2-(dimethylamino)ethyl)sulfamoyl)-1-((5-methoxythiazolo[5,4-b]pyridin-2-yl)carbamoyl)spiro[indoline-3,3'-pyrrolidine]-1'-carboxylate (Example 348), (R)-1'-acetyl-5-chloro-N-(5-chlorothiazol-2-yl)spiro[indoline-3,3'-pyrrolidine]-1-carboxamide (Example 349), (R)-5-chloro-N-(5-chlorothiazol-2-yl)-1'-formyl spiro[indoline-3,3'-pyrrolidine]-1-carboxamide (Example 350), (S)-methyl 5-chloro-1-((5-chlorothiazol-2-yl)carbamoyl)spiro[indoline-3,3'-pyrrolidine]-1'-carboxylate (Example 351), (S)-5-chloro-N-(5-chlorothiazol-2-yl)-1'-(methylsulfonyl)spiro[indoline-3,3'-pyrrolidine]-1-carboxamide (Example 352), (R)-1'-(2-aminoacetyl)-5-chloro-N-(5-chlorothiazol-2-yl)spiro[indoline-3,3'-pyrrolidine]-1-carboxamide (Example 353), (R)-1'-acetyl-5-chloro-N-(5-fluorothiazol-2-yl)spiro[indoline-3,3'-pyrrolidine]-1-carboxamide (Example 354), (S)-methyl 5-chloro-1-((5-fluorothiazol-2-yl)carbamoyl)spiro[indoline-3,3'-pyrrolidine]-1'-carboxylate (Example 355), (S)-methyl 5-chloro-1-((5-methylthiazol-2-yl)carbamoyl)spiro[indoline-3,3'-pyrrolidine]-1'-carboxylate (Example 356), (S)-methyl 5-chloro-1-((5-((3-ethoxy-3-oxopropyl)thio)thiazol-2-yl)carbamoyl)spiro[indoline-3,3'-pyrrolidine]-1'-carboxylate (Example 357), (S)-3-((2-(5-chloro-1'-(methoxycarbonyl)spiro[indoline-3,3'-pyrrolidin]-1-ylcarboxamido)thiazol-5-yl)thio)propionic acid (Example 358), (R)-ethyl 3-((2-(1'-acetyl-5-chlorospiro[indoline-3,3'-pyrrolidin]-1-ylcarboxamido)thiazol-5-yl)thio)propanoate (Example 359), (R)-3-((2-(1'-acetyl-5-chlorospiro[indoline-3,3'-pyrrolidin]-1-ylcarboxamido)thiazol-5-yl)thio)propionic acid (Example 360), (R)-t-butyl-3-((2-(1'-acetyl-5-chlorospiro[indoline-3,3'-pyrrolidin]-1-ylcarboxamido)thiazol-5-yl)thio)propanoate (Example 361), (S)-methyl 1-((5-((3-(t-butoxy)-3-oxopropyl)thio)thiazol-2-yl)carbamoyl)-5-chlorospiro[indoline-3,3'-pyrrolidine]-1'-carboxylate (Example 362), 1'-acetyl-5-chloro-N-(5-methyl-1H-pyrazol-3-yl)spiro[indoline-3,3'-pyrrolidine]-1-carboxamide (Example 363), 1'-acetyl-5-cyano-N-(5-fluorothiazol-2-yl)spiro[indoline-3,3'-pyrrolidine]-1-carboxamide (Example 364), 5-cyano-N-(5-fluorothiazol-2-yl)-1'-(2-hydroxyacetyl)spiro[indoline-3,3'-pyrrolidine]-1-carboxamide (Example 365), 5-chloro-1'-(2-hydroxyacetyl)-N-(5-methoxythiazol-2-yl)spiro[indoline-3,3'-pyrrolidine]-1-carboxamide (Example 366), 5-chloro-N-(5-fluorothiazol-2-yl)-1'-(2-(methylamino)-2-oxoacetyl)spiro[indoline-3,3'-pyrrolidine]-1-carboxamide (Example 367), 5-chloro-N-(5-fluorothiazol-2-yl)-1'-(2-hydroxyacetyl)spiro[indoline-3,3'-pyrrolidine]-1-carboxamide (Example 368), 1'-acetyl-5-cyano-N-(5-methoxythiazol-2-yl)spiro[indoline-3,3'-pyrrolidine]-1-carboxamide (Example 369), 5-chloro-N-(5-methoxythiazol-2-yl)-1'-(2-(methylamino)-2-oxoacetyl)spiro[indoline-3,3'-pyrrolidine]-1-carboxamide (Example 370), 5-cyano-1'-(2-hydroxyacetyl)-N-(5-methoxythiazol-2-yl)spiro[indoline-3,3'-pyrrolidine]-1-carboxamide (Example 371), 5-cyano-N-(5-methoxythiazol-2-yl)-1'-(2-(methylamino)-2-oxoacetyl)spiro[indoline-3,3'-pyrrolidine]-1-carboxamide (Example 372), 5-chloro-N1-(5-chlorothiazol-2-yl)-N1'-methyl spiro[indoline-3,3'-pyrrolidine]-1,1'-dicarboxamide (Example 373), (R)-5-chloro-N1-(5-fluorothiazol-2-yl)-N1'-methyl spiro[indoline-3,3'-pyrrolidine]-1,1'-dicarboxamide (Example 374), 5-cyano-N-(5-fluorothiazol-2-yl)-1'-(2-(methylamino)-2-oxoacetyl)spiro[indoline-3,3'-pyrrolidine]-1-carboxamide (Example 375), (R)—N1-(5-chlorothiazol-2-yl)-5-cyano-N1'-methyl spiro[indoline-3,3'-pyrrolidine]-1,1'-dicarboxamide (Example 376), (R)-5-cyano-N1-(5-fluorothiazol-2-yl)-N1'-methyl spiro[indoline-3,3'-pyrrolidine]-1,1'-dicarboxamide (Example 377), 5-chloro-N-(5-chlorothiazol-2-yl)-1'-(2-oxopropanoyl)spiro[indoline-3,3'-pyrrolidine]-1-carboxamide (Example 378), 5-chloro-N1-(5-chlorothiazol-2-yl)-N1'-ethyl spiro[indoline-3,3'-pyrrolidine]-1,1'-dicarboxamide (Example 379), (R)-5-chloro-N1-(5-methoxythiazol-2-yl)-N1'-methyl spiro[indoline-3,3'-pyrrolidine]-1,1'-dicarboxamide (Example 380), (R)-5-cyano-N1-(5-methoxythiazol-2-yl)-N1'-methyl spiro[indoline-3,3'-pyrrolidine]-1,1'-dicarboxamide (Example 381), (R)-5-chloro-N1'-methyl-N1-(5-methylthiazol-2-yl)spiro[indoline-3,3'-pyrrolidine]-1,1'-dicarboxamide (Example 382), N1-(5-chlorothiazol-2-yl)-N1'-methyl-5-(methylsulfonyl)spiro[indoline-3,3'-pyrrolidine]-1,1'-dicarboxamide (Example 383), 5-chloro-N-(5-chlorothiazol-2-yl)-1'-(2-(dimethylamino)-2-oxoacetyl)spiro[indoline-3,3'-pyrrolidine]-1-carboxamide (Example 384), 5-chloro-N-(5-chlorothiazol-2-yl)-1'-(2,2-difluoroacetyl)spiro[indoline-3,3'-pyrrolidine]-1-carboxamide (Example 385), 1'-acetyl-5-chloro-N-(isoxazol-3-yl)spiro[indoline-3,3'-pyrrolidine]-1-carboxamide (Example 386), 1'-acetyl-5-chloro-N-(4,5,6,7-tetrahydrobenzo[d]thiazol-2-yl)spiro[indoline-3,3'-pyrrolidine]-1-carboxamide (Example 387), 1'-acetyl-5-chloro-N-(4,5-dihydrothiazol-2-yl)spiro[indoline-3,3'-pyrrolidine]-1-carboxamide (Example 388), 1'-acetyl-5-chloro-N-(5-methylpyrazin-2-yl)spiro[indoline-3,3'-pyrrolidine]-1-carboxamide (Example 389), (R)-5-chloro-N1'-methyl-N1-(5-methylpyrazin-2-yl)spiro[indoline-3,3'-pyrrolidine]-1,1'-dicarboxamide (Example 390), 1'-acetyl-5-chloro-N-(6-chloropyrazin-2-yl)spiro[indoline-3,3'-pyrrolidine]-1-carboxamide (Example 391), 1'-acetyl-N-(5-bromopyrazin-2-yl)-5-chlorospiro[indoline-3,3'-pyrrolidine]-1-carboxamide (Example 392), 1'-acetyl-5-chloro-N-(pyrazin-2-yl)spiro[indoline-3,3'-pyrrolidine]-1-carboxamide (Example 393), 1'-acetyl-5-chloro-N-(5-methoxypyrazin-2-yl)spiro[indoline-3,3'-pyrrolidine]-1-carboxamide (Example 394), 1'-acetyl-5-chloro-N-(5-chloropyrazin-2-yl)spiro[indoline-3,3'-pyrrolidine]-1-carboxamide (Example 395), 1'-acetyl-5-chloro-N-(pyridazin-3-yl)spiro[indoline-3,3'-pyrrolidine]-1-carboxamide (Example 396), ethyl 4-((1'-acetyl-1-((5-chlorothiazol-2-yl)carbamoyl)spiro[indoline-3,3'-pyrrolidin]-5-yl)oxy)butanoate (Example 397), 4-((1'-acetyl-1-((5-chlorothiazol-2-yl)carbamoyl)spiro[indoline-3,3'-pyrrolidin]-5-yl)oxy)butanoic acid (Example 398), 1'-acetyl-5-(4-(azetidin-1-yl)-4-oxobutoxy)-N-(5-chlorothiazol-2-yl)spiro[indoline-3,3'-pyrrolidine]-1-carboxamide (Example 399), 1'-acetyl-N-(5-chlorothiazol-2-yl)-5-(4-(methylamino)-4-oxobutoxy)spiro[indoline-3,3'-pyrrolidine]-1-carboxamide (Example 400), 1'-acetyl-1-((5-chlorothiazol-2-yl)carbamoyl)spiro[indoline-3,3'-pyrrolidine]-5-carboxylic acid (Example 401), 1'-acetyl-N1-(5-chlorothiazol-2-yl)-N-5-methyl spiro[indoline-3,3'-pyrrolidine]-1,5-dicarboxamide (Example 402), 3-(N-benzyl-1-((5-chlorothiazol-2-yl)carbamoyl)-1'-(methylcarbamoyl)spiro[indoline-3,3'-pyrrolidin]-5-ylcarboxamido)propanoic acid (Example 403), 1'-acetyl-N-(5-chlorothiazol-2-yl)-5-(hydroxymethyl)spiro[indoline-3,3'-pyrrolidine]-1-carboxamide (Example 404), 1'-acetyl-N-(5-chlorothiazol-2-yl)-5-(1-hydroxyethyl)spiro[indoline-3,3'-pyrrolidine]-1-carboxamide (Example 405), 1',5-diacetyl-N-(5-chlorothiazol-2-yl)spiro[indoline-3,3'-pyrrolidine]-1-carboxamide (Example 406), 1'-acetyl-N-(5-chlorothiazol-2-yl)-5-(2-hydroxypropan-2-yl)spiro[indoline-3,3'-pyrrolidine]-1-carboxamide (Example 407), 2-(1'-acetyl-1-((5-chlorothiazol-2-yl)carbamoyl)spiro[indoline-3,3'-pyrrolidin]-5-yl)acetic acid (Example 408), 1'-acetyl-5-(2-(azetidin-1-yl)-2-oxoethyl)-N-(5-chlorothiazol-2-yl)spiro[indoline-3,3'-pyrrolidine]-1-carboxamide (Example 409), (E)-ethyl 3-(1'-acetyl-1-((5-chlorothiazol-2-yl)carbamoyl)spiro[indoline-3,3'-pyrrolidin]-5-yl)acrylate (Example 410), (E)-1'-acetyl-5-(3-(azetidin-1-yl)-3-oxoprop-1-en-1-yl)-N-(5-chlorothiazol-2-yl)spiro[indoline-3,3'-pyrrolidine]-1-carboxamide (Example 411), 3-(1'-acetyl-1-((5-chlorothiazol-2-yl)carbamoyl)spiro[indoline-3,3'-pyrrolidin]-5-yl)propanoic acid (Example 412), 1'-acetyl-5-(3-(azetidin-1-yl)-3-oxopropyl)-N-(5-chlorothiazol-2-yl)spiro[indoline-3,3'-pyrrolidine]-1-carboxamide (Example 413), 5-(3-(azetidin-1-yl)-3-oxopropyl)-1'-(2-hydroxyacetyl)-N-(5-methoxythiazol-2-yl)spiro[indoline-3,3'-pyrrolidine]-1-carboxamide (Example 414), 5-(3-(azetidin-1-yl)-3-oxopropyl)-1'-(2-hydroxyacetyl)-N-(5-methylthiazol-2-yl)spiro[indoline-3,3'-pyrrolidine]-1-carboxamide (Example 415), 5-(3-(azetidin-1-yl)-3-oxopropyl)-N1-(5-chlorothiazol-2-yl)-N1'-methyl spiro[indoline-3,3'-pyrrolidine]-1,1'-dicarboxamide (Example 416), 5-(3-(azetidin-1-yl)-3-oxopropyl)-N1-(5-methoxythiazol-2-yl)-N1'-methyl spiro[indoline-3,3'-pyrrolidine]-1,1'-dicarboxamide (Example 417), ethyl 4-(1'-acetyl-1-((5-chlorothiazol-2-yl)carbamoyl)spiro[indoline-3,3'-pyrrolidin]-5-yl)butanoate (Example 418), ethyl 4-(1-((5-chlorothiazol-2-yl)carbamoyl)-1'-(methylcarbamoyl)spiro[indoline-3,3'-pyrrolidin]-5-yl)butanoate (Example 419), ethyl 4-(1'-(methylcarbamoyl)-1-((5-methylpyrazin-2-yl)carbamoyl)spiro[indoline-3,3'-pyrrolidin]-5-yl)butanoate (Example 420), 4-(1'-acetyl-1-((5-chlorothiazol-2-yl)carbamoyl)spiro[indoline-3,3'-pyrrolidin]-5-yl)butanoic acid (Example 421), 4-(1-((5-chlorothiazol-2-yl)carbamoyl)-1'-(methylcarbamoyl)spiro[indoline-3,3'-pyrrolidin]-5-yl)butanoic acid (Example 422), 1'-acetyl-5-(4-(azetidin-1-yl)-4-oxobutyl)-N-(5-chlorothiazol-2-yl)spiro[indoline-3,3'-pyrrolidine]-1-carboxamide (Example 423), 5-(4-(azetidin-1-yl)-4-oxobutyl)-N1-(5-chlorothiazol-2-yl)-N1'-methylspiro[indoline-3,3'-pyrrolidine]-1,1'-dicarboxamide (Example 424), 5-(4-(azetidin-1-yl)-4-oxobutyl)-N1'-methyl-N1-(5-methylpyrazin-2-yl)spiro[indoline-3,3'-pyrrolidine]-1,1'-dicarboxamide (Example 425), ethyl 5-(1'-acetyl-1-((5-chlorothiazol-2-yl)carbamoyl)spiro[indoline-3,3'-pyrrolidin]-5-yl)pentanoate (Example 426), 5-(1'-acetyl-1-((5-chlorothiazol-2-yl)carbamoyl)spiro[indoline-3,3'-pyrrolidin]-5-yl)pentanoic acid (Example 427), 1'-acetyl-5-(5-(azetidin-1-yl)-5-oxopentyl)-N-(5-chlorothiazol-2-yl)spiro[indoline-3,3'-pyrrolidine]-1-carboxamide (Example 428), 1'-acetyl-N-(5-chlorothiazol-2-yl)-5-(4-(methylsulfonyl)butyl)spiro[indoline-3,3'-pyrrolidine]-1-carboxamide (Example 429), 1'-acetyl-5-((3-(azetidine-1-carbonyl)cyclobutyl)methyl)-N-(5-chlorothiazol-2-yl)spiro[indoline-3,3'-pyrrolidine]-1-carboxamide (Example 430), 1'-acetyl-N-(5-chlorothiazol-2-yl)-5-(trifluoromethyl)spiro[indoline-3,3'-pyrrolidine]-1-carboxamide (Example 431), N1-(5-chlorothiazol-2-yl)-N1'-methyl-5-(trifluoromethyl)spiro[indoline-3,3'-pyrrolidine]-1,1'-dicarboxamide (Example 432), N1'-methyl-N1-(5-methylthiazol-2-yl)-5-(trifluoromethyl)spiro[indoline-3,3'-pyrrolidine]-1,1'-dicarboxamide (Example 433), N1'-methyl-N1-(5-methylpyrazin-2-yl)-5-(trifluoromethyl)spiro[indoline-3,3'-pyrrolidine]-1,1'-dicarboxamide (Example 434), 1'-(2-hydroxyacetyl)-N-(5-methylpyrazin-2-yl)-5-(trifluoromethyl)spiro[indoline-3,3'-pyrrolidine]-1-carboxamide (Example 435), 1'-acetyl-N-(5-fluorothiazol-2-yl)-5-(trifluoromethyl)spiro[indoline-3,3'-pyrrolidine]-1-carboxamide (Example 436), 1'-acetyl-N-(5-methoxythiazol-2-yl)-5-(trifluoromethyl) spiro[indoline-3,3'-pyrrolidine]-1-carboxamide (Example 437), N1-(5-fluorothiazol-2-yl)-N1'-methyl-5-(trifluoromethyl) spiro[indoline-3,3'-pyrrolidine]-1,1'-dicarboxamide (Example 438), N1-(5-methoxythiazol-2-yl)-N1'-methyl-5-(trifluoromethyl) spiro[indoline-3,3'-pyrrolidine]-1,1'-dicarboxamide (Example 439), 1'-(2-(methylamino)-2-oxoacetyl)-N-(5-methylpyrazin-2-yl)-5-(trifluoromethyl)spiro[indoline-3,3'-pyrrolidine]-1-carboxamide (Example 440), 1'-(2-hydroxyacetyl)-N-(5-methoxythiazol-2-yl)-5-(trifluoromethyl)spiro[indoline-3,3'-pyrrolidine]-1-carboxamide (Example 441), N-(5-methoxythiazol-2-yl)-1'-(2-(methylamino)-2-oxoacetyl)-5-(trifluoromethyl)spiro[indoline-3,3'-pyrrolidine]-1-carboxamide (Example 442), N-(5-chlorothiazol-2-yl)-1'-(2-(methylamino)-2-oxoacetyl)-5-(trifluoromethyl)spiro[indoline-3,3'-pyrrolidine]-1-carboxamide (Example 443), 1'-acetyl-N-(5-methylpyrazin-2-yl)-5-(trifluoromethyl)spiro[indoline-3,3'-pyrrolidine]-1-carboxamide (Example 444), N1'-((1-acetylazetidin-3-yl)methyl)-N1-(5-chlorothiazol-2-yl)-5-(trifluoromethyl)spiro[indoline-3,3'-pyrrolidine]-1,1'-dicarboxamide (Example 445), N1'-((1-acetylazetidin-3-yl)methyl)-N1-(5-fluorothiazol-2-yl)-5-(trifluoromethyl)spiro[indoline-3,3'-pyrrolidine]-1,1'-dicarboxamide (Example 446), N1'-((1-acetylazetidin-3-yl)methyl)-N1-(5-methoxythiazol-2-yl)-5-(trifluoromethyl)spiro[indoline-3,3'-pyrrolidine]-1,1'-dicarboxamide (Example 447), N1'-((1-acetylazetidin-3-yl)methyl)-N1-(5-methylpyrazin-2-yl)-5-(trifluoromethyl)spiro[indoline-3,3'-pyrrolidine]-1,1'-dicarboxamide (Example 448), 5-chloro-N-(5-chlorothiazol-2-yl)-1'-(methylcarbamothioyl)spiro[indoline-3,3'-pyrrolidine]-1-carboxamide (Example 449), 5-chloro-N-(5-chlorothiazol-2-yl)-1'-(2-ethoxy-3,4-dioxocyclobut-1-en-1-yl)spiro[indoline-3,3'-pyrrolidine]-1-carboxamide (Example 450), 5-chloro-N-(5-chlorothiazol-2-yl)-1'-(2-(methylamino)-3,4-dioxo cyclobut-1-en-1-yl)spiro[indoline-3,3'-pyrrolidine]-1-carboxamide (Example 451), 1'-acetyl-N-(5-((3-aminopropyl)thio)thiazol-2-yl)-5-chlorospiro[indoline-3,3'-pyrrolidine]-1-carboxamide (Example 452), N-(5-((3-acetamidopropyl)thio)thiazol-2-yl)-1'-acetyl-5-chlorospiro[indoline-3,3'-pyrrolidine]-1-carboxamide (Example 453), methyl 5-chloro-1-((5-((3-(cyclopropanecarboxamido)propyl)thio)thiazol-2-yl)carbamoyl)spiro[indoline-3,3'-pyrrolidine]-1'-carboxylate (Example 454), methyl 5-chloro-1-((5-((3-((methoxycarbonyl)amino)propyl)thio)thiazol-2-yl)carbamoyl)spiro[indoline-3,3'-pyrrolidine]-1'-carboxylate (Example 455), 1'-acetyl-5-chloro-N-(5-cyanothiazol-2-yl)spiro[indoline-3,3'-pyrrolidine]-1-carboxamide (Example 456), ethyl 2-(5-chloro-1-((5-chlorothiazol-2-yl)carbamoyl)spiro[indoline-3,3'-pyrrolidin]-1'-ylcarboxamido)acetate (Example 457), 2-(5-chloro-1-((5-chlorothiazol-2-yl)carbamoyl)spiro[indoline-3,3'-pyrrolidin]-1'-ylcarboxamido)acetic acid (Example 458), 5-chloro-N1-(5-chlorothiazol-2-yl)-N1'-(2-hydroxyethyl) spiro[indoline-3,3'-pyrrolidine]-1,1'-dicarboxamide (Example 459), N1'-(2-(azetidin-1-yl)-2-oxoethyl)-5-chloro-N1-(5-chlorothiazol-2-yl)spiro[indoline-3,3'-pyrrolidine]-1,1'-dicarboxamide (Example 460), 5-chloro-N1-(5-chlorothiazol-2-yl)-N1'-(2-(methylamino)-2-oxoethyl)spiro[indoline-3,3'-pyrrolidine]-1,1'-dicarboxamide (Example 461), ethyl 3-(5-chloro-1-((5-chlorothiazol-2-yl)carbamoyl)spiro[indoline-3,3'-pyrrolidin]-1'-ylcarboxamido)propanoate (Example 462), 3-(5-chloro-1-((5-chlorothiazol-2-yl)carbamoyl)spiro[indoline-3,3'-pyrrolidin]-1'-ylcarboxamido)propanoic acid (Example 463), 5-chloro-N1-(5-chlorothiazol-2-yl)-N1'-(3-hydroxypropyl) spiro[indoline-3,3'-pyrrolidine]-1,1'-dicarboxamide (Example 464), 5-chloro-N1-(5-chlorothiazol-2-yl)-N1'-(3-(methylamino)-3-oxopropyl)spiro[indoline-3,3'-pyrrolidine]-1,1'-dicarboxamide (Example 465), N1'-(3-(azetidin-1-yl)-3-oxopropyl)-5-chloro-N1-(5-chlorothiazol-2-yl)spiro[indoline-3,3'-pyrrolidine]-1,1'-dicarboxamide (Example 466), 5-chloro-N1-(5-chlorothiazol-2-yl)-N1'-(2-(methylsulfonyl) ethyl)spiro[indoline-3,3'-pyrrolidine]-1,1'-dicarboxamide (Example 467), ethyl 4-(5-chloro-1-((5-chlorothiazol-2-yl)carbamoyl)spiro[indoline-3,3'-pyrrolidin]-1'-ylcarboxamido)butanoate (Example 468), 4-(5-chloro-1-((5-chlorothiazol-2-yl)carbamoyl)spiro[indoline-3,3'-pyrrolidin]-1'-ylcarboxamido)butanoic acid (Example 469), 5-chloro-N1-(5-chlorothiazol-2-yl)-N1'-(4-hydroxybutyl) spiro[indoline-3,3'-pyrrolidine]-1,1'-dicarboxamide (Example 470), N1'-(4-(azetidin-1-yl)-4-oxobutyl)-5-chloro-N1-(5-chlorothiazol-2-yl)spiro[indoline-3,3'-pyrrolidine]-1,1'-dicarboxamide (Example 471), 5-chloro-N1-(5-chlorothiazol-2-yl)-N1'-(4-(methylamino)-4-oxobutyl)spiro[indoline-3,3'-pyrrolidine]-1,1'-dicarboxamide (Example 472), ethyl 1-(5-chloro-1-((5-chlorothiazol-2-yl)carbamoyl)spiro [indoline-3,3'-pyrrolidin]-1'-ylcarboxamido)cyclopropanecarboxylate (Example 473), 1-(5-chloro-1-((5-chlorothiazol-2-yl)carbamoyl)spiro[indoline-3,3'-pyrrolidin]-1'-ylcarboxamido)cyclopropanecarboxylic acid (Example 474), 5-chloro-N1-(5-chlorothiazol-2-yl)-N1'-(1-(methylcarbamoyl)cyclopropyl)spiro[indoline-3,3'-pyrrolidine]-1,1'-dicarboxamide (Example 475), N1'-((1-acetylazetidin-3-yl)methyl)-5-chloro-N1-(5-chlorothiazol-2-yl)spiro[indoline-3,3'-pyrrolidine]-1,1'-dicarboxamide (Example 476), 5-chloro-N-(5-chlorothiazol-2-yl)-1'-((S)-2,3-dihydroxypropanoyl)spiro[indoline-3,3'-pyrrolidine]-1-carboxamide (Example 477), 5-chloro-N-(5-chlorothiazol-2-yl)-1'-((R)-2,3-dihydroxypropanoyl)spiro[indoline-3,3'-pyrrolidine]-1-carboxamide (Example 478), 5-chloro-N-(5-chlorothiazol-2-yl)-1'-(3-hydroxypropanoyl) spiro[indoline-3,3'-pyrrolidine]-1-carboxamide (Example 479), 5-chloro-N1-(5-chlorothiazol-2-yl)-N1'-methoxyspiro[indoline-3,3'-pyrrolidine]-1,1'-dicarboxamide (Example 480), 5-chloro-N1-(5-chlorothiazol-2-yl)-N1'-hydroxyspiro[indoline-3,3'-pyrrolidine]-1,1'-dicarboxamide (Example 481), 5-chloro-N-(5-chlorothiazol-2-yl)-1'-(N-methylsulfamoyl) spiro[indoline-3,3'-pyrrolidine]-1-carboxamide (Example 482), (R)-1'-acetyl-5-cyano-N-(5-fluorothiazol-2-yl)spiro[indoline-3,3'-pyrrolidine]-1-carboxamide (Example 483), (R)-5-chloro-N1-(5-chlorothiazol-2-yl)-N1'-methyl spiro[indoline-3,3'-pyrrolidine]-1,1'-dicarboxamide (Example 484), (R)—N1'-methyl-N1-(5-methylpyrazin-2-yl)-5-(trifluoromethyl)spiro[indoline-3,3'-pyrrolidine]-1,1'-dicarboxamide (Example 485), (R)-1'-acetyl-N-(5-methoxythiazol-2-yl)-5-(trifluoromethyl)spiro[indoline-3,3'-pyrrolidine]-1-carboxamide (Example 486), (R)—N1-(5-fluorothiazol-2-yl)-N1'-methyl-5-(trifluoromethyl)spiro[indoline-3,3'-pyrrolidine]-1,1'-dicarboxamide (Example 487), (S)—N1-(5-methoxythiazol-2-yl)-N1'-methyl-5-(trifluoromethyl)spiro[indoline-3,3'-pyrrolidine]-1,1'-dicarboxamide (Example 488), and, (R)—N1-(5-methoxythiazol-2-yl)-N1'-methyl-5-(trifluoromethyl)spiro[indoline-3,3'-pyrrolidine]-1,1'-dicarboxamide (Example 489).

If the compound of the present invention has geometric isomers or optical isomers, such isomers are also included in the scope of the present invention. These isomers are separated according to an ordinary method.

The salt of the compound represented by the general formula (1) is not particularly limited, as long as it is a pharmaceutically acceptable salt. When the compound is treated as an acidic compound, examples of the salt of the compound represented by the general formula (1) include: alkaline metal salts or alkaline-earth metal salts, such as sodium, potassium, magnesium, or calcium; and salts with organic bases such as trimethylamine, triethylamine, pyridine, picoline, N-methylpyrrolidine, N-methyl piperidine, or N-methyl morpholine. When the compound is treated as a basic compound, examples of the salt of the compound represented by the general formula (1) include: acid-added salts with mineral acids, such as hydrochloride, hydrobromide, hydroiodide, sulfate, nitrate, or phosphate; and acid-added salts with organic acids, such as benzoate, methanesulfonate, ethanesulfonate, benzenesulfonate, p-toluenesulfonate, maleate, fumarate, tartrate, citrate, or acetate.

An example of the solvate of the compound represented by the general formula (1) or a salt thereof is a hydrate. However, examples of the solvate are not limited thereto.

It is to be noted that a compound that is metabolized in a living body and is converted to the compound represented by the general formula (1), namely, a prodrug is also included in the present invention. Examples of a group capable of forming the prodrug of the compound of the present invention include groups described in "Progress in Medicine," Life-science Medica, 1985, Vol. 5, pp. 2157-2161, and groups described in "Iyakuhin no Kaihatsu (Development of Pharmaceutical Products)," Hirokawa Shoten, 1990, Vol. 7, Bunshi Sekkei (Molecular Designing), pp. 163-198.

The above described compound represented by the general formula (1), or a salt thereof, or a solvate of the compound or the salt can be produced by various known methods. The production method is not particularly limited, and they can be produced, for example, according to reaction steps as described below. In addition, upon performing the following reactions, functional groups other than those in the reaction site may previously be protected as necessary, and they may be then deprotected at a suitable stage. Such protection and deprotection can be carried out with reference to commonly used methods (e.g. the method described in Protective Groups in Organic Synthesis Third Edition, John Wiley & Sons, Inc., 1999). Further, reactions in individual steps may be carried out by ordinary methods (e.g. the method described in Comprehensive Organic Transformations Second Edition, John Wiley & Sons, Inc.; 1999), and isolation and purification may be carried out by an ordinary method appropriately selected from crystallization, recrystallization, chromatography, and the like, or by a combination thereof.

(Method for Producing the Compound Represented by the General Formula (1))

The compound represented by the general formula (1) of the present invention can be produced by the method illustrated in reaction pathway diagram 1 as shown below. Specifically, a compound represented by general formula (13) is allowed to react with an amino-heteroaryl derivative represented by general formula (14) to obtain a urea compound represented by general formula (15) (A-1). A protecting group is removed from the urea compound represented by general formula (15) to obtain an amine compound represented by general formula (16) (A-2). A reaction reagent is allowed to react with the amine compound represented by general formula (16), so as to produce the compound represented by the general formula (1) of the present invention (A-3).

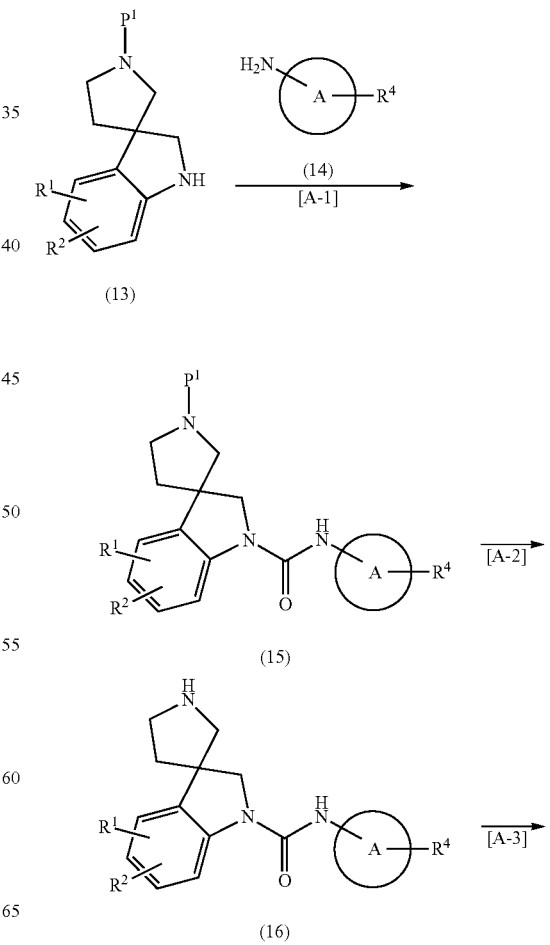

[Reaction Pathway Diagram 1]

-continued

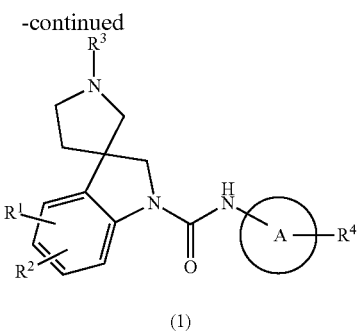

(1)

[wherein ring A, R¹, R², R³, and R⁴ have the same definitions as those in the above described general formula (1), and P¹ represents a protecting group for the amino group (a benzyl group, a benzyloxycarbonyl group, a t-butoxycarbonyl group, etc.)].

(A-1) Step A-1 is a step of allowing the compound (13) to react with the compound (14) in the presence of an ureation reagent to produce the compound (15). The used ureation reagent is not particularly limited. Examples of the ureation reagent include phosgene, triphosgene, carbonyldiimidazole, 4-nitrophenyl chloroformate, and phenyl chloroformate. Of these, carbonyldiimidazole is preferable. The used solvent is not particularly limited. Examples of the solvent include organic solvents such as tetrahydrofuran, dioxane, cyclopentylmethyl ether, dichloromethane, dichloroethane, or N,N'-dimethylformamide. Of these, tetrahydrofuran is preferable. In addition, bases such as triethylamine or pyridine may also be used, as necessary. The reaction temperature is −30° C. to 150° C., and preferably 0° C. to 100° C. The reaction time is 1 minute to 48 hours, and preferably 30 minutes to 24 hours.

(A-2) Step A-2 is a step of removing the protecting group P¹ from the compound (15) obtained in Step A-1 to produce the compound (16). Methods and conditions for such deprotection are different depending on the type of the protecting group P¹. For example, a benzyl group and a benzyloxycarbonyl group can be removed by catalytic hydrogenation, and a t-butoxycarbonyl group can be removed with acid. Such deprotection can be carried out with reference to a method commonly used in organic chemistry (e.g. the method described in Protective Groups in Organic Synthesis Third Edition, John Wiley & Sons, Inc., 1999).

(A-3) Step A-3 is a step of subjecting the compound (16) obtained in Step A-2 to alkylation with halogenated alkyl, or reductive amination with an aldehyde compound, or a condensation reaction with a carboxylic acid compound, or acylation with an acyl chloride compound, or carbamation with a chloroformic acid compound, or an ureation reaction with an ureation reagent, or a sulfonamidation reaction with a sulfonyl chloride compound, so as to produce the compound (1). The reaction can be carried out with reference to an ordinary method (e.g. the method described in Comprehensive Organic Transformations Second Edition, John Wiley & Sons, Inc.; 1999).

The compound (13) used as a raw material can be produced by a method described in known methods (International Publication WO2009/089454 etc.) or a method similar thereto. In addition, by using, as a raw material, tryptamine, 5-bromotryptamine, 5-methoxytryptamine, 5-trifluoromethyloxytryptamine, 5-cyanotryptamine, etc., instead of 5-chlorotryptamine, various compounds corresponding to the compound (13) can also be produced.

Moreover, differing from the above described methods, the compound represented by the general formula (1) of the present invention can also be produced by the method illustrated in reaction pathway diagram 2 as shown below. Specifically, a protecting group is bound to a compound represented by general formula (13) to obtain a compound represented by general formula (17) (B-1). The protecting group is removed from the compound represented by general formula (17) to obtain an amine compound represented by general formula (18) (B-2). A reaction reagent is allowed to react with the compound represented by general formula (18) to obtain a compound represented by general formula (19) (B-3). A protecting group is removed from the compound represented by general formula (19) to obtain an amine compound represented by general formula (20) (B-4). An aminoheteroaryl derivative represented by general formula (14) is allowed to react with the compound represented by general formula (20), so as to produce the compound represented by the general formula (1) of the present invention (B-5).

[Reaction Pathway Diagram 2]

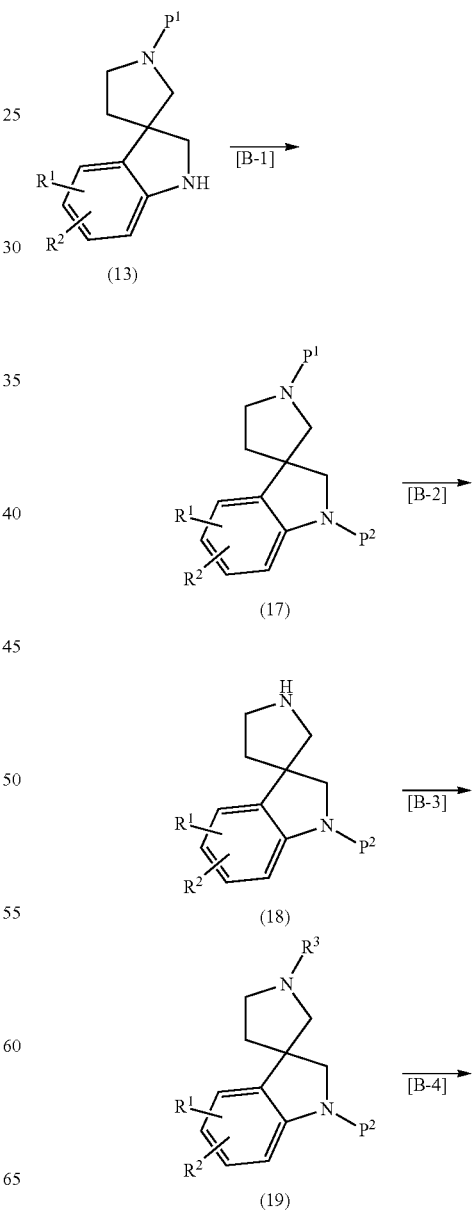

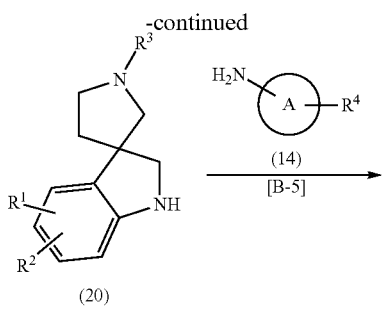

(20)

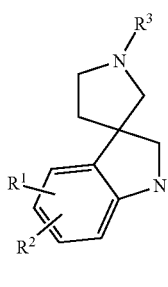

(1)

[wherein ring A, R$^1$, R$^2$, R$^3$, and R$^4$ have the same definitions as those in the above described general formula (1), P$^1$ and P$^2$ each represent a protecting group for the amino group (a benzyl group, a benzyloxycarbonyl group, a t-butoxycarbonyl group, etc.)].

(B-1) Step B-1 is a step of protecting the amino group of the compound (13) by P$^2$ to produce the compound (17). Methods and conditions for such protection are different depending on the type of the protecting group P$^2$. Such protection can be carried out with reference to a method commonly used in organic chemistry (e.g. the method described in Protective Groups in Organic Synthesis Third Edition, John Wiley & Sons, Inc., 1999).

(B-2) Step B-2 is a step of removing the protecting group P$^1$ from the compound (17) obtained in Step B-1 to produce the compound (18). Methods and conditions for such deprotection are different depending on the type of the protecting group P$^1$. For example, a benzyl group and a benzyloxycarbonyl group can be removed by catalytic hydrogenation, and a t-butoxycarbonyl group can be removed with acid. Such deprotection can be carried out with reference to a method commonly used in organic chemistry (e.g. the method described in Protective Groups in Organic Synthesis Third Edition, John Wiley & Sons, Inc., 1999).

(B-3) Step B-3 is a step of subjecting the compound (18) obtained in Step B-2 to alkylation with halogenated alkyl, or reductive amination with an aldehyde compound, or a condensation reaction with a carboxylic acid compound, or acylation with an acyl halide compound, or carbamation with a haloformic acid compound, or an ureation reaction with an ureation reagent, or a sulfonamidation reaction with a sulfonyl halide, so as to produce the compound (19) The reaction can be carried out with reference to an ordinary method (e.g. the method described in Comprehensive Organic Transformations Second Edition, John Wiley & Sons, Inc.; 1999).

(B-4) Step B-4 is a step of removing the protecting group P$^2$ from the compound (19) obtained in Step B-3 to produce the compound (20). Methods and conditions for such deprotection are different depending on the type of the protecting group P$^2$. For example, a benzyl group and a benzyloxycarbonyl group can be removed by catalytic hydrogenation, and a t-butoxycarbonyl group can be removed with acid. Such deprotection can be carried out with reference to a method commonly used in organic chemistry (e.g. the method described in Protective Groups in Organic Synthesis Third Edition, John Wiley & Sons, Inc., 1999).

(B-5) Step B-5 is a step of allowing the compound (20) obtained in Step B-4 to react with the compound (14) in the presence of an ureation reagent to produce the compound (1). The used ureation reagent is not particularly limited. Examples of the ureation reagent include phosgene, triphosgene, carbonyldiimidazole, 4-nitrophenyl chloroformate, and phenyl chloroformate. The used solvent is not particularly limited. Examples of the solvent include organic solvents such as tetrahydrofuran, dioxane, cyclopentylmethyl ether, dichloromethane, and dichloroethane. The reaction temperature is −30° C. to 150° C., and preferably 0° C. to 100° C. The reaction time is 1 minute to 48 hours, and preferably 30 minutes to 24 hours.

Moreover, the compounds represented by general formula (19), which can also be represented by general formula (23), can be produced by the method illustrated in reaction pathway diagram 3 as shown below. Specifically, a compound represented by general formula (21) is subjected to demethylation to obtain a phenol compound represented by general formula (22) (C-1). The compound represented by general formula (22) is subjected to alkylation to obtain the compound represented by general formula (23) (C-2)

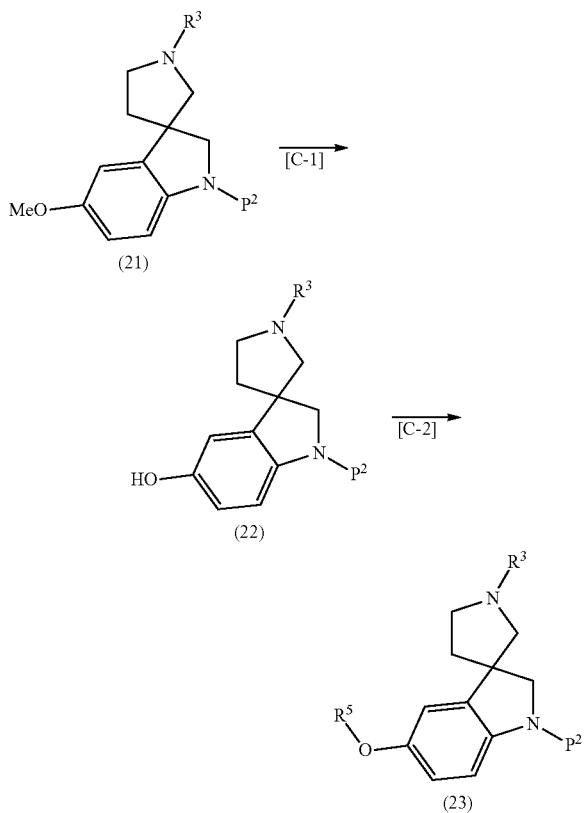

[Reaction Pathway Diagram 3]

[wherein R$^3$ and R$^5$ have the same definitions as those in the above described general formula (1), and P$^2$ represents a protecting group for the amino group (a benzyl group, a benzyloxycarbonyl group, a t-butoxycarbonyl group, etc.)].

(C-1) Step C-1 is a method of producing the compound represented by general formula (22) by performing a reaction on the compound (21) that can be produced by a method described in known methods (International Publication WO2009/089454 etc.) or a method similar thereto under demethylation conditions. Such demethylation can be carried out with reference to a method commonly used in organic chemistry (e.g. the method described in Protective Groups in Organic Synthesis Third Edition, John Wiley & Sons, Inc., 1999).

(C-2) Step C-2 is a method of producing the compound represented by general formula (23) by subjecting the compound represented by general formula (22) to alkylation and arylation. For example, for introduction of an alkyl group into the aforementioned compound, a reaction of the compound with halogenated alkyl can be applied, and for introduction of an aryl group into the aforementioned compound, general cross-coupling reactions using transition metal, which include the Suzuki-Miyaura Reaction (Chem. Rev., 95, 2457-2483 (1995)) as a typical example, can be applied. Regarding the reaction of introducing an alkyl group, halogenated alkyl is allowed to act on the compound in the presence of a base. The used base is not particularly limited. Examples of the base that can be used herein include: alkali metal carbonates such as lithium carbonate, sodium carbonate, potassium carbonate, cesium carbonate, or sodium hydrogen carbonate; and organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent that can be used herein include N,N-dimethylformamide, N,N-dimethylacetamide, N-methylpyrrolidone, dimethyl sulfoxide, dioxane, tetrahydrofuran, acetonitrile, propionitrile, dichloroethane, and dichloromethane. The reaction temperature is −30° C. to 150° C., and preferably 0° C. to 120° C. The reaction time is 10 minutes to 12 hours, and preferably 30 minutes to 6 hours. For the reaction of introducing an aryl group into the compound, a coupling reaction with a boronic acid reagent that is carried out in a solvent or with no solvent, in the presence or absence of a base, and in the presence of a metal catalyst, can be applied. During this reaction, microwave irradiation may also be carried out. Examples of the metal catalyst used herein include: palladium complexes such as tris(dibenzylideneacetone)dipalladium(0), tris(dibenzylideneacetone) (chloroform)dipalladium(0), [1,1'-bis(diphenylphosphino) ferrocene]dichloropalladium(II), or tetrakis (triphenylphosphine)palladium(0); and copper reagents such as copper acetate, cuprous iodide, cuprous bromide, or cuprous cyanide. These substances may be used singly. However, these metal catalysts may also be used in combination with a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine, or N-methylglycine. The used base is not particularly limited. Examples of the base that can be used herein include: alkali metal hydrides such as lithium hydride, sodium hydride, or potassium hydride; alkali metals such as metallic lithium, metallic sodium, or metallic potassium; alkali metal hydroxides such as lithium hydroxide, sodium hydroxide, or potassium hydroxide; alkali metal carbonates such as lithium carbonate, sodium carbonate, potassium carbonate, or cesium carbonate; alkali metal fluorides such as potassium fluoride or cesium fluoride; organic metal bases such as lithium diisopropylamide, sodium diisopropylamide, potassium diisopropylamide, lithium hexamethyldisilazide, sodium hexamethyldisilazide, potassium hexamethyldisilazide, t-butoxy sodium, t-butoxy potassium, n-butyl lithium, sec-butyl lithium, or t-butyl lithium; and organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent include tetrahydrofuran, toluene, dioxane, N,N-dimethylformamide, N,N-dimethylacetamide, N-methylpyrrolidone, dimethyl sulfoxide, dichloromethane, and water. These solvents can be used singly or in combination. The reaction temperature is 0° C. to 200° C., and preferably 10° C. to 100° C. The reaction time is 1 minute to 5 days, and preferably 30 minutes to 24 hours.

Moreover, the compounds represented by general formula (19), which can also be represented by general formula (27), can be produced by the method illustrated in reaction pathway diagram 4 as shown below. Specifically, a compound represented by general formula (24) is subjected to chlorosulfonylation to obtain a compound represented by general formula (25) (D-1). The compound represented by general formula (25) is allowed to react with an amine compound represented by general formula (26) to obtain a compound represented by general formula (27) (D-2).

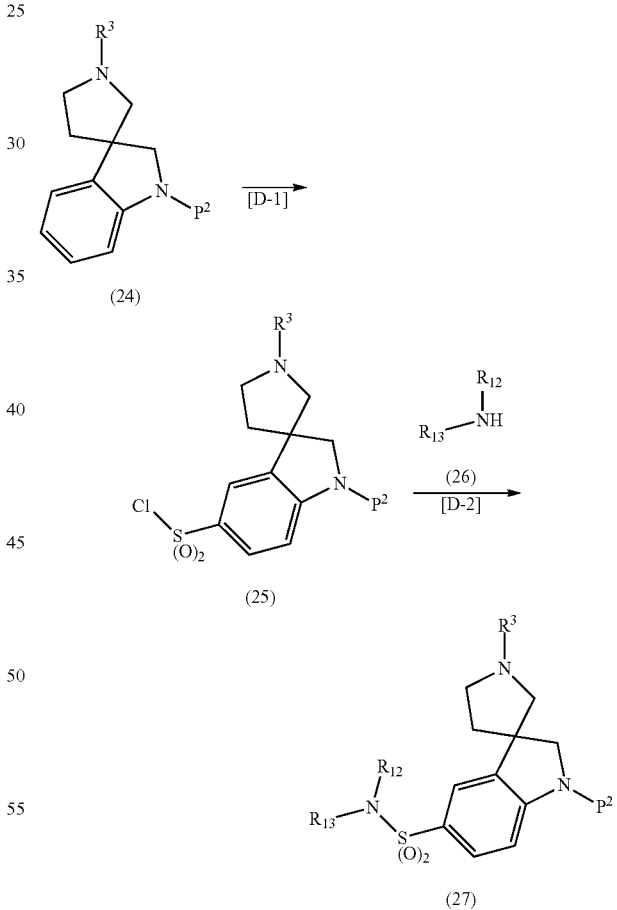

[Reaction Pathway Diagram 4]

[wherein $R^3$ has the same definition as that in the above described general formula (1), $R^{12}$ and $R^{13}$ each represent a $C_{1-6}$ alkyl group optionally having a substituent, a $C_{3-8}$ cycloalkyl group or a 5-10 membered heterocyclic ring, and $P^2$ represents a protecting group for the amino group (a benzyl group, a benzyloxycarbonyl group, a t-butoxycarbonyl group, etc.)].

(D-1) Step D-1 is a method of producing the compound represented by general formula (25) by subjecting the compound (24) that can be produced by a method described in known methods (International Publication WO2009/089454 etc.) or a method similar thereto to chlorosulfonylation. The used chlorosulfonylation reagent is not particularly limited, and an example of such a reagent is chlorosulfonic acid. The used solvent is not particularly limited. Examples of the solvent include organic solvents such as carbon tetrachloride, dichloromethane, or dichloroethane. Of these, dichloromethane is preferable. The reaction temperature is −30° C. to 150° C., and preferably 0° C. to 100° C. The reaction time is 1 minute to 48 hours, and preferably 30 minutes to 24 hours.

(D-2) Step D-2 is a method of producing the compound represented by general formula (27) by allowing the compound represented by general formula (25) to react with the amine compound represented by general formula (26) in the presence of a base. The used base is not particularly limited. Examples of the base that can be used herein include: alkali metal carbonates such as lithium carbonate, sodium carbonate, potassium carbonate, cesium carbonate, or sodium hydrogen carbonate; and organic bases such as 1,8-diazabicyclo[5.4.0]undec-7-ene (DBU), 1,5-diazabicyclo[4.3.0]non-5-ene (DBN), triethylamine, N,N-diisopropylethylamine, N,N-diisopropylpentylamine, trimethylamine, or pyridine. The used solvent is not particularly limited. Examples of the solvent that can be used herein include N,N-dimethylformamide, N,N-dimethylacetamide, N-methylpyrrolidone, dimethyl sulfoxide, dioxane, tetrahydrofuran, acetonitrile, propionitrile, dichloroethane, and dichloromethane. The reaction temperature is −30° C. to 150° C., and preferably 0° C. to 100° C. The reaction time is 10 minutes to 12 hours, and preferably 30 minutes to 6 hours.

Moreover, the compounds represented by general formula (19), which can also be represented by general formula (29), can be produced by the method illustrated in reaction pathway diagram 5 as shown below. Specifically, a compound represented by general formula (25) is reduced and is then alkylated, so as to obtain a compound represented by general formula (28) (E-1). The compound represented by general formula (28) is oxidized to obtain a compound represented by general formula (29) (E-2).

[Reaction Pathway Diagram 5]

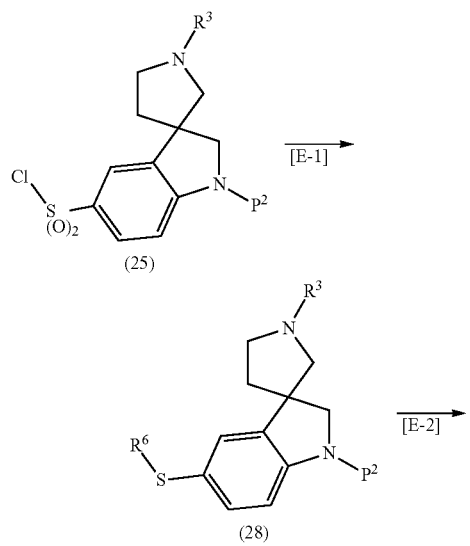

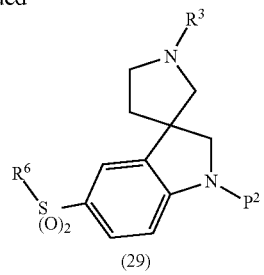

[wherein $R^3$ and $R^6$ have the same definitions as those in the above described general formula (1), and $P^2$ represents a protecting group for the amino group (a benzyl group, a benzyloxycarbonyl group, a t-butoxycarbonyl group, etc.)].

(E-1) Step E-1 is a method of producing the compound represented by general formula (28) by reducing the compound represented by general formula (25) and then alkylating it. The used reducing agent is not particularly limited. Examples of the reducing agent include: phosphorus such as triphenylphosphine or tributylphosphine; metals such as zinc or tin; catalytic hydrogenation; lithium aluminum; and sodium borohydride. The used solvent is not particularly limited. For example, tetrahydrofuran, dioxane, and water can be used singly or in combination. The reaction temperature is −30° C. to 150° C., and preferably 0° C. to 120° C. The reaction time is 10 minutes to 12 hours, and preferably 30 minutes to 6 hours. In the alkylation reaction, halogenated alkyl is allowed to act on the aforementioned compound in the presence of a base. The used base is not particularly limited. Examples of the base that can be used herein include: alkali metal carbonates such as lithium carbonate, sodium carbonate, potassium carbonate, cesium carbonate, or sodium hydrogen carbonate; and organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent that can be used herein include N,N-dimethylformamide, N,N-dimethylacetamide, N-methylpyrrolidone, dimethyl sulfoxide, dioxane, tetrahydrofuran, acetonitrile, propionitrile, dichloroethane, and dichloromethane. The reaction temperature is −30° C. to 150° C., and preferably 0° C. to 120° C. The reaction time is 10 minutes to 12 hours, and preferably 30 minutes to 6 hours.

(E-2) Step E-2 is a method of producing the compound represented by general formula (29) by oxidizing the compound represented by general formula (28). The used oxidizing agent is not particularly limited. Examples of the oxidizing agent include hydrogen peroxide solution, peracetic acid, pertrifluoroacetic acid, dimethyl dioxirane, Oxone (trade name), m-chloroperbenzoic acid, magnesium bis(peroxyphthalate) hexahydrate, potassium permanganate, and chromium(VI) oxide. Of these, m-chloroperbenzoic acid is preferable. The used solvent is not particularly limited. For example, dichloroethane or dichloromethane can be used. The reaction temperature is −30° C. to 150° C., and preferably 0° C. to 100° C. The reaction time is 10 minutes to 12 hours, and preferably 30 minutes to 6 hours.

Moreover, the compounds represented by general formula (14), which can also be represented by general formula (34), can be produced by the method illustrated in reaction pathway diagram 6 as shown below. Specifically, a protecting group is bound to a compound represented by general formula (30) to obtain a compound represented by general formula (31)

(F-1). The compound represented by general formula (31) is reduced to obtain an alcohol compound represented by general formula (32) (F-2). A protecting group is bound to the compound represented by general formula (32) to obtain a compound represented by general formula (33) (F-3). A protecting group is removed from the compound represented by general formula (33), so as to obtain an amine compound represented by general formula (34) (F-4).

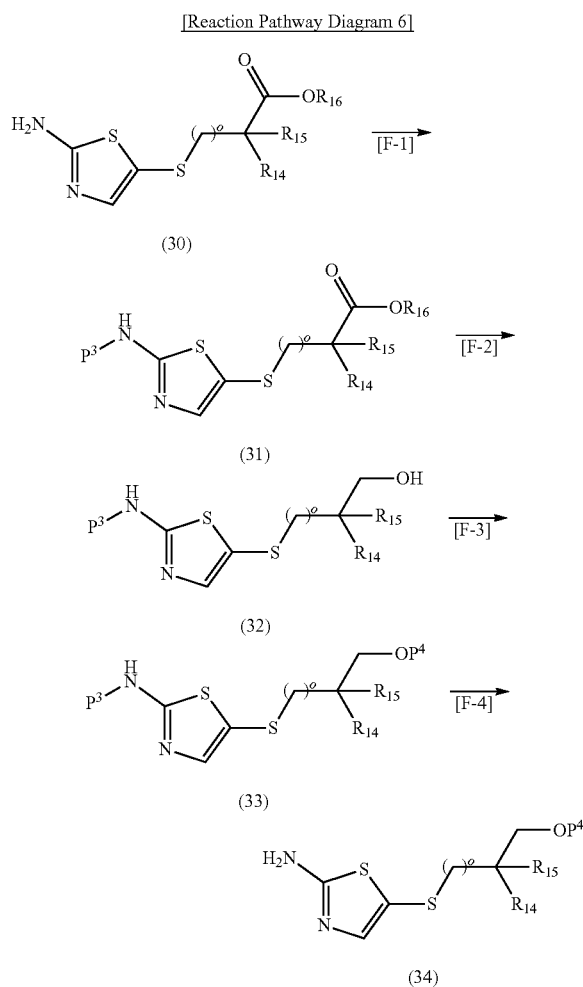

[wherein $R^{14}$ and $R^{15}$ each represent a hydrogen atom or a $C_{1-6}$ alkyl group, $R^{16}$ represents a $C_{1-6}$ alkyl group, $P^3$ represents a protecting group for the amino group (a benzyl group, a benzyloxycarbonyl group, a t-butoxycarbonyl group, etc.), $P^4$ represents a protecting group for the alcohol group (a t-butyldimethylsilyl group etc.), and o represents an integer of 0 to 2].

(F-1) Step F-1 is a step of protecting the amino group of the compound represented by general formula (30) by $P^3$, so as to produce the compound (31). Methods and conditions for such protection are different depending on the type of the protecting group $P^3$. Such protection can be carried out with reference to a method commonly used in organic chemistry (e.g. the method described in Protective Groups in Organic Synthesis Third Edition, John Wiley & Sons, Inc., 1999).

(F-2) Step F-2 is a step of reducing the compound represented by general formula (31), so as to produce the compound (32). The used reducing agent is not particularly limited. Examples of the reducing agent include lithium aluminum hydride, diisobutyl aluminum hydride, and sodium borohydride. The used solvent is not particularly limited. For example, tetrahydrofuran, dioxane, and diethyl ether can be used singly or in combination. The reaction temperature is −30° C. to 150° C., and preferably 0° C. to 120° C. The reaction time is 10 minutes to 12 hours, and preferably 30 minutes to 6 hours.

(F-3) Step F-3 is a step of protecting the alcohol group of the compound represented by general formula (32) by $P^4$, so as to produce the compound (33). Methods and conditions for such protection are different depending on the type of the protecting group $P^4$. Such protection can be carried out with reference to a method commonly used in organic chemistry (e.g. the method described in Protective Groups in Organic Synthesis Third Edition, John Wiley & Sons, Inc., 1999).

(F-4) Step F-4 is a step of deprotecting the compound represented by general formula (33), so as to produce the compound (34). Methods and conditions for such deprotection are different depending on the type of the protecting group $P^4$. Such deprotection can be carried out with reference to a method commonly used in organic chemistry (e.g. the method described in Protective Groups in Organic Synthesis Third Edition, John Wiley & Sons, Inc., 1999).

Moreover, the compounds represented by general formula (13), which can also be represented by general formula (39), can be produced by the method illustrated in reaction pathway diagram 7 as shown below. Specifically, a compound represented by general formula (35) is halogenated to obtain a compound represented by general formula (36) (G-1). The compound represented by general formula (36) is subjected to sulfidation to obtain a sulfide compound represented by general formula (37) (G-2) The compound represented by general formula (37) is oxidized to obtain a compound represented by general formula (38) (G-3). A protecting group is removed from the compound represented by general formula (38), so as to obtain an amine compound represented by general formula (39) (F-4).

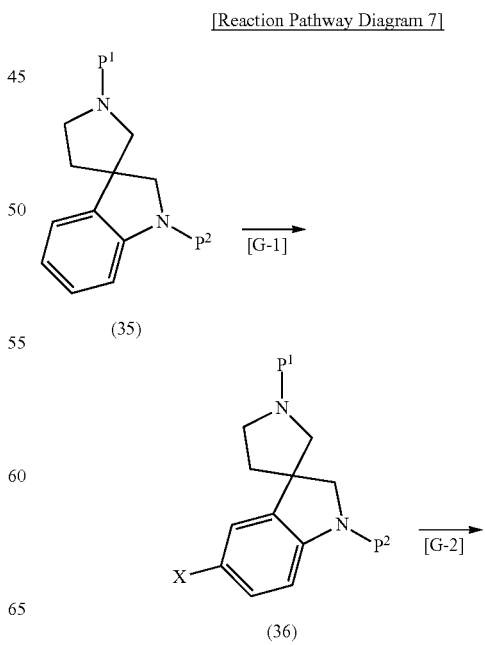

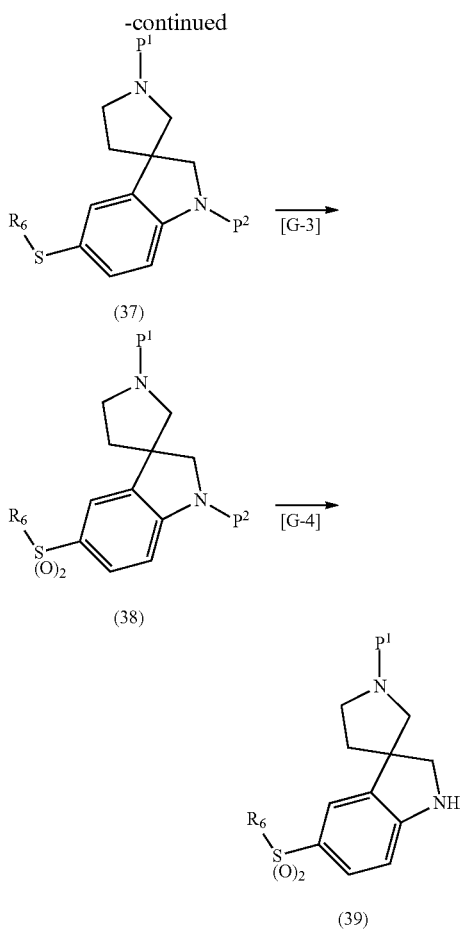

[wherein R⁶ has the same definition as that in the above described general formula (1), X represents a halogen group, and P¹ and P² each represent a protecting group for the amino group (a benzyl group, a benzyloxycarbonyl group, a t-butoxycarbonyl group, etc.)].

(G-1) Step G-1 is a step of halogenating the compound represented by general formula (35) to produce the compound (36). The used halogenating agent is not particularly limited. Examples of the halogenating agent include chlorine, bromine, iodine, N-bromosuccinimide, N-chlorosuccinimide, N-iodosuccinimide, and pyridinium bromide perbromide. The used solvent is not particularly limited. For example, methylene chloride, tetrahydrofuran, dioxane, diethyl ether, methanol, ethanol, isopropanol, t-butanol, and water can be used singly or in combination. The reaction temperature is −30° C. to 150° C., and preferably 0° C. to 120° C. The reaction time is 10 minutes to 48 hours, and preferably 30 minutes to 24 hours.

(G-2) Step G-2 is a step of subjecting the compound represented by general formula (36) to a sulfidation reaction with thioalkoxide in the presence or absence of a base and in the presence of a metal catalyst, so as to produce the compound (37). The used metal catalyst is not particularly limited. Examples of the metal catalyst used herein include: palladium complexes such as tris(dibenzylideneacetone)dipalladium(0), tris(dibenzylideneacetone) (chloroform)dipalladium(0), [1,1'-bis(diphenylphosphino)ferrocene] dichloropalladium(II), tetrakis(triphenylphosphine) palladium(0), palladium diacetate, or palladium chloride; and copper reagents such as copper acetate, cuprous iodide, cuprous bromide, or cuprous cyanide. These substances may be used singly. Otherwise, these substances may also be used in combination with a ligand such as triphenylphosphine, xantphos, tri(o-tolyl)phosphine, S-Phos, X-Phos, BINAP, (2-biphenyl)di-t-butylphosphine, (2-biphenyl)dicyclohexylphosphine, tetramethylethylenediamine, N,N'-dimethylethylenediamine, glycine, N,N-dimethylglycine, or N-methylglycine. The used base is not particularly limited. Examples of the base that can be used herein include: alkali metal hydrides such as lithium hydride, sodium hydride, or potassium hydride; alkali metals such as metallic lithium, metallic sodium, or metallic potassium; alkali metal hydroxides such as lithium hydroxide, sodium hydroxide, or potassium hydroxide; alkali metal carbonates such as lithium carbonate, sodium carbonate, potassium carbonate, or cesium carbonate; alkali metal fluorides such as potassium fluoride or cesium fluoride; organic metal bases such as lithium diisopropylamide, sodium diisopropylamide, potassium diisopropylamide, lithium hexamethyldisilazide, sodium hexamethyldisilazide, potassium hexamethyldisilazide, t-butoxy sodium, t-butoxy potassium, n-butyl lithium, sec-butyl lithium, or t-butyl lithium; and organic bases such as 1,8-diazabicyclo [5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent include tetrahydrofuran, toluene, xylene, dioxane, N,N-dimethylformamide, N,N-dimethylacetamide, N-methylpyrrolidone, dimethyl sulfoxide, dichloromethane, and water. These solvents can be used singly or in combination. The reaction temperature is 0° C. to 300° C., and preferably 10° C. to 200° C. The reaction time is 1 minute to 5 days, and preferably 30 minutes to 24 hours.

(G-3) Step G-3 is a step of oxidizing the compound represented by general formula (37) to produce the compound (38). The oxidizing agent used in oxidation is not particularly limited. Examples of the oxidizing agent include hydrogen peroxide solution, peracetic acid, pertrifluoroacetic acid, dimethyl dioxirane, Oxone (trade name), m-chloroperbenzoic acid, magnesium bis(peroxyphthalate) hexahydrate, potassium permanganate, and chromium(VI) oxide. Of these, m-chloroperbenzoic acid is preferable. The used solvent is not particularly limited. For example, dichloromethane, dichloroethane, or chloroform can be used. Of these, dichloromethane is preferable. The reaction temperature is −30° C. to 50° C., and preferably −10° C. to 30° C. The reaction time is 5 minutes to 40 hours, and preferably 10 minutes to 24 hours.

(G-4) Step G-4 is a step of removing the protecting group P² from the compound represented by general formula (38) to produce the compound (39). Methods and conditions for such deprotection are different depending on the type of the protecting group P². For example, a benzyl group and a benzyloxycarbonyl group can be removed by catalytic hydrogenation, and a t-butoxycarbonyl group can be removed with acid. Such deprotection can be carried out with reference to a method commonly used in organic chemistry (e.g. the method described in Protective Groups in Organic Synthesis Third Edition, John Wiley & Sons, Inc., 1999).

Moreover, differing from the above described methods, the compound represented by the general formula (13) can also be produced by the method illustrated in reaction pathway diagram 8 as shown below. Specifically, a compound represented by general formula (40) and a compound represented by general formula (41) are subjected to a coupling reaction to obtain a compound represented by general formula (42) (H-1). Then, the compound represented by general formula

(42) is subjected to an intramolecular cyclization reaction, so as to produce the compound represented by the general formula (13) (H-2).

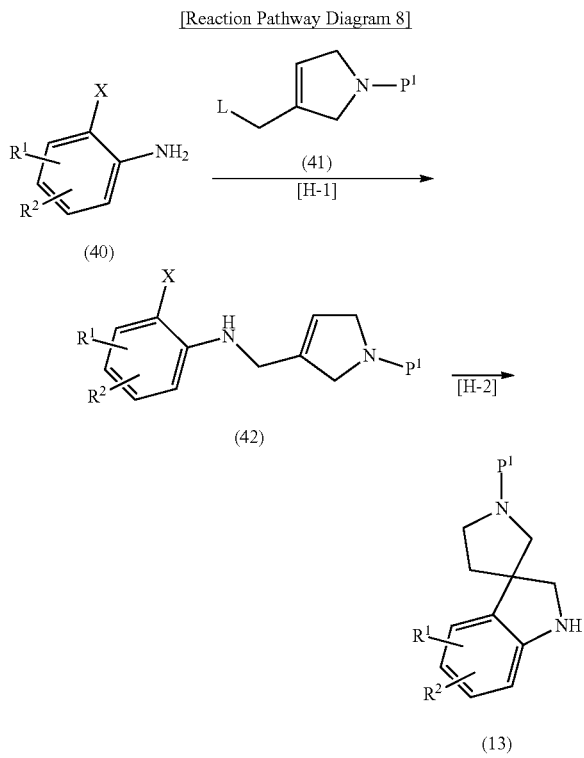

[Reaction Pathway Diagram 8]

[wherein $R^1$ and $R^2$ have the same definitions as those in the above described general formula (1), X represents a halogen group, L represents a leaving group, and $P^1$ represents a protecting group for the amino group (a benzyl group, a benzyloxycarbonyl group, a t-butoxycarbonyl group, etc.)].
(H-1) Step H-1 is a step of coupling the compound represented by general formula (40) and the compound represented by general formula (41) in the presence of a base, so as to produce the compound (42). The used base is not particularly limited. Examples of the base that can be used herein include: alkali metal hydrides such as lithium hydride, sodium hydride, or potassium hydride; alkali metal carbonates such as lithium carbonate, sodium carbonate, potassium carbonate, cesium carbonate, or sodium hydrogen carbonate; and organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent that can be used herein include N,N-dimethylformamide, N,N-dimethylacetamide, N-methylpyrrolidone, dimethyl sulfoxide, dioxane, tetrahydrofuran, acetonitrile, propionitrile, dichloroethane, and dichloromethane. The reaction temperature is −30° C. to 150° C., and preferably −10° C. to 50° C. The reaction time is 10 minutes to 24 hours, and preferably 30 minutes to 12 hours.
(H-2) Step H-2 is a step of performing the intramolecular circularization of the compound represented by general formula (42) using a radical reaction reagent or a transition metal catalyst, so as to produce the compound (13). In the case of a radical reaction, the used radical reaction reagent is not particularly limited. For example, tributyl tin hydride or tris(trimethylsilyl)silane can be used. As a radical reaction initiator, azobisisobutyronitrile, 1,1'-azobis(cyclohexanecarbonitrile), triethylborane, diethylzinc, or the like can be used. The used solvent is not particularly limited, and for example, toluene or benzene can be used. The reaction temperature is −30° C. to 300° C., and preferably 0° C. to 150° C. The reaction time is 10 minutes to 48 hours, and preferably 30 minutes to 24 hours. The used solvent is not particularly limited. Examples of the solvent include tetrahydrofuran, toluene, xylene, dioxane, N,N-dimethylformamide, N,N-dimethylacetamide, N-methylpyrrolidone, dimethyl sulfoxide, dichloromethane, and water. These solvents can be used singly or in combination. The reaction temperature is 0° C. to 300° C., and preferably 10° C. to 200° C. The reaction time is 1 minute to 5 days, and preferably 30 minutes to 24 hours.

It is to be noted that the compound (41) used as a raw material can be produced by the method described in known methods (European Journal of Organic Chemistry, 4264-((276; 2008 etc.) or a method similar thereto.

Moreover, the compounds represented by general formula (17), which can also be represented by general formula (43), can be produced by the method illustrated in reaction pathway diagram 9 as shown below. Specifically, a compound represented by general formula (36), and an organic metal reagent or an alkenyl compound, are subjected to a coupling reaction using a metal catalyst, to obtain a compound represented by general formula (43) (I-1)

[Reaction Pathway Diagram 9]

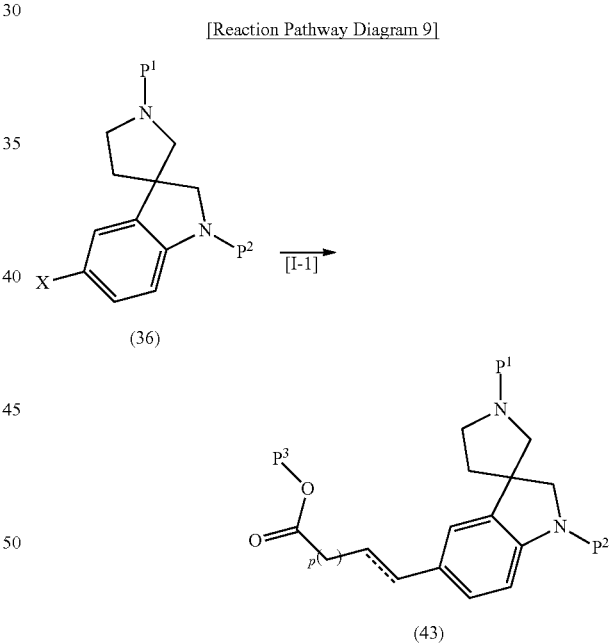

[wherein X represents a halogen group, $P^1$ and $P^2$ each represent a protecting group for the amino group (a benzyl group, a benzyloxycarbonyl group, a t-butoxycarbonyl group, etc.), $P^3$ represents a protecting group for the carboxyl group (an alkyl group, a silyl group, etc.), and p represents an integer of 0 to 2].
(I-1) Step I-1 is a step of subjecting the compound represented by general formula (36) to a coupling reaction using a metal catalyst, so as to produce the compound (43). As such coupling reactions using a metal catalyst, common cross-coupling reactions using a transition metal, which include Heck-Mizoroki reaction (Chem. Rev., 100, 3009-3060 (2000)) and Negishi reaction (Tetrahedron, 48, 9577-9648 (1992)) as typical examples, can be applied herein. Examples of the metal catalyst used in a coupling reaction with an alkene compound reagent or an organic zinc reagent include: palladium complexes such as tris(dibenzylideneacetone)dipalladium(0), tris(dibenzylideneacetone) (chloroform)dipalladium(0), [1,1'-bis(diphenylphosphino)ferrocene] dichloropalladium(II), tetrakis(triphenylphosphine)palladium(0), palladium diacetate, or palladium chloride; and copper reagents such as copper acetate, cuprous iodide, cuprous bromide, or cuprous cyanide. These substances may be used singly. However, these metal catalysts may also be used in combination with a ligand such as triphenylphosphine, xantphos, tri(o-tolyl)phosphine, S-Phos, X-Phos, BINAP, (2-biphenyl)di-t-butylphosphine, (2-biphenyl)dicyclohexylphosphine, tetramethylethylenediamine, N,N'-dimethylethylenediamine, glycine, N,N-dimethylglycine, or N-methylglycine. The used base is not particularly limited. Examples of the base that can be used herein include: alkali metal hydrides such as lithium hydride, sodium hydride, or potassium hydride; alkali metals such as metallic lithium, metallic sodium, or metallic potassium; alkali metal hydroxides such as lithium hydroxide, sodium hydroxide, or potassium hydroxide; alkali metal carbonates such as lithium carbonate, sodium carbonate, potassium carbonate, or cesium carbonate; alkali metal fluorides such as potassium fluoride or cesium fluoride; organic metal bases such as lithium diisopropylamide, sodium diisopropylamide, potassium diisopropylamide, lithium hexamethyldisilazide, sodium hexamethyldisilazide, potassium hexamethyldisilazide, t-butoxy sodium, t-butoxy potassium, n-butyl lithium, sec-butyl lithium, or t-butyl lithium; and organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, or pyridine. The used solvent is not particularly limited. Examples of the solvent include tetrahydrofuran, toluene, dioxane, N,N-dimethylformamide, N,N-dimethylacetamide, N-methylpyrrolidone, dimethyl sulfoxide, dichloromethane, and water. These solvents can be used singly or in combination. The reaction temperature is 0° C. to 200° C., and preferably 10° C. to 150° C. The reaction time is 1 minute to 5 days, and preferably 30 minutes to 24 hours.

Reaction intermediates and products of interest, which were obtained from each of the above described reactions, can be isolated and purified, as necessary, by applying purification methods commonly used in organic synthetic chemistry, such as filtration, extraction, washing, drying, concentration, recrystallization, or various types of chromatography. In addition, in the case of reaction intermediates, they can also be subjected to the subsequent reaction without being particularly purified.

Moreover, various types of isomers can be isolated by applying an ordinary method of utilizing differences in physicochemical properties among the isomers. A racemic mixture can be induced to an optically pure isomer by a common racemic resolution method, such as a method which comprises inducing a racemic mixture to diastereomeric salts with common optically active acid such as tartaric acid and then subjecting the salts to optical resolution, or a method using optically active column chromatography. Furthermore, a diastereomeric mixture can be divided, for example, by fractionated crystallization or various types of chromatography. Further, an optically active compound can also be produced by using suitable optically active raw materials.

The obtained compound (1) can be converted to salts according to an ordinary method. In addition, it can also be converted to a solvate in solvents such as a reaction solvent or a recrystallization solvent, or a hydrate.

As a pharmaceutical preparation comprising, as an active ingredient, the compound represented by the general formula (1) of the present invention, or a salt thereof, or a solvate of the compound or the salt, the aforementioned active ingredient may be used singly. However, in general, pharmaceutically acceptable carriers, additives, and the like are mixed with the active ingredient, and the thus obtained mixture is used as a pharmaceutical preparation. The dosage form of a pharmaceutical composition is not particularly limited, and it can be selected, as appropriate, depending on therapeutic purpose. For example, the dosage form may be any one of an oral agent, an injection, a suppository, an ointment, an inhalant, eye drops, nasal drops, and a patch. A pharmaceutical composition suitable for each of these dosage forms can be produced by known pharmaceutical formulation methods.

In the case of preparing a solid preparation for oral administration, an excipient, and as necessary, a binder, a disintegrant, a lubricant, a coloring agent, a corrigent, a flavoring agent, and the like are added to the compound represented by the general formula (1), and thereafter, a tablet, a coated tablet, a granule, a powder agent, a capsule, and the like can be produced from the obtained mixture according to an ordinary method. Additives commonly used in the present technical field can be used herein. Examples of the excipient used herein include lactose, saccharose, sodium chloride, glucose, starch, calcium carbonate, kaoline, microcrystalline cellulose, and silicic acid. Examples of the binder used herein include water, ethanol, propanol, simple syrup, glucose solution, starch solution, gelatin solution, carboxymethylcellulose, hydroxypropylcellulose, hydroxypropyl starch, methylcellulose, ethylcellulose, shellac, calcium phosphate, and polyvinyl pyrrolidone. Examples of the disintegrant used herein include dry starch, sodium alginate, agar powder, sodium hydrogen carbonate, calcium carbonate, sodium lauryl sulfate, monoglyceride stearate, and lactose. Examples of the lubricant used herein include purified talc, stearate, borax, and polyethylene glycol. Examples of the corrigent used herein include saccharose, bitter orange peel, citric acid, and tartaric acid.

In the case of preparing a liquid preparation for oral administration, a corrigent, a buffer, a stabilizer, a flavoring agent, and the like are added to the compound represented by the general formula (1), and thereafter, an oral liquid agent, a syrup agent, an elixir agent, and the like can be produced from the obtained mixture according to an ordinary method. Examples of the corrigent used herein are the same as those described above. An example of the buffer used herein is sodium citrate, and examples of the stabilizer used herein include Tragacanth, gum Arabic, and gelatin.

In the case of preparing an injection, a pH adjuster, a buffer, a stabilizer, an isotonizing agent, a regional anesthetic, and the like are added to the compound represented by the general formula (1), and thereafter, hypodermic, intramuscular and intravenous injections can be produced from the obtained mixture according to an ordinary method. Examples of the pH adjuster and buffer used herein include sodium citrate, sodium acetate, and sodium phosphate. Examples of the stabilizer used herein include sodium pyrosulfite, EDTA, thioglycolic acid, and thiolactic acid. Examples of the regional anesthetic used herein include procaine hydrochloride and lidocaine hydrochloride. Examples of the isotonizing agent used herein include sodium chloride and glucose.

In the case of preparing a suppository, known suppository carriers such as polyethylene glycol, lanolin, cacao butter, or fatty acid triglyceride, and as necessary, a surfactant such as Tween (R) are added to the compound represented by the general formula (1), and thereafter, suppositories can be produced from the obtained mixture according to an ordinary method.

In the case of preparing an ointment, commonly used base, stabilizer, wetting agent, preservative, etc. are mixed into the compound represented by the general formula (1), as necessary, and thereafter, the obtained mixture is blended to produce an ointment according to an ordinary method. Examples of the base used herein include liquid paraffin, white petrolatum, white beeswax, octyl dodecyl alcohol, and paraffin. Examples of the preservative used herein include methyl p-hydroxybenzoate, ethyl p-hydroxybenzoate, and propyl p-hydroxybenzoate.

Other than the aforementioned dosage forms, the compound represented by the general formula (1) can also be processed into an inhalant, eye drops, or nasal drops according to ordinary methods.

The compound represented by the general formula (1) of the present invention is administered via oral administration or parenteral administration. The dose of the pharmaceutical preparation of the present invention is different depending on the body weight, age, sex, and symptoms of a patient, etc. In general, in the case of an adult patient, the compound represented by the general formula (1) is preferably administered at a dose of 0.01 to 1000 mg/day, and preferably 0.1 to 300 mg/day, in one to three divided doses.

EXAMPLES

Hereinafter, the present invention will be more specifically described in the following Examples and Test Examples. However, these examples are not intended to limit the scope of the present invention. It is to be noted that abbreviations used in the following examples have the following meanings.
s: singlet
d: doublet
t: triplet
q: quartet
quint: quintet
m: multiplet
br: broad
J: coupling constant
Hz: Hertz
$CDCl_3$: deuterated chloroform
DMSO-$d_6$: deuterated dimethyl sulfoxide
$CD_3OD$: deuterated methanol
$^1$H-NMR: proton nuclear magnetic resonance

Example 1

Production of t-butyl 5-bromo-1-((5-chlorothiazol-2-yl)carbamoyl)spiro[indoline-3,3'-pyrrolidine]-1'-carboxylate 2-Amino-5-chlorothiazole hydrochloride (1.00 g, 5.80 mmol) was dissolved in methylene chloride (50 mL), and the obtained solution was then washed with a saturated aqueous solution of sodium hydrogen carbonate. The resulting solution was dried over anhydrous sodium sulfate and was then filtered. After that, pyridine (0.47 mL, 5.80 mmol) and 4-nitrophenyl chloroformate (1.18 g, 5.80 mmol) were added to the filtrate, and the obtained mixture was then stirred at room temperature for 3 hours. Thereafter, a solid was collected by filtration, was then washed with methylene chloride, and was then dried to obtain 4-nitrophenyl (5-chlorothiazol-2-yl)carbamate (980 mg, 56%) in the form of a white solid. t-Butyl 5-bromospiro[indoline-3,3'-pyrrolidine]-1'-carboxylate (65.1 mg, 0.184 mmol) synthesized by a method described in the known method (International Publication WO2009/089454) or a method similar thereto was dissolved in N,N'-dimethylformamide (2 mL). Thereafter, 4-nitrophenyl (5-chlorothiazol-2-yl)carbamate (55.2 mg, 0.184 mmol) and triethylamine (13 µL, 0.092 mmol) were added to the above obtained solution, and the obtained mixture was then stirred at 50° C. for 3 hours. Thereafter, the reaction solution was diluted with water, and was then extracted with ethyl acetate. The organic layer was washed with brine, and was then dried over anhydrous sodium sulfate, followed by concentration in vacuo. The obtained residue was purified by silica gel column chromatography (hexane:ethyl acetate=2:1) to obtain the captioned compound (60.0 mg, 64%) in the form of a white solid.

$^1$H-NMR (400 MHz, $CDCl_3$) δ: 1.44 (9H, s), 2.05 (1H, m), 2.21 (1H, m), 3.41-3.99 (6H, m), 7.13 (1H, s), 7.25 (1H, s), 7.35 (1H, d, J=8.4 Hz), 7.89 (1H, d, J=8.4 Hz).

Example 2

Production of 5-bromo-N-(5-chlorothiazol-2-yl)spiro[indoline-3,3'-pyrrolidine]-1-carboxamide The t-butyl 5-bromo-1-((5-chlorothiazol-2-yl)carbamoyl)spiro[indoline-3,3'-pyrrolidine]-1'-carboxylate (54.2 mg, 0.105 mmol) obtained in Example 1 was dissolved in methylene chloride (0.5 mL). Thereafter, trifluoroacetic acid (0.5 mL) was added to the above obtained solution at room temperature, and the obtained mixture was then stirred for 1 hour. The reaction solution was neutralized with a saturated aqueous solution of sodium hydrogen carbonate, and a solid was then collected by filtration, followed by drying, to obtain the captioned compound (43.2 mg, 100%) in the form of a white solid.

$^1$H-NMR (400 MHz, $CD_3OD$) δ: 2.25-2.29 (2H, m), 3.33-3.62 (4H, m), 4.10 (1H, d, J=10.9 Hz), 4.13 (1H, d, J=10.9 Hz), 7.22 (1H, s), 7.38 (1H, dd, J=8.7, 2.0 Hz), 7.48 (1H, d, J=2.0 Hz), 7.94 (1H, d, J=8.7 Hz).

Example 3

Production of 1'-acetyl-5-bromo-N-(5-chlorothiazol-2-yl)spiro[indoline-3,3'-pyrrolidine]-1-carboxamide The 5-bromo-N-(5-chlorothiazol-2-yl)spiro[indoline-3,3'-pyrrolidine]-1-carboxamide (48.2 mg, 0.105 mmol) obtained in Example 2 was dissolved in methylene chloride (1.0 mL). Thereafter, triethylamine (34.4 µL, 0.315 mmol) and acetyl chloride (7.5 µL, 0.105 mmol) were added to the above obtained solution under cooling on ice, and the obtained mixture was then stirred for 1 hour. The reaction solution was diluted with water, and was then extracted with methylene chloride. The organic layer was washed with brine, and was then dried over anhydrous sodium sulfate, followed by concentration in vacuo. The obtained residue was purified by silica gel column chromatography (chloroform:methanol=10:1) to obtain the captioned compound (45.0 mg, 94%) in the form of a white solid.

$^1$H-NMR (400 MHz, $CDCl_3$) δ: 2.08-2.36 (5H, m), 3.48-4.12 (6H, m), 7.17 (1H, s), 7.25-7.28 (1H, m), 7.39-7.43 (1H, m), 7.93-7.99 (1H, m).

Production of Examples 4 to 16, 18, 21, and 22

The below captioned compounds were all obtained in the form of a white solid by performing the same reactions and/or treatments as those in Example 3, with the exception that each raw material compound was used instead of acetyl chloride.

Example 4

(The compound in the parentheses that is described below the captioned compound is a raw material compound that was used instead of acetyl chloride. The same shall apply hereafter.)

5-Bromo-N-(5-chlorothiazol-2-yl)-1'-propionylspiro[indoline-3,3'-pyrrolidine]-1-carboxamide (Propionyl chloride)

Example 5

5-Bromo-1'-butyryl-N-(5-chlorothiazol-2-yl)spiro[indoline-3,3'-pyrrolidine]-1-carboxamide (Butyryl chloride)

Example 6

5-Bromo-N-(5-chlorothiazol-2-yl)-1'-pentanoylspiro[indoline-3,3'-pyrrolidine]-1-carboxamide (Valeryl chloride)

Example 7

5-Bromo-N-(5-chlorothiazol-2-yl)-1'-isobutyrylspiro[indoline-3,3'-pyrrolidine]-1-carboxamide (Isobutyril chloride)

Example 8

5-Bromo-N-(5-chlorothiazol-2-yl)-1'-(cyclopropanecarbonyl)spiro[indoline-3,3'-pyrrolidine]-1-carboxamide (Cyclopropanecarbonyl chloride)
$^1$H-NMR (400 MHz, CDCl$_3$) δ: 0.79-1.12 (5H, m), 2.09-2.38 (2H, m), 3.49-4.11 (6H, m), 7.18 (1H, s), 7.27-7.31 (1H, m), 7.39-7.44 (1H, m), 7.92-7.98 (1H, m).

Example 9

5-Bromo-N-(5-chlorothiazol-2-yl)-1'-(cyclobutanecarbonyl)spiro[indoline-3,3'-pyrrolidine]-1-carboxamide (Cyclobutanecarbonyl chloride)

Example 10

5-Bromo-N-(5-chlorothiazol-2-yl)-1'-(cyclopentanecarbonyl)spiro[indoline-3,3'-pyrrolidine]-1-carboxamide (Cyclopentanecarbonyl chloride)

Example 11

5-Bromo-N-(5-chlorothiazol-2-yl)-1'-(cyclohexanecarbonyl)spiro[indoline-3,3'-pyrrolidine]-1-carboxamide (Cyclohexanecarbonyl chloride)

Example 12

1'-Benzoyl-5-bromo-N-(5-chlorothiazol-2-yl)spiro[indoline-3,3'-pyrrolidine]-1-carboxamide (Benzoyl chloride)
$^1$H-NMR (400 MHz, CDCl$_3$) δ: 2.11-2.40 (2H, m), 3.57-4.22 (6H, m), 7.00-7.57 (8H, m), 7.90-7.95 (1H, m).

Example 13

Methyl 5-bromo-1-((5-chlorothiazol-2-yl)carbamoyl)spiro[indoline-3,3'-pyrrolidine]-1'-carboxylate (Methyl chloroformate)

Example 14

5-Bromo-N-(5-chlorothiazol-2-yl)-1'-(2,2,2-trifluoroacetyl)spiro[indoline-3,3'-pyrrolidine]-1-carboxamide (Trifluoroacetic anhydride)
$^1$H-NMR (400 MHz, CDCl$_3$) δ: 2.28-2.37 (2H, m), 3.70-4.06 (6H, m), 7.16 (1H, s), 7.42-7.45 (1H, m), 7.96-8.00 (1H, m).

Example 15

5-Bromo-N1-(5-chlorothiazol-2-yl)-N1',N1'-dimethylspiro[indoline-3,3'-pyrrolidine]-1,1'-dicarboxamide (Dimethylcarbamoyl chloride)
$^1$H-NMR (400 MHz, CDCl$_3$) δ: 2.06-2.29 (2H, m), 2.88 (6H, s), 3.47-3.72 (4H, m), 3.89 (1H, d, J=1 Hz), 4.00 (1H, d, J=10 Hz), 7.18 (1H, s), 7.29 (1H, d, J=2.2 Hz), 7.39 (1H, dd, J=8.7, 2.2 Hz), 7.96 (1H, d, J=8.7 Hz).

Example 16

5-Bromo-N1-(5-chlorothiazol-2-yl)spiro[indoline-3,3'-pyrrolidine]-1,1'-dicarboxamide (Chlorosulfonyl isocyanate)
$^1$H-NMR (400 MHz, DMSO-d$_6$) δ: 1.95-2.36 (2H, m), 3.37-3.77 (4H, m), 3.99-4.15 (2H, m), 7.42-7.58 (3H, m), 7.88 (1H, s).

Example 18

5-Bromo-N-(5-chlorothiazol-2-yl)-1'-(2-methoxyacetyl)spiro[indoline-3,3'-pyrrolidine]-1-carboxamide (Methoxyacetyl chloride)
$^1$H-NMR (400 MHz, DMSO-d$_6$) δ: 2.02-2.33 (2H, m), 3.44-3.71 (6H, m), 3.96-4.14 (5H, m), 7.42-7.57 (3H, m), 7.88-7.91 (1H, m).

Example 21

5-Bromo-N-(5-chlorothiazol-2-yl)-1'-(methylsulfonyl)spiro[indoline-3,3'-pyrrolidine]-1-carboxamide (Methanesulfonyl chloride)
$^1$H-NMR (400 MHz, DMSO-d$_6$) δ: 2.15-2.27 (5H, m), 3.04 (3H, s), 3.22-3.59 (4H, m), 4.09-4.15 (2H, m), 7.41 (1H, d, J=8.8 Hz), 7.49 (1H, s), 7.66 (1H, s), 7.89 (1H, d, J=8.8 Hz).

Example 22

5-Bromo-N-(5-chlorothiazol-2-yl)-1'-(ethylsulfonyl)spiro[indoline-3,3'-pyrrolidine]-1-carboxamide (Ethanesulfonyl chloride)

Example 17

Production of 5-bromo-N-(5-chlorothiazol-2-yl)-1'-(2-hydroxyacetyl)spiro[indoline-3,3'-pyrrolidine]-1-carboxamide Step 1: 5-Bromo-N-(5-chlorothiazol-2-yl)-1'-(2-acetoxyacetyl)spiro[indoline-3,3'-pyrrolidine]-1-carboxamide was obtained in the form of a white solid by performing the same reactions and/or treatments as those in Example 3, with the exception that acetoxyacetyl chloride was used instead of acetyl chloride.
$^1$H-NMR (400 MHz, CDCl$_3$) δ: 2.02-2.43 (5H, m), 3.43-4.20 (6H, m), 4.44-4.85 (2H, m), 7.11-7.29 (3H, m), 7.98-8.08 (1H, m).

Step 2: 5-Bromo-N-(5-chlorothiazol-2-yl)-1'-(2-acetoxyacetyl)spiro[indoline-3,3'-pyrrolidine]-1-carboxamide (64.0 mg, 0.136 mmol) was dissolved in a mixed solvent of tetrahydrofuran (2 mL) and methanol (1 mL). Thereafter, an aqueous solution of sodium hydroxide (2 M, 0.5 mL) was added to the above obtained solution at room temperature, and the obtained mixture was then stirred for 30 minutes. Thereafter, the reaction solution was diluted with water, and was then extracted with ethyl acetate. The organic layer was washed with brine, and was then dried over anhydrous sodium sulfate, followed by concentration in vacuo. The obtained residue was purified by silica gel column chromatography (chloroform:methanol=100:1→7:1) to obtain the captioned compound (37.8 mg, 65%) in the form of a white solid.

Example 19

Production of t-butyl (2-(5-bromo-1-((5-chlorothiazol-2-yl)carbamoyl)spiro[indoline-3,3'-pyrrolidin]-1'-yl)-2-oxoethyl)carbamate The 5-bromo-N-(5-chlorothiazol-2-yl)spiro[indoline-3,3'-pyrrolidine]-1-carboxamide (40 mg, 0.097 mmol) obtained in Example 2 was dissolved in methylene chloride (1.0 mL). Thereafter, triethylamine (27.0 µL, 0.194 mmol), N-Boc glycine (20 mg, 0.116 mmol), and 1-ethyl-3-(3-dimethylaminopropyl)carbodiimide hydrochloride (22 mg, 0.116 mmol) were added to the above obtained solution at room temperature, and the obtained mixture was then stirred for 12 hours. Thereafter, the reaction solution was diluted with water, and was then extracted with chloroform. The resultant was dried over anhydrous sodium sulfate and was then concentrated in vacuo. The obtained residue was purified by silica gel column chromatography (chloroform:methanol=10:1) to obtain the captioned compound (22.0 mg, 40%) in the form of a white solid.
$^1$H-NMR (400 MHz, DMSO-d$_6$) δ: 1.39 (9H, d, J=8.0 Hz), 2.06-2.24 (2H, m), 3.51-3.75 (6H, m), 4.07-4.17 (2H, m), 6.84-6.88 (1H, m), 7.43-7.59 (3H, m), 7.87 (1H, br).

Example 20

Production of 1'-(2-aminoacetyl)-5-bromo-N-(5-chlorothiazol-2-yl)spiro[indoline-3,3'-pyrrolidine]-1-carboxamide The t-butyl (2-(5-bromo-1-((5-chlorothiazol-2-yl)carbamoyl)spiro[indoline-3,3'-pyrrolidin]-1'-yl)-2-oxoethyl)carbamate (18 mg, 0.032 mmol) obtained in Example 19 was dissolved in ethyl acetate (0.5 mL). Thereafter, a 4 N solution of HCl/ethyl acetate (200 µL, 0.800 mmol) was added to the above obtained solution at room temperature, and the obtained mixture was then stirred for 7 hours. Thereafter, the reaction solution was neutralized, was then filtered, and was then concentrated in vacuo. The obtained residue was purified by silica gel column chromatography (chloroform:ammonia-methanol=10:1) to obtain the captioned compound in the form of a light yellow solid.
$^1$H-NMR (400 MHz, CD$_3$OD) δ: 2.11-2.39 (2H, m), 3.47-3.88 (6H, m), 4.03-4.13 (2H, m), 7.20 (1H, s), 7.35-7.42 (2H, m), 7.95 (1H, dd, J=2.4, 8.8 Hz).

Example 23

Production of 5-bromo-N-(5-chlorothiazol-2-yl)-1'-formylspiro[indoline-3,3'-pyrrolidine]-1-carboxamide The 5-bromo-N-(5-chlorothiazol-2-yl)spiro[indoline-3,3'-pyrrolidine]-1-carboxamide (160 mg, 0.387 mmol) obtained in Example 2 was dissolved in N,N'-dimethylformamide (4.0 mL). Thereafter, formic acid (22.0 µL, 0.581 mmol) and 1-ethyl-3-(3-dimethylaminopropyl)carbodiimide hydrochloride (148 mg, 0.774 mmol) were added to the above obtained solution, and the thus obtained mixture was then stirred for 18 hours. Thereafter, the reaction solution was diluted with water, and was then extracted with ethyl acetate. The organic layer was washed with brine, and was then dried over anhydrous sodium sulfate, followed by concentration in vacuo. The obtained residue was purified by silica gel column chromatography (chloroform:methanol=20:1) to obtain the captioned compound (92.8 mg, 54%) in the form of a white solid.

Example 24

Production of 5-bromo-N-(5-chlorothiazol-2-yl)-1'-methylspiro[indoline-3,3'-pyrrolidine]-1-carboxamide The 5-bromo-N-(5-chlorothiazol-2-yl)spiro[indoline-3,3'-pyrrolidine]-1-carboxamide (48.2 mg, 0.105 mmol) obtained in Example 2 was dissolved in N,N'-dimethylformamide (1.0 mL). Thereafter, potassium carbonate (43.5 mg, 0.315 mmol) and methyl iodide (30.0 mg, 0.210 mmol) were added to the above obtained solution at room temperature, and the obtained mixture was then stirred for 3 hours. Thereafter, the reaction solution was diluted with water, and was then extracted with methylene chloride. The organic layer was washed with brine, and was then dried over anhydrous sodium sulfate, followed by concentration in vacuo. The obtained residue was purified by silica gel column chromatography (chloroform:methanol=10:1) to obtain the captioned compound (11.0 mg, 35%) in the form of a white solid.

$^1$H-NMR (400 MHz, CDCl$_3$) δ: 2.04-2.11 (1H, m), 2.23-2.30 (1H, m), 2.41 (3H, s), 2.52 (1H, d, J=9.3 Hz), 2.59 (2H, dd, J=15.6, 9.0 Hz), 2.80 (1H, d, J=9.3 Hz), 2.93-2.99 (1H, m), 3.90 (1H, d, J=9.3 Hz), 4.11 (1H, d, J=9.3 Hz), 7.23 (1H, s), 7.35 (1H, d, J=8.5 Hz), 7.37 (1H, s), 7.88 (1H, d, J=8.5 Hz).

Production of Examples 25 to 28 and 30 to 33

The below captioned compounds were all obtained in the form of a white solid by performing the same reactions and/or treatments as those in Examples 1, 2, and 3, with the exception that each raw material compound was used instead of 2-amino-5-chlorothiazole hydrochloride. Example 25 (The compound in the parentheses that is described below the captioned compound is a raw material compound that was used instead of 2-amino-5-chlorothiazole hydrochloride. The same shall apply hereafter.)

1'-Acetyl-5-bromo-N-(thiazol-2-yl)spiro[indoline-3,3'-pyrrolidine]-1-carboxamide (2-Aminothiazole)

Example 26

1'-Acetyl-5-bromo-N-(5-fluorothiazol-2-yl)spiro[indoline-3,3'-pyrrolidine]-1-carboxamide (2-Amino-5-fluorothiazole hydrochloride)

Example 27

1'-Acetyl-5-bromo-N-(5-methoxythiazolo[5,4-b]pyridin-2-yl)spiro[indoline-3,3'-pyrrolidine]-1-carboxamide (5-Methoxythiazolo[5,4-b]pyridin-2-amine synthesized by a method described in the known methods (International Publication WO2004/050645 etc.) or a method similar thereto)

Example 28

Ethyl 2-((2-(1'-acetyl-5-bromospiro[indoline-3,3'-pyrrolidin]-1-ylcarboxamido)thiazol-5-yl)thio)acetate (Ethyl 2-((2-aminothiazol-5-yl)thio)acetate synthesized by a method described in the known methods (International Publication WO2005/066145 etc.) or a method similar thereto)

$^1$H-NMR (400 MHz, CDCl$_3$) δ: 1.27 (3H, t, J=7.2 Hz), 2.08-2.34 (5H, m), 3.45 (2H, s), 3.57-3.67 (3H, m), 3.80-4.10 (3H, m), 4.19 (2H, q, J=7.2 Hz), 7.25-7.28 (1H, m), 7.39-7.41 (2H, m), 7.93-7.98 (1H, m), 9.09 (1H, brs).

Example 30

1'-Acetyl-5-bromo-N-(1-methyl-1H-pyrazol-3-yl)spiro[indoline-3,3'-pyrrolidine]-1-carboxamide (1-Methyl-1H-pyrazole-3-amine)

Example 31

1'-Acetyl-5-bromo-N-(1H-pyrazol-3-yl)spiro[indoline-3,3'-pyrrolidine]-1-carboxamide (1H-Pyrazole-3-amine)
$^1$H-NMR (400 MHz, CDCl$_3$) δ: 1.90-2.22 (5H, m), 3.38-3.82 (6H, m), 6.66 (1H, s), 7.14-7.43 (3H, m), 7.86-7.92 (1H, m), 8.63-8.71 (1H, m).

Example 32

1'-Acetyl-5-bromo-N-(pyridin-2-yl)spiro[indoline-3,3'-pyrrolidine]-1-carboxamide (2-Aminopyridine)

Example 33

1'-Acetyl-5-bromo-N-(5-chloropyridin-2-yl)spiro[indoline-3,3'-pyrrolidine]-1-carboxamide (2-Amino-5-chloropyridine)

Example 29

Production of 2-((2-(1'-acetyl-5-bromospiro[indoline-3,3'-pyrrolidin]-1-ylcarboxamido)thiazol-5-yl)thio)acetic acid The ethyl 2-((2-(1'-acetyl-5-bromospiro[indoline-3,3'-pyrrolidin]-1-ylcarboxamido)thiazol-5-yl)thio)acetate (91 mg, 0.169 mmol) obtained in Example 28 was dissolved in ethanol (1.0 mL) and tetrahydrofuran (4.0 mL). Thereafter, a 2 M aqueous solution of sodium hydroxide (1 mL) was added to the above obtained solution at room temperature, and the obtained mixture was then stirred for 18 hours. Thereafter, the reaction solution was diluted with water, and was then washed with diethyl ether. The water phase was converted to be acidic by addition of hydrochloric acid, and the precipitated solid was collected by filtration and was then washed with water. The obtained solid was dried in vacuo to obtain the captioned compound (53 mg, 61%) in the form of a white solid.

$^1$H-NMR (400 MHz, DMSO-d$_6$) δ: 1.91-2.33 (5H, m), 3.37-3.74 (6H, m), 4.02-4.19 (2H, m), 7.42 (1H, d, J=7.3 Hz), 7.50 (1H, s), 7.55 (d, d, J=7.3 Hz), 7.90 (1H, s).

Example 34

Production of 6-(1'-acetyl-5-bromospiro[indoline-3,3'-pyrrolidin]-1-ylcarboxamido)nicotinic acid The captioned compound was obtained in the form of a white solid by performing the same reactions and/or treatments as those in Examples 1, 2, 3, and 29, with the exception that methyl 6-aminonicotinate was used instead of 2-amino-5-chlorothiazole hydrochloride.

$^1$H-NMR (400 MHz, CD$_3$OD) δ: 2.09-2.41 (5H, m), 3.48-3.87 (4H, m), 4.13-4.29 (2H, m), 7.39-7.48 (2H, m), 7.90-7.94 (1H, m), 8.06 (1H, d, J=8.7 Hz), 8.28 (1H, d, J=8.7 Hz), 8.86 (1H, s).

Example 35

Production of methyl 5-bromo-1-(thiazol-2-ylcarbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that 2-aminothiazole was used instead of 2-amino-5-chlorothiazole hydrochloride, and that methyl chloroformate was used instead of acetyl chloride.

Example 36

Production of methyl 5-bromo-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that 2-amino-5-fluorothiazole hydrochloride was used instead of 2-amino-5-chlorothiazole hydrochloride, and that methyl chloroformate was used instead of acetyl chloride.

Example 37

Production of methyl 5-bromo-1-((5-((2-ethoxy-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that ethyl 2-((2-aminothiazol-5-yl)thio)acetate was used instead of 2-amino-5-chlorothiazole hydrochloride, and that methyl chloroformate was used instead of acetyl chloride.

Example 38

Production of 2-((2-(5-bromo-1'-(methoxycarbonyl)spiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the methyl 5-bromo-1-((5-((2-ethoxy-2-oxoethyl)thio)thiazol-2-yl)carbamoyl)spiro[indoline-3,3'-pyrrolidine]-1'-carboxylate obtained in Example 37 was used instead of ethyl 2-((2-(1'-acetyl-5-bromospiro[indoline-3,3'-pyrrolidin]-1-ylcarboxamido)thiazol-5-yl)thio)acetate.

Example 39

Production of 1'-acetyl-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exception that the t-butyl 5-chlorospiro[indoline-3,3'-pyrrolidine]-1'-carboxylate synthesized by a method described in the known method (International Publication WO2009/089454) or a method similar thereto was used instead of t-butyl 5-bromospiro[indoline-3,3'-pyrrolidine]-1'-carboxylate.

Example 40

Production of 5-chloro-N-(5-chlorothiazol-2-yl)-1'-formylspiro[indoline-3,3'-pyrrolidine]-1-carboxamide The captioned compound was obtained in the form of a white solid by performing the same reactions and/or treatments as those in Example 23, with the exception that the 5-chloro-N-(5-chlorothiazol-2-yl)spiro[indoline-3,3'-pyrrolidine]-1-carboxamide obtained as an intermediate of Example 39 was used instead of 5-bromo-N-(5-chlorothiazol-2-yl)spiro[indoline-3,3'-pyrrolidine]-1-carboxamide.

Example 41

Production of methyl 5-chloro-1-((5-chlorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 42

Production of 5-chloro-N-(5-chlorothiazol-2-yl)-1'-(methylsulfonyl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that methanesulfonyl chloride was used instead of acetyl chloride.

Example 43

Production of ethyl 2-(5-chloro-1-((5-chlorothiazol-2-yl)carbamoyl)spiro[indoline-3,3'-pyrrolidin]-1'-yl)-2-oxoacetate The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that ethyl chloroglyoxylate was used instead of acetyl chloride.

$^1$H-NMR (400 MHz, CDCl$_3$) δ: 1.24-1.39 (3H, m), 2.14-2.24 (1H, m), 2.30-2.38 (1H, m), 3.62-4.37 (8H, m), 7.14-7.17 (2H, m), 7.27-7.30 (1H, m), 8.02 (1H, dd, J=8.4, 16.0 Hz).

Example 44

Production of 2-(5-chloro-1-((5-chlorothiazol-2-yl)carbamoyl)spiro[indoline-3,3'-pyrrolidin]-1'-yl)-2-oxoacetic acid The captioned compound was obtained in the form of a white solid by performing the same reactions and/or treatments as those in Example 29, with the exception that the ethyl 2-(5-chloro-1-((5-chlorothiazol-2-yl)carbamoyl)spiro[indoline-3,3'-pyrrolidin]-1'-yl)-2-oxoacetate obtained in Example 43 was used instead of ethyl 2-((2-(1'-acetyl-5-bromospiro[indoline-3,3'-pyrrolidin]-1-ylcarboxamido)thiazol-5-yl)thio)acetate.

$^1$H-NMR (400 MHz, DMSO-d$_6$) δ: 2.12-2.20 (1H, m), 2.27-2.32 (1H, m), 3.52-3.88 (4H, m), 4.06-4.16 (2H, m), 7.30 (1H, d, J=8.8 Hz), 7.49 (2H, s), 7.94 (1H, br).

Example 45

Production of 1'-(2-amino-2-oxoacetyl)-5-chloro-N-(5-chlorothiazol-2-yl)spiro[indoline-3,3'-pyrrolidine]-1-carboxamide A saturated solution of ammonia-methanol (0.5 mL) and tetrahydrofuran (0.5 mL) were added to the ethyl 2-(5-chloro-1-((5-chlorothiazol-2-yl)carbamoyl)spiro[indoline-3,3'-pyrrolidin]-1'-yl)-2-oxoacetate (50 mg, 0.106 mmol) obtained in Example 43, and the obtained mixture was then stirred at room temperature for 14 hours. Thereafter, the reaction solution was concentrated in vacuo, and the obtained residue was then washed with chloroform to obtain the captioned compound (29.0 mg, 62%) in the form of a white solid.

Example 46

Production of 5-chloro-N-(5-chlorothiazol-2-yl)-1'-(2-(methylamino)-2-oxoacetyl)spiro[indoline-3,3'-pyrrolidine]-1-carboxamide The captioned compound was obtained in the form of a white solid by performing the same reactions and/or treatments as those in Example 45, with the exception that a solution of methylamine-tetrahydrofuran was used instead of the saturated solution of ammonia-methanol.

$^1$H-NMR (400 MHz, DMSO-d$_6$) δ: 2.16-2.33 (2H, m), 2.66 (3H, dd, J=4.8, 18.4 Hz), 3.54-3.56 (1H, m), 3.69-3.80 (2H, m), 4.09 (3H, br), 7.30 (1H, d, J=8.0 Hz), 7.48 (2H, s), 7.93 (1H, dd, J=4.8 Hz), 8.64-8.69 (1H, m).

Example 47

Production of 1'-(2-aminoacetyl)-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Examples 19 and 20, with the exception that 5-chloro-N-(5-chlorothiazol-2-yl)spiro[indoline-3,3'-pyrrolidine]-1-carboxamide was used instead of 5-bromo-N-(5-chlorothiazol-2-yl)spiro[indoline-3,3'-pyrrolidine]-1-carboxamide.

Example 48

Production of 5-chloro-N-(5-chlorothiazol-2-yl)-1'-(2-(methylamino)acetyl)spiro[indoline-3,3'-pyrrolidine]-1-carboxamide The captioned compound was obtained in the form of a white solid by performing the same reactions and/or treatments as those in Examples 19 and 20, with the exceptions that 5-chloro-N-(5-chlorothiazol-2-yl)spiro[indoline-3,3'-pyrrolidine]-1-carboxamide was used instead of 5-bromo-N-(5-chlorothiazol-2-yl)spiro[indoline-3,3'-pyrrolidine]-1-carboxamide, and that N-Boc-N-methyl glycine was used instead of N-Boc glycine.

Example 49

Production of 5-chloro-N-(5-chlorothiazol-2-yl)-1'-(2-(dimethylamino)acetyl)spiro[indoline-3,3'-pyrrolidine]-1-carboxamide The captioned compound was obtained in the form of a white solid by performing the same reactions and/or treatments as those in Example 19, with the exceptions that 5-chloro-N-(5-chlorothiazol-2-yl)spiro[indoline-3,3'-pyrrolidine]-1-carboxamide was used instead of 5-bromo-N-(5-chlorothiazol-2-yl)spiro[indoline-3,3'-pyrrolidine]-1-carboxamide, and that N,N-dimethyl glycine was used instead of N-Boc glycine.

$^1$H-NMR (400 MHz, CDCl$_3$) δ: 2.05-2.36 (8H, m), 3.04-3.22 (2H, m), 3.53-4.13 (6H, m), 7.11-7.16 (2H, m), 7.23-7.28 (1H, m), 7.97-8.04 (1H, m).

Example 50

Production of 1'-(2-acetamidoacetyl)-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Example 3, with the exception that the 1'-(2-aminoacetyl)-5-chloro-N-(5-chlorothiazol-2-yl)spiro[indoline-3,3'-pyrrolidine]-1-carboxamide obtained in Example 47 was used instead of 5-bromo-N-(5-chlorothiazol-2-yl)spiro[indoline-3,3'-pyrrolidine]-1-carboxamide.

$^1$H-NMR (400 MHz, CDCl$_3$) δ: 1.88-2.32 (5H, m), 3.40-3.96 (6H, m), 4.16-4.28 (1H, m), 4.52-4.78 (1H, m), 7.05-7.29 (3H, m), 7.73 (1H, br), 7.98-8.10 (1H, m).

Example 51

Production of 1'-(2-aminopropanoyl)-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Examples 19 and 20, with the exceptions that 5-chloro-N-(5-chlorothiazol-2-yl)spiro[indoline-3,3'-pyrrolidine]-1-carboxamide was used instead of bromo-N-(5-chlorothiazol-2-yl)spiro[indoline-3,3'-pyrrolidine]-1-carboxamide, and that N-Boc alanine was used instead of N-Boc glycine.

Example 52

Production of (R)-2-(5-chloro-1-((5-chlorothiazol-2-yl)carbamoyl)spiro[indoline-3,3'-pyrrolidin]-1'-yl)-2-oxoethyl acetate Step 1: (S)-t-Butyl 5-chloro-1-((5-chlorothiazol-2-yl)carbamoyl)spiro[indoline-3,3'-pyrrolidine]-1'-carboxylate was obtained in the form of a white solid by performing the same reactions and/or treatments as those in Example 1, with the exception that the (S)-t-butyl 5-chlorospiro[indoline-3,3'-pyrrolidine]-1'-carboxylate synthesized by a method described in the known methods (International Publication WO2006/090261 etc.) or a method similar thereto was used instead of t-butyl 5-bromospiro[indoline-3,3'-pyrrolidine]-1'-carboxylate.

$^1$H-NMR (400 MHz, DMSO-$d_6$) δ: 1.38 (9H, s), 2.01 (1H, m), 2.15 (1H, m), 3.22-3.54 (4H, m), 4.04 (2H, br), 7.21 (1H, d, J=8.0 Hz), 7.38 (1H, br), 7.41 (1H, s), 7.83 (1H, d, J=8.0 Hz).

Step 2: The captioned compound was obtained in the form of a white solid by performing the same reactions and/or treatments as those in Examples 2 and 3, with the exceptions that (S)-t-butyl 5-chloro-1-((5-chlorothiazol-2-yl)carbamoyl)spiro[indoline-3,3'-pyrrolidine]-1'-carboxylate was used instead of t-butyl 5-bromo-1-((5-chlorothiazol-2-yl)carbamoyl)spiro[indoline-3,3'-pyrrolidine]-1'-carboxylate, and that acetoxyacetyl chloride was used instead of acetyl chloride.

$^1$H-NMR (400 MHz, CDCl$_3$) δ: 2.06-2.33 (7H, m), 3.45-4.20 (6H, m), 4.44-4.85 (2H, m), 7.11-7.29 (3H, m), 7.98-8.08 (1H, m).

Example 53

Production of (R)-5-chloro-N-(5-chlorothiazol-2-yl)-1'-(2-hydroxyacetyl)spiro[indoline-3,3'-pyrrolidine]-1-carboxamide The captioned compound was obtained in the form of a white solid by performing the same reactions and/or treatments as those in Step 2 of Example 17, with the exception that the (R)-2-(5-chloro-1-((5-chlorothiazol-2-yl)carbamoyl)spiro[indoline-3,3'-pyrrolidin]-1'-yl)-2-oxoethyl acetate obtained in Example 52 was used instead of 2-(5-bromo-1-((5-chlorothiazol-2-yl)carbamoyl)spiro[indoline-3,3'-pyrrolidin]-1'-yl)-2-oxoethyl acetate.

$^1$H-NMR (400 MHz, DMSO-$d_6$) δ: 2.03-2.25 (2H, m), 3.27-3.68 (4H, m), 3.90-4.15 (4H, m), 4.61-4.69 (1H, m), 7.23-7.25 (1H, m), 7.42-7.44 (2H, m), 7.89-7.91 (1H, m).

Example 54

Production of (R)-5-chloro-N-(5-chlorothiazol-2-yl)-1'-(2-methoxyacetyl)spiro[indoline-3,3'-pyrrolidine]-1-carboxamide The captioned compound was obtained in the form of a white solid by performing the same reactions and/or treatments as those in Example 3, with the exceptions that the (R)-5-chloro-N-(5-chlorothiazol-2-yl)spiro[indoline-3,3'-pyrrolidine]-1-carboxamide obtained as an intermediate of Example 52 was used instead of 5-bromo-N-(5-chlorothiazol-2-yl)spiro[indoline-3,3'-pyrrolidine]-1-carboxamide, and that methoxyacetyl chloride was used instead of acetyl chloride.

$^1$H-NMR (400 MHz, DMSO-$d_6$) δ: 2.03-2.30 (2H, m), 3.25-3.70 (7H, m), 3.94-4.15 (4H, m), 7.25-7.27 (1H, m), 7.40-7.44 (2H, m), 7.89-7.91 (1H, m)

Example 55

Production of (2R)-1-(5-chloro-1-((5-chlorothiazol-2-yl)carbamoyl)spiro[indoline-3,3'-pyrrolidin]-1'-yl)-1-oxopropan-2-yl acetate The captioned compound was obtained in the form of a white solid by performing the same reactions and/or treatments as those in Step 1 of Example 17, with the exceptions that (R)-2-acetoxypropionic acid chloride was used instead of acetoxyacetic acid chloride, and that 5-chloro-N-(5-chlorothiazol-2-yl)spiro[indoline-3,3'-pyrrolidine]-1-carboxamide was used instead of 5-bromo-N-(5-chlorothiazol-2-yl)spiro[indoline-3,3'-pyrrolidine]-1-carboxamide.

Example 56

Production of 5-chloro-N-(5-chlorothiazol-2-yl)-1'-((R)-2-hydroxypropanoyl)spiro[indoline-3,3'-pyrrolidine]-1-carboxamide The captioned compound was obtained in the form of a white solid by performing the same reactions and/or treatments as those in Step 2 of Example 17, with the exception that the (2R)-1-(5-chloro-1-((5-chlorothiazol-2-yl)carbamoyl)spiro[indoline-3,3'-pyrrolidin]-1'-yl)-1-oxopropan-2-yl acetate obtained in Example 55 was used instead of 5-bromo-N-(5-chlorothiazol-2-yl)-1'-(2-acetoxyacetyl)spiro[indoline-3,3'-pyrrolidine]-1-carboxamide.

Example 57

Production of t-butyl 2-(5-chloro-1-((5-chlorothiazol-2-yl)carbamoyl)spiro[indoline-3,3'-pyrrolidin]-1'-yl)acetate Step 1: t-Butyl 5-chlorospiro[indoline-3,3'-pyrrolidine]-1'-carboxylate (19.3 g, 62.5 mmol) was dissolved in methylene chloride (193 mL). Thereafter, pyridine (6.1 mL, 75.0 mmol) and trifluoroacetic anhydride (9.5 mL, 68.75 mmol) were added to the above obtained solution under cooling on ice, and the obtained mixture was then stirred for 10 minutes. Thereafter, the reaction solution was diluted with water, and was then extracted with chloroform. The organic layer was dried over anhydrous sodium sulfate, and was then concentrated in vacuo. The obtained residue was purified by silica gel column chromatography (n-hexane:ethyl acetate=5:1) to obtain t-butyl 5-chloro-1-(2,2,2-trifluoroacetyl)spiro[indoline-3,3'-pyrrolidine]-1'-carboxylate (23.8 g, 94%) in the form of a light yellow oily product.

$^1$H-NMR (400 MHz, CDCl$_3$) δ: 1.47 (9H, s), 2.03-2.12 (1H, m), 2.12-2.68 (1H, m), 3.41-3.80 (4H, m), 4.08-4.20 (2H, m), 7.20 (1H, s), 7.31 (1H, dd, J=2.4 Hz, 8.8 Hz), 8.16 (1H, d, J=8.8 Hz).

Step 2: t-Butyl 2-(5-chloro-1-(2,2,2-trifluoroacetyl)spiro[indoline-3,3'-pyrrolidin]-1'-yl)acetate was obtained in the form of a colorless oily product by performing the same reactions and/or treatments as those in Examples 2 and 3, with the exceptions that t-butyl 5-chloro-1-(2,2,2-trifluoroacetyl)spiro[indoline-3,3'-pyrrolidine]-1'-carboxylate was used instead of t-butyl 5-bromo-1-((5-chlorothiazol-2-yl)carbamoyl)spiro[indoline-3,3'-pyrrolidine]-1'-carboxylate, and that t-butyl bromoacetate was used instead of acetyl chloride.

$^1$H-NMR (400 MHz, CDCl$_3$) δ: 1.48 (9H, s), 2.04-2.14 (1H, m), 2.18-2.28 (1H, m), 2.78 (1H, d, J=11.2 Hz), 2.81-2.89 (1H, m), 2.99 (1H, d, J=11.2 Hz), 3.00-3.20 (1H, m), 3.31 (2H, s), 4.12 (1H, d, J=11.2 Hz), 4.34 (1H, d, J=10.8 Hz), 7.24-7.28 (1H, m), 7.34 (1H, d, J=2.4 Hz), 8.11 (1H, d, J=8.8 Hz).

Step 3: Methanol (10.7 mL), water (3.6 mL), and potassium carbonate (0.4 g, 2.86 mmol) were added to t-butyl 2-(5-chloro-1-(2,2,2-trifluoroacetyl)spiro[indoline-3,3'-pyrrolidin]-1'-yl)acetate (0.6 g, 1.43 mmol), and the obtained mixture was then stirred at room temperature for 1.5 hours. Thereafter, the reaction solution was diluted with ethyl acetate, and was then washed with water and brine. The organic layer was concentrated in vacuo to obtain t-butyl 2-(5-chlorospiro[indoline-3,3'-pyrrolidin]-1'-yl)acetate (0.47 g, >100%) in the form of a light brown oily product.

$^1$H-NMR (400 MHz, CDCl$_3$) δ: 1.47 (9H, s), 2.01-2.07 (2H, m), 2.67 (1H, d, J=11.2 Hz), 2.72-2.81 (1H, m), 2.97-3.04 (1H, m), 3.28 (2H, d, J=2.8 Hz), 3.43-3.50 (1H, m), 3.60-3.65 (1H, m), 3.71 (1H, brs), 6.53 (1H, d, J=8.4 Hz), 6.98 (1H, dd, J=2.0 Hz, 8.4 Hz), 7.13 (1H, d, J=2.0 Hz).

Step 4: The captioned compound was obtained in the form of a white solid by performing the same reactions and/or treatments as those in Example 1, with the exception that t-butyl 2-(5-chlorospiro[indoline-3,3'-pyrrolidin]-1'-yl)acetate was used instead of t-butyl 5-bromospiro[indoline-3,3'-pyrrolidine]-1'-carboxylate.

Example 58

Production of methyl 2-(5-chloro-1-((5-chlorothiazol-2-yl)carbamoyl)spiro[indoline-3,3'-pyrrolidin]-1'-yl)acetate The captioned compound was obtained in the form of a white solid by performing the same reactions and/or treatments as those in Example 57, with the exception that methyl bromoacetate was used instead of t-butyl bromoacetate.

$^1$H-NMR (400 MHz, CDCl$_3$) δ: 2.03-2.14 (1H, m), 2.24-2.33 (1H, m), 2.77 (1H, d, J=9.2 Hz), 2.80-2.88 (1H, m), 3.03 (1H, d, J=8.8 Hz), 3.12-3.21 (1H, m), 3.44 (2H, d, J=2.0 Hz), 3.74 (3H, s), 3.93 (1H, d, J=11.2 Hz), 4.17 (1H, d, J=11.2 Hz), 7.20-7.24 (3H, m), 7.95 (1H, d, J=8.8 Hz).

Example 59

Production of 2-(5-chloro-1-((5-chlorothiazol-2-yl)carbamoyl)spiro[indoline-3,3'-pyrrolidin]-1'-yl)acetic acid The captioned compound was obtained in the form of a white solid by performing the same reactions and/or treatments as those in Example 2, with the exception that the t-butyl 2-(5-chloro-1-((5-methylthiazol-2-yl)carbamoyl)spiro[indoline-3,3'-pyrrolidin]-1'-yl)acetate obtained in Example 57 was used instead of t-butyl 5-bromo-1-((5-chlorothiazol-2-yl)carbamoyl)spiro[indoline-3,3'-pyrrolidine]-1'-carboxylate.

$^1$H-NMR (400 MHz, DMSO-d$_6$) δ: 2.00-2.18 (2H, m), 2.79-3.00 (4H, m), 3.30-3.40 (2H, m), 4.08 (1H, d, J=11.2 Hz), 4.19 (1H, d, J=10.4 Hz), 7.24 (1H, dd, J=2.4 Hz, 8.8 Hz), 7.40 (1H, d, J=2.4 Hz), 7.47 (1H, s), 7.90 (1H, d, J=8.8 Hz)

Example 60

Production of 1'-(2-amino-2-oxoethyl)-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Example 45, with the exception that the methyl 2-(5-chloro-1-((5-chlorothiazol-2-yl)carbamoyl)spiro[indoline-3,3'-pyrrolidin]-1'-yl)acetate obtained in Example 58 was used instead of ethyl 2-(5-chloro-1-((5-chlorothiazol-2-yl)carbamoyl)spiro[indoline-3,3'-pyrrolidin]-1'-yl)-2-oxoacetate.

$^1$H-NMR (400 MHz, DMSO-d$_6$) δ: 1.98-2.08 (1H, m), 2.10-2.20 (1H, m), 2.68-2.93 (4H, m), 3.09 (2H, s), 4.06 (1H, d, J=10.8 Hz), 4.26 (1H, d, J=10.8 Hz), 7.14-7.24 (2H, br), 7.25 (1H, dd, J=2.0 Hz, 8.4 Hz), 7.45 (1H, d, J=2.0 Hz), 7.48 (1H, s), 7.90 (1H, J=8.0 Hz).

Example 61

Production of 5-chloro-N-(5-chlorothiazol-2-yl)-1'-(2-(methylamino)-2-oxoethyl)spiro[indoline-3,3'-pyrrolidine]-1-carboxamide The captioned compound was obtained in the form of a white solid by performing the same reactions and/or treatments as those in Example 45, with the exceptions that the methyl 2-(5-chloro-1-((5-chlorothiazol-2-yl)carbamoyl)spiro[indoline-3,3'-pyrrolidin]-1'-yl)acetate obtained in Example 58 was used instead of ethyl 2-(5-chloro-1-((5-chlorothiazol-2-yl)carbamoyl)spiro[indoline-3,3'-pyrrolidin]-1'-yl)-2-oxoacetate, and that a solution of methylamine-tetrahydrofuran was used instead of a saturated solution of ammonia-methanol.

Example 62

Production of 5-chloro-N-(5-chlorothiazol-2-yl)-1'-(2-cyanoacetyl)spiro[indoline-3,3'-pyrrolidine]-1-carboxamide The captioned compound was obtained in the form of a white solid by performing the same reactions and/or treatments as those in Example 23, with the exceptions that the 5-chloro-N-(5-chlorothiazol-2-yl)spiro[indoline-3,3'-pyrrolidine]-1-carboxamide obtained as an intermediate of Example 39 was used instead of 5-bromo-N-(5-chlorothiazol-2-yl)spiro[indoline-3,3'-pyrrolidine]-1-carboxamide, and that cyanoacetic acid was used instead of formic acid.

$^1$H-NMR (400 MHz, DMSO-d$_6$) δ: 2.04-2.36 (2H, m), 3.34-3.56 (2H, m), 3.63-3.78 (2H, m), 3.86-4.24 (4H, m), 7.26-7.34 (1H, m), 7.42-7.52 (2H, m), 7.88-7.98 (1H, m)

Example 63

Production of 1'-acetyl-N-(5-chlorothiazol-2-yl)-5-methoxyspiro[indoline-3,3'-pyrrolidine]-1-carboxamide The captioned compound was obtained in the form of a white solid by performing the same reactions and/or treatments as those in Examples 1, 2, and 3, with the exception that

Example 64

Production of 1'-acetyl-5-methoxy-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-methoxyspiro[indoline-3,3'-pyrrolidine]-1'-carboxylate was used instead of t-butyl 5-bromospiro[indoline-3,3'-pyrrolidine]-1'-carboxylate, and that the 5-methoxythiazolo[5,4-b]pyridin-2-amine synthesized by a method described in the known methods (International Publication WO2004/050645 etc.) was used instead of 2-amino-5-chlorothiazole hydrochloride.

$^1$H-NMR (400 MHz, CDCl$_3$) δ: 2.07-2.36 (5H, m), 3.45-4.21 (9H, m), 6.71-6.85 (2H, m), 7.17 (1H, s), 7.89-8.00 (1H, m), 9.29 (1H, brs).

Example 64

Production of 1'-acetyl-5-methoxy-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-methoxyspiro[indoline-3,3'-pyrrolidine]-1'-carboxylate was used instead of t-butyl 5-bromospiro[indoline-3,3'-pyrrolidine]-1'-carboxylate, and that the 5-methoxythiazolo[5,4-b]pyridin-2-amine synthesized by a method described in the known methods (International Publication WO2004/050645 etc.) was used instead of 2-amino-5-chlorothiazole hydrochloride.

Example 65

Production of 1'-acetyl-N-(5-chlorothiazol-2-yl)-5-fluorospiro[indoline-3,3'-pyrrolidine]-1-carboxamide The captioned compound was obtained in the form of a white solid by performing the same reactions and/or treatments as those in Examples 1, 2, and 3, with the exception that the t-butyl 5-fluorospiro[indoline-3,3'-pyrrolidine]-1'-carboxylate synthesized by a method described in the known methods (International Publication WO2009/089454 etc.) or a method similar thereto was used instead of t-butyl 5-bromospiro[indoline-3,3'-pyrrolidine]-1'-carboxylate.

Example 66

Production of 1'-acetyl-5-fluoro-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that the 5-methoxythiazolo[5,4-b]pyridin-2-amine synthesized by a method described in the known methods (International Publication WO2004/050645 etc.) was used instead of 2-amino-5-chlorothiazole hydrochloride.

Example 67

Production of 1'-acetyl-5-chloro-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that the 5-methoxythiazolo[5,4-b]pyridin-2-amine synthesized by a method described in the known methods (International Publication WO2004/050645 etc.) was used instead of 2-amino-5-chlorothiazole hydrochloride.

Example 68

Production of 1'-acetyl-5-chloro-N-(5-fluorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

$^1$H-NMR (400 MHz, DMSO-d$_6$) δ: 1.88-2.31 (5H, m), 3.25-3.79 (4H, m), 3.97-4.23 (2H, m), 7.23-7.32 (2H, m), 7.39-7.47 (1H, m), 7.89-7.99 (1H, m).

Example 69

Production of 5-chloro-N-(5-fluorothiazol-2-yl)-1'-formylspiro[indoline-3,3'-pyrrolidine]-1-carboxamide The captioned compound was obtained in the form of a white solid by performing the same reactions and/or treatments as those in Examples 1, 2, and 23, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 70

Production of 5-chloro-N-(5-fluorothiazol-2-yl)-1'-(methylsulfonyl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, that 2-amino-5-fluorothiazole hydrochloride was used instead of 2-amino-5-chlorothiazole hydrochloride, and that methanesulfonyl chloride was used instead of acetyl chloride.

Example 71

Production of methyl 5-chloro-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, that 2-amino-5-fluorothiazole hydrochloride was used instead of 2-amino-5-chlorothiazole hydrochloride, and that methyl chloroformate was used instead of acetyl chloride.

Example 72

Production of methyl 5-chloro-1-((4-methylthiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, that 2-amino-4-methylthiazole was used instead of 2-amino-5-chlorothiazole hydrochloride, and that methyl chloroformate was used instead of acetyl chloride.

Example 73

Production of methyl 5-chloro-1-((5-methylthiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, that 2-amino-5-methylthiazole was used instead of 2-amino-5-chlorothiazole hydrochloride, and that methyl chloroformate was used instead of acetyl chloride.

Example 74

Production of (R)-1'-acetyl-5-chloro-N-(5-methylthiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that 2-amino-5-methylthiazole was used instead of 2-amino-5-chlorothiazole hydrochloride, and that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate.

Example 75

Production of N-(5-chlorothiazol-2-yl)-5-fluoro-1'-formylspiro[indoline-3,3'-pyrrolidine]-1-carboxamide The captioned compound was obtained in the form of a white solid by performing the same reactions and/or treatments as those in Examples 1, 2, and 23, with the exception that t-butyl 5-fluorospiro[indoline-3,3'-pyrrolidine]-1'-carboxylate was used instead of t-butyl 5-bromospiro[indoline-3,3'-pyrrolidine]-1'-carboxylate.

Example 76

Production of 5-fluoro-N-(5-fluorothiazol-2-yl)-1'-formylspiro[indoline-3,3'-pyrrolidine]-1-carboxamide The captioned compound was obtained in the form of a white solid by performing the same reactions and/or treatments as those in Examples 1, 2, and 23, with the exceptions that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 77

Production of 1'-acetyl-5-fluoro-N-(5-fluorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 78

Production of N-(5-chlorothiazol-2-yl)-5-fluoro-1'-(methylsulfonyl)spiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that methanesulfonyl chloride was used instead of acetyl chloride.

Example 79

Production of 5-fluoro-N-(5-fluorothiazol-2-yl)-1'-(methylsulfonyl)spiro[indoline-3,3'-pyrrolidine]-1-carboxamide The captioned compound was obtained in the form of a white solid by performing the same reactions and/or treatments as those in Examples 1, 2, and 3, with the exceptions that 2-amino-5-fluorothiazole hydrochloride was used instead of 2-amino-5-chlorothiazole hydrochloride, that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that methanesulfonyl chloride was used instead of acetyl chloride.

Example 80

Production of methyl 1-((5-chlorothiazol-2-yl)carbamoyl)-5-fluorospiro[indoline-3,3'-pyrrolidine]-1'-carboxylate The captioned compound was obtained in the form of a white solid by performing the same reactions and/or treatments as those in Examples 1, 2, and 3, with the exceptions that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 81

Production of methyl 5-fluoro-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that 2-amino-5-fluorothiazole hydrochloride was used instead of 2-amino-5-chlorothiazole hydrochloride, that t-butyl 5-fluorospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 82

Production of ethyl 2-(5-chloro-1'-(methoxycarbonylspiro[indoline-3,3'-pyrrolidin]-1-ylcarboxamido)thiazole-4-carboxylate The captioned compound was obtained in the form of a white solid by performing the same reactions and/or treatments as those in Examples 1, 2, and 3, with the exceptions that ethyl 2-aminothiazole-4-carboxylate was used instead of 2-amino-5-chlorothiazole hydrochloride, that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 83

Production of 2-(5-chloro-1'-(methoxycarbonyl)spiro[indoline-3,3'-pyrrolidin]-1-ylcarboxamido)thiazole-4-carboxylic acid The captioned compound was obtained in the form of a white solid by performing the same reactions and/or treatments as those in Step 2 of Example 17, with the exception that the ethyl 2-(5-chloro-1'-(methoxycarbonylspiro[indoline-3,3'-pyrrolidin]-1-ylcarboxamido)thiazole-4-carboxylate obtained in Example 82 was used instead of 5-bromo-N-(5-chlorothiazol-2-yl)-1'-(2-acetoxyacetyl)spiro[indoline-3,3'-pyrrolidine]-1-carboxamide.

Example 84

Production of methyl 1-((4-carbamoylthiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the ethyl 2-(5-chloro-1'-(methoxycarbonylspiro[indoline-3,3'-pyrrolidin]-1-ylcarboxamido)thiazole-4-carboxylate obtained in Example 82 was used instead of ethyl 2-(5-chloro-1-((5-chlorothiazol-2-yl)carbamoyl)spiro[indoline-3,3'-pyrrolidin]-1'-yl)-2-oxoacetate.

Example 85

Production of methyl 5-chloro-1-((4-(dimethylcarbamoyl)thiazol-2-yl)carbamoyl)spiro[indoline-3,3'-pyrrolidine]-1'-carboxylate The 2-(5-chloro-1'-(methoxycarbonyl)spiro[indoline-3,3'-pyrrolidin]-1-ylcarboxamido)thiazole-4-carboxylic acid (30 mg, 0.069 mmol) obtained in Example 83 was dissolved in methylene chloride (1 mL). Thereafter, triethylamine (24 µL, 0.10 mmol), dimethylamine hydrochloride (8.2 mg, 0.10 mmol), and 1-ethyl-3-(3-dimethylaminopropyl)carbodiimide hydrochloride (19 mg, 0.10 mmol) were added to the above obtained solution, and the thus obtained mixture was then stirred at room temperature for 13 hours. Thereafter, the reaction solution was concentrated in vacuo, and the obtained residue was then purified by silica gel column chromatography (chloroform:methanol=10:1) to obtain the captioned compound (26 mg, 81%) in the form of a light yellow amorphous product.

$^1$H-NMR (400 MHz, CDCl$_3$) δ: 2.06-2.26 (2H, m), 3.10-3.19 (6H, m), 3.42-3.77 (7H, m), 3.88-4.06 (2H, m), 7.10 (1H, s), 7.24 (1H, d, J=8.8 Hz), 7.36 (1H, s), 8.02 (1H, d, J=8.8 Hz), 9.47 (1H, br)

Examples 86 to 88

The below captioned compounds were all obtained in the form of a white solid by performing the same reactions and/or treatments as those in Example 85, with the exception that each raw material compound was used instead of dimethylamine hydrochloride.

Example 86

(The compound in the parentheses that is described below the captioned compound is a raw material compound that was used instead of dimethylamine hydrochloride. The same shall apply hereafter.)

Methyl 5-chloro-1-((4-(pyrrolidine-1-carbonyl)thiazol-2-yl)carbamoyl)spiro[indoline-3,3'-pyrrolidine]-1'-carboxylate (Pyrrolidine)

$^1$H-NMR (400 MHz, CDCl$_3$) δ: 1.91-2.22 (6H, m), 3.43-3.76 (11H, m), 3.94-4.07 (2H, m), 7.10 (1H, s), 7.23 (1H, d, J=8.8 Hz), 7.42 (1H, s), 8.03 (1H, d, J=8.8 Hz), 9.55 (1H, br).

Example 87

Methyl 5-chloro-1-((4-(piperidine-1-carbonyl)thiazol-2-yl)carbamoyl)spiro[indoline-3,3'-pyrrolidine]-1'-carboxylate (Piperidine)

Example 88

Methyl 5-chloro-1-((4-(morpholine-4-carbonyl)thiazol-2-yl)carbamoyl)spiro[indoline-3,3'-pyrrolidine]-1'-carboxylate (Morpholine)
$^1$H-NMR (400 MHz, CDCl$_3$) δ: 2.12 (1H, br), 2.22-2.30 (1H, m), 3.52-3.81 (15H, m), 3.96-4.05 (2H, m), 7.13 (1H, s), 7.26 (1H, d, J=8.8 Hz), 7.48 (1H, s), 8.01 (1H, d, J=8.8 Hz), 8.72 (1H, br).

Example 89

Production of methyl 5-chloro-1-((4-(hydroxymethyl)thiazol-2-yl)carbamoyl)spiro[indoline-3,3'-pyrrolidine]-1'-carboxylate Step 1: Methyl 5-chlorospiro[indoline-3,3'-pyrrolidine]-1'-carboxylate was obtained in the form of a white solid by performing the same reactions and/or treatments as those in Steps 2 and 3 of Example 57, with the exception that methyl chloroformate was used instead of t-butyl bromoacetate.
$^1$H-NMR (400 MHz, CDCl$_3$) δ: 1.95-2.12 (2H, m), 3.38-3.80 (10H, m), 6.54 (1H, d, J=8.0 Hz), 6.97 (1H, s), 6.99 (1H, d, J=8.0 Hz).

Step 2: Methyl 5-chlorospiro[indoline-3,3'-pyrrolidine]-1'-carboxylate (100 mg, 0.37 mmol) was dissolved in N,N'-dimethylformamide (0.5 mL). Thereafter, 4-nitrophenyl chloroformate (75 mg, 0.37 mmol) and pyridine (30 μL, 0.37 mmol) were added to the above obtained solution, and the thus obtained mixture was then stirred at room temperature for 13 hours. Thereafter, the (2-aminothiazol-4-yl)methyl acetate (65 mg, 0.37 mmol) synthesized by a method described in the known methods (International Publication WO2006/011631 etc.) or a method similar thereto was dissolved in N,N'-dimethylformamide (1.4 mL), and the obtained solution was then added to the reaction solution. The obtained mixture was stirred at room temperature for 24 hours. Thereafter, the reaction solution was diluted with water, and was then extracted with ethyl acetate. The organic layer was successively washed with a saturated aqueous solution of sodium hydrogen carbonate and brine, and was then dried over anhydrous sodium sulfate, followed by concentration in vacuo, to obtain a residue. The obtained residue was dissolved in methanol (1 mL), and thereafter, potassium carbonate (51 mg, 0.37 mmol) was added to the mixed solution at room temperature. The obtained mixture was stirred for 2 hours. Thereafter, the reaction solution was diluted with water, and was then extracted with chloroform. The resultant was dried over anhydrous sodium sulfate, and was then concentrated in vacuo. The obtained residue was purified by silica gel column chromatography (chloroform:methanol=100:0→10:1) to obtain the captioned compound (26.5 mg, 17%) in the form of a light yellow amorphous product.

Example 90

Production of methyl 5-chloro-1-((4-((dimethylamino)methyl)thiazol-2-yl)carbamoyl)spiro[indoline-3,3'-pyrrolidine]-1'-carboxylate The methyl 5-chlorospiro[indoline-3,3'-pyrrolidine]-1'-carboxylate (20 mg, 0.076 mmol) obtained in Step 1 of Example 89 was dissolved in tetrahydrofuran (1.0 mL). Thereafter, the 4-((dimethylamino)methyl)thiazole-2-amine (12 mg, 0.076 mmol) synthesized by a method described in the known methods (International Publication WO2008/086047 etc.) or a method similar thereto, carbonyldiimidazole (24 mg, 0.152 mmol), and dimethylaminopyridine (1.0 mg, 0.008 mmol) were added to the above obtained solution, and the thus obtained mixture was then stirred at 45° C. for 12 hours. Thereafter, the reaction solution was concentrated in vacuo, and the obtained residue was then purified by silica gel column chromatography (chloroform:methanol=10:1) to obtain the captioned compound (12 mg, 34%) in the form of a white solid.
$^1$H-NMR (400 MHz, CDCl$_3$) δ: 2.08 (2H, br), 2.17-2.27 (7H, m), 3.39-3.76 (11H, m), 3.95-4.04 (2H, m), 6.51 (1H, s), 7.09 (1H, d, J=2.0 Hz), 7.23 (1H, dd, J=2.0, 8.8 Hz), 8.04 (1H, d, J=8.8 Hz).

Production of Examples 91, 93, 102, 104, 108, 109, 117 to 121, 124, 127, 129, 136, 138, 139, 142, 145, 149, 156, 159, 161, 162, 180, 181, and 184

The below captioned compounds were all obtained in the form of a white solid by performing the same reactions and/or treatments as those in Example 90, with the exception that each raw material compound was used instead of 4-((dimethylamino)methyl)thiazole-2-amine.

Example 91

(The compound in the parentheses that is described below the captioned compound is a raw material compound that was used instead of 4-((dimethylamino)methyl)thiazole-2-amine. The same shall apply hereafter.)

Methyl 5-chloro-1-((4-(piperidin-1-ylmethyl)thiazol-2-yl)carbamoyl)spiro[indoline-3,3'-pyrrolidine]-1'-carboxylate (4-(Piperidin-1-ylmethyl)thiazole-2-amine synthesized by a method described in the known methods (International Publication WO2008/086047 etc.) or a method similar thereto)
$^1$H-NMR (400 MHz, CDCl$_3$) δ: 1.45 (2H, br), 1.57-1.63 (4H, m), 2.05-2.24 (2H, m), 2.40 (4H, br), 3.41-3.76 (9H, m), 3.97-4.06 (2H, m), 6.44 (1H, s), 7.09 (1H, d, J=2.0 Hz), 7.22 (1H, dd, J=2.0, 8.8 Hz), 8.06 (1H, d, J=8.8 Hz).

Example 93

Methyl 5-chloro-1-((4-(2-methoxy-2-oxoethyl)thiazol-2-yl)carbamoyl)spiro[indoline-3,3'-pyrrolidine]-1'-carboxylate (Methyl 2-amino-4-thiazoleacetate)

Example 102

1-(2-(5-Chloro-1'-(methoxycarbonyl)spiro[indoline-3,3'-pyrrolidin]-1-ylcarboxamido)thiazol-4-yl)ethane-1,2-diyl diacetate (1-(2-Aminothiazol-4-yl)ethane-1,2-diyl diacetate synthesized by a method described in the known methods (International Publication WO2007/026761 etc.) or a method similar thereto)
$^1$H-NMR (400 MHz, CDCl$_3$) δ: 2.04-2.30 (8H, m), 3.50-3.77 (7H, m), 4.01-4.05 (2H, m), 4.36-4.51 (2H, m), 6.06 (1H, dt, J=1.0, 1.0 Hz), 6.89 (1H, s), 7.26 (1H, dd, J=2.0, 8.8 Hz), 8.00 (1H, d, J=8.8 Hz), 8.59 (1H, br).

Example 104

Methyl 5-chloro-1-((4-(3-ethoxy-3-oxopropyl)thiazol-2-yl)carbamoyl)spiro[indoline-3,3'-pyrrolidine]-1'-carboxylate (Ethyl 2-aminothiazole-4-propanoate)

Example 108

Methyl 1-((4-butylthiazol-2-yl)carbamoyl)-5-chlorospiro[indoline-3,3'-pyrrolidine]-1'-carboxylate (2-Amino-4-butylthiazole synthesized by a method described in the known methods (Helvetica Chimica Acta, 32, 35-8; 1949 etc.) or a method similar thereto)

Example 109

Ethyl 2-(5-chloro-1'-(methoxycarbonyl)spiro[indoline-3,3'-pyrrolidin]-1-ylcarboxamido)thiazole-5-carboxylate (Ethyl 2-aminothiazole-5-carboxylate)

Example 117

Methyl 5-chloro-1-((5-(2-hydroxypropan-2-yl)thiazol-2-yl)carbamoyl)spiro[indoline-3,3'-pyrrolidine]-1'-carboxylate (2-Amino-α,α-dimethyl-5-thiazolemethanol)
$^1$H-NMR (400 MHz, CDCl$_3$) δ: 1.63 (6H, s), 2.03 (1H, m), 2.18 (1H, m), 3.33-61 (7H, m), 3.86 (1H, d, J=10.0 Hz), 3.95 (1H, d, J=10.0 Hz), 7.07-7.09 (2H, m), 7.22 (1H, m), 8.01 (1H, m).

Example 118

Methyl 5-chloro-1-((5-(1,1,1,3,3,3-hexafluoro-2-hydroxypropan-2-yl)thiazol-2-yl)carbamoyl)spiro[indoline-3,3'-pyrrolidine]-1'-carboxylate (2-Amino-α,α-bis(trifluoromethyl)-5-thiazolemethanol)
$^1$H-NMR (400 MHz, DMSO-d$_6$) δ: 2.03 (1H, m), 2.16 (1H, m), 3.25-3.41 (2H, m), 3.51-3.57 (5H, m), 4.10 (2H, br), 7.10 (1H, d, J=8.4 Hz), 7.27 (1H, s), 7.58 (1H, s), 7.89 (1H, d, J=8.0 Hz), 9.14 (1H, s).

Example 119

Methyl 5-chloro-1-((5-(((diethylamino)methyl)thiazol-2-yl)carbamoyl)spiro[indoline-3,3'-pyrrolidine]-1'-carboxylate (5-((Diethylamino)methyl)thiazole-2-amine)

Example 120

Methyl 5-chloro-1-((5-(2-hydroxyethyl)thiazol-2-yl)carbamoyl)spiro[indoline-3,3'-pyrrolidine]-1'-carboxylate (2-Amino-5-thiazoleethanol)

Example 121

Methyl 5-chloro-1-((5-(3-ethoxy-3-oxopropyl)thiazol-2-yl)carbamoyl)spiro[indoline-3,3'-pyrrolidine]-1'-carboxylate (Ethyl 2-aminothiazole-5-propanoate synthesized by a method described in the known methods (International Publication WO2001/098282 etc.) or a method similar thereto)

Example 124

Methyl 5-chloro-1-((5-(4-methoxy-4-oxobutyl)thiazol-2-yl)carbamoyl)spiro[indoline-3,3'-pyrrolidine]-1'-carboxylate (Methyl 2-aminothiazole-5-butanoate synthesized by a method described in the known methods (International Publication WO2001/098282 etc.) or a method similar thereto)
$^1$H-NMR (400 MHz, CDCl$_3$) δ: 1.95-2.09 (3H, m), 2.18-2.25 (1H, m), 2.38 (2H, t, J=7.2 Hz), 2.77 (2H, t, J=7.2 Hz), 3.46-3.76 (10H, m), 3.95-4.04 (2H, m), 6.94 (1H, s), 7.10 (1H, s), 7.24 (1H, dd, J=2.0, 8.8 Hz), 8.02 (1H, d, J=8.8 Hz).

Example 127

Methyl 5-chloro-1-((5-(methylthio)thiazol-2-yl)carbamoyl)spiro[indoline-3,3'-pyrrolidine]-1'-carboxylate (5-(Methylthio)thiazole-2-amine synthesized by a method described in the known methods (International Publication WO2005/066145 etc.) or a method similar thereto)
$^1$H-NMR (400 MHz, CDCl$_3$) δ: 2.08 (1H, m), 2.21 (1H, m), 2.40 (3H, s), 3.43-3.75 (7H, m), 3.90 (1H, d, J=10.0 Hz), 4.00 (1H, d, J=10.0 Hz), 4.09 (1H, d, J=7.2 Hz), 4.12 (1H, d, J=7.2 Hz), 7.11 (1H, s), 7.21-7.26 (2H, m), 7.98 (1H, d, J=8.4 Hz)

Example 129

Methyl 5-chloro-1-((5-((2-methoxy-2-oxoethyl)thio)thiazol-2-yl)carbamoyl)spiro[indoline-3,3'-pyrrolidine]-1'-carboxylate (Methyl 2-((2-aminothiazol-5-yl)thio)acetate synthesized by a method described in the known methods (International Publication WO2005/066145 etc.) or a method similar thereto)

Example 136

Methyl 5-chloro-1-((5-((2-((tetrahydro-2H-pyran-2-yl)oxy)ethyl)thio)thiazol-2-yl)carbamoyl)spiro[indoline-3,3'-pyrrolidine]-1'-carboxylate (5-((2-((Tetrahydro-2H-pyran-2-yl)oxy)ethyl)thio)thiazole-2-amine synthesized by a method described in the known methods (International Publication WO2005/066145 etc.) or a method similar thereto)

Example 138

Methyl 5-chloro-1-((5-((2-methoxyethyl)thio)thiazol-2-yl)carbamoyl)spiro[indoline-3,3'-pyrrolidine]-1'-carboxylate (5-((2-Methoxyethyl)thio)thiazole-2-amine)

Example 139

Methyl 5-chloro-1-((5-((1-ethoxy-1-oxopropan-2-yl)thio)thiazol-2-yl)carbamoyl)spiro[indoline-3,3'-pyrrolidine]-1'-carboxylate (Ethyl 2-((2-aminothiazol-5-yl)thio)propanoate synthesized by a method described in the known methods (International Publication WO2005/066145 etc.) or a method similar thereto)

Example 142

Methyl 5-chloro-1-((5-((1-ethoxy-2-methyl-1-oxopropan-2-yl)thio)thiazol-2-yl)carbamoyl)spiro[indoline-3,3'-pyrrolidine]-1'-carboxylate (Ethyl 2-((2-aminothiazol-5-yl)thio)-2-methylpropanoate synthesized by a method described in the known methods (International Publication WO2007/006814 etc.) or a method similar thereto)

Example 145

Methyl 5-chloro-1-((5-((1-ethoxy-1-oxobutan-2-yl)thio)thiazol-2-yl)carbamoyl)spiro[indoline-3,3'-pyrrolidine]-1'-carboxylate (Ethyl 2-((2-aminothiazol-5-yl)thio)butanoate synthesized by a method described in the known methods (International Publication WO2005/066145 etc.) or a method similar thereto)

Example 149

Methyl 5-chloro-1-((5-((3-ethoxy-3-oxopropyl)thio)thiazol-2-yl)carbamoyl)spiro[indoline-3,3'-pyrrolidine]-1'-carboxylate (Ethyl 3-((2-aminothiazol-5-yl)thio)propanoate synthesized by a method described in the known methods (International Publication WO2005/066145 etc.) or a method similar thereto)

Example 156

Methyl 5-chloro-1-((5-((3-ethoxy-2,2-dimethyl-3-oxopropyl)thio)thiazol-2-yl)carbamoyl)spiro[indoline-3,3'-pyrrolidine]-1'-carboxylate (Ethyl 3-((2-aminothiazol-5-yl)thio)-2,2-dimethylpropanoate synthesized by a method described in the known methods (International Publication WO2008/084044 etc.) or a method similar thereto)

Example 159

Methyl 5-chloro-1-((5-((4-ethoxy-4-oxobutyl)thio)thiazol-2-yl)carbamoyl)spiro[indoline-3,3'-pyrrolidine]-1'-carboxylate (Ethyl 4-((2-aminothiazol-5-yl)thio)butanoate synthesized by a method described in the known methods (International Publication WO2005/066145 etc.) or a method similar thereto)

Example 161

Methyl 5-chloro-1-((5-((3-hydroxypropyl)thio)thiazol-2-yl)carbamoyl)spiro[indoline-3,3'-pyrrolidine]-1'-carboxylate (3-((2-Aminothiazol-5-yl)thio)propan-1-ol synthesized by a method described in the known methods (International Publication WO2007/007886 etc.) or a method similar thereto)

$^1$H-NMR (400 MHz, CDCl$_3$) δ: 1.67 (1H, brs), 1.83-1.90 (2H, m), 1.99-2.26 (2H, m), 2.82 (2H, t, J=6.6 Hz), 3.46 (2H, t, J=6.6 Hz), 3.49-3.76 (7H, m), 3.95-4.03 (2H, m), 7.12 (1H, s), 7.25 (1H, d, J=8.8 Hz), 7.31 (1H, s), 8.00 (1H, d, J=8.8 Hz).

Example 162

Methyl 5-chloro-1-((5-((3-methoxypropyl)thio)thiazol-2-yl)carbamoyl)spiro[indoline-3,3'-pyrrolidine]-1'-carboxylate (5-((3-Methoxypropyl)thio)thiazole-2-amine)

$^1$H-NMR (400 MHz, CDCl$_3$) δ: 1.92-1.99 (2H, m), 2.08-2.27 (2H, m), 2.80 (2H, t, J=6.7 Hz), 3.50-3.75 (7H, m), 3.77 (3H, s), 3.90-4.03 (2H, m), 4.23 (2H, t, J=6.7 Hz), 7.11 (1H, s), 7.24 (1H, d, J=8.4 Hz), 7.32 (1H, s), 7.99 (1H, d, J=8.4 Hz).

Example 180

Methyl 5-chloro-1-((5-((3-(dimethylamino)propyl)thio)thiazol-2-yl)carbamoyl)spiro[indoline-3,3'-pyrrolidine]-1'-carboxylate (5-((3-(Dimethylamino)propyl)thio)thiazole-2-amine synthesized by a method described in the known methods (International Publication WO2009/133687 etc.))

$^1$H-NMR (400 MHz, CDCl$_3$) δ: 1.77 (2H, quint, J=7.31 Hz), 2.01-2.13 (1H, m), 2.16-2.29 (7H, m), 2.39 (2H, t, J=7.31 Hz), 2.76 (2H, t, J=7.31 Hz), 3.42-3.83 (7H, m), 3.91-4.07 (2H, m), 7.10 (1H, s), 7.21 (1H, d, J=8.3 Hz), 7.24 (1H, s), 7.99 (1H, d, J=8.3 Hz).

Example 181

Methyl 5-chloro-1-((5-methoxythiazol-2-yl)carbamoyl)spiro[indoline-3,3'-pyrrolidine]-1'-carboxylate (2-Amino-5-methoxythiazole)

$^1$H-NMR (400 MHz, CDCl$_3$) δ: 2.08 (1H, br), 2.18-2.26 (1H, m), 3.47-4.01 (12H, m), 6.59 (1H, s), 7.10 (1H, s), 7.23 (1H, dd, J=2.0, 8.8 Hz), 7.99 (1H, d, J=8.8 Hz).

Example 184

Methyl 5-chloro-1-((5-(3-(methoxycarbonyl)phenoxy)thiazol-2-yl)carbamoyl)spiro[indoline-3,3'-pyrrolidine]-1'-carboxylate (Methyl 3-((2-aminothiazol-5-yl)oxy)benzoate synthesized by a method described in the known methods (International Publication WO2008/005914 etc.))
$^1$H-NMR (400 MHz, CDCl$_3$) δ: 2.04-2.16 (1H, m), 2.19-2.31 (1H, m), 3.47-3.85 (7H, m), 3.88-4.06 (2H, m), 7.02 (1H, s), 7.12 (1H, s), 7.22-7.29 (1H, m), 7.31 (1H, d, J=7.8 Hz), 7.41 (1H, dd, J=7.8, 7.8 Hz), 7.74 (1H, brs), 7.80 (1H, d, J=7.8 Hz). 7.95 (1H, d, J=8.8 Hz).

Example 92

Production of 1'-acetyl-5-chloro-N-(4-(2-hydroxypropan-2-yl)thiazol-2-yl)spiro[indoline-3,3'-pyrrolidine]-1-carboxamide The captioned compound was obtained in the form of a white solid by performing the same reactions and/or treatments as those in Steps 2 and 3 of Example 57 and Example 90, with the exceptions that acetyl chloride was used instead of t-butyl bromoacetate, and that 2-amino-α,α-dimethyl-4-thiazolemethanol was used instead of 4-((dimethylamino)methyl)thiazole-2-amine.

Example 94

Production of 2-(2-(5-chloro-1'-(methoxycarbonyl)spiro[indoline-3,3'-pyrrolidin]-1-ylcarboxamido)thiazol-4-yl)acetic acid The captioned compound was obtained in the form of a white solid by performing the same reactions and/or treatments as those in Step 2 of Example 17, with the exception that the methyl 5-chloro-1-((4-(2-methoxy-2-oxoethyl)thiazol-2-yl)carbamoyl)spiro[indoline-3,3'-pyrrolidine]-1'-carboxylate obtained in Example 93 was used instead of 5-bromo-N-(5-chlorothiazol-2-yl)-1'-(2-acetoxyacetyl)spiro[indoline-3,3'-pyrrolidine]-1-carboxamide.

Example 95

Production of methyl 1-((4-(2-amino-2-oxoethyl)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((4-(2-methoxy-2-oxoethyl)thiazol-2-yl)carbamoyl)spiro[indoline-3,3'-pyrrolidine]-1'-carboxylate obtained in Example 93 was used instead of ethyl 2-(5-chloro-1-((5-chlorothiazol-2-yl)carbamoyl)spiro[indoline-3,3'-pyrrolidin]-1'-yl)-2-oxoacetate.
$^1$H-NMR (400 MHz, CDCl$_3$) δ: 2.04 (2H, br), 2.15-2.21 (1H, m), 3.39-3.75 (9H, m), 4.03-4.15 (2H, m), 6.79 (1H, s), 7.02-7.23 (4H, m), 8.03 (1H, d, J=8.8 Hz), 10.5 (1H, br).

Example 96

Production of methyl 5-chloro-1-((4-(2-(dimethylamino)-2-oxoethyl)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 2-(2-(5-chloro-1'-(methoxycarbonyl)spiro[indoline-3,3'-pyrrolidin]-1-ylcarboxamido)thiazol-4-yl)acetic acid obtained in Example 94 was used instead of 2-(5-chloro-1'-(methoxycarbonyl)spiro[indoline-3,3'-pyrrolidin]-1-ylcarboxamido)thiazole-4-carboxylic acid.

Production of Examples 97 to 100

The below captioned compounds were all obtained in the form of a white solid by performing the same reactions and/or treatments as those in Example 85, with the exceptions that 2-(2-(5-chloro-1'-(methoxycarbonyl)spiro[indoline-3,3'-pyrrolidin]-1-ylcarboxamido)thiazol-4-yl)acetic acid was used instead of 2-(5-chloro-1'-(methoxycarbonyl)spiro[indoline-3,3'-pyrrolidin]-1-ylcarboxamido)thiazole-4-carboxylic acid, and that each raw material compound was used instead of dimethylamine hydrochloride.

Example 97

Methyl 1-((4-(2-(azetidin-1-yl)-2-oxoethyl)thiazol-2-yl)carbamoyl)-5-chloro-spiro[indoline-3,3'-pyrrolidine]-1'-carboxylate (Azetidine)
$^1$H-NMR (400 MHz, CDCl$_3$) δ: 2.06 (1H, br), 2.14-2.29 (3H, m), 3.44-3.76 (9H, m), 3.96-4.02 (4H, m), 4.18 (2H, t, J=3.6 Hz), 6.52 (1H, s), 7.07 (1H, s), 7.17 (1H, dd, J=2.4, 8.8 Hz), 7.98 (1H, d, J=8.8 Hz).

Example 98

Methyl 5-chloro-1-((4-(2-oxo-2-(pyrrolidin-1-yl)ethyl)thiazol-2-yl)carbamoyl)spiro[indoline-3,3'-pyrrolidine]-1'-carboxylate (Pyrrolidine)

Example 99

Methyl 5-chloro-1-((4-(2-oxo-2-(piperidin-1-yl)ethyl)thiazol-2-yl)carbamoyl)spiro[indoline-3,3'-pyrrolidine]-1'-carboxylate (Piperidine)

Example 100

Methyl 5-chloro-1-((4-(2-morpholino-2-oxoethyl)thiazol-2-yl)carbamoyl)spiro[indoline-3,3'-pyrrolidine]-1'-carboxylate (Morpholine)

Example 101

Production of methyl 5-chloro-1-((4-(2-hydroxyethyl)thiazol-2-yl)carbamoyl)spiro[indoline-3,3'-pyrrolidine]-1'-carboxylate The captioned compound was obtained in the form of a white solid by performing the same reactions and/or treatments as those in Example 89, with the exception that the 2-(2-aminothiazol-4-yl)ethyl acetate synthesized by a method described in the known methods (International Pub-

Example 103

Production of methyl 5-chloro-1-((4-(1,2-dihydroxyethyl)thiazol-2-yl)carbamoyl)spiro[indoline-3,3'-pyrrolidine]-1'-carboxylate The captioned compound was obtained in the form of a white solid by performing the same reactions and/or treatments as those in Step 2 of Example 17, with the exception that the 1-(2-(5-chloro-1'-(methoxycarbonyl)spiro[indoline-3,3'-pyrrolidin]-1'-ylcarboxamido)thiazol-4-yl)ethane-1,2-diyl diacetate obtained in Example 102 was used instead of 5-bromo-N-(5-chlorothiazol-2-yl)-1'-(2-acetoxyacetyl)spiro[indoline-3,3'-pyrrolidine]-1-carboxamide.

Example 105

Production of 3-(2-(5-chloro-1'-(methoxycarbonyl)spiro[indoline-3,3'-pyrrolidin]-1'-ylcarboxamido)thiazol-4-yl)propionic acid The captioned compound was obtained in the form of a white solid by performing the same reactions and/or treatments as those in Step 2 of Example 17, with the exception that the methyl 5-chloro-1-((4-(3-ethoxy-3-oxopropyl)thiazol-2-yl)carbamoyl)spiro[indoline-3,3'-pyrrolidine]-1'-carboxylate obtained in Example 104 was used instead of 5-bromo-N-(5-chlorothiazol-2-yl)-1'-(2-acetoxyacetyl)spiro[indoline-3,3'-pyrrolidine]-1-carboxamide.

Example 106

Production of methyl 1-((4-(3-amino-3-oxopropyl)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((4-(3-ethoxy-3-oxopropyl)thiazol-2-yl)carbamoyl)spiro[indoline-3,3'-pyrrolidine]-1'-carboxylate obtained in Example 104 was used instead of ethyl 2-(5-chloro-1-((5-chlorothiazol-2-yl)carbamoyl)spiro[indoline-3,3'-pyrrolidin]-1'-yl)-2-oxoacetate.

Example 107

Production of methyl 5-chloro-1-((4-(3-(dimethylamino)-3-oxopropyl)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 3-(2-(5-chloro-1'-(methoxycarbonyl)spiro[indoline-3,3'-pyrrolidin]-1'-ylcarboxamido)thiazol-4-yl)propionic acid obtained in Example 105 was used instead of 2-(5-chloro-1'-(methoxycarbonyl)spiro[indoline-3,3'-pyrrolidin]-1'-ylcarboxamido)thiazole-4-carboxylic acid.

$^1$H-NMR (400 MHz, CDCl$_3$) δ: 2.08-2.21 (2H, m), 2.67 (2H, t, J=5.6 Hz), 2.89-3.02 (8H, m), 3.45-3.76 (7H, m), 4.01-4.09 (2H, m), 6.22 (1H, s), 7.07 (1H, s), 7.20 (1H, d, J=8.3 Hz), 8.09 (1H, d, J=8.3 Hz).

Example 110

Production of 2-(5-chloro-1'-(methoxycarbonyl)spiro[indoline-3,3'-pyrrolidin]-1'-ylcarboxamido)thiazole-5-carboxylic acid The captioned compound was obtained in the form of a white solid by performing the same reactions and/or treatments as those in Step 2 of Example 17, with the exception that the ethyl 2-(5-chloro-1'-(methoxycarbonyl)spiro[indoline-3,3'-pyrrolidin]-1'-ylcarboxamido)thiazole-5-carboxylate obtained in Example 109 was used instead of 5-bromo-N-(5-chlorothiazol-2-yl)-1'-(2-acetoxyacetyl)spiro[indoline-3,3'-pyrrolidine]-1-carboxamide.

Example 111

Production of methyl 1-((5-carbamoylthiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the ethyl 2-(5-chloro-1'-(methoxycarbonyl)spiro[indoline-3,3'-pyrrolidin]-1'-ylcarboxamido)thiazole-5-carboxylate obtained in Example 109 was used instead of ethyl 2-(5-chloro-1-((5-chlorothiazol-2-yl)carbamoyl)spiro[indoline-3,3'-pyrrolidin]-1'-yl)-2-oxoacetate.

$^1$H-NMR (400 MHz, DMSO-d$_6$) δ: 2.02-2.14 (1H, m), 2.14-2.31 (1H, m), 3.24-3.71 (7H, m), 3.94-4.29 (2H, m), 7.23-7.52 (3H, m), 7.71-7.91 (1H, m), 7.91-8.09 (2H, m).

Example 112

Production of methyl 5-chloro-1-((5-(dimethylcarbamoyl)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 2-(5-chloro-1'-(methoxycarbonyl)spiro[indoline-3,3'-pyrrolidin]-1'-ylcarboxamido)thiazole-5-carboxylic acid obtained in Example 110 was used instead of 2-(5-chloro-1'-(methoxycarbonyl)spiro[indoline-3,3'-pyrrolidin]-1'-ylcarboxamido)thiazole-4-carboxylic acid.

Production of Examples 113 to 116

The below captioned compounds were all obtained in the form of a white solid by performing the same reactions and/or treatments as those in Example 85, with the exceptions that 2-(5-chloro-1'-(methoxycarbonyl)spiro[indoline-3,3'-pyrrolidin]-1'-ylcarboxamido)thiazole-5-carboxylic acid was used instead of 2-(5-chloro-1'-(methoxycarbonyl)spiro[indoline-3,3'-pyrrolidin]-1'-ylcarboxamido)thiazole-4-carboxylic acid, and that each raw material compound was used instead of dimethylamine hydrochloride.

Example 113

Methyl 1-((5-(azetidine-1-carbonyl)thiazol-2-yl)carbamoyl)-5-chlorospiro[indoline-3,3'-pyrrolidine]-1'-carboxylate (Azetidine)

Example 114

Methyl 5-chloro-1-((5-(pyrrolidine-1-carbonyl)thiazol-2-yl)carbamoyl)spiro[indoline-3,3'-pyrrolidine]-1'-carboxylate (Pyrrolidine)

Example 115

Methyl 5-chloro-1-((5-(piperidine-1-carbonyl)thiazol-2-yl)carbamoyl)spiro[indoline-3,3'-pyrrolidine]-1'-carboxylate (Piperidine)

Example 116

Methyl 5-chloro-1-((5-(morpholine-4-carbonyl)thiazol-2-yl)carbamoyl)spiro[indoline-3,3'-pyrrolidine]-1'-carboxylate (Morpholine)

Example 122

Production of 3-(2-(5-chloro-1'-(methoxycarbonyl)spiro[indoline-3,3'-pyrrolidin]-1-ylcarboxamido)thiazol-5-yl)propionic acid The captioned compound was obtained in the form of a white solid by performing the same reactions and/or treatments as those in Step 2 of Example 17, with the exception that the methyl 5-chloro-1-((5-(3-ethoxy-3-oxopropyl)thiazol-2-yl)carbamoyl)spiro[indoline-3,3'-pyrrolidine]-1'-carboxylate obtained in Example 121 was used instead of 5-bromo-N-(5-chlorothiazol-2-yl)-1'-(2-acetoxyacetyl)spiro[indoline-3,3'-pyrrolidine]-1-carboxamide.

Example 123

Production of methyl 1-((5-(3-amino-3-oxopropyl)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((5-(3-ethoxy-3-oxopropyl)thiazol-2-yl)carbamoyl)spiro[indoline-3,3'-pyrrolidine]-1'-carboxylate obtained in Example 121 was used instead of ethyl 2-(5-chloro-1-((5-chlorothiazol-2-yl)carbamoyl)spiro[indoline-3,3'-pyrrolidin]-1'-yl)-2-oxoacetate.

Example 125

Production of 4-(2-(5-chloro-1'-(methoxycarbonyl)spiro[indoline-3,3'-pyrrolidin]-1-ylcarboxamido)thiazol-5-yl)butyric acid The captioned compound was obtained in the form of a white solid by performing the same reactions and/or treatments as those in Step 2 of Example 17, with the exception that the methyl 5-chloro-1-((5-(4-methoxy-4-oxobutyl)thiazol-2-yl)carbamoyl)spiro[indoline-3,3'-pyrrolidine]-1'-carboxylate obtained in Example 124 was used instead of 5-bromo-N-(5-chlorothiazol-2-yl)-1'-(2-acetoxyacetyl)spiro[indoline-3,3'-pyrrolidine]-1-carboxamide.

$^1$H-NMR (400 MHz, DMSO-$d_6$) δ: 1.79 (2H, quint, J=7.2 Hz), 2.05-2.09 (1H, m), 2.16-2.28 (3H, m), 2.66 (2H, t, J=7.2 Hz), 3.38-3.64 (9H, m), 7.07 (1H, s), 7.25 (1H, dd, J=1.6, 8.0 Hz), 7.38 (1H, d, J=1.6 Hz), 7.99 (1H, d, J=8.0 Hz)

Example 126

Production of methyl 5-chloro-1-((5-(4-(dimethylamino)-4-oxobutyl)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 4-(2-(5-chloro-1'-(methoxycarbonyl)spiro[indoline-3,3'-pyrrolidin]-1-ylcarboxamido)thiazol-5-yl)butyric acid obtained in Example 125 was used instead of 2-(5-chloro-1'-(methoxycarbonyl)spiro[indoline-3,3'-pyrrolidin]-1-ylcarboxamido)thiazole-4-carboxylic acid.

Example 128

Production of methyl 5-chloro-1-((5-(methylsulfonyl)thiazol-2-yl)carbamoyl)spiro[indoline-3,3'-pyrrolidine]-1'-carboxylate The methyl 5-chloro-1-((5-(methylthio)thiazol-2-yl)carbamoyl)spiro[indoline-3,3'-pyrrolidine]-1'-carboxylate (41.0 mg, 0.093 mmol) obtained in Example 127 was dissolved in methylene chloride (4 mL). Thereafter, meta-chloroperbenzoic acid (64.0 mg, 0.37 mmol) was added to the above obtained solution, and the thus obtained mixture was then stirred at room temperature for 2 hours. Thereafter, the reaction solution was diluted with an aqueous solution of sodium sulfite, and was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain the captioned compound (22.0 mg, 50%) in the form of a white solid.

$^1$H-NMR (400 MHz, CDCl$_3$) δ: 2.13 (1H, m), 2.26 (1H, m), 3.21 (3H, s), 3.54-3.76 (7H, m), 4.01 (1H, m), 4.10 (1H, m), 7.15 (1H, s), 7.21-7.26 (1H, m), 7.95 (1H, s), 8.00 (1H, m).

Example 130

Production of 2-((2-(5-chloro-1'-(methoxycarbonyl)spiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the methyl 5-chloro-1-((5-((2-methoxy-2-oxoethyl)thio)thiazol-2-yl)carbamoyl)spiro[indoline-3,3'-pyrrolidine]-1'-carboxylate obtained in Example 129 was used instead of ethyl 2-((2-(1'-acetyl-5-bromospiro[indoline-3,3'-pyrrolidin]-1-ylcarboxamido)thiazol-5-yl)thio)acetate.

Example 131

Production of methyl 5-chloro-1-((5-((2-(dimethylamino)-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 2-((2-(5-chloro-1'-(methoxycarbonyl)spiro[indoline-3,3'-pyrrolidin]-1-ylcarboxamido)thiazol-5-yl)thio)acetic acid obtained in Example 130 was used instead of 2-(5-chloro-1'-(methoxycarbonyl)spiro[indoline-3,3'-pyrrolidin]-1-ylcarboxamido)thiazole-4-carboxylic acid.

$^1$H-NMR (400 MHz, CDCl$_3$) δ: 2.17-2.25 (2H, m), 3.00 (3H, s), 3.10 (3H, s), 3.47-3.55 (2H, m), 3.58-3.76 (7H, m), 4.04-4.15 (2H, m), 7.02-7.07 (2H, m), 7.21-7.26 (1H, m), 7.79-7.86 (1H, m).

Example 132

Production of methyl 1-((5-((2-amino-2-oxoethyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((5-((2-methoxy-2-oxoethyl)thio)thiazol-2-yl)carbamoyl)spiro[indoline-3,3'-pyrrolidine]-1'-carboxylate obtained in Example 129 was used instead of ethyl 2-(5-chloro-1-((5-chlorothiazol-2-yl)carbamoyl)spiro[indoline-3,3'-pyrrolidin]-1'-yl)-2-oxoacetate.

Example 133

Production of methyl 5-chloro-1-((5-((2-(methylamino)-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 46, with the exception that the methyl 5-chloro-1-((5-((2-methoxy-2-oxoethyl)thio)thiazol-2-yl)carbamoyl)spiro[indoline-3,3'-pyrrolidine]-1'-carboxylate obtained in Example 129 was used instead of ethyl 2-(5-chloro-1-((5-chlorothiazol-2-yl)carbamoyl)spiro[indoline-3,3'-pyrrolidin]-1'-yl)-2-oxoacetate.

Example 134

Production of methyl 1-((5-((2-(azetidin-1-yl)-2-oxoethyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 85, with the exceptions that the 2-((2-(5-chloro-1'-(methoxycarbonyl)spiro[indoline-3,3'-pyrrolidin]-1-ylcarboxamido)thiazol-5-yl)thio)acetic acid obtained in Example 130 was used instead of 2-(5-chloro-1'-(methoxycarbonyl)spiro[indoline-3,3'-pyrrolidin]-1-ylcarboxamido)thiazole-4-carboxylic acid, and that azetidine was used instead of dimethylamine hydrochloride.

Example 135

Production of methyl 5-chloro-1-((5-((2-morpholino-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exceptions that the 2-((2-(5-chloro-1'-(methoxycarbonyl)spiro[indoline-3,3'-pyrrolidin]-1-ylcarboxamido)thiazol-5-yl)thio)acetic acid obtained in Example 130 was used instead of 2-(5-chloro-1'-(methoxycarbonyl)spiro[indoline-3,3'-pyrrolidin]-1-ylcarboxamido)thiazole-4-carboxylic acid, and that morpholine was used instead of dimethylamine hydrochloride.

$^1$H-NMR (400 MHz, CDCl$_3$) δ: 2.16-2.27 (2H, m), 3.48-3.76 (17H, m), 4.00-4.13 (2H, m), 7.04-7.09 (2H, m), 7.21-7.26 (1H, m), 7.77-7.85 (1H, m).

Example 137

Production of methyl 5-chloro-1-((5-((2-hydroxyethyl)thio)thiazol-2-yl)carbamoyl)spiro[indoline-3,3'-pyrrolidine]-1'-carboxylate The methyl 5-chloro-1-((5-((2-((tetrahydro-2H-pyran-2-yl)oxy)ethyl)thio)thiazol-2-yl)carbamoyl)spiro[indoline-3,3'-pyrrolidine]-1'-carboxylate (90.0 mg, 0.163 mmol) obtained in Example 136 was dissolved in tetrahydrofuran (1 mL) and methanol (1 mL). Thereafter, a 12 N aqueous solution of hydrochloric acid (0.2 mL) was added to the above obtained solution, and the thus obtained mixture was then stirred at room temperature for 10 minutes. Thereafter, the reaction solution was neutralized with a saturated aqueous solution of sodium hydrogen carbonate, and was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain the captioned compound (63.0 mg, 82%) in the form of a white solid.

Example 140

Production of 2-((2-(5-chloro-1'-(methoxycarbonyl)spiro[indoline-3,3'-pyrrolidin]-1-ylcarboxamido)thiazol-5-yl)thio)propionic acid The captioned compound was obtained in the form of a white solid by performing the same reactions and/or treatments as those in Step 2 of Example 17, with the exception that the methyl 5-chloro-1-((5-((1-ethoxy-1-oxopropan-2-yl)thio)thiazol-2-yl)carbamoyl)spiro[indoline-3,3'-pyrrolidine]-1'-carboxylate obtained in Example 139 was used instead of 5-bromo-N-(5-chlorothiazol-2-yl)-1'-(2-acetoxyacetyl)spiro[indoline-3,3'-pyrrolidine]-1-carboxamide.

Example 141

Production of methyl 5-chloro-1-((5-((1-hydroxypropan-2-yl)thio)thiazol-2-yl)carbamoyl)spiro[indoline-3,3'-pyrrolidine]-1'-carboxylate Step 1: Lithium aluminum hydride (97 mg, 2.56 mmol) was suspended in tetrahydrofuran (5 mL). Thereafter, under cooling on ice, a tetrahydrofuran (6 mL) solution of ethyl 2-((2-aminothiazol-5-yl)thio)propanoate (0.2 g, 0.85 mmol) was added to the obtained suspension, and the thus obtained mixture was then stirred for 30 minutes. Thereafter, sodium sulfate and water were added to the reaction solution, and the obtained mixture was then stirred. Insoluble matters were removed by filtration, and the filtrate was then concentrated in vacuo. The obtained residue was purified by preparative thin-layer chromatography (chloroform:methanol=5:1) to obtain 2-((2-aminothiazol-5-yl)thio)propan-1-ol (103 mg, 63%) in the form of a yellow oily product.

$^1$H-NMR (400 MHz, CDCl$_3$) δ: 1.26 (3H, d, J=6.8 Hz), 2.91-3.02 (1H, m), 3.52 (1H, dd, J=7.3, 11.2 Hz), 3.60 (1H, dd, J=5.4, 11.2 Hz), 5.01-5.21 (2H, brs), 7.10 (1H, s).

Step 2: 2-((2-Aminothiazol-5-yl)thio)propan-1-ol (101 mg, 0.53 mmol) was dissolved in N,N-dimethylformamide (5 mL). Thereafter, imidazole (72 mg, 1.06 mmol) and t-butyldimethylsilyl chloride (100 mg, 0.64 mmol) were added to the above obtained solution, and the thus obtained mixture was then stirred at room temperature for 14.5 hours. Thereafter, the reaction solution was diluted with water, and was then extracted with ethyl acetate. The organic layer was washed with water and brine, and was then dried over anhydrous magnesium sulfate, followed by concentration in vacuo. The obtained residue was purified by preparative thin-layer chromatography (chloroform:methanol=10:1) to obtain 5-((1-(((t-butyldimethylsilyl)oxy)propan-2-yl)thio) thiazole-2-amine (141 mg, 87%) in the form of a yellow oily product.

$^1$H-NMR (400 MHz, CDCl$_3$) δ: 0.44 (3H, s), 0.49 (3H, s), 0.89 (9H, s), 1.25 (3H, d, J=6.8 Hz), 2.82-2.95 (1H, m), 3.50 (1H, dd, J=7.8, 10.2 Hz), 3.72 (1H, dd, J=5.9, 10.2 Hz), 4.93-5.11 (2H, brs), 7.07 (1H, s).

Step 3: Methyl 1-((5-((1-((t-butyldimethylsilyl)oxy)propan-2-yl)thio)thiazol-2-yl)carbamoyl)-5-chlorospiro[indoline-3,3'-pyrrolidine]-1'-carboxylate was obtained in the form of a light yellow amorphous product by performing the same reactions and/or treatments as those in Example 90, with the exception that 5-((1-((t-butyldimethylsilyl)oxy)propan-2-yl)thio)thiazole-2-amine was used instead of 4-((dimethylamino)methyl)thiazole-2-amine.

$^1$H-NMR (400 MHz, CDCl$_3$) δ: 0.05 (3H, s), 0.05 (3H, s), 0.89 (9H, s), 1.27 (3H, d, J=6.8 Hz), 2.03-2.14 (1H, m), 2.17-2.30 (1H, m), 2.94-3.05 (1H, m), 3.43-3.84 (9H, m), 3.89-4.06 (2H, m), 7.12 (1H, s), 7.22-7.28 (1H, m), 7.30 (1H, s), 8.00 (1H, d, J=8.8 Hz).

Step 4: Methyl 1-((5-((1-((t-butyldimethylsilyl)oxy)propan-2-yl)thio)thiazol-2-yl)carbamoyl)-5-chlorospiro[indoline-3,3'-pyrrolidine]-1'-carboxylate (200 mg, 0.34 mmol) was dissolved in tetrahydrofuran (10 mL). Thereafter, a tetrahydrofuran solution (0.2 mL, 1.7 mmol) of tetrabutylammonium fluoride (1 mol/mL) was added to the above obtained solution, and the thus obtained mixture was then stirred at room temperature for 11.3 hours. Thereafter, the reaction solution was concentrated in vacuo, and the obtained residue was then purified by preparative thin-layer chromatography (chloroform:methanol=10:1) to obtain the captioned compound (0.12 g, 72%) in the form of a white amorphous product.

$^1$H-NMR (400 MHz, CDCl$_3$) δ: 1.29 (3H, d, J=6.8 Hz), 1.99-2.16 (1H, m), 2.16-2.34 (1H, m), 2.99-3.11 (1H, m), 3.43-3.85 (9H, m), 3.88-4.07 (2H, m), 7.13 (1H, s), 7.22-7.30 (1H, m), 7.34 (1H, s), 7.99 (1H, d, J=8.8 Hz).

Example 143

Production of 2-((2-(5-chloro-1'-(methoxycarbonyl)spiro[indoline-3,3'-pyrrolidin]-1-ylcarboxamido)thiazol-5-yl)thio)-2-methylpropionic acid The captioned compound was obtained in the form of a white solid by performing the same reactions and/or treatments as those in Step 2 of Example 17, with the exception that the methyl 5-chloro-1-((5-((1-ethoxy-2-methyl-1-oxopropan-2-yl)thio)thiazol-2-yl)carbamoyl)spiro[indoline-3,3'-pyrrolidine]-1'-carboxylate obtained in Example 142 was used instead of 5-bromo-N-(5-chlorothiazol-2-yl)-1'-(2-acetoxyacetyl)spiro[indoline-3,3'-pyrrolidine]-1-carboxamide.

Example 144

Production of methyl 5-chloro-1-((5-((1-hydroxy-2-methylpropan-2-yl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 141, with the exception that ethyl 2-((2-aminothiazol-5-yl)thio)-2-methylpropanoate was used instead of ethyl 2-((2-aminothiazol-5-yl)thio)propanoate.

Example 146

Production of 2-((2-(5-chloro-1'-(methoxycarbonyl)spiro[indoline-3,3'-pyrrolidin]-1-ylcarboxamido)thiazol-5-yl)thio)butyric acid The captioned compound was obtained in the form of a white solid by performing the same reactions and/or treatments as those in Step 2 of Example 17, with the exception that the methyl 5-chloro-1-((5-((1-ethoxy-1-oxobutan-2-yl)thio)thiazol-2-yl)carbamoyl)spiro[indoline-3,3'-pyrrolidine]-1'-carboxylate obtained in Example 145 was used instead of 5-bromo-N-(5-chlorothiazol-2-yl)-1'-(2-acetoxyacetyl)spiro[indoline-3,3'-pyrrolidine]-1-carboxamide.

Example 147

Production of methyl 5-chloro-1-((5-((1-(dimethylamino)-1-oxobutan-2-yl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 2-((2-(5-chloro-1'-(methoxy)carbonylspiro[indoline-3,3'-pyrrolidin]-1-ylcarboxamido)thiazol-5-yl)thio)butyric acid obtained in Example 146 was used instead of 2-(5-chloro-1'-(methoxycarbonyl)spiro[indoline-3,3'-pyrrolidin]-1-ylcarboxamido)thiazole-4-carboxylic acid.

Example 148

Production of methyl 5-chloro-1-((5-((1-hydroxybutan-2-yl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 141, with the exception that ethyl 2-((2-aminothiazol-5-yl)thio)butanoate was used instead of ethyl 2-((2-aminothiazol-5-yl)thio)propanoate.

Example 150

Production of 3-((2-(5-chloro-1'-(methoxycarbonyl)spiro[indoline-3,3'-pyrrolidin]-1-ylcarboxamido)thiazol-5-yl)thio)propionic acid The captioned compound was obtained in the form of a white solid by performing the same reactions and/or treatments as those in Step 2 of Example 17, with the exception that the methyl 5-chloro-1-((5-((3-ethoxy-3-oxoethyl)thio) thiazol-2-yl)carbamoyl)spiro[indoline-3,3'-pyrrolidine]-1'-carboxylate obtained in Example 149 was used instead of 5-bromo-N-(5-chlorothiazol-2-yl)-1'-(2-acetoxyacetyl)spiro [indoline-3,3'-pyrrolidine]-1-carboxamide.

Example 151

Production of methyl 5-chloro-1-((5-((3-(methylamino)-3-oxopropyl)thio)thiazol-2-yl)carbamoyl) spiro[indoline-3,3'-pyrrolidine]-1'-carboxylate The captioned compound was obtained in the form of a white solid by performing the same reactions and/or treatments as those in Example 46, with the exception that the methyl 5-chloro-1-((5-((3-ethoxy-3-oxoethyl)thio)thiazol-2-yl)carbamoyl)spiro[indoline-3,3'-pyrrolidine]-1'-carboxylate obtained in Example 149 was used instead of ethyl 2-(5-chloro-1-((5-chlorothiazol-2-yl)carbamoyl)spiro[indoline-3,3'-pyrrolidin]-1'-yl)-2-oxoacetate.
$^1$H-NMR (400 MHz, CDCl$_3$) δ: 2.10-2.40 (2H, m), 2.49 (2H, t, J=7.2 Hz), 2.82 (3H, d, J=4.2 Hz), 3.02 (2H, t, J=7.2 Hz), 3.55-3.83 (7H, m), 3.93-4.07 (2H, m), 5.74 (1H, br), 7.10-7.12 (1H, m), 7.20-7.25 (1H, m), 7.30-7.33 (1H, m), 7.93-8.00 (1H, m).

Example 152

Production of methyl 5-chloro-1-((5-((3-(dimethylamino)-3-oxopropyl)thio)thiazol-2-yl)carbamoyl) spiro[indoline-3,3'-pyrrolidine]-1'-carboxylate The captioned compound was obtained in the form of a white solid by performing the same reactions and/or treatments as those in Example 85, with the exception that the 3-((2-(5-chloro-1'-(methoxycarbonyl)spiro[indoline-3,3'-pyrrolidin]-1-ylcarboxamido)thiazol-5-yl)thio)propionic acid obtained in Example 150 was used instead of 2-(5-chloro-1'-(methoxycarbonyl)spiro[indoline-3,3'-pyrrolidin]-1-ylcarboxamido)thiazole-4-carboxylic acid.

Example 153

Production of methyl 1-((5-((3-(azetidin-1-yl)-3-oxopropyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 85, with the exceptions that the 3-((2-(5-chloro-1'-(methoxycarbonyl)spiro[indoline-3,3'-pyrrolidin]-1-ylcarboxamido)thiazol-5-yl)thio)propionic acid obtained in Example 150 was used instead of 2-(5-chloro-1'-(methoxycarbonyl)spiro[indoline-3,3'-pyrrolidin]-1-ylcarboxamido)thiazole-4-carboxylic acid, and that azetidine was used instead of dimethylamine hydrochloride.

Example 154

Production of methyl 5-chloro-1-((5-((3-morpholino-3-oxopropyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exceptions that the 3-((2-(5-chloro-1'-(methoxycarbonyl)spiro[indoline-3,3'-pyrrolidin]-1-ylcarboxamido)thiazol-5-yl)thio)propionic acid obtained in Example 150 was used instead of 2-(5-chloro-1'-(methoxycarbonyl)spiro[indoline-3,3'-pyrrolidin]-1-ylcarboxamido)thiazole-4-carboxylic acid, and that morpholine was used instead of dimethylamine hydrochloride.
$^1$H-NMR (400 MHz, CDCl$_3$) δ: 2.03-2.18 (1H, m), 2.18-2.34 (1H, m), 2.64 (3H, t, J=7.3 Hz), 3.05 (3H, t, J=7.3 Hz), 3.31-3.89 (15H, m), 3.91-4.10 (2H, m), 7.13 (1H, s), 7.20-7.38 (2H, m), 7.99 (1H, d, J=8.8 Hz).

Example 155

Production of methyl 1-((5-((3-amino-3-oxopropyl) thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((5-((3-ethoxy-3-oxoethyl)thio)thiazol-2-yl)carbamoyl)spiro[indoline-3,3'-pyrrolidine]-1'-carboxylate obtained in Example 149 was used instead of ethyl 2-(5-chloro-1-((5-chlorothiazol-2-yl)carbamoyl)spiro[indoline-3,3'-pyrrolidin]-1'-yl)-2-oxoacetate.

Example 157

Production of 3-((2-(5-chloro-1'-(methoxycarbonyl) spiro[indoline-3,3'-pyrrolidin]-1-ylcarboxamido) thiazol-5-yl)thio)-2,2-dimethylpropionic acid The captioned compound was obtained in the form of a white solid by performing the same reactions and/or treatments as those in Step 2 of Example 17, with the exception that the methyl 5-chloro-1-((5-((3-ethoxy-2,2-dimethyl-3-oxopropyl)thio)thiazol-2-yl)carbamoyl)spiro[indoline-3,3'-pyrrolidine]-1'-carboxylate obtained in Example 156 was used instead of 5-bromo-N-(5-chlorothiazol-2-yl)-1'-(2-acetoxyacetyl)spiro[indoline-3,3'-pyrrolidine]-1-carboxamide.

Example 158

Production of methyl 5-chloro-1-((5-((3-hydroxy-2,2-dimethylpropyl)thio)thiazol-2-yl)carbamoyl)spiro [indoline-3,3'-pyrrolidine]-1'-carboxylate The captioned compound was obtained in the form of a white solid by performing the same reactions and/or treatments as those in Example 141, with the exception that ethyl 3-((2-aminothiazol-5-yl)thio)-2,2-dimethylpropanoate was used instead of ethyl 2-((2-aminothiazol-5-yl)thio)propanoate.

Example 160

Production of 4-((2-(5-chloro-1'-(methoxycarbonyl) spiro[indoline-3,3'-pyrrolidin]-1-ylcarboxamido) thiazol-5-yl)thio)butyric acid The captioned compound was obtained in the form of a white solid by performing the same reactions and/or treatments as those in Step 2 of Example 17, with the exception that the methyl 5-chloro-1-((5-((4-ethoxy-4-oxobutyl)thio) thiazol-2-yl)carbamoyl)spiro[indoline-3,3'-pyrrolidine]-1'-carboxylate obtained in Example 159 was used instead of 5-bromo-N-(5-chlorothiazol-2-yl)-1'-(2-acetoxyacetyl)spiro[indoline-3,3'-pyrrolidine]-1-carboxamide.

Example 163

Production of methyl 1-((5-((4-amino-4-oxobutyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 45, with the exception that the methyl 5-chloro-1-((5-((4-ethoxy-4-oxobutyl)thio)thiazol-2-yl)carbamoyl)spiro[indoline-3,3'-pyrrolidine]-1'-carboxylate obtained in Example 159 was used instead of ethyl 2-(5-chloro-1-((5-chlorothiazol-2-yl)carbamoyl)spiro[indoline-3,3'-pyrrolidin]-1'-yl)-2-oxoacetate.

Example 164

Production of methyl 5-chloro-1-((5-((4-(methylamino)-4-oxobutyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 46, with the exception that the methyl 5-chloro-1-((5-((4-ethoxy-4-oxobutyl)thio)thiazol-2-yl)carbamoyl)spiro[indoline-3,3'-pyrrolidine]-1'-carboxylate obtained in Example 159 was used instead of ethyl 2-(5-chloro-1-((5-chlorothiazol-2-yl)carbamoyl)spiro[indoline-3,3'-pyrrolidin]-1'-yl)-2-oxoacetate.
$^1$H-NMR (400 MHz, CDCl$_3$) δ: 1.94 (2H, tt, J=7.2 Hz, 7.2 Hz), 2.05-2.28 (2H, m), 2.32 (2H, t, J=7.2 Hz), 2.77 (2H, d, J=7.2 Hz), 2.80 (3H, t, J=2.4 Hz), 3.46-3.84 (7H, m), 3.93-4.06 (2H, m), 5.58 (1H, br), 7.10-7.14 (1H, m), 7.21-7.26 (1H, m), 7.28-7.32 (1H, m), 7.90-8.00 (1H, m)

Example 165

Production of methyl 5-chloro-1-((5-((4-(dimethylamino)-4-oxobutyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exception that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid.

Example 166

Production of methyl 5-chloro-1-((5-((4-morpholino-4-oxobutyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exceptions that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid, and that morpholine was used instead of dimethylamine hydrochloride.

Example 167

Production of methyl 1-((5-((4-(azetidin-1-yl)-4-oxobutyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 85, with the exceptions that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid, and that azetidine was used instead of dimethylamine hydrochloride.

Example 168

Production of methyl 5-chloro-1-((5-((4-(methoxyamino)-4-oxobutyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exceptions that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid, and that O-methylhydroxylamine hydrochloride was used instead of dimethylamine hydrochloride.
$^1$H-NMR (400 MHz, CDCl$_3$) δ: 1.95 (2H, quint, J=7.1 Hz), 2.03-2.16 (1H, m), 2.16-2.32 (2H, m), 2.50-2.69 (1H, m), 2.74-2.86 (2H, m), 3.45-3.86 (10H, m), 3.92-4.11 (2H, m), 7.12 (1H, s), 7.23 (1H, d, J=8.5 Hz), 7.30 (1H, s), 7.97 (1H, d, J=8.5 Hz).

Example 169

Production of methyl 5-chloro-1-((5-((4-(hydroxyamino)-4-oxobutyl)thio)thiazol-2-yl)carbamoyl)spiro[indoline-3,3'-pyrrolidine]-1'-carboxylate Step 1: Methyl 5-chloro-1-((5-((4-oxo-4-(((tetrahydro-2H-pyran-2-yl)oxy)amino)butyl)thio)thiazol-2-yl)carbamoyl)spiro[indoline-3,3'-pyrrolidine]-1'-carboxylate was obtained in the form of a white amorphous product by performing the same reactions and/or treatments as those in Example 85, with the exceptions that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid, and that O-(tetrahydro-2H-pyran-2-yl)hydroxylamine was used instead of dimethylamine hydrochloride.
$^1$H-NMR (400 MHz, CDCl$_3$) δ: 1.50-1.71 (2H, m), 1.73-1.88 (3H, m), 1.89-2.00 (2H, m), 2.02-2.16 (1H, m), 2.18-2.32 (2H, m), 2.74-2.84 (2H, m), 3.46-3.84 (9H, m), 3.87-4.08 (4H, m), 4.90-5.01 (1H, m), 7.12 (1H, s), 7.19-7.28 (1H, m), 7.31 (1H, s), 7.98 (1H, d, J=8.5 Hz).
Step 2: The captioned compound was obtained in the form of a white solid by performing the same reactions and/or treatments as those in Example 137, with the exception that methyl 5-chloro-1-((5-((4-oxo-4-(((tetrahydro-2H-pyran-2-yl)oxy)amino)butyl)thio)thiazol-2-yl)carbamoyl)spiro[indoline-3,3'-pyrrolidine]-1'-carboxylate was used instead of methyl 5-chloro-1-((5-((2-((tetrahydro-2H-pyran-2-yl)oxy)ethyl)thio)thiazol-2-yl)carbamoyl)spiro[indoline-3,3'-pyrrolidine]-1'-carboxylate.

$^1$H-NMR (400 MHz, DMSO-d$_6$) δ: 1.74 (2H, quint, J=7.31 Hz), 2.00-2.15 (3H, m), 2.15-2.29 (1H, m), 2.71 (2H, t, J=7.31 Hz), 3.22-3.74 (7H, m), 4.01-4.21 (2H, m), 7.28 (1H, d, J=7.1 Hz), 7.42 (1H, s), 7.47 (1H, s), 7.89-8.06 (1H, m), 8.69 (1H, s), 10.39 (1H, s).

Example 170

Production of methyl 5-chloro-1-((5-((4-(3-hydroxyazetidin-1-yl)-4-oxobutyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 85, with the exceptions that the 4-((2-(5-chloro-1'-(methoxycarbonyl)spiro[indoline-3,3'-pyrrolidin]-1-ylcarboxamido)thiazol-5-yl)thio)butyric acid obtained in Example 160 was used instead of 2-(5-chloro-1'-(methoxycarbonyl)spiro[indoline-3,3'-pyrrolidin]-1-ylcarboxamido)thiazole-4-carboxylic acid, and that 3-hydroxyazetidine hydrochloride was used instead of dimethylamine hydrochloride.

$^1$H-NMR (400 MHz, CDCl$_3$) δ: 1.82-2.02 (2H, m), 2.02-2.41 (4H, m), 2.71-2.90 (2H, m), 3.43-3.92 (8H, m), 3.92-4.16 (3H, m), 4.18-4.29 (1H, m), 4.29-4.43 (1H, m), 4.58-4.72 (1H, m), 7.11 (1H, m), 7.18-7.39 (2H, m), 7.94 (1H, d, J=8.8 Hz).

Example 171

Production of ethyl 4-((2-(1'-acetyl-5-chlorospiro[indoline-3,3'-pyrrolidin]-1-ylcarboxamido)thiazol-5-yl)thio)butanoate Step 1: 1-(5-Chlorospiro[indoline-3,3'-pyrrolidin]-1'-yl)ethanone was obtained in the form of a white solid by performing the same reactions and/or treatments as those in Steps 2 and 3 of Example 57, with the exception that acetyl chloride was used instead of t-butyl bromoacetate.

$^1$H-NMR (400 MHz, CDCl$_3$) δ: 2.03-2.21 (5H, m), 3.42-3.83 (7H m), 6.54-6.60 (1H, m), 6.95-7.04 (2H, m).

Step 2: The captioned compound was obtained in the form of a white solid by performing the same reactions and/or treatments as those in Example 90, with the exceptions that 1-(5-chlorospiro[indoline-3,3'-pyrrolidin]-1'-yl)ethanone was used instead of methyl 5-chlorospiro[indoline-3,3'-pyrrolidine]-1'-carboxylate, and that ethyl 4-((2-aminothiazol-5-yl)thio)butanoate was used instead of 4-((dimethylamino)methyl)thiazole-2-amine.

Example 172

Production of 4-((2-(1'-acetyl-5-chlorospiro[indoline-3,3'-pyrrolidin]-1-ylcarboxamido)thiazol-5-yl)thio)butyric acid The captioned compound was obtained in the form of a white solid by performing the same reactions and/or treatments as those in Step 2 of Example 17, with the exception that the ethyl 4-((2-(1'-acetyl-5-chlorospiro[indoline-3,3'-pyrrolidin]-1-ylcarboxamido)thiazol-5-yl)thio)butanoate obtained in Example 171 was used instead of 5-bromo-N-(5-chlorothiazol-2-yl)-1'-(2-acetoxyacetyl)spiro[indoline-3,3'-pyrrolidine]-1-carboxamide.

Example 173

Production of 1'-acetyl-5-chloro-N-(5-((4-(methylamino)-4-oxobutyl)thio)thiazol-2-yl)spiro[indoline-3,3'-pyrrolidine]-1-carboxamide The captioned compound was obtained in the form of a white solid by performing the same reactions and/or treatments as those in Example 46, with the exception that the ethyl 4-((2-(1'-acetyl-5-chlorospiro[indoline-3,3'-pyrrolidin]-1-ylcarboxamido)thiazol-5-yl)thio)butanoate obtained in Example 171 was used instead of ethyl 2-(5-chloro-1-((5-chlorothiazol-2-yl)carbamoyl)spiro[indoline-3,3'-pyrrolidin]-1'-yl)-2-oxoacetate.

Example 174

Production of methyl 1-((5-((2-aminoethyl)thio)thiazol-2-yl)carbamoyl)-5-chlorospiro[indoline-3,3'-pyrrolidine]-1'-carboxylate Step 1: Methyl 5-chloro-1-((5-((2-(1,3-dioxoisoindolin-2-yl)ethyl)thio)thiazol-2-yl)carbamoyl)spiro[indoline-3,3'-pyrrolidine]-1'-carboxylate was obtained in the form of a yellow solid by performing the same reactions and/or treatments as those in Example 90, with the exception that 2-(2-((2-aminothiazol-5-yl)thio)ethyl)isoindoline-1,3-dione was used instead of 4-((dimethylamino)methyl)thiazole-2-amine.

$^1$H-NMR (400 MHz, DMSO-d$_6$) δ: 2.03-2.14 (1H, m), 2.14-2.30 (1H, m), 3.02 (2H, t, J=6.6 Hz), 3.20-3.50 (2H, m), 3.52-3.68 (5H, m), 3.79 (2H, t, J=6.6 Hz), 3.98-4.17 (2H, m), 7.29 (1H, d, J=7.3 Hz), 7.42 (1H, s), 7.49 (1H, s), 7.79-7.90 (4H, m), 7.90-8.01 (1H, m).

Step 2: Methyl 5-chloro-1-((5-((2-(1,3-dioxoisoindolin-2-yl)ethyl)thio)thiazol-2-yl)carbamoyl)spiro[indoline-3,3'-pyrrolidine]-1'-carboxylate (56 mg, 0.094 mmol) was dissolved in ethanol (3 mL). Thereafter, hydrazine monohydrate (0.007 mL, 0.14 mmol) was added to the above obtained solution, and the thus obtained mixture was then stirred at 90° C. for 3 hours. Thereafter, insoluble matters were removed by filtration, and the reaction solution was then concentrated in vacuo. The obtained residue was purified by preparative thin-layer column chromatography (chloroform:saturated ammonium methanol=10:1) to obtain the captioned compound (20 mg, 46%) in the form of a white solid.

Example 175

Production of methyl 1-((5-((2-acetamidoethyl)thio)thiazol-2-yl)carbamoyl)-5-chlorospiro[indoline-3,3'-pyrrolidine]-1'-carboxylate The captioned compound was obtained in the form of a white solid by performing the same reactions and/or treatments as those in Example 3, with the exception that the methyl 1-((5-((2-aminoethyl)thio)thiazol-2-yl)carbamoyl)-5-chlorospiro[indoline-3,3'-pyrrolidine]-1'-carboxylate obtained in Example 174 was used instead of 5-bromo-N-(5-chlorothiazol-2-yl)spiro[indoline-3,3'-pyrrolidine]-1-carboxamide.

Example 176

Production of methyl 1-((5-((3-aminopropyl)thio)
thiazol-2-yl)carbamoyl)-5-chlorospiro[indoline-3,3'-
pyrrolidine]-1'-carboxylate The captioned compound was obtained in the form of a white solid by performing the same reactions and/or treatments as those in Example 174, with the exception that the 2-(2-((2-aminothiazol-5-yl)thio)propyl)isoindoline-1,3-dione synthesized by a method described in the known methods (International Publication WO2005/066145 etc.) or a reaction similar thereto was used instead of 2-(2-((2-aminothiazol-5-yl)thio)ethyl)isoindoline-1,3-dione.

$^1$H-NMR (400 MHz, DMSO-$d_6$) δ: 1.75 (2H, quint, J=7.3 Hz), 1.95-2.09 (1H, m), 2.09-2.27 (1H, m), 2.65 (2H, t, J=7.3 Hz), 2.82 (2H, t, J=7.3 Hz), 3.11-3.68 (7H, m), 3.88-3.97 (2H, m), 7.16 (1H, dd, J=2.2, 8.5 Hz), 7.22 (1H, s), 7.25 (1H, d, J=2.2 Hz), 8.02 (1H, d, J=8.5 Hz).

Example 177

Production of methyl 1-((5-((3-acetamidopropyl)
thio)thiazol-2-yl)carbamoyl)-5-chlorospiro[indoline-
3,3'-pyrrolidine]-1'-carboxylate The captioned compound was obtained in the form of a white solid by performing the same reactions and/or treatments as those in Example 3, with the exception that the methyl 1-((5-((3-aminopropyl)thio)thiazol-2-yl)carbamoyl)-5-chlorospiro[indoline-3,3'-pyrrolidine]-1'-carboxylate obtained in Example 176 was used instead of 5-bromo-N-(5-chlorothiazol-2-yl)spiro[indoline-3,3'-pyrrolidine]-1-carboxamide.

$^1$H-NMR (400 MHz, CDCl$_3$) δ: 1.82 (2H, quint, J=7.3 Hz), 1.98 (3H, s), 2.03-2.16 (1H, m), 2.16-2.30 (1H, m), 2.75 (2H, t, J=6.8 Hz), 3.35 (2H, q, J=6.8 Hz), 3.45-3.86 (7H, m), 3.95-4.08 (2H, m), 5.73 (1H, brs), 7.12 (1H, s), 7.24 (1H, dd, J=2.2, 8.8 Hz), 7.31 (1H, s), 8.00 (1H, d, J=8.8 Hz).

Example 178

Production of methyl 5-chloro-1-((5-((3-(methylsulfonamido)propyl)thio)thiazol-2-yl)carbamoyl)spiro
[indoline-3,3'-pyrrolidine]-1'-carboxylate The captioned compound was obtained in the form of a white solid by performing the same reactions and/or treatments as those in Example 3, with the exceptions that the methyl 1-((5-((3-aminopropyl)thio)thiazol-2-yl)carbamoyl)-5-chlorospiro[indoline-3,3'-pyrrolidine]-1'-carboxylate obtained in Example 176 was used instead of 5-bromo-N-(5-chlorothiazol-2-yl)spiro[indoline-3,3'-pyrrolidine]-1-carboxamide, and that methanesulfonic acid chloride was used instead of acetyl chloride.

Example 179

Production of methyl 5-chloro-1-((5-((3-(cyclopropanesulfonamido)propyl)thio)thiazol-2-yl)carbamoyl)spiro[indoline-3,3'-pyrrolidine]-1'-carboxylate The captioned compound was obtained in the form of a white solid by performing the same reactions and/or treatments as those in Example 3, with the exceptions that the methyl 1-((5-((3-aminopropyl)thio)thiazol-2-yl)carbamoyl)-5-chlorospiro[indoline-3,3'-pyrrolidine]-1'-carboxylate obtained in Example 176 was used instead of 5-bromo-N-(5-chlorothiazol-2-yl)spiro[indoline-3,3'-pyrrolidine]-1-carboxamide, and that cyclopropanesulfonyl chloride was used instead of acetyl chloride.

$^1$H-NMR (400 MHz, CDCl$_3$) δ: 0.96-1.08 (2H, m), 1.11-1.18 (2H, m), 1.89 (2H, quint, J=7.3 Hz), 2.06-2.18 (1H, m), 2.18-2.29 (1H, m), 2.34-2.46 (1H, m), 2.84 (2H, t, J=7.3 Hz), 3.29 (2H, q, J=7.3 Hz), 3.44-3.88 (7H, m), 3.96-4.12 (2H, m), 7.10 (1H, s), 7.16 (1H, d, J=8.5 Hz), 7.29 (1H, s), 7.90 (1H, d, J=8.5 Hz)

Example 182

Production of 1'-acetyl-5-chloro-N-(5-methoxythiazol-2-yl)spiro[indoline-3,3'-pyrrolidine]-1-carboxamide The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that 2-amino-5-methoxythiazole was used instead of 4-((dimethylamino)methyl)thiazole-2-amine.

Example 183

Production of 1'-acetyl-5-chloro-N-(5-ethoxythiazol-2-yl)spiro[indoline-3,3'-pyrrolidine]-1-carboxamide The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that 2-amino-5-ethoxythiazole was used instead of 4-((dimethylamino)methyl)thiazole-2-amine.

Example 185

Production of 3-((2-(5-chloro-1'-(methoxycarbonyl)
spiro[indoline-3,3'-pyrrolidin]-1-ylcarboxamido)
thiazol-5-yl)oxy)benzoic acid The captioned compound was obtained in the form of a white solid by performing the same reactions and/or treatments as those in Step 2 of Example 17, with the exception that the methyl 5-chloro-1-((5-((5-(methoxycarbonyl)phenoxy)thiazol-2-yl)carbamoyl)spiro[indoline-3,3'-pyrrolidine]-1'-carboxylate obtained in Example 184 was used instead of 5-bromo-N-(5-chlorothiazol-2-yl)-1'-(2-acetoxyacetyl)spiro[indoline-3,3'-pyrrolidine]-1-carboxamide.

$^1$H-NMR (400 MHz, DMSO-$d_6$) δ: 2.01-2.14 (1H, m), 2.14-2.29 (1H, m), 3.29-3.67 (7H, m), 4.03-4.18 (2H, m), 7.16 (1H, dd, J=2.0, 8.8 Hz), 7.32 (1H, s), 7.39-746 (2H, m), 7.52-7.59 (2H, m), 7.73 (1H, d, J=7.8 Hz), 7.85-7.97 (1H, m).

Example 186

Production of methyl 1-((5-(3-carbamoylphenoxy)
thiazol-2-yl)carbamoyl)-5-chlorospiro[indoline-3,3'-
pyrrolidine]-1'-carboxylate The captioned compound was obtained in the form of a white solid by performing the same reactions and/or treatments as those in Example 45, with the exception that the methyl 5-chloro-1-((5-(methoxycarbonyl)phenoxy)thiazol-2-yl)carbamoyl)spiro[indoline-3,3'-pyrrolidine]-1'-carboxylate obtained in Example 184 was used instead of ethyl 2-(5-chloro-1-((5-chlorothiazol-2-yl)carbamoyl)spiro[indoline-3,3'-pyrrolidin]-1'-yl)-2-oxoacetate.

$^1$H-NMR (400 MHz, CDCl$_3$) δ: 1.97-2.16 (1H, m), 2.16-2.28 (1H, m), 3.43-3.85 (7H, m), 3.98-4.19 (2H, m), 6.09-6.39 (2H, m), 7.01 (1H, s), 7.10 (1H, brs), 7.16-7.22 (1H, m), 7.23-7.36 (1H, m), 7.43 (1H, dd, J=7.8, 7.8 Hz), 7.51 (1H, d, J=7.8 Hz), 7.60 (1H, brs), 7.92 (1H, brs).

Example 187

Production of methyl 3-((2-(1'-acetyl-5-chlorospiro[indoline-3,3'-pyrrolidin]-1-ylcarboxamido)thiazol-5-yl)oxy)benzoate The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that methyl 3-((2-aminothiazol-5-yl)benzoate was used instead of 4-((dimethylamino)methyl)thiazole-2-amine.

Example 188

Production of 3-((2-(1'-acetyl-5-chlorospiro[indoline-3,3'-pyrrolidin]-1-ylcarboxamido)thiazol-5-yl)oxy)benzoic acid The captioned compound was obtained in the form of a white solid by performing the same reactions and/or treatments as those in Step 2 of Example 17, with the exception that the methyl 3-((2-(1'-acetyl-5-chlorospiro[indoline-3,3'-pyrrolidin]-1-ylcarboxamido)thiazol-5-yl)oxy)benzoate obtained in Example 187 was used instead of 5-bromo-N-(5-chlorothiazol-2-yl)-1'-(2-acetoxyacetyl)spiro[indoline-3,3'-pyrrolidine]-1-carboxamide.

Example 189

Production of methyl 4-((2-(1'-acetyl-5-chlorospiro[indoline-3,3'-pyrrolidin]-1-ylcarboxamido)thiazol-5-yl)oxy)benzoate The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that the methyl 4-((2-aminothiazol-5-yl)oxy)benzoate synthesized by a method described in the known methods (International Publication WO2008/005914 etc.) or a reaction similar thereto was used instead of 4-((dimethylamino)methyl)thiazole-2-amine.

Example 190

Production of 4-((2-(1'-acetyl-5-chlorospiro[indoline-3,3'-pyrrolidin]-1-ylcarboxamido)thiazol-5-yl)oxy)benzoic acid The captioned compound was obtained in the form of a white solid by performing the same reactions and/or treat-ments as those in Step 2 of Example 17, with the exception that the methyl 4-((2-(1'-acetyl-5-chlorospiro[indoline-3,3'-pyrrolidin]-1-ylcarboxamido)thiazol-5-yl)oxy)benzoate obtained in Example 189 was used instead of 5-bromo-N-(5-chlorothiazol-2-yl)-1'-(2-acetoxyacetyl)spiro[indoline-3,3'-pyrrolidine]-1-carboxamide.

Example 191

Production of methyl 4-((2-(1'-acetyl-5-chlorospiro[indoline-3,3'-pyrrolidin]-1-ylcarboxamido)thiazol-5-yl)oxy)-2-fluorobenzoate The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that the methyl 4-((2-aminothiazol-5-yl)oxy)-2-fluorobenzoate synthesized by a method described in the known methods (International Publication WO2008/005914 etc.) or a reaction similar thereto was used instead of 4-((dimethylamino)methyl)thiazole-2-amine.

Example 192

Production of 4-((2-(1'-acetyl-5-chlorospiro[indoline-3,3'-pyrrolidin]-1-ylcarboxamido)thiazol-5-yl)oxy)-2-fluorobenzoic acid The captioned compound was obtained in the form of a white solid by performing the same reactions and/or treatments as those in Step 2 of Example 17, with the exception that the methyl 4-((2-(1'-acetyl-5-chlorospiro[indoline-3,3'-pyrrolidin]-1-ylcarboxamido)thiazol-5-yl)oxy)-2-fluorobenzoate obtained in Example 191 was used instead of 5-bromo-N-(5-chlorothiazol-2-yl)-1'-(2-acetoxyacetyl)spiro[indoline-3,3'-pyrrolidine]-1-carboxamide.

$^1$H-NMR (400 MHz, DMSO-d$_6$) δ: 1.94-2.30 (5H, m), 3.28-3.80 (4H, m), 3.98-4.24 (2H, m), 7.24-7.7.40 (2H, m), 7.37 (1H, s), 7.40-7.46 (1H, m), 7.77-7.86 (2H, m), 7.88-7.98 (1H, br).

Example 193

Production of methyl 5-((2-(1'-acetyl-5-chlorospiro[indoline-3,3'-pyrrolidin]-1-ylcarboxamido)thiazol-5-yl)oxy)nicotinate The captioned compound was obtained in the form of a white solid by performing the same reactions and/or treatments as those in Example 90, with the exceptions that the 1-(5-chlorospiro[indoline-3,3'-pyrrolidin]-1'-yl)ethanone obtained in Step 1 of Example 171 was used instead of methyl 5-chlorospiro[indoline-3,3'-pyrrolidine]-1'-carboxylate, and that the methyl 5-((2-aminothiazol-5-yl)oxy)nicotinate synthesized by a method described in the known methods (International Publication WO2008/005914 etc.) or a method similar thereto was used instead of 4-((dimethylamino)methyl)thiazole-2-amine.

Example 194

Production of 5-((2-(1'-acetyl-5-chlorospiro[indoline-3,3'-pyrrolidin]-1-ylcarboxamido)thiazol-5-yl)oxy)nicotinic acid The captioned compound was obtained in the form of a white solid by performing the same reactions and/or treatments as those in Step 2 of Example 17, with the exception that the methyl 5-((2-(1'-acetyl-5-chlorospiro[indoline-3,3'-pyrrolidin]-1-ylcarboxamido)thiazol-5-yl)oxy)nicotinate obtained in Example 193 was used instead of 5-bromo-N-(5-chlorothiazol-2-yl)-1'-(2-acetoxyacetyl)spiro[indoline-3,3'-pyrrolidine]-1-carboxamide.

Example 195

Production of methyl 1-((5-chlorothiazol-2-yl)carbamoyl)-5-cyanospiro[indoline-3,3'-pyrrolidine]-1'-carboxylate The captioned compound was obtained in the form of a white solid by performing the same reactions and/or treatments as those in Examples 1, 2, and 3, with the exceptions that the t-butyl 5-cyanospiro[indoline-3,3'-pyrrolidine]-1'-carboxylate synthesized by a method described in the known methods (International Publication WO2009/089454 etc.) or a method similar thereto was used instead of t-butyl 5-bromospiro[indoline-3,3'-pyrrolidine]-1'-carboxylate, and that methyl chloroformate was used instead of acetyl chloride.

$^1$H-NMR (400 MHz, CDCl$_3$) δ: 2.13-2.26 (2H, m), 3.54-4.13 (9H, m), 7.16 (1H, s), 7.41 (1H, s), 7.61 (1H, d, J=8.5 Hz), 8.18 (1H, d, J=8.5 Hz), 9.38 (1H, brs).

Example 196

Production of 1'-acetyl-N-(5-chlorothiazol-2-yl)-5-cyanospiro[indoline-3,3'-pyrrolidine]-1-carboxamide The captioned compound was obtained in the form of a white solid by performing the same reactions and/or treatments as those in Examples 1, 2, and 3, with the exception that t-butyl 5-cyanospiro[indoline-3,3'-pyrrolidine]-1'-carboxylate was used instead of t-butyl 5-bromospiro[indoline-3,3'-pyrrolidine]-1'-carboxylate.

Example 197

Production of 1'-acetyl-N-(5-chlorothiazol-2-yl)-5-(trifluoromethoxy)spiro[indoline-3,3'-pyrrolidine]-1-carboxamide The captioned compound was obtained in the form of a white solid by performing the same reactions and/or treatments as those in Examples 1, 2, and 3, with the exception that the t-butyl 5-trifluoromethoxyspiro[indoline-3,3'-pyrrolidine]-1'-carboxylate synthesized by a method described in the known methods (International Publication WO2009/089454 etc.) or a method similar thereto was used instead of t-butyl 5-bromospiro[indoline-3,3'-pyrrolidine]-1'-carboxylate.

$^1$H-NMR (400 MHz, CDCl$_3$) δ: 2.08-2.37 (5H, m), 3.49-4.13 (6H, m), 6.91-7.01 (1H, m), 7.14-7.17 (21H, m), 8.04-8.10 (1H, m).

Example 198

Production of 1'-acetyl-N-(5-chlorothiazol-2-yl)-5-(4-fluorophenoxy)spiro[indoline-3,3'-pyrrolidine]-1-carboxamide Step 1: 1-(1'-Acetyl-5-methoxyspiro[indoline-3,3'-pyrrolidin]-1-yl)-2,2,2-trifluoroethanone was obtained in the form of a yellow oily product by performing the same reactions and/or treatments as those in Steps 1 and 2 of Example 57, with the exceptions that the t-butyl 5-methoxyspiro[indoline-3,3'-pyrrolidine]-1'-carboxylate synthesized by a method described in the known methods (International Publication WO2009/089454 etc.) or a method similar thereto was used instead of t-butyl 5-chlorospiro[indoline-3,3'-pyrrolidine]-1'-carboxylate, and that acetyl chloride was used instead of t-butyl bromoacetate.

$^1$H-NMR (400 MHz, CDCl$_3$) δ: 2.05-2.33 (5H, m), 3.37-3.92 (7H, m), 4.09-4.19 (2H, m), 6.74-6.77 (1H, m), 6.85-6.89 (1H, m), 8.14-8.17 (1H, m).

Step 2: 1-(1'-Acetyl-5-methoxyspiro[indoline-3,3'-pyrrolidin]-1-yl)-2,2,2-trifluoroethanone (2.74 g, 8.00 mmol) was dissolved in methylene chloride (50 mL). Thereafter, 1 M boron tribromide (40 mL, 40.0 mmol) was added to the above obtained solution at −78° C., and the thus obtained mixture was then stirred at −20° C. for 3 hours. Thereafter, the reaction solution was poured into ice water, and was then extracted with chloroform. The organic layer was washed with water and brine, and was then dried over anhydrous sodium sulfate, followed by concentration in vacuo. The obtained residue was purified by silica gel column chromatography (chloroform:methanol=20:1) to obtain 1-(1'-acetyl-5-hydroxyspiro[indoline-3,3'-pyrrolidin]-1-yl)-2,2,2-trifluoroethanone (2.39 g, 91%) in the form of a dark brown solid.

$^1$H-NMR (400 MHz, CDCl$_3$) δ: 2.07-2.27 (5H, m), 3.50-3.83 (4H, m), 4.08-4.20 (2H, m), 6.74 (1H, s), 6.80-6.86 (1H, m), 8.06-8.10 (1H, m), 8.16 (0.5H, s), 8.30 (0.5H, s).

Step 3: 1-(1'-Acetyl-5-hydroxyspiro[indoline-3,3'-pyrrolidin]-1-yl)-2,2,2-trifluoroethanone (40 mg, 0.122 mmol) was dissolved in methylene chloride (1.5 mL). Thereafter, 4-fluorophenylboronic acid (34 mg, 0.244 mmol), copper(II) acetate (22 mg, 0.122 mmol), triethylamine (62 mg, 0.610 mmol), and molecular sieves 4A (40 mg) were added to the above obtained solution, and the thus obtained mixture was then stirred at room temperature for 18 hours. Thereafter, the reaction solution was concentrated in vacuo, and the obtained residue was then purified by silica gel column chromatography (ethyl acetate) to obtain 1-(1'-acetyl-5-(4-fluorophenoxy)spiro[indoline-3,3'-pyrrolidin]-1-yl)-2,2,2-trifluoroethanone (30 mg, 56%) in the form of a light yellow solid.

$^1$H-NMR (400 MHz, CDCl$_3$) δ: 2.04-2.31 (5H, m), 3.46-3.89 (4H, m), 4.11-4.22 (2H, m), 6.80-7.08 (6H, m), 8.17 (1H, dd, J=8.8, 1.2 Hz).

Step 4: The captioned compound was obtained in the form of a light brown solid by performing the same reactions and/or treatments as those in Steps 3 and 4 of Example 57, with the exception that 1-(1'-acetyl-5-(4-fluorophenoxy)spiro[indoline-3,3'-pyrrolidin]-1-yl)-2,2,2-trifluoroethanone was used instead of t-butyl 2-(5-chloro-1-(2,2,2-trifluoroacetyl)spiro[indoline-3,3'-pyrrolidin]-1'-yl)acetate.

$^1$H-NMR (400 MHz, CDCl$_3$) δ: 1.99-2.49 (12H, m), 3.02 (4H, br), 3.56-3.94 (7H, m), 4.09-4.23 (2H, m), 7.52-7.54 (1H, m), 7.68-7.88 (2H, m), 8.17-8.21 (2H, m), 8.30-8.32 (1H, m), 8.88 (1H, s).

Production of Examples 199, 201, 203, 205, 207, 209, 210, 212, 214, 215, 217, 219, 220, and 222

The below captioned compounds were all obtained in the form of a white solid by performing the same reactions and/or treatments as those in Steps 3 and 4 of Example 198, with the exception that each raw material compound was used instead of 4-fluorophenylboronic acid.

Example 199

(The compound in the parentheses that is described below the captioned compound is a raw material compound that was used instead of 4-fluorophenylboronic acid. The same shall apply hereafter.)

1'-Acetyl-N-(5-chlorothiazol-2-yl)-5-phenoxyspiro[indoline-3,3'-pyrrolidine]-1-carboxamide (Phenylboronic acid)
$^1$H-NMR (400 MHz, CDCl$_3$) δ: 2.07-2.35 (5H, m), 3.54-4.11 (6H, m), 6.83-6.98 (4H, m), 7.11 (1H, t, J=7.3 Hz), 7.19 (1H, s), 7.34 (2H, t, J=7.3 Hz), 7.96-8.02 (1H, m).

Example 201

1'-Acetyl-N-(5-chlorothiazol-2-yl)-5-(3-fluorophenoxy)spiro[indoline-3,3'-pyrrolidine]-1-carboxamide (3-Fluorophenylboronic acid)

Example 203

1'-Acetyl-N-(5-chlorothiazol-2-yl)-5-(o-tolyloxy)spiro[indoline-3,3'-pyrrolidine]-1-carboxamide (2-Tolylboronic acid)

Example 205

1'-Acetyl-N-(5-chlorothiazol-2-yl)-5-(m-tolyloxy)spiro[indoline-3,3'-pyrrolidine]-1-carboxamide (3-Tolylboronic acid)

Example 207

1'-Acetyl-N-(5-chlorothiazol-2-yl)-5-(p-tolyloxy)spiro[indoline-3,3'-pyrrolidine]-1-carboxamide (4-Tolylboronic acid)

Example 209

1'-Acetyl-N-(5-chlorothiazol-2-yl)-5-(2-(trifluoromethyl)phenoxy)spiro[indoline-3,3'-pyrrolidine]-1-carboxamide (2-(Trifluoromethyl)phenylboronic acid)
$^1$H-NMR (400 MHz, CDCl$_3$) δ: 2.07-2.36 (5H, m), 3.49-4.14 (6H, m), 6.85-6.98 (3H, m), 7.15-7.18 (2H, m), 7.45 (1H, t, J=7.8 Hz), 7.66-7.69 (1H, m), 8.01-8.07 (1H, m), 9.53 (1H, brs).

Example 210

1'-Acetyl-N-(5-chlorothiazol-2-yl)-5-(3-(trifluoromethyl)phenoxy)spiro[indoline-3,3'-pyrrolidine]-1-carboxamide (3-(Trifluoromethyl)phenylboronic acid)

Example 212

1'-Acetyl-N-(5-chlorothiazol-2-yl)-5-(4-(trifluoromethyl)phenoxy)spiro[indoline-3,3'-pyrrolidine]-1-carboxamide (4-(Trifluoromethyl)phenylboronic acid)

Example 214

1'-Acetyl-N-(5-chlorothiazol-2-yl)-5-(2-methoxyphenoxy)spiro[indoline-3,3'-pyrrolidine]-1-carboxamide (2-Methoxyphenylboronic acid)

Example 215

1'-Acetyl-N-(5-chlorothiazol-2-yl)-5-(3-methoxyphenoxy)spiro[indoline-3,3'-pyrrolidine]-1-carboxamide (3-Methoxyphenylboronic acid)

Example 217

1'-Acetyl-N-(5-chlorothiazol-2-yl)-5-(4-methoxyphenoxy)spiro[indoline-3,3'-pyrrolidine]-1-carboxamide (4-Methoxyphenylboronic acid)

Example 219

1'-Acetyl-N-(5-chlorothiazol-2-yl)-5-(2-(methylsulfonyl)phenoxy)spiro[indoline-3,3'-pyrrolidine]-1-carboxamide (2-(Methylsulfonyl)phenylboronic acid)

Example 220

1'-Acetyl-N-(5-chlorothiazol-2-yl)-5-(3-(methylsulfonyl)phenoxy)spiro[indoline-3,3'-pyrrolidine]-1-carboxamide (3-(Methylsulfonyl)phenylboronic acid)

Example 222

1'-Acetyl-N-(5-chlorothiazol-2-yl)-5-(4-(methylsulfonyl)phenoxy)spiro[indoline-3,3'-pyrrolidine]-1-carboxamide (4-(Methylsulfonyl)phenylboronic acid)
$^1$H-NMR (400 MHz, CDCl$_3$) δ: 2.05-2.37 (5H, m), 3.07 (3H, s), 3.49-4.89 (6H, m), 6.89-6.92 (1H, m), 7.00-7.02 (1H, m), 7.05 (2H, d, J=8.9 Hz), 7.19-7.20 (1H, m), 7.89 (2H, d, J=8.9 Hz), 8.07-8.13 (1H, m).

Example 200

Production of 1'-acetyl-N-(5-methoxythiazolo[5,4-b]pyridin-2-yl)-5-phenoxyspiro[indoline-3,3'-pyrrolidine]-1-carboxamide The captioned compound was obtained in the form of a white solid by performing the same reactions and/or treatments as those in Steps 3 and 4 of Example 198, with the exceptions that phenylboronic acid was used instead of 4-fluorophenylboronic acid, and that 5-methoxythiazolo[5,4-b]pyridin-2-amine was used instead of the 2-amino-5-chlorothiazole hydrochloride in Example 1, which was cited in Example 57.

Production of Examples 202, 204, 206, 208, 211, 213, 216, 218, 221, and 223

The below captioned compounds were all obtained in the form of a white solid by performing the same reactions and/or treatments as those in Example 200, with the exception that each raw material compound was used instead of phenylboronic acid.

Example 202

(The compound in the parentheses that is described below the captioned compound is a raw material compound that was used instead of phenylboronic acid. The same shall apply hereafter.)

1'-Acetyl-5-(3-fluorophenoxy)-N-(5-methoxythiazolo[5,4-b]pyridin-2-yl)spiro[indoline-3,3'-pyrrolidine]-1-carboxamide (3-Fluorophenylboronic acid)

Example 204

1'-Acetyl-N-(5-methoxythiazolo[5,4-b]pyridin-2-yl)-5-(o-tolyloxy)spiro[indoline-3,3'-pyrrolidine]-1-carboxamide (2-Tolylboronic acid)

Example 206

1'-Acetyl-N-(5-methoxythiazolo[5,4-b]pyridin-2-yl)-5-(m-tolyloxy)spiro[indoline-3,3'-pyrrolidine]-1-carboxamide (3-Tolylboronic acid)

Example 208

1'-Acetyl-N-(5-methoxythiazolo[5,4-b]pyridin-2-yl)-5-(p-tolyloxy)spiro[indoline-3,3'-pyrrolidine]-1-carboxamide (4-Tolylboronic acid)
$^1$H-NMR (400 MHz, CDCl$_3$) δ: 2.05-2.31 (5H, m), 2.34 (3H, s), 3.49-3.89 (4H, m), 3.40 (3H, s), 4.01-4.14 (2H, m), 6.76-6.96 (5H, m), 7.14 (2H, d, J=6.8 Hz), 7.75 (1H, s), 7.97-8.03 (1H, m).

Example 211

1'-Acetyl-N-(5-methoxythiazolo[5,4-b]pyridin-2-yl)-5-(3-(trifluoromethyl)phenoxy)spiro[indoline-3,3'-pyrrolidine]-1-carboxamide (3-(Trifluoromethyl)phenylboronic acid)

Example 213

1'-Acetyl-N-(5-methoxythiazolo[5,4-b]pyridin-2-yl)-5-(4-(trifluoromethyl)phenoxy)spiro[indoline-3,3'-pyrrolidine]-1-carboxamide (4-(Trifluoromethyl)phenylboronic acid)

Example 216

1'-Acetyl-5-(3-methoxyphenoxy)-N-(5-methoxythiazolo[5,4-b]pyridin-2-yl)spiro[indoline-3,3'-pyrrolidine]-1-carboxamide (3-Methoxyphenylboronic acid)

Example 218

1'-Acetyl-5-(4-methoxyphenoxy)-N-(5-methoxythiazolo[5,4-b]pyridin-2-yl)spiro[indoline-3,3'-pyrrolidine]-1-carboxamide (4-Methoxyphenylboronic acid)
$^1$H-NMR (400 MHz, CDCl$_3$) δ: 2.07-2.29 (5H, m), 3.53-3.79 (4H, m), 3.81 (3H, s), 4.00 (3H, s), 4.02-4.23 (2H, m), 6.76-6.82 (2H, m), 6.88-6.96 (5H, m), 7.72-7.78 (1H, m), 7.96-8.03 (1H, m).

Example 221

1'-Acetyl-N-(5-methoxythiazolo[5,4-b]pyridin-2-yl)-5-(3-(methylsulfonyl)phenoxy)spiro[indoline-3,3'-pyrrolidine]-1-carboxamide (3-(Methylsulfonyl)phenylboronic acid)

Example 223

1'-Acetyl-N-(5-methoxythiazolo[5,4-b]pyridin-2-yl)-5-(4-(methylsulfonyl)phenoxy)spiro[indoline-3,3'-pyrrolidine]-1-carboxamide (4-(methylsulfonyl)phenylboronic acid)

Example 224

Production of 1'-acetyl-N-(5-chlorothiazol-2-yl)-5-ethoxyspiro[indoline-3,3'-pyrrolidine]-1-carboxamide Step 1: The 1-(1'-acetyl-5-hydroxyspiro[indoline-3,3'-pyrrolidin]-1-yl)-2,2,2-trifluoroethanone (40 mg, 0.122 mmol) obtained in Step 2 of Example 198 was dissolved in N,N-dimethylformamide (0.5 mL). Thereafter, cesium carbonate (52 mg, 0.159 mmol) and iodoethane (23 mg, 0.146 mmol) were added to the above obtained solution, and the thus obtained mixture was then stirred at room temperature for 18 hours. Thereafter, ethyl acetate was added to the reaction solution, and the reaction mixture was then washed with water and brine. The resultant was dried over anhydrous sodium sulfate. The solvent was distilled away, and the obtained residue was then purified by silica gel column chromatography (ethyl acetate) to obtain 1-(1'-acetyl-5-ethoxyspiro[indoline-3,3'-pyrrolidin]-1-yl)-2,2,2-trifluoroethanone (24 mg, 54%) in the form of a colorless oily product.

¹H-NMR (400 MHz, CDCl₃) δ: 1.42 (3H, t, J=7.0 Hz), 2.05-2.32 (5H, m), 3.57-3.99 (4H, m), 4.03 (2H, q, J=7.0 Hz), 4.09-4.19 (2H, m), 6.74-6.87 (2H, m), 8.12-8.14 (1H, m).

Step 2: The captioned compound (17 mg, 100%) was obtained in the form of a reddish brown solid by performing the same reactions and/or treatments as those in Step 4 of Example 198, with the exception that 1-(1'-acetyl-5-ethoxyspiro[indoline-3,3'-pyrrolidin]-1-yl)-2,2,2-trifluoroethanone was used instead of 1-(1'-acetyl-5-(4-fluorophenoxy)phenoxyspiro[indoline-3,3'-pyrrolidin]-1-yl)-2,2,2-trifluoroethanone.

Example 225

Production of 1'-acetyl-5-ethoxy-N-(5-methoxythiazolo[5,4-b]pyridin-2-yl)spiro[indoline-3,3'-pyrrolidine]-1-carboxamide The captioned compound was obtained in the form of a reddish brown solid by performing the same reactions and/or treatments as those in Step 4 of Example 198, with the exceptions that 5-methoxythiazolo[5,4-b]pyridin-2-amine was used instead of the 2-amino-5-chlorothiazole hydrochloride in Example 1, which was cited in Example 57, and that 1-(1'-acetyl-5-ethoxyspiro[indoline-3,3'-pyrrolidin]-1-yl)-2,2,2-trifluoroethanone was used instead of 1-(1'-acetyl-5-(4-fluorophenoxy)phenoxyspiro[indoline-3,3'-pyrrolidin]-1-yl)-2,2,2-trifluoroethanone.

Example 226

Production of methyl 1-((5-chlorothiazol-2-yl)carbamoyl)-5-(2,2,2-trifluoroethoxy)spiro[indoline-3,3'-pyrrolidine]-1'-carboxylate The captioned compound was obtained in the form of a white solid by performing the same reactions and/or treatments as those in Steps 1 and 2 of Example 198 and Example 224, with the exceptions that methyl chloroformate was used instead of acetyl chloride, and that 2,2,2-trifluoroethyl-4-methylbenzene sulfonate was used instead of iodomethane.

Production of Examples 227, 229, 231, 232, and 234

The below captioned compounds were all obtained in the form of a white solid by performing the same reactions and/or treatments as those in Example 224, with the exception that each raw material compound was used instead of iodoethane.

Example 227

(The compound in the parentheses that is described below the captioned compound is a raw material compound that was used instead of iodoethane. The same shall apply hereafter.)

1'-Acetyl-N-(5-chlorothiazol-2-yl)-5-isopropoxyspiro[indoline-3,3'-pyrrolidine]-1-carboxamide (2-Iodopropane)

Example 229

1'-Acetyl-5-benzyloxy-N-(5-chlorothiazol-2-yl)spiro[indoline-3,3'-pyrrolidine]-1-carboxamide (Benzyl bromide)
¹H-NMR (400 MHz, CDCl₃) δ: 2.06-2.33 (5H, m), 3.47-4.08 (6H, m), 5.04 (2H, s), 6.77-6.93 (2H, m), 7.16 (1H, s), 7.32-7.43 7.89-7.96 (1H, m), 9.50 (1H, brs).

Example 231

1'-Acetyl-N-(5-chlorothiazol-2-yl)-5-(1-phenylethoxy)spiro[indoline-3,3'-pyrrolidine]-1-carboxamide ((1-Bromoethyl)benzene)

Example 232

1'-Acetyl-N-(5-chlorothiazol-2-yl)-5-phenethoxyspiro[indoline-3,3'-pyrrolidine]-1-carboxamide (Phenethyl bromide)

Example 234

1'-Acetyl-N-(5-chlorothiazol-2-yl)-5-((1-phenylpropan-2-yl)oxy)spiro[indoline-3,3'-pyrrolidine]-1-carboxamide (2-Bromo-1-phenylpropane)

Production of Examples 228, 230, 233, and 235

The below captioned compounds were all obtained in the form of a white solid by performing the same reactions and/or treatments as those in Example 225, with the exception that each raw material compound was used instead of iodoethane.

Example 228

(The compound in the parentheses that is described below the captioned compound is a raw material compound that was used instead of iodoethane. The same shall apply hereafter.)

1'-Acetyl-5-isopropoxy-N-(5-methoxythiazolo[5,4-b]pyridin-2-yl)spiro[indoline-3,3'-pyrrolidine]-1-carboxamide (2-Iodopropane)

Example 230

1'-Acetyl-5-benzyloxy-N-(5-methoxythiazolo[5,4-b]pyridin-2-yl)spiro[indoline-3,3'-pyrrolidine]-1-carboxamide (Benzyl bromide)

Example 233

1'-Acetyl-N-(5-methoxythiazolo[5,4-b]pyridin-2-yl)-5-phenethoxyspiro[indoline-3,3'-pyrrolidine]-1-carboxamide (Phenethyl bromide)

Example 235

1'-Acetyl-N-(5-methoxythiazolo[5,4-b]pyridin-2-yl)-5-((1-phenylpropan-2-yl)oxy)spiro[indoline-3,3'-pyrrolidine]-1-carboxamide (2-Bromo-1-phenylpropane)

Example 236

Production of 1'-acetyl-N-(5-chlorothiazol-2-yl)-5-((4-methylpiperazin-1-yl)sulfonyl)spiro[indoline-3,3'-pyrrolidine]-1-carboxamide Step 1: 1-(1'-Acetylspiro[indoline-3,3'-pyrrolidin]-1-yl)-2,2,2-trifluoroethanone was obtained in the form of a white solid by performing the same reactions and/or treatments as those in Steps 1 and 2 of Example 57, with the exceptions that t-butyl spiro[indoline-3,3'-pyrrolidine]-1'-carboxylate was used instead of t-butyl 5-chlorospiro[indoline-3,3'-pyrrolidine]-1'-carboxylate, and that acetyl chloride was used instead of t-butyl bromoacetate.

$^1$H-NMR (400 MHz, CDCl$_3$) δ: 2.07-2.35 (5H, m), 3.55-3.82 (4H, m), 4.11-4.21 (2H, m), 7.21-7.27 (2H, m), 7.33-7.40 (1H, m), 8.21-8.24 (1H, m).

Step 2: 1-(1'-Acetylspiro[indoline-3,3'-pyrrolidin]-1-yl)-2,2,2-trifluoroethanone (1.19 g, 3.81 mmol) was dissolved in methylene chloride (10 mL). Thereafter, chlorosulfonic acid (1.27 mL, 19 mmol) was added to the above obtained solution under cooling on ice, and the thus obtained mixture was then stirred for 30 minutes. Thereafter, while stirring, the reaction solution was added dropwise to ice water, and was then extracted with chloroform. The obtained organic layer was washed with brine, and was then dried over anhydrous sodium sulfate, followed by concentration in vacuo. The obtained residue was dissolved in methylene chloride (20 mL). Thereafter, N,N-diisopropylethylamine (0.7 mL, 4 mmol) and 1-methylpiperazine (0.22 mL, 2 mmol) were added to the above obtained solution under cooling on ice, and the thus obtained mixture was then stirred at room temperature for 15 hours. Thereafter, the reaction solution was diluted with water, and was then extracted with chloroform. The obtained organic layer was washed with brine, and was then dried over anhydrous sodium sulfate, followed by concentration in vacuo. The obtained residue was dissolved in methanol (3 mL), and a saturated solution of ammonium-methanol (3 mL) was then added to the above obtained solution, followed by stirring the mixture at room temperature for 30 minutes. Thereafter, the reaction solution was concentrated in vacuo, and the obtained residue was then purified by silica gel column chromatography (chloroform:methanol=10:1) to obtain 1-(5-((4-methylpiperazin-1-yl)sulfonyl)spiro[indoline-3,3'-pyrrolidin]-1'-yl)ethanone (559 mg, 82%) in the form of a white solid.

$^1$H-NMR (400 MHz, CDCl$_3$) δ: 2.01-2.33 (8H, m), 2.48 (2H, br), 2.98 (2H, br), 3.40-3.84 (6H, m), 4.52 (1H, br), 6.62-6.65 (1H, m), 7.34-7.35 (1H, m), 7.45-7.49 (1H, m).

Step 3: The captioned compound was obtained in the form of a white solid by performing the same reactions and/or treatments as those in Example 1, with the exception that 1-(5-((4-methylpiperazin-1-yl)sulfonyl)spiro[indoline-3,3'-pyrrolidin]-1'-yl)ethanone was used instead of t-butyl 5-bromospiro[indoline-3,3'-pyrrolidine]-1'-carboxylate.

Production of Examples 237 to 239 and 241 to 244

The below captioned compounds were all obtained in the form of a white solid by performing the same reactions and/or treatments as those in Step 3 of Example 236, with the exception that each raw material compound was used instead of the 2-amino-5-chlorothiazole hydrochloride in Example 1, which was cited in Step 3 of Example 236. Example 237 (The compound in the parentheses that is described below the captioned compound is a raw material compound that was used instead of 2-amino-5-chlorothiazole hydrochloride. The same shall apply hereafter.)

1'-Acetyl-5-((4-methylpiperazin-1-yl)sulfonyl)-N-(thiazol-2-yl)spiro[indoline-3,3'-pyrrolidine]-1-carboxamide (2-Aminothiazole)

Example 238

1'-Acetyl-N-(5-fluorothiazol-2-yl)-5-((4-methylpiperazin-1-yl)sulfonyl)spiro[indoline-3,3'-pyrrolidine]-1-carboxamide (2-Amino-5-fluorothiazole)

Example 239

Ethyl 2-((2-(1'-acetyl-5-((4-methylpiperazin-1-yl)sulfonyl)spiro[indoline-3,3'-pyrrolidin]-1-ylcarboxamido)thiazol-5-yl)thio)acetate (Ethyl 2-((2-aminothiazol-5-yl)thio)acetate)

Example 241

1'-Acetyl-N-(1-methyl-1H-pyrazol-3-yl)-5-((4-methylpiperazin-1-yl)sulfonyl)spiro[indoline-3,3'-pyrrolidine]-1-carboxamide (1-Methyl-1H-pyrazole-3-amine)

Example 242

1'-Acetyl-5-((4-methylpiperazin-1-yl)sulfonyl)-N-(pyridin-2-yl)spiro[indoline-3,3'-pyrrolidine]-1-carboxamide (2-Aminopyridine)

Example 243

Methyl 6-(1'-acetyl-5-((4-methylpiperazin-1-yl)sulfonyl)spiro[indoline-3,3'-pyrrolidin]-1-ylcarboxamido)nicotinate (Methyl 6-aminonicotinate)

$^1$H-NMR (400 MHz, CDCl$_3$) δ: 1.99-2.49 (12H, m), 3.02 (4H, br), 3.56-3.94 (7H, m), 4.09-4.23 (2H, m), 7.52-7.54 (1H, m), 7.68-7.88 (2H, m), 8.17-8.21 (2H, m), 8.30-8.32 (1H, m), 8.88 (1H, s).

Example 244

1'-Acetyl-N-(5-methoxythiazolo[5,4-b]pyridin-2-yl)-5-((4-methylpiperazin-1-yl)sulfonyl)spiro[indoline-3,3'-pyrrolidine]-1-carboxamide (5-Methoxythiazolo[5,4-b]pyridin-2-amine)

Example 240

Production of 2-((2-(1'-acetyl-5-((4-methylpiperazin-1-yl)sulfonyl)spiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the ethyl 2-((2-(1'-acetyl-5-((4-methylpiperazin-1-yl)sulfonyl)spiro[indoline-3,3'-pyrrolidin]-1-ylcarboxamido)thiazol-5-yl)thio)acetate obtained in Example 239 was used instead of ethyl 2-((2-(1'-acetyl-5-bromospiro[indoline-3,3'-pyrrolidin]-1-ylcarboxamido)thiazol-5-yl)thio)acetate.

Production of Examples 245 to 251, 253 to 256, 258, 260, 262, 264, 266, 268, 270, 272, 274, 276, and 284

The below captioned compounds were all obtained in the form of a white solid by performing the same reactions and/or treatments as those in Steps 2 and 3 of Example 236, with the exception that each raw material compound was used instead of 1-methylpiperazine.

Example 245

(The compound in the parentheses that is described below the captioned compound is a raw material compound that was used instead of 1-methylpiperazine. The same shall apply hereafter.)

1'-Acetyl-N-(5-chlorothiazol-2-yl)-5-(N,N-diethylsulfamoyl)spiro[indoline-3,3'-pyrrolidine]-1-carboxamide (Diethylamine)
$^1$H-NMR (400 MHz, CDCl$_3$) δ: 1.07-1.13 (6H, m), 2.02-2.36 (5H, m), 3.14-3.22 (4H, m), 3.40-4.15 (6H, m), 7.13-7.14 (1H, m), 7.59-7.62 (1H, m), 7.67-7.72 (1H, m), 8.15-8.21 (1H, m).

Example 246

1'-Acetyl-N-(5-chlorothiazol-2-yl)-5-(N-cyclopentylsulfamoyl)spiro[indoline-3,3'-pyrrolidine]-1-carboxamide (Cyclopentanamine)
$^1$H-NMR (400 MHz, CDCl$_3$) δ: 1.28-1.79 (8H, m), 2.03-2.31 (5H, m), 3.43-3.82 (5H, m), 4.03-4.17 (2H, m), 7.12-7.13 (1H, m), 7.62-7.63 (1H, m), 7.71-7.75 (1H, m), 8.14-8.18 (1H, m).

Example 247

1'-Acetyl-N-(5-chlorothiazol-2-yl)-5-(N-(2-methoxyethyl)sulfamoyl)spiro[indoline-3,3'-pyrrolidine]-1-carboxamide (2-Methoxyethanamine)

Example 248

1'-Acetyl-N-(5-chlorothiazol-2-yl)-5-(N-(3-methoxypropyl)sulfamoyl)spiro[indoline-3,3'-pyrrolidine]-1-carboxamide (3-Methoxypropanamine)
$^1$H-NMR (400 MHz, CDCl$_3$) δ: 1.68-1.73 (2H, m), 2.01-2.32 (5H, m), 2.98-3.05 (2H, m), 3.23 (3H, s), 3.33-3.37 (2H, m), 3.41-3.86 (4H, m), 4.02-4.18 (2H, m), 5.75-5.83 (1H, m), 7.13-7.14 (1H, m), 7.60-7.64 (1H, m), 7.71-7.80 (1H, m), 8.10-8.18 (1H, m).

Example 249

1'-Acetyl-N-(5-chlorothiazol-2-yl)-5-(pyrrolidin-1-ylsulfonyl)spiro[indoline-3,3'-pyrrolidine]-1-carboxamide (Pyrrolidine)

Example 250

1'-Acetyl-N-(5-chlorothiazol-2-yl)-5-(piperidin-1-ylsulfonyl)spiro[indoline-3,3'-pyrrolidine]-1-carboxamide (Piperidine)
$^1$H-NMR (400 MHz, DMSO-d$_6$) δ: 1.45 (4H, br), 1.92-2.25 (5H, m), 2.81 (4H, br), 3.33-3.80 (4H, m), 4.01-4.15 (2H, m), 7.40 (1H, s), 7.50-7.55 (2H, m), 8.02-8.05 (1H, m).

Example 251

1'-Acetyl-5-(N-benzylsulfamoyl)-N-(5-chlorothiazol-2-yl)spiro[indoline-3,3'-pyrrolidine]-1-carboxamide (Benzylamine)

Example 253

1'-Acetyl-N-(5-chlorothiazol-2-yl)-5-(N-(2-(dimethylamino)ethyl)sulfamoyl)spiro[indoline-3,3'-pyrrolidine]-1-carboxamide (N,N-Dimethylethane-1,2-diamine)

Example 254

1'-Acetyl-N-(5-chlorothiazol-2-yl)-5-(N-(cyclohexylmethyl)sulfamoyl)spiro[indoline-3,3'-pyrrolidine]-1-carboxamide (Cyclohexylmethanamine)
$^1$H-NMR (400 MHz, CDCl$_3$) δ: 0.79-0.85 (2H, m), 1.08-1.28 (4H, m), 1.66-1.69 (5H, m), 2.01-2.30 (5H, m), 2.68-2.76 (2H, m), 3.48-4.22 (6H, m), 5.85-5.90 (1H, m), 7.14 (1H, s), 7.59-7.78 (2H, m), 8.16-8.20 (1H, m).

Example 255

1'-Acetyl-N-(5-chlorothiazol-2-yl)-5-(N,N-dipropylsulfamoyl)spiro[indoline-3,3'-pyrrolidine]-1-carboxamide (Dipropylamine)

Example 256

1'-Acetyl-N-(5-chlorothiazol-2-yl)-5-(N-(pyridin-2-ylmethyl)sulfamoyl)spiro[indoline-3,3'-pyrrolidine]-1-carboxamide (Pyridin-2-ylmethanamine)

Example 258

1'-Acetyl-N-(5-chlorothiazol-2-yl)-5-(N-(pyridin-3-ylmethyl)sulfamoyl)spiro[indoline-3,3'-pyrrolidine]-1-carboxamide (Pyridin-3-ylmethanamine)
$^1$H-NMR (400 MHz, DMSO-$d_6$) δ: 1.90-2.18 (5H, m), 3.32-3.71 (4H, m), 3.98-4.19 (4H, m), 7.20-7.23 (1H, m), 7.59 (1H, s), 7.54-7.68 (3H, m), 8.00-8.09 (1H, m), 8.34-8.40 (2H, m).

Example 260

1'-Acetyl-N-(5-chlorothiazol-2-yl)-5-(N-(pyridin-4-ylmethyl)sulfamoyl)spiro[indoline-3,3'-pyrrolidine]-1-carboxamide (Pyridin-4-ylmethanamine)

Example 262

1'-Acetyl-N-(5-chlorothiazol-2-yl)-5-(N-(2-methoxybenzyl)sulfamoyl)spiro[indoline-3,3'-pyrrolidine]-1-carboxamide (2-Methoxybenzylamine)

Example 264

1'-Acetyl-N-(5-chlorothiazol-2-yl)-5-(N-(3-methoxybenzyl)sulfamoyl)spiro[indoline-3,3'-pyrrolidine]-1-carboxamide (3-Methoxybenzylamine)

Example 266

1'-Acetyl-N-(5-chlorothiazol-2-yl)-5-(N-(4-methoxybenzyl)sulfamoyl)spiro[indoline-3,3'-pyrrolidine]-1-carboxamide (4-Methoxybenzylamine)

Example 268

1'-Acetyl-N-(5-chlorothiazol-2-yl)-5-(N-(2-fluorobenzyl)sulfamoyl)spiro[indoline-3,3'-pyrrolidine]-1-carboxamide (2-Fluorobenzylamine)

Example 270

1'-Acetyl-N-(5-chlorothiazol-2-yl)-5-(N-(furan-2-ylmethyl)sulfamoyl)spiro[indoline-3,3'-pyrrolidine]-1-carboxamide (Furan-2-ylmethanamine)

Example 272

1'-Acetyl-N-(5-chlorothiazol-2-yl)-5-(N-(thiophen-2-ylmethyl)sulfamoyl)spiro[indoline-3,3'-pyrrolidine]-1-carboxamide (Thiophen-2-ylmethanamine)
$^1$H-NMR (400 MHz, CDCl$_3$) δ: 2.02-2.33 (5H, m), 3.43-3.80 (4H, m) 4.02-4.40 (4H, m), 6.75-6.72 (2H, m), 7.17-7.18 (1H, m), 7.55-7.57 (1H, m), 7.76-7.78 (1H, m), 8.16-8.19 (1H, m).

Example 274

1'-Acetyl-N-(5-chlorothiazol-2-yl)-5-(N-(2-methoxyethyl)-N-methylsulfamoyl)spiro[indoline-3,3'-pyrrolidine]-1-carboxamide (2-Methoxy-N-methylethanamine)

Example 276

1'-Acetyl-5-(N-benzyl-N-methylsulfamoyl)-N-(5-chlorothiazol-2-yl)spiro[indoline-3,3'-pyrrolidine]-1-carboxamide (N-Methylbenzylamine)

Example 284

1'-Acetyl-N-(5-chlorothiazol-2-yl)-5-(N-phenethylsulfamoyl)spiro[indoline-3,3'-pyrrolidine]-1-carboxamide (Phenethylamine)

Example 252

Production of 1'-acetyl-5-(N-benzylsulfamoyl)-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Steps 2 and 3 of Example 236, with the exceptions that benzylamine was used instead of 1-methylpiperazine, and that 5-methoxythiazolo[5,4-b]pyridin-2-amine was used instead of the 2-amino-5-chlorothiazole hydrochloride in Example 1, which was cited in Step 3 of Example 236.

Examples 257, 259, 261, 263, 265, 267, 269, 271, 273, 275, 277, 285, 286, 288 to 290, 292, 294, 296, 298 to 301, and 305

The below captioned compounds were all obtained in the form of a white solid by performing the same reactions and/or treatments as those in Example 252, with the exception that each raw material compound was used instead of benzylamine.

Example 257

(The compound in the parentheses that is described below the captioned compound is a raw material compound that was used instead of benzylamine. The same shall apply hereafter.)

1'-Acetyl-N-(5-methoxythiazolo[5,4-b]pyridin-2-yl)-5-(N-(pyridin-2-ylmethyl) sulfamoyl)spiro[indoline-3,3'-pyrrolidine]-1-carboxamide (Pyridin-2-ylmethanamine)

Example 259

1'-Acetyl-N-(5-methoxythiazolo[5,4-b]pyridin-2-yl)-5-(N-(pyridin-3-ylmethyl)sulfamoyl)spiro[indoline-3,3'-pyrrolidine]-1-carboxamide (Pyridin-3-ylmethanamine)

Example 261

1'-Acetyl-N-(5-methoxythiazolo[5,4-b]pyridin-2-yl)-5-(N-(pyridin-4-ylmethyl)sulfamoyl)spiro[indoline-3,3'-pyrrolidine]-1-carboxamide (Pyridin-4-ylmethanamine)

Example 263

1'-Acetyl-5-(N-(2-methoxybenzyl)sulfamoyl)-N-(5-methoxythiazolo[5,4-b]pyridin-2-yl)spiro[indoline-3,3'-pyrrolidine]-1-carboxamide (2-Methoxybenzylamine)

$^1$H-NMR (400 MHz, DMSO-$d_6$) δ: 1.97-2.33 (5H, m), 3.44-3.88 (7H, m), 3.88-4.01 (5H, m), 4.03-4.40 (2H, m), 6.86-6.92 (4H, m), 7.19-7.21 (2H, m), 7.64-8.12 (5H, m).

Example 265

1'-Acetyl-5-(N-(3-methoxybenzyl)sulfamoyl)-N-(5-methoxythiazolo[5,4-b]pyridin-2-yl)spiro[indoline-3,3'-pyrrolidine]-1-carboxamide (3-Methoxybenzylamine)

Example 267

1'-Acetyl-5-(N-(4-methoxybenzyl)sulfamoyl)-N-(5-methoxythiazolo[5,4-b]pyridin-2-yl)spiro[indoline-3,3'-pyrrolidine]-1-carboxamide (4-Methoxybenzylamine)

Example 269

1'-Acetyl-5-(N-(2-fluorobenzyl)sulfamoyl)-N-(5-methoxythiazolo[5,4-b]pyridin-2-yl)spiro[indoline-3,3'-pyrrolidine]-1-carboxamide (2-Fluorobenzylamine)

$^1$H-NMR (400 MHz, DMSO-$d_6$) δ: 1.95-2.32 (5H, m), 3.32-3.78 (4H, m), 3.92 (3H, s), 4.02-4.33 (4H, m), 6.89-6.90 (1H, m), 7.07-7.10 (2H, m), 7.25-7.34 (2H, m), 7.66-7.73 (2H, m), 8.03-8.09 (2H, m).

Example 271

1'-Acetyl-5-(N-(furan-2-ylmethyl)sulfamoyl)-N-(5-methoxythiazolo[5,4-b]pyridin-2-yl)spiro[indoline-3,3'-pyrrolidine]-1-carboxamide (Furan-2-ylmethanamine)

$^1$H-NMR (400 MHz, DMSO-$d_6$) δ: 1.92-2.32 (5H, m), 3.34-3.77 (4H, m), 3.92 (3H, s), 4.01-4.40 (4H, m), 6.15-6.16 (1H, m), 6.30-6.32 (1H, m), 6.88-6.90 (1H, m), 7.49-7.50 (1H, m), 7.69 (2H, br), 8.00-8.20 (2H, m).

Example 273

1'-Acetyl-N-(5-methoxythiazolo[5,4-b]pyridin-2-yl)-5-(N-(thiophen-2-ylmethyl)sulfamoyl)spiro[indoline-3,3'-pyrrolidine]-1-carboxamide (Thiophen-2-ylmethanamine)

$^1$H-NMR (400 MHz, DMSO-$d_6$) δ: 1.97-2.32 (5H, m), 3.40-3.80 (4H, m), 3.91 (3H, s), 4.08-4.22 (4H, m), 6.83-6.92 (3H, m), 7.39 (1H, s), 7.63-7.88 (2H, m), 8.09-8.22 (2H, m).

Example 275

1'-Acetyl-5-(N-(2-methoxyethyl)-N-methylsulfamoyl)-N-(5-methoxythiazolo[5,4-b]pyridin-2-yl)spiro[indoline-3,3'-pyrrolidine]-1-carboxamide (2-Methoxy-N-methylethanamine)

$^1$H-NMR (400 MHz, CDCl$_3$) δ: 2.02-2.35 (5H, m), 2.81-2.83 (3H, m), 3.19-3.26 (2H, m), 3.32-3.33 (3H, m), 3.49-4.50 (11H, m), 6.68-6.78 (1H, m), 7.52-7.73 (3H, m), 8.25-8.30 (1H, m).

Example 277

1'-Acetyl-5-(N-benzyl-N-methylsulfamoyl)-N-(5-methoxythiazolo[5,4-b]pyridin-2-yl)spiro[indoline-3,3'-pyrrolidine]-1-carboxamide (N-Methylbenzylamine)

Example 285

1'-Acetyl-N-(5-methoxythiazolo[5,4-b]pyridin-2-yl)-5-(N-phenethylsulfamoyl)spiro[indoline-3,3'-pyrrolidine]-1-carboxamide (Phenethylamine)

Example 286 t-Butyl 3-(1'-acetyl-N-benzyl-((5-methoxythiazolo[5,4-b]pyridin-2-yl)carbamoyl)spiro[indoline-3,3'-pyrrolidin]-5-ylsulfonamido)propanoate (t-Butyl 3-(benzylamino)propanoate)

Example 288

1'-Acetyl-5-(N-benzyl-N-(2-methoxyethyl)sulfamoyl)-N-(5-methoxythiazolo[5,4-b]pyridin-2-yl)spiro[indoline-3,3'-pyrrolidine]-1-carboxamide (N-Benzyl-2-methoxyethanamine)
$^1$H-NMR (400 MHz, CDCl$_3$) δ: 2.02-2.32 (5H, m), 3.11-3.15 (3H, m), 3.327-3.34 (4H, m), 3.50-3.92 (4H, m), 3.98 (3H, s), 4.04-4.22 (2H, m), 4.39-4.43 (2H, m), 6.76-6.80 (1H, m), 7.25-7.30 (5H, m), 7.59-7.60 (1H, m), 7.66-7.70 (1H, m), 7.75-7.79 (1H, m), 8.20-8.26 (1H, m).

Example 289

1'-Acetyl-5-(N-benzyl-N-(3-methoxypropyl)sulfamoyl)-N-(5-methoxythiazolo[5,4-b]pyridin-2-yl)spiro[indoline-3,3'-pyrrolidine]-1-carboxamide (N-Benzyl-3-methoxypropanamine)
$^1$H-NMR (400 MHz, CDCl$_3$) δ: 1.55-1.63 (2H, m), 2.02-2.32 (5H, m), 3.15-3.23 (7H, m), 3.49-3.90 (4H, m), 3.94 (3H, s), 4.03-4.23 (2H, m), 4.30-4.33 (2H, m), 6.72-6.74 (1H, m), 7.25-7.33 (5H, m), 7.56 (1H, s), 7.63-7.75 (2H, m), 8.22-8.26 (1H, m).

Example 290 t-Butyl 3-(1'-acetyl-N-(2-methoxyethyl)-1-((5-methoxythiazolo[5,4-b]pyridin-2-yl)carbamoyl)spiro[indoline-3,3'-pyrrolidin]-5-ylsulfonamido)propanoate (t-Butyl 3-((2-methoxyethyl)amino)propanoate)

Example 292 t-Butyl 3-(1'-Acetyl-N-(3-methoxypropyl)-1-((5-methoxythiazolo[5,4-b]pyridin-2-yl)carbamoyl)spiro[indoline-3,3'-pyrrolidin]-5-ylsulfonamido)propanoate (t-Butyl 3-((3-methoxypropyl)amino)propanoate)

Example 294 t-Butyl 4-(1'-acetyl-N-benzyl-1-((5-methoxythiazolo[5,4-b]pyridin-2-yl)carbamoyl)spiro[indoline-3,3'-pyrrolidin]-5-ylsulfonamido)butanoate (t-Butyl 4-(benzylamino)butanoate)

Example 296 t-Butyl 3-(1'-acetyl-N-(cyclopropylmethyl)-1-((5-methoxythiazolo[5,4-b]pyridin-2-yl)carbamoyl)spiro[indoline-3,3'-pyrrolidin]-5-ylsulfonamido)propanoate (t-Butyl 3-((cyclopropylmethyl)amino)propanoate synthesized by a method described in the known methods (International Publication WO2007/041366 etc.) or a reaction similar thereto)

Example 298

1'-Acetyl-5-(N-benzyl-N-(2-(dimethylamino)ethyl)sulfamoyl)-N-(5-methoxythiazolo[5,4-b]pyridin-2-yl)carbamoyl)spiro[indoline-3,3'-pyrrolidine]-1-carboxamide (N-Benzyl-N',N'-dimethylethane-1,2-diamine)

Example 299

1'-Acetyl-5-(N-(cyclopropylmethyl)-N-(2-(dimethylamino)ethyl)sulfamoyl)-N-(5-methoxythiazolo[5,4-b]pyridin-2-yl)spiro[indoline-3,3'-pyrrolidine]-1-carboxamide (N-Cyclopropylmethyl-N',N'-dimethylethane-1,2-diamine)

Example 300

1'-Acetyl-5-(N-(cyclopropylmethyl)-N-(2-methoxyethyl)sulfamoyl)-N-(5-methoxythiazolo[5,4-b]pyridin-2-yl)spiro[indoline-3,3'-pyrrolidine]-1-carboxamide (N-Cyclopropylmethyl-2-methoxyethanamine)
$^1$H-NMR (400 MHz, CDCl$_3$) δ: 0.20 (1H, m), 0.50 (1H, m), 0.88 (1H, m), 2.12-2.30 (5H, m), 3.05-3.10 (2H, m), 3.29-3.30 (3H, m), 3.42-3.47 (2H, m), 3.53-3.92 (6H, m), 3.98 (3H, s), 4.07-4.20 (2H, m), 6.76-6.79 (1H, m), 7.61-7.76 (3H, m), 8.22-8.28 (1H, m).

Example 301

1'-Acetyl-5-(N-(cyclopropylmethyl)-N-(3-methoxypropyl)sulfamoyl)-N-(5-methoxythiazolo[5,4-b]pyridin-2-yl)spiro[indoline-3,3'-pyrrolidine]-1-carboxamide (N-Cyclopropylmethyl-3-methoxypropanamine)

Example 305 t-Butyl 3-(1'-acetyl-N-(2-(dimethylamino)ethyl)-1-((5-methoxythiazolo[5,4-b]pyridin-2-yl)carbamoyl)spiro[indoline-3,3'-pyrrolidin]-5-ylsulfonamido)propanoate (t-Butyl 3-((2-(dimethylamino)ethyl)amino)propanoate)

Example 278

Production of 1'-acetyl-5-(N-benzyl-N-methylsulfamoyl)-N-(5-fluorothiazol-2-yl)spiro[indoline-3,3'-pyrrolidine]-1-carboxamide The captioned compound was obtained in the form of a white solid by performing the same reactions and/or treatments as those in Steps 2 and 3 of Example 236, with the exceptions that N-methylbenzylamine was used instead of 1-methylpiperazine, and that 2-amino-5-fluorothiazole was used instead of the 2-amino-5-chlorothiazole hydrochloride in Example 1, which was cited in Step 3 of Example 236.

Examples 279 and 281 to 283

The below captioned compounds were all obtained in the form of a white solid by performing the same reactions and/or

Example 279

Ethyl 2-((2-(1'-acetyl-5-(N-benzyl-N-methylsulfamoyl)spiro[indoline-3,3'-pyrrolidin]-1-ylcarboxamido)thiazol-5-yl)thio)acetate (Ethyl 2-((2-aminothiazol-5-yl)thio)acetate)

Example 281

1'-Acetyl-5-(N-benzyl-N-methylsulfamoyl)-N-(1-methyl-1H-pyrazol-3-yl)spiro[indoline-3,3'-pyrrolidine]-1-carboxamide (1-Methyl-1H-pyrazole-3-amine)

Example 282

1'-Acetyl-5-(N-benzyl-N-methylsulfamoyl)-N-(5-methyl-1,3,4-thiadiazol-2-yl)spiro[indoline-3,3'-pyrrolidine]-1-carboxamide (5-Methyl-1,3,4-thiadiazole-2-amine)
$^1$H-NMR (400 MHz, CDCl$_3$) δ: 2.02-2.44 (5H, m), 2.59-2.64 (6H, m), 3.56-3.95 (4H, m), 4.08-4.16 (2H, m), 4.42-4.51 (2H, m), 7.27-7.36 (5H, m), 7.62-7.66 (1H, m), 7.76-7.80 (1H, m), 8.27-8.32 (1H, m).

Example 283

Methyl 6-(1'-acetyl-5-(N-benzyl-N-methylsulfamoyl)spiro[indoline-3,3'-pyrrolidin]-1-ylcarboxamido)nicotinate(methyl 6-aminonicotinate)

Example 280

Production of 2-((2-(1'-acetyl-5-(N-benzyl-N-methylsulfamoyl)spiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the ethyl 2-((2-(1'-acetyl-5-(N-benzyl-N-methylsulfamoyl)spiro[indoline-3,3'-pyrrolidin]-1-ylcarboxamido)thiazol-5-yl)thio)acetate obtained in Example 279 was used instead of ethyl 2-((2-(1'-acetyl-5-bromospiro[indoline-3,3'-pyrrolidin]-1-ylcarboxamido)thiazol-5-yl)thio)acetate.

Example 287

Production of 3-(1'-acetyl-N-benzyl-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the t-butyl 3-(1'-acetyl-N-benzyl-((5-methoxythiazolo[5,4-b]pyridin-2-yl)carbamoyl)spiro[indoline-3,3'-pyrrolidin]5-ylsulfonamido)propanoate obtained in Example 286 was used instead of t-butyl 5-bromo-1-((5-chlorothiazol-2-yl)carbamoyl)spiro[indoline-3,3'-pyrrolidine]-1'-carboxylate.

Example 291

Production of 3-(1'-acetyl-N-(2-methoxyethyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the t-butyl 3-(1'-acetyl-N-(2-methoxyethyl)-1-((5-methoxythiazolo[5,4-b]pyridin-2-yl)carbamoylspiro[indoline-3,3'-pyrrolidin]-5-ylsulfonamido)propanoate obtained in Example 290 was used instead of t-butyl 5-bromo-1-((5-chlorothiazol-2-yl)carbamoyl)spiro[indoline-3,3'-pyrrolidine]-1'-carboxylate.

Example 293

Production of 3-(1'-acetyl-N-(3-methoxypropyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the t-butyl 3-(1'-acetyl-N-(3-methoxypropyl)-1-((5-methoxythiazolo[5,4-b]pyridin-2-yl)carbamoylspiro[indoline-3,3'-pyrrolidin]-5-ylsulfonamido)propanoate obtained in Example 292 was used instead of t-butyl 5-bromo-1-((5-chlorothiazol-2-yl)carbamoyl)spiro[indoline-3,3'-pyrrolidine]-1'-carboxylate.

Example 295

Production of 4-(1'-acetyl-N-benzyl-1-((5-methoxythiazolo[5,4-b]pyridin-2-yl)carbamoyl)spiro[indoline-3,3'-pyrrolidin]-5-ylsulfonamido)butyric acid The captioned compound was obtained in the form of a white solid by performing the same reactions and/or treatments as those in Example 2, with the exception that the t-butyl 4-((1'-acetyl-N-benzyl-1-((5-methoxythiazolo[5,4-b]pyridin-2-yl)carbamoyl)spiro[indoline-3,3'-pyrrolidin]-5-ylsulfonamido)butanoate obtained in Example 294 was used instead of t-butyl 5-bromo-1-((5-chlorothiazol-2-yl)carbamoyl)spiro[indoline-3,3'-pyrrolidine]-1'-carboxylate.

Example 297

Production of 3-(1'-acetyl-N-(cyclopropylmethyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the t-butyl 3-((1'-acetyl-N-(cyclopropylmethyl)-1-((5-methoxythiazolo[5,4-b]pyridin-2-yl)carbamoyl)spiro[indoline-3,3'-pyrrolidin]-5-ylsulfonamido)propanoate obtained in Example 296 was used instead of t-butyl 5-bromo-1-((5-chlorothiazol-2-yl)carbamoyl)spiro[indoline-3,3'-pyrrolidine]-1'-carboxylate.

Example 302

Production of 1'-acetyl-5-(N-(cyclopropylmethyl)-N-(2-hydroxyethyl)sulfamoyl)-N-(5-methoxythiazolo[5,4-b]pyridin-2-yl)spiro[indoline-3,3'-pyrrolidine]-1-carboxamide Step 1: 1'-Acetyl-5-(N-(2-((t-butyldimethylsilyl)oxy)ethyl)-N-(cyclopropylmethyl)sulfamoyl)-N-(5-methoxythiazolo[5,4-b]pyridin-2-yl)spiro[indoline-3,3'-pyrrolidine]-1-carboxamide was obtained in the form of a white solid by performing the same reactions and/or treatments as those in Steps 2 and 3 of Example 236, with the exceptions that the 2-((t-butyldimethylsilyl)oxy)-N-(cyclopropylmethyl)ethanamine synthesized by a method described in the known methods (International Publication WO2003/043981 etc.) or a reaction similar thereto was used instead of 1-methylpiperazine, and that 5-methoxythiazolo[5,4-b]pyridin-2-amine was used instead of the 2-amino-5-chlorothiazole hydrochloride in Example 1, which was cited in Step 3 of Example 236.

$^1$H-NMR (400 MHz, CDCl$_3$) δ: 0.05 (6H, s), 0.18-0.22 (2H, m), 0.49-0.54 (2H, m), 0.88 (9H, s), 1.70 (1H, brs), 2.11-2.35 (5H, m), 3.07-3.18 (2H, m), 3.28-3.37 (2H, m), 3.51-3.96 (6H, m), 4.00 (3H, s), 4.06-4.23 (2H, m), 6.78 (1H, dd, J=9.0, 2.2 Hz), 7.61 (1H, dd, J=9.0, 2.2 Hz), 7.70-7.77 (2H, m), 8.22-8.28 (1H, m).

Step 2: The captioned compound was obtained in the form of a white solid by performing the same reactions and/or treatments as those in Step 4 of Example 141, with the exception that 1'-acetyl-5-(N-(2-((t-butyldimethylsilyl)oxy)ethyl)-N-(cyclopropylmethyl)sulfamoyl)-N-(5-methoxythiazolo[5,4-b]pyridin-2-yl)spiro[indoline-3,3'-pyrrolidine]-1-carboxamide was used instead of methyl 1-((5-((1-((t-butyldimethylsilyl)oxy)propan-2-yl)thio)thiazol-2-yl)carbamoyl)-5-chlorospiro[indoline-3,3'-pyrrolidine]-1'-carboxylate.

$^1$H-NMR (400 MHz, CDCl$_3$) δ: 0.16-0.21 (2H, m), 0.50-0.55 (2H, m), 0.88-0.92 (1H, m), 2.05-2.35 (6H, m), 3.08 (2H, dd, J=10.7, 6.8 Hz), 3.33-3.41 (2H, m), 3.51-3.91 (6H, m), 3.98 (3H, s), 4.07-4.24 (2H, m), 6.77 (1H, d, J=8.8 Hz), 7.62 (3H, m), 8.21-8.27 (1H, m).

Example 303

Production of 1'-acetyl-5-(N-benzyl-N-(2-hydroxyethyl)sulfamoyl)-N-(5-methoxythiazolo[5,4-b]pyridin-2-yl)spiro[indoline-3,3'-pyrrolidine]-1-carboxamide The captioned compound was obtained in the form of a white solid by performing the same reactions and/or treatments as those in Example 302, with the exception that the 2-((t-butyldimethylsilyl)oxy)-N-benzylethanamine synthesized by a method described in the known methods (International Publication WO2006/125972 etc.) or a reaction similar thereto was used instead of 2-((t-butyldimethylsilyl)oxy)-N-(cyclopropylmethyl)ethanamine.

$^1$H-NMR (400 MHz, CDCl$_3$) δ: 1.81 (1H, brs), 2.05-2.33 (5H, m), 3.22-3.31 (2H, m), 3.49-3.91 (6H, m), 3.99 (3H, s), 4.09-4.39 (4H, m), 6.77 (1H, d, J=8.8 Hz), 7.27-7.31 (5H, m), 7.62-7.70 (2H, m), 7.78 (1H, t, J=8.8 Hz), 8.24-8.30 (1H, m).

Example 304

Production of 3-(1'-acetyl-N-(2-hydroxyethyl)-1-((5-methoxythiazolo[5,4-b]pyridin-2-yl)carbamoyl)spiro[indoline-3,3'-pyrrolidin]-5-ylsulfonamido)propionic acid Step 1: t-Butyl-3-(1'-acetyl-N-(2-((t-butyldimethylsilyl)oxy)ethyl)-1-((5-methoxythiazolo[5,4-b]pyridin-2-yl)carbamoyl)spiro[indoline-3,3'-pyrrolidin]-5-ylsulfonamido)propanoate was obtained in the form of a light yellow oily product by performing the same reactions and/or treatments as those in Steps 2 and 3 of Example 236, with the exceptions that the t-butyl 3-((2-((t-butyldimethylsilyl)oxy)ethyl)amino)propanoate synthesized by a method described in the known methods (International Publication WO2007/041366 etc.) or a reaction similar thereto was used instead of 1-methylpiperazine, and that 5-methoxythiazolo[5,4-b]pyridin-2-amine was used instead of the 2-amino-5-chlorothiazole hydrochloride in Example 1, which was cited in Step 3 of Example 236.

$^1$H-NMR (400 MHz, CDCl$_3$) δ: 0.05 (6H, s), 0.87 (9H, s), 1.43 (9H, s), 2.11-2.34 (5H, m), 2.45 (2H, t, J=6.7 Hz), 2.62 (2H, t, J=6.5 Hz), 2.74 (2H, t, J=6.5 Hz), 2.89 (2H, t, J=6.7 Hz), 3.56-3.93 (4H, m), 3.99 (3H, s), 4.09-4.25 (2H, m), 6.78 (1H, dd, J=9.7, 2.4 Hz), 7.62 (1H, dd, J=9.7, 2.4 Hz), 7.69-7.73 (2H, m), 8.24-8.31 (1H, m)

Step 2: The captioned compound was obtained in the form of a white solid by performing the same reactions and/or treatments as those in Example 2, with the exception that t-butyl-3-(1'-acetyl-N-(2-((t-butyldimethylsilyl)oxy)ethyl)-1-((5-methoxythiazolo[5,4-b]pyridin-2-yl)carbamoyl)spiro[indoline-3,3'-pyrrolidin]-5-ylsulfonamido)propanoate was used instead of t-butyl 5-bromo-1-((5-chlorothiazol-2-yl)carbamoyl)spiro[indoline-3,3'-pyrrolidine]-1'-carboxylate.

$^1$H-NMR (400 MHz, CD$_3$OD) δ: 2.10-2.49 (5H, m), 2.62 (2H, t, J=7.3 Hz), 3.26-3.32 (2H, m), 3.44-3.89 (8H, m), 3.93 (3H, s), 4.11-4.25 (2H, m), 6.77 (1H, dd, J=8.6, 1.7 Hz), 7.70-7.76 (3H, m), 8.21 (1H, dd, J=8.6, 1.7 Hz).

Example 306

Production of methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Example 236, with the exceptions that methyl chloroformate was used instead of the acetyl chloride in Example 3, cited in Steps 1 and 2 of Example 57 which was cited in Step 1 of Example 236, that t-butyl 3-(benzylamino)propanoate was used instead of 1-methylpiperazine, and that 5-methoxythiazolo[5,4-b]pyridin-2-amine was used instead of the 2-amino-5-chlorothiazole hydrochloride in Example 1, which was cited in Step 3 of Example 236.

$^1$H-NMR (400 MHz, CDCl$_3$) δ: 1.38 (9H, s), 2.12 (1H, m), 2.30 (1H, m), 2.42 (2H, t, J=9.2 Hz), 3.38 (2H, t, J=9.2 Hz), 3.47-3.88 (7H, m), 4.01 (3H, s), 4.02-4.32 (2H, m), 4.35 (2H, s), 6.78 (1H, d, J=8.2 Hz), 7.25-7.70 (5H, m), 7.59 (1H, s), 7.71 (1H, m), 7.94 (1H, d, J=8.8 Hz), 8.25 (1H, d, J=8.6 Hz).

Example 307

Production of 3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate obtained in Example 306 was used instead of t-butyl 5-bromo-1-((5-chlorothiazol-2-yl)carbamoyl)spiro[indoline-3,3'-pyrrolidine]-1'-carboxylate.

$^1$H-NMR (400 MHz, DMSO-d$_6$) δ: 2.14 (1H, m), 2.27-2.31 (3H, m), 3.33 (2H, t, J=7.8 Hz), 3.44-3.64 (7H, m), 3.92 (3H, s), 4.22 (2H, m), 4.36 (2H, s), 6.86 (1H, d, J=8.8 Hz), 7.28-2.33 (5H, m), 7.72-7.76 (2H, m), 7.84 (1H, d, J=8.8 Hz), 8.17 (1H, d, J=8.1 Hz), 8.24 (1H, s).

Example 308

Production of 5-(N-benzyl-N-(2-(dimethylamino)ethyl)sulfamoyl)-N-(5-fluorothiazol-2-yl)-1'-formyl-spiro[indoline-3,3'-pyrrolidine]-1-carboxamide The captioned compound was obtained in the form of a white solid by performing the same reactions and/or treatments as those in Examples 2, 23, and Steps 2 and 3 of Example 236, with the exceptions that t-butyl spiro[indoline-3,3'-pyrrolidine]-1'-carboxylate was used instead of t-butyl 5-bromo-1-((5-chlorothiazol-2-yl)carbamoyl)spiro[indoline-3,3'-pyrrolidine]-1'-carboxylate, that N-benzyl-N',N'-dimethylethane-1,2-diamine was used instead of 1-methylpiperazine, and that 2-amino-5-fluorothiazole was used instead of 2-amino-5-chlorothiazole hydrochloride.

$^1$H-NMR (400 MHz, CDCl$_3$) δ: 2.05-2.41 (8H, m), 3.22-4.11 (8H, m), 3.45-4.13 (8H, m), 4.38 (2H, s), 6.91-6.93 (1H, m), 7.29-7.34 (5H, m), 7.62-7.63 (1H, m), 7.81-7.84 (1H, m), 8.19-8.35 (2H, m).

Example 309

Production of 5-(N-benzyl-N-(2-hydroxyethyl)sulfamoyl)-N-(5-fluorothiazol-2-yl)-1'-formylspiro[indoline-3,3'-pyrrolidine]-1-carboxamide The captioned compound was obtained in the form of a light yellow solid by performing the same reactions and/or treatments as those in Example 308, with the exception that 2-((t-butyldimethylsilyl)oxy)-N-benzylethanamine was used instead of N-benzyl-N',N'-dimethylethane-1,2-diamine.

Example 310

Production of 1'-acetyl-N-(5-chlorothiazol-2-yl)-5-(cyclopentylsulfonyl)spiro[indoline-3,3'-pyrrolidine]-1-carboxamide Step 1: The 1'-acetyl-1-(2,2,2-trifluoroacetyl)spiro[indoline-3,3'-pyrrolidine]-5-sulfonyl chloride (101 mg, 0.25 mmol) obtained as an intermediate in Step 2 of Example 236 was dissolved in tetrahydrofuran (3 mL). Thereafter, water (0.1 mL) and triphenylphosphine (0.23 g, 0.86 mmol) were added to the above obtained solution, and the thus obtained mixture was then stirred at 50° C. for 4 hours. Thereafter, the reaction solution was diluted with water, and was then extracted with ethyl acetate. The organic layer was washed with brine, and was then dried over anhydrous magnesium sulfate, followed by concentration in vacuo. The obtained residue was purified by preparative thin-layer chromatography (chloroform:methanol=20:1) to obtain 1-(1'-acetyl-5-mercaptospiro[indoline-3,3'-pyrrolidin]-1-yl)-2,2,2-trifluoroethanone (26 mg, 31%) in the form of a colorless oily product.

$^1$H-NMR (400 MHz, CDCl$_3$) δ: 2.03-2.37 (5H, m), 3.51-4.23 (6H, m), 7.10-7.19 (1H, m), 7.23-7.31 (1H, m), 8.05-8.13 (1H, m).

Step 2: 1-(1'-Acetyl-5-mercaptospiro[indoline-3,3'-pyrrolidin]-1-yl)-2,2,2-trifluoroethanone (26 mg, 0.076 mmol) was dissolved in dimethylformamide (1 mL). Thereafter, potassium carbonate (32 mg, 0.23 mmol) and cyclopentane bromide (23 mg, 0.15 mmol) were added to the above obtained solution, and the thus obtained mixture was then stirred at room temperature for 1.5 hours. Thereafter, the reaction solution was diluted with water, and was then extracted with ethyl acetate. The organic layer was washed with brine, and was then dried over anhydrous magnesium sulfate, followed by concentration in vacuo. The obtained residue was purified by preparative thin-layer chromatography (chloroform:methanol=20:1) to obtain 1-(1'-acetyl-5-(cyclopentylthio)spiro[indoline-3,3'-pyrrolidin]-1-yl)-2,2,2-trifluoroethanone (13 mg, 42%) in the form of a colorless oily product.

$^1$H-NMR (400 MHz, CDCl$_3$) δ: 1.52-1.87 (6H, m), 1.95-2.37 (8H, m), 3.49-4.23 (6H, m), 7.17-7.22 (1H, m), 7.31-7.39 (1H, m), 8.10-8.18 (1H, m).

Step 3: 1-(1'-Acetyl-5-(cyclopentylthio)spiro[indoline-3,3'-pyrrolidin]-1-yl)-2,2,2-trifluoroethanone (13 mg, 0.032 mmol) was dissolved in methylene chloride (1 mL). Thereafter, sodium hydrogen carbonate (8 mg, 0.096 mmol) was added to the above obtained solution, and then, under cooling on ice, m-chloroperbenzoic acid (11 mg, 0.064 mmol) was further added thereto. The thus obtained mixture was stirred at room temperature for 1 hour. Thereafter, the reaction solution was diluted with water, and was then extracted with ethyl acetate. The organic layer was washed with a saturated aqueous solution of sodium hydrogen carbonate, water, and brine, and was then dried over anhydrous magnesium sulfate, followed by concentration in vacuo. The obtained residue was purified by preparative thin-layer chromatography (chloroform:methanol=10:1). The obtained colorless oily product was dissolved in methanol (1 mL). A saturated solution of ammonium-methanol (0.5 mL) was added to the above obtained solution, and the thus obtained mixture was then stirred at room temperature for 15 minutes. Thereafter, the reaction solution was concentrated in vacuo, and the obtained residue was then purified by preparative thin-layer chromatography (chloroform:methanol=10:1) to obtain 1-(5-(cyclopentylsulfonyl)spiro[indoline-3,3'-pyrrolidin]-1'-yl)ethanone (2 mg, 17%) in the form of a colorless oily product.

$^1$H-NMR (400 MHz, CDCl$_3$) δ: 1.47-1.94 (6H, m), 1.94-2.35 (7H, m), 3.34-3.90 (7H, m), 4.23-4.39 (1H, brs), 6.62-6.71 (1H, m), 7.48-7.55 (1H, m), 7.58-7.66 (1H, m).

Step 4: The captioned compound was obtained in the form of a white solid by performing the same reactions and/or treatments as those in Example 1, with the exception that 1-(5-(cyclopentylsulfonyl)spiro[indoline-3,3'-pyrrolidin]-1'-yl)ethanone was used instead of t-butyl 5-bromospiro[indoline-3,3'-pyrrolidine]-1'-carboxylate.

¹H-NMR (400 MHz, CDCl₃) δ: 1.40-1.94 (6H, m), 1.94-2.46 (7H, m), 3.38-4.21 (7H, m), 7.14-7.20 (1H, m), 7.65-7.72 (1H, m), 7.81-7.87 (1H, m), 8.22-8.30 (1H, m).

Example 311

Production of 1'-acetyl-N-(5-chlorothiazol-2-yl)-5-(methylsulfonyl)spiro[indoline-3,3'-pyrrolidine]-1-carboxamide The captioned compound was obtained in the form of a white solid by performing the same reactions and/or treatments as those in Example 310, with the exception that iodomethane was used instead of cyclopentane bromide.

¹H-NMR (400 MHz, CDCl₃) δ: 2.09-2.38 (5H, m), 3.06-3.08 (3H, m), 3.49-4.21 (6H, m), 7.16-7.17 (1H, m), 7.71-7.74 (1H, m), 7.86-7.89 (1H, m), 8.25-8.31 (1H, m).

Example 312

Production of (S)-methyl 5,6-dichloro-1-((5-chlorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that the (S)-t-butyl 5,6-dichlorospiro[indoline-3,3'-pyrrolidine]-1'-carboxylate synthesized by a method described in the known methods (International Publication WO2006/090261 etc.) or a method similar thereto was used instead of t-butyl 5-bromospiro[indoline-3,3'-pyrrolidine]-1'-carboxylate, and that methyl chloroformate was used instead of acetyl chloride.

Example 313

Production of (S)-methyl 5,6-dichloro-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5,6-dichlorospiro[indoline-3,3'-pyrrolidine]-1'-carboxylate was used instead of t-butyl 5-bromospiro[indoline-3,3'-pyrrolidine]-1'-carboxylate, that methyl chloroformate was used instead of acetyl chloride, and that 2-amino-5-fluorothiazole hydrochloride was used instead of 2-amino-5-chlorothiazole hydrochloride.

¹H-NMR (400 MHz, CDCl₃) δ: 2.02-2.18 (2H, m), 3.46-3.75 (7H, m), 4.10-4.15 (2H, m), 6.82 (1H, s), 7.07 (1H, s), 7.30 (1H, s)

Example 314

Production of methyl 5,6-dibromo-1-((5-chlorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that the t-butyl 5,6-dibromospiro[indoline-3,3'-pyrrolidine]-1'-carboxylate synthesized by a method described in the known methods (International Publication WO2009/089454 etc.) or a method similar thereto was used instead of t-butyl 5-bromospiro[indoline-3,3'-pyrrolidine]-1'-carboxylate, and that methyl chloroformate was used instead of acetyl chloride.

Example 315

Production of 1'-acetyl-N-(5-chlorothiazol-2-yl)-5-phenylspiro[indoline-3,3'-pyrrolidine]-1-carboxamide The captioned compound was obtained in the form of a white solid by performing the same reactions and/or treatments as those in Examples 1, 2, and 3, with the exception that the t-butyl 5-phenylspiro[indoline-3,3'-pyrrolidine]-1'-carboxylate synthesized by a method described in the known methods (International Publication WO2009/089454 etc.) or a method similar thereto was used instead of t-butyl 5-bromospiro[indoline-3,3'-pyrrolidine]-1'-carboxylate.

¹H-NMR (400 MHz, CDCl₃) δ: 2.06-2.45 (5H, m), 3.53-4.16 (6H, m), 7.20 (1H, s), 7.32-7.40 (2H, m), 7.40-7.48 (2H, m), 7.51-7.58 (3H, m), 8.04-8.12 (1H, m)

Example 316

Production of 1'-acetyl-N-(5-methoxythiazolo[5,4-b]pyridin-2-yl)-5-phenylspiro[indoline-3,3'-pyrrolidine]-1-carboxamide The captioned compound was obtained in the form of a white solid by performing the same reactions and/or treatments as those in Examples 1, 2, and 3, with the exceptions that t-butyl 5-phenylspiro[indoline-3,3'-pyrrolidine]-1'-carboxylate was used instead of t-butyl 5-bromospiro[indoline-3,3'-pyrrolidine]-1'-carboxylate, and that 5-methoxythiazolo[5,4-b]pyridin-2-amine was used instead of 2-amino-5-chlorothiazole hydrochloride.

Example 317

Production of (R)-1'-acetyl-5-bromo-N-(5-chlorothiazol-2-yl)spiro[indoline-3,3'-pyrrolidine]-1-carboxamide The captioned compound was obtained in the form of a white solid by performing the same reactions and/or treatments as those in Example 3, with the exception that the (S)-t-butyl 5-bromospiro[indoline-3,3'-pyrrolidine]-1'-carboxylate synthesized by a method described in the known methods (International Publication WO2006/090261 etc.) or a method similar thereto was used instead of t-butyl 5-bromospiro[indoline-3,3'-pyrrolidine]-1'-carboxylate.

Example 318

Production of (S)-1'-acetyl-5-bromo-N-(5-chlorothiazol-2-yl)spiro[indoline-3,3'-pyrrolidine]-1-carboxamide The captioned compound was obtained in the form of a white solid by performing the same reactions and/or treatments as those in Example 3, with the exception that the (R)-t-butyl 5-bromospiro[indoline-3,3'-pyrrolidine]-1'-carboxylate synthesized by a method described in the known methods (International Publication WO2006/090261 etc.) or a method similar thereto was used instead of t-butyl 5-bromospiro[indoline-3,3'-pyrrolidine]-1'-carboxylate.

Example 319

Production of (R)-methyl 5-bromo-1-((5-chlorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 320

Production of (S)-methyl 5-bromo-1-((5-chlorothiazol-2-yl)carbamoyl)spiro[indoline-3,3'-pyrrolidin]-1'-ylcarboxylate The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.
$^1$H-NMR (400 MHz, CDCl$_3$) δ: 2.03-2.28 (2H, m), 3.48-3.99 (9H, m), 7.17 (1H, s), 7.25 (1H, d, J=2.0 Hz), 7.39 (1H, dd, J=8.8 Hz, 2.0 Hz), 7.91 (1H, d, J=8.8 Hz), 8.47 (1H, brs).

Example 321

Production of (R)-ethyl 2-((2-(1'-acetyl-5-bromospiro[indoline-3,3'-pyrrolidin]-1-ylcarboxamido)thiazol-5-yl)thio)acetate The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that ethyl 2-((2-aminothiazol-5-yl)thio)acetate was used instead of 2-amino-5-chlorothiazole hydrochloride.

Example 322

Production of (S)-ethyl 2-((2-(1'-acetyl-5-bromospiro[indoline-3,3'-pyrrolidin]-1-ylcarboxamido)thiazol-5-yl)thio)acetate The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that ethyl 2-((2-aminothiazol-5-yl)thio)acetate was used instead of 2-amino-5-chlorothiazole hydrochloride.

Example 323

Production of (R)-2-((2-(1'-acetyl-5-bromospiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the (R)-ethyl 2-((2-(1'-acetyl-5-bromospiro[indoline-3,3'-pyrrolidin]-1-ylcarboxamido)thiazol-5-yl)thio)acetate obtained in Example 321 was used instead of ethyl 2-((2-(1'-acetyl-5-bromospiro[indoline-3,3'-pyrrolidin]-1-ylcarboxamido)thiazol-5-yl)thio)acetate.

Example 324

Production of (S)-2-((2-(1'-acetyl-5-bromospiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the (S)-ethyl 2-((2-(1'-acetyl-5-bromospiro[indoline-3,3'-pyrrolidin]-1-ylcarboxamido)thiazol-5-yl)thio)acetate obtained in Example 322 was used instead of ethyl 2-((2-(1'-acetyl-5-bromospiro[indoline-3,3'-pyrrolidin]-1-ylcarboxamido)thiazol-5-yl)thio)acetate.

Example 325

Production of (R)-1'-acetyl-5-bromo-N-(thiazol-2-yl)spiro[indoline-3,3'-pyrrolidin]-1-ylcarboxamide The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that 2-aminothiazole was used instead of 2-amino-5-chlorothiazole hydrochloride.

Example 326

Production of (S)-1'-acetyl-5-bromo-N-(thiazol-2-yl)spiro[indoline-3,3'-pyrrolidin]-1-ylcarboxamide The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that 2-aminothiazole was used instead of 2-amino-5-chlorothiazole hydrochloride.

Example 327

Production of (R)-1'-acetyl-5-bromo-N-(5-fluorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 328

Production of (S)-1'-acetyl-5-bromo-N-(5-fluorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 329

Production of (R)-methyl 5-bromo-1-(thiazol-2-ylcarbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 330

Production of (S)-methyl 5-bromo-1-(thiazol-2-ylcarbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

Example 331

Production of (R)-methyl 5-bromo-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, that 2-amino-5-fluorothiazole hydrochloride was used instead of 2-amino-5-chlorothiazole hydrochloride, and that methyl chloroformate was used instead of acetyl chloride.

Example 332

Production of (S)-methyl 5-bromo-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, that 2-amino-5-fluorothiazole hydrochloride was used instead of 2-amino-5-chlorothiazole hydrochloride, and that methyl chloroformate was used instead of acetyl chloride.

Example 333

Production of (R)-methyl 5-bromo-1-((5-((2-ethoxy-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (R)-t-butyl 5-bromospiro[indoline-3,3'-pyrrolidine]-1'-carboxylate was used instead of t-butyl 5-bromospiro[indoline-3,3'-pyrrolidine]-1'-carboxylate, that the ethyl 2-((2-aminothiazol-5-yl)thio)acetate synthesized by a method described in the known methods (International Publication WO2005/066145 etc.) was used instead of 2-amino-5-chlorothiazole hydrochloride, and that methyl chloroformate was used instead of acetyl chloride.

Example 334

Production of (S)-methyl 5-bromo-1-((5-((2-ethoxy-2-oxoethyl)thio)thiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-bromospiro[indoline-3,3'-pyrrolidine]-1'-carboxylate was used instead of t-butyl 5-bromospiro[indoline-3,3'-pyrrolidine]-1'-carboxylate, that the ethyl 2-((2-aminothiazol-5-yl)thio)acetate synthesized by a method described in the known methods (International Publication WO2005/066145 etc.) was used instead of 2-amino-5-chlorothiazole hydrochloride, and that methyl chloroformate was used instead of acetyl chloride.

$^1$H-NMR (400 MHz, CDCl$_3$) δ: 1.26 (3H, t, J=7.2 Hz), 2.03-2.27 (2H, m), 3.44 (s, 3H), 3.46-3.75 (6H, m), 3.92-4.01 (2H, m), 4.17 (2H, q, J=7.2 Hz), 7.29 (1H, s), 7.38 (1H, d, J=8.8 Hz), 7.39 (1H, s), 7.92 (1H, d, J=8.8 Hz), 8.57 (1H, brs).

Example 335

Production of (R)-2-((2-(5-bromo-1'-(methoxycarbonyl)spiro[indoline-3,3'-pyrrolidin]-1-ylcarboxamido)thiazol-5-yl)thio)acetic acid The captioned compound was obtained in the form of a white solid by performing the same reactions and/or treatments as those in Example 29, with the exception that the (R)-methyl 5-bromo-1-((5-((2-ethoxy-2-oxoethyl)thio)thiazol-2-yl)carbamoyl)spiro[indoline-3,3'-pyrrolidine]-1'-carboxylate obtained in Example 333 was used instead of ethyl 2-((2-(1'-acetyl-5-bromospiro[indoline-3,3'-pyrrolidin]-1-ylcarboxamido)thiazol-5-yl)thio)acetate.

Example 336

Production of (S)-2-((2-(5-bromo-1'-(methoxycarbonyl)spiro[indoline-3,3'-pyrrolidin]-1-ylcarboxamido)thiazol-5-yl)thio)acetic acid The captioned compound was obtained in the form of a light yellow amorphous product by performing the same reactions and/or treatments as those in Example 29, with the exception that the (S)-methyl 5-bromo-1-((5-((2-ethoxy-2-oxoethyl)thio)thiazol-2-yl)carbamoyl)spiro[indoline-3,3'-pyrrolidine]-1'-carboxylate obtained in Example 334 was used instead of ethyl 2-((2-(1'-acetyl-5-bromospiro[indoline-3,3'-pyrrolidin]-1-ylcarboxamido)thiazol-5-yl)thio)acetate.

$^1$H-NMR (400 MHz, CDCl$_3$) δ: 2.01-2.24 (2H, m), 3.31-3.64 (9H, m), 4.09 (2H, s), 7.40 (1H, d, J=8.3 Hz), 7.50 (1H, s), 7.53 (1H, s), 7.91 (d, J=8.3 Hz), 11.5 (1H, brs).

Example 337

Production of (R)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Example 306, with the exception that the (R)-t-butyl spiro[indoline-3,3'-pyrrolidine]-1'-carboxylate synthesized by a method described in the known methods (International Publication WO2006/090261 etc.) or a method similar thereto was used instead of the t-butyl 5-bromospiro[indoline-3,3'-pyrrolidine]-1'-carboxylate obtained as an intermediate of Example 306.

Example 338

Production of (S)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Example 306, with the exception that the (S)-t-butyl spiro[indoline-3,3'-pyrrolidine]-1'-carboxylate synthesized by a method described in the known methods (International Publication WO2006/090261 etc.) or a method similar thereto was used instead of the t-butyl 5-bromospiro[indoline-3,3'-pyrrolidine]-1'-carboxylate obtained as an intermediate of Example 306.

Example 339

Production of (R)-3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the (R)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate obtained in Example 337 was used instead of t-butyl 5-bromo-1-((5-chlorothiazol-2-yl)carbamoyl)spiro[indoline-3,3'-pyrrolidine]-1'-carboxylate.

Example 340

Production of (S)-3-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)propionic acid The captioned compound was obtained in the form of a white solid by performing the same reactions and/or treatments as those in Example 2, with the exception that the (S)-methyl 5-(N-benzyl-N-(3-(t-butoxy)-3-oxopropyl)sulfamoyl)-1-((5-methoxythiazolo[5,4-b]pyridin-2-yl)carbamoyl)spiro[indoline-3,3'-pyrrolidine]-1'-carboxylate obtained in Example 338 was used instead of t-butyl 5-bromo-1-((5-chlorothiazol-2-yl)carbamoyl)spiro[indoline-3,3'-pyrrolidine]-1'-carboxylate.

$^1$H-NMR (400 MHz, DMSO-d$_6$) δ: 2.14 (1H, m), 2.26-2.29 (3H, m), 3.25-3.64 (9H, m), 3.92 (3H, s), 4.22-4.40 (4H, m), 6.87 (1H, d, J=8.8 Hz), 7.29-7.37 (5H, m), 7.77-7.88 (3H, m), 8.19 (1H, m).

Example 341

Production of (R)-4-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)butyric acid The captioned compound was obtained in the form of a white solid by performing the same reactions and/or treatments as those in Steps 2 and 3 of Example 236, with the exceptions that t-butyl 4-(benzylamino)butanoate was used instead of 1-methylpiperazine, that (R)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.

Example 342

Production of (S)-4-(N-benzyl-1'-(methoxycarbonyl)-1-((5-methoxythiazolo[5,4-b]pyridin-2-yl)carbamoyl)spiro[indoline-3,3'-pyrrolidin]-5-ylsulfonamido)butyric acid The captioned compound was obtained in the form of a white solid by performing the same reactions and/or treatments as those in Steps 2 and 3 of Example 236, with the exceptions that t-butyl 4-(benzylamino)butanoate was used instead of 1-methylpiperazine, that (S)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.

$^1$H-NMR (400 MHz, CDCl$_3$) δ: 1.68 (2H, br), 2.12 (1H, m), 2.15-2.27 (3H, m), 3.12 (2H, br), 3.40-3.82 (7H, m), 3.91 (3H, s), 4.05-4.40 (4H, m), 6.77 (1H, d, J=8.8 Hz), 7.24-7.30 (5H, m), 7.51 (1H, s), 7.62-7.75 (2H, m), 8.19 (1H, d, J=8.6 Hz).

Example 343

Production of (R)-methyl 5-(N-benzyl-N-(2-methoxyethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Steps 2 and 3 of Example 236, with the exceptions that N-benzyl-2-methoxyethanamine was used instead of 1-methylpiperazine, that (R)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.

Example 344

Production of (S)-methyl 5-(N-benzyl-N-(2-methoxyethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Steps 2 and 3 of Example 236, with the exceptions that N-benzyl-2-methoxyethanamine was used instead of 1-methylpiperazine, that (S)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.
$^1$H-NMR (400 MHz, CDCl$_3$) δ: 2.03 (1H, m), 2.18 (1H, m), 3.13 (3H, s), 3.41-3.45 (4H, m), 3.47-3.78 (7H, m), 3.93 (3H, s), 3.98-4.12 (2H, m), 4.39 (2H, s), 6.76 (1H, d, J=8.8 Hz), 7.23-7.31 (5H, m), 7.53 (1H, s), 7.66 (1H, d, J=8.2 Hz), 7.75 (1H, d, J=8.5 Hz), 8.18 (1H, d, J=8.8 Hz).

Example 345

Production of (S)-methyl 5-(N-benzyl-N-(2-hydroxyethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Example 302, with the exceptions that the 2-((t-butyldimethylsilyl)oxy)-N-benzylethanamine synthesized by a method described in the known methods (International Publication WO2006/125972 etc.) or a reaction similar thereto was used instead of 2-((t-butyldimethylsilyl)oxy)-N-(cyclopropylmethyl)ethanamine, that (S)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.
$^1$H-NMR (400 MHz, CDCl$_3$) δ: 2.11 (1H, br), 2.24 (1H, br), 3.27 (2H, m), 3.25-3.76 (9H, m), 4.00 (3H, s), 4.05-4.13 (2H, m), 4.38 (2H, s), 6.78 (1H, d, J=8.8 Hz), 7.26-7.33 (5H, m), 7.52 (1H, s), 7.71 (1H, d, J=8.8 Hz), 7.79 (1H, d, J=8.3 Hz), 8.25 (1H, d, 8.8 Hz).

Example 346

Production of (R)-methyl 5-(N-benzyl-N-(2-hydroxyethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Example 303, with the exceptions that the 2-((t-butyldimethylsilyl)oxy)-N-benzylethanamine synthesized by a method described in the known methods (International Publication WO2006/125972 etc.) or a reaction similar thereto was used instead of 2-((t-butyldimethylsilyl)oxy)-N-(cyclopropylmethyl)ethanamine, that (R)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.

Example 347

Production of (S)-methyl 5-(N-benzyl-N-(2-(dimethylamino)ethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Steps 2 and 3 of Example 236, with the exceptions that N-benzyl-N',N'-dimethylethane-1,2-diamine was used instead of 1-methylpiperazine, that (S)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.
$^1$H-NMR (400 MHz, CDCl$_3$) δ: 2.08 (6H, s), 2.19-2.31 (4H, m), 3.20 (2H, m), 3.43-3.76 (7H, m), 3.99 (3H, s), 4.04-4.15 (2H, m), 4.35 (2H, m), 6.78 (1H, d, J=8.8 Hz), 7.27-7.30 (5H, m), 7.61 (1H, s), 7.68 (1H, d, J=8.8 Hz), 7.78 (1H, d, J=8.3 Hz), 8.25 (1H, d, J=7.8 Hz).

Example 348

Production of (R)-methyl 5-(N-benzyl-N-(2-(dimethylamino)ethyl)sulfamoyl)-1-((5-methoxythiazolo[5,4-b]pyridin-2-yl)carbamoyl)spiro[indoline-3,3'-pyrrolidine]-1'-carboxylate The captioned compound was obtained in the form of a white solid by performing the same reactions and/or treatments as those in Steps 2 and 3 of Example 236, with the exceptions that N-benzyl-N',N'-dimethylethane-1,2-diamine was used instead of 1-methylpiperazine, that (R)-t-butyl spiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of the acetyl chloride in Example 1, which was cited in Step 3 of Example 236.

Example 349

Production of (R)-1'-acetyl-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exception that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate.

Example 350

Production of (R)-5-chloro-N-(5-chlorothiazol-2-yl)-1'-formylspiro[indoline-3,3'-pyrrolidine]-1-carboxamide The captioned compound was obtained in the form of a white solid by performing the same reactions and/or treatments as those in Examples 1, 2, and 23, with the exception that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate.

$^1$H-NMR (400 MHz, DMSO-$d_6$) δ: 2.07-2.37 (2H, m), 3.26-3.67 (3H, m), 3.75-3.90 (1H, m), 3.95-4.23 (2H, m), 7.26-7.34 (1H, m), 7.39-7.53 (2H, m), 7.88-8.00 (1H, m), 8.18-8.29 (1H, m).

Example 351

Production of (S)-methyl 5-chloro-1-((5-chlorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and that methyl chloroformate was used instead of acetyl chloride.

$^1$H-NMR (400 MHz, DMSO-$d_6$) δ: 2.01-2.32 (2H, m), 3.24-3.71 (7H, m), 3.99-4.23 (2H, m), 7.29 (1H, d, J=8.3 Hz), 7.45 (1H, s), 7.50 (1H, s), 7.92 (1H, d, J=8.3 Hz), 11.10-11.52 (1H, brs).

Example 352

Production of (S)-5-chloro-N-(5-chlorothiazol-2-yl)-1'-(methylsulfonyl)spiro[indoline-3,3'-pyrrolidine]-1-carboxamide The captioned compound was obtained in the form of a white solid by performing the same reactions and/or treatments as those in Examples 1, 2, and 3, with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and that methanesulfonic acid chloride was used instead of acetyl chloride.

Example 353

Production of (R)-1'-(2-aminoacetyl)-5-chloro-N-(5-chlorothiazol-2-yl)spiro[indoline-3,3'-pyrrolidine]-1-carboxamide The captioned compound was obtained in the form of a white solid by performing the same reactions and/or treatments as those in Examples 1, 2, 19, and 20, with the exception that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate.

$^1$H-NMR (400 MHz, CDCl$_3$) δ: 1.99-2.17 (1H, m), 2.17-2.34 (1H, m), 3.37-4.18 (9H, m), 6.92 (1H, d, J=2.4 Hz), 7.12 (1H, s), 7.20-7.35 (1H, m), 7.97 (1H, d, J=8.8 Hz), 8.79-9.04 (1H, brs).

Example 354

Production of (R)-1'-acetyl-5-chloro-N-(5-fluorothiazol-2-yl)spiro[indoline-3,3'-pyrrolidine]-1-carboxamide The captioned compound was obtained in the form of a white solid by performing the same reactions and/or treatments as those in Examples 1, 2, and 3, with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

Example 355

Production of (S)-methyl 5-chloro-1-((5-fluorothiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 2-amino-5-fluorothiazole hydrochloride was used instead of 2-amino-5-chlorothiazole hydrochloride.

$^1$H-NMR (400 MHz, CDCl$_3$) δ: 1.99-2.17 (1H, m), 2.17-2.34 (1H, m), 3.37-4.18 (9H, m), 6.92 (1H, d, J=2.4 Hz), 7.12 (1H, s), 7.20-7.35 (1H, m), 7.97 (1H, d, J=8.8 Hz), 8.79-9.04 (1H, brs).

Example 356

Production of (S)-methyl 5-chloro-1-((5-methylthiazol-2-yl)carbamoyl)spiro[indoline-3,3'-pyrrolidine]-1'-carboxylate The captioned compound was obtained in the form of a white solid by performing the same reactions and/or treatments as those in Examples 1, 2, and 3, with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 2-amino-5-methylthiazole was used instead of 2-amino-5-chlorothiazole hydrochloride.

Example 357

Production of (S)-methyl 5-chloro-1-((5-((3-ethoxy-3-oxopropyl)thio)thiazol-2-yl)carbamoyl)spiro[indoline-3,3'-pyrrolidine]-1'-carboxylate The captioned compound was obtained in the form of a white solid by performing the same reactions and/or treatments as those in Steps 2 and 3 of Example 57 with the exception that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and thereafter, by performing the same reactions and/or treatments as those in Example 90 with the exception that the ethyl 3-((2-aminothiazol-5-yl)thio)propanoate synthesized by a method described in the known methods (International Publication WO2005/066145 etc.) or a method similar thereto was used instead of 4-((dimethylamino)methyl)thiazole-2-amine.

Example 358

Production of (S)-3-((2-(5-chloro-1'-(methoxycarbonyl)spiro[indoline-3,3'-pyrrolidin]-1-ylcarboxamido) thiazol-5-yl)thio)propionic acid The captioned compound was obtained in the form of a white solid by performing the same reactions and/or treatments as those in Step 2 of Example 17, with the exception that the (S)-methyl 5-chloro-1-((5-((3-ethoxy-3-oxopropyl) thio)thiazol-2-yl)carbamoyl)spiro[indoline-3,3'-pyrrolidine]-1'-carboxylate obtained in Example 357 was used instead of 5-bromo-N-(5-chlorothiazol-2-yl)-1'-(2-acetoxyacetyl)spiro[indoline-3,3'-pyrrolidine]-1-carboxamide.

Example 359

Production of (R)-ethyl 3-((2-(1'-acetyl-5-chlorospiro[indoline-3,3'-pyrrolidin]-1-ylcarboxamido) thiazol-5-yl)thio)propanoate The captioned compound was obtained in the form of a white solid by performing the same reactions and/or treatments as those in Steps 2 and 3 of Example 57 with the exceptions that (S)-t-butyl 5-chlorospiro[indoline-3,3'-pyrrolidine]-1'-carboxylate was used instead of t-butyl 5-chlorospiro[indoline-3,3'-pyrrolidine]-1'-carboxylate and that acetyl chloride was used instead of t-butyl bromoacetate, and thereafter, by performing the same reactions and/or treatments as those in Example 90 with the exception that the ethyl 3-((2-aminothiazol-5-yl)thio)propanoate synthesized by a method described in the known methods (International Publication WO2005/066145 etc.) or a method similar thereto was used instead of 4-((dimethylamino)methyl)thiazole-2-amine.

Example 360

Production of (R)-3-((2-(1'-acetyl-5-chlorospiro[indoline-3,3'-pyrrolidin]-1-ylcarboxamido)thiazol-5-yl)thio)propionic acid The captioned compound was obtained in the form of a white solid by performing the same reactions and/or treatments as those in Step 2 of Example 17, with the exception that the (R)-ethyl 3-((2-(1'-acetyl-5-chlorospiro[indoline-3, 3'-pyrrolidin]-1-ylcarboxamido)thiazol-5-yl)thio)propanoate obtained in Example 359 was used instead of 5-bromo-N-(5-chlorothiazol-2-yl)-1'-(2-acetoxyacetyl)spiro [indoline-3,3'-pyrrolidine]-1-carboxamide.

Example 361

Production of (R)-t-butyl 3-((2-(1'-acetyl-5-chlorospiro[indoline-3,3'-pyrrolidin]-1-ylcarboxamido) thiazol-5-yl)thio)propanoate The captioned compound was obtained in the form of a white solid by performing the same reactions and/or treatments as those in Steps 2 and 3 of Example 57 with the exceptions that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate and that acetyl chloride was used instead of t-butyl bromoacetate, and thereafter, by performing the same reactions and/or treatments as those in Example 90 with the exception that the t-butyl 3-((2-aminothiazol-5-yl)thio)propanoate synthesized by a method described in the known methods (International Publication WO2005/066145 etc.) or a method similar thereto was used instead of 4-((dimethylamino)methyl)thiazole-2-amine.

Example 362

Production of (S)-methyl 1-((5-((3-(t-butoxy)-3-oxopropyl)thio)thiazol-2-yl)carbamoyl)-5-chlorospiro [indoline-3,3'-pyrrolidine]-1'-carboxylate The captioned compound was obtained in the form of a white solid by performing the same reactions and/or treatments as those in Steps 2 and 3 of Example 57 with the exception that (S)-t-butyl 5-chlorospiro[indoline-3,3'-pyrrolidine]-1'-carboxylate was used instead of t-butyl 5-bromospiro[indoline-3,3'-pyrrolidine]-1'-carboxylate, and thereafter, by performing the same reactions and/or treatments as those in Example 90 with the exception that t-butyl 3-((2-aminothiazol-5-yl)thio)propanoate was used instead of 4-((dimethylamino)methyl)thiazole-2-amine.

Production of Examples 363, 364, 369, 386, 387, 388, 389, 391, 392, 393, 394, 395, 396, 436, 437, 444, 456, 483, and 486

The below captioned compounds were all obtained in the form of a white solid by performing the same reactions and/or treatments as those in Examples 1, 2, and 3, with the exception that the below mentioned raw material compounds were used instead of t-butyl 5-bromospiro[indoline-3,3'-pyrrolidine]-1'-carboxylate and 2-amino-5-chlorothiazole hydrochloride.

Example 363

1'-Acetyl-5-chloro-N-(5-methyl-1H-pyrazol-3-yl) spiro[indoline-3,3'-pyrrolidine]-1-carboxamide t-Butyl 5-chlorospiro[indoline-3,3'-pyrrolidine]-1'-carboxylate and 3-amino-5-methylpyrazole The compounds in the parentheses that are described below the captioned compound are successively raw material compounds that were used instead of t-butyl 5-bromospiro[indoline-3,3'-pyrrolidine]-1'-carboxylate and 2-amino-5-chlorothiazole hydrochloride. The same shall apply hereafter.

Example 364

1'-Acetyl-5-cyano-N-(5-fluorothiazol-2-yl)spiro[indoline-3,3'-pyrrolidine]-1-carboxamide t-Butyl 5-cyanospiro[indoline-3,3'-pyrrolidine]-1'-carboxylate and 2-amino-5-fluorothiazole hydrochloride Example 369

1'-Acetyl-5-cyano-N-(5-methoxythiazol-2-yl)spiro [indoline-3,3'-pyrrolidine]-1-carboxamide t-Butyl 5-cyanospiro[indoline-3,3'-pyrrolidine]-1'-carboxylate and 2-amino-5-methoxythiazole

Example 386

1'-Acetyl-5-chloro-N-(isoxazol-3-yl)spiro[indoline-3,3'-pyrrolidine]-1-carboxamide t-Butyl 5-chlorospiro[indoline-3,3'-pyrrolidine]-1'-carboxylate and 3-aminoisoxazole $^1$H-NMR (400 MHz, DMSO-d$_6$) δ: 1.92-2.34 (5H, m), 3.27-3.79 (4H, m), 4.04-4.25 (2H, m), 6.87-6.91 (1H, m), 7.25-7.32 (1H, m), 7.41-7.49 (1H, m), 7.87-7.95 (1H, m), 8.76 (1H, br), 9.86 (1H, br).

Example 387

1'-Acetyl-5-chloro-N-(4,5,6,7-tetrahydrobenzo[d]thiazol-2-yl)spiro[indoline-3,3'-pyrrolidine]-1-carboxamide t-Butyl 5-chlorospiro[indoline-3,3'-pyrrolidine]-1'-carboxylate and 4,5,6,7-tetrahydro-1,3-benzothiazole-2-amine $^1$H-NMR (400 MHz, CDCl$_3$) δ: 1.85 (4H, br), 2.08-2.33 (5H, m), 2.57 (4H, m), 3.54-3.92 (4H, m), 4.01-4.13 (2H, m), 7.07 (1H, m), 7.22 (1H, m), 8.05 (1H, m).

Example 388

1'-Acetyl-5-chloro-N-(4,5-dihydrothiazol-2-yl)spiro[indoline-3,3'-pyrrolidine]-1-carboxamide t-Butyl 5-chlorospiro[indoline-3,3'-pyrrolidine]-1'-carboxylate and 2-amino-2-thiazoline $^1$H-NMR (400 MHz, CDCl$_3$) δ: 2.01-2.25 (5H, m), 3.30 (2H, t, J=7.6 Hz), 3.48-3.89 (6H, m), 3.97-4.17 (2H, m), 7.06 (1H, dd, J=2.2, 12.0 Hz), 7.17-7.24 (1H, m), 8.00-8.09 (1H, m).

Example 389

1'-Acetyl-5-chloro-N-(5-methylpyrazin-2-yl)spiro[indoline-3,3'-pyrrolidine]-1-carboxamide t-Butyl 5-chlorospiro[indoline-3,3'-pyrrolidine]-1'-carboxylate and 2-amino-5-methylpyrazine $^1$H-NMR (400 MHz, CDCl$_3$) δ: 2.08-2.38 (5H, m), 2.53 (3H, s), 3.58-3.69 (2H, m), 3.73-3.92 (2H, m), 3.99-4.10 (2H, m), 7.11 (2H, m), 7.92 (1H, m), 8.09 (1H, m), 9.32 (1H, m).

Example 391

1'-Acetyl-5-chloro-N-(6-chloropyrazin-2-yl)spiro[indoline-3,3'-pyrrolidine]-1-carboxamide t-Butyl 5-chlorospiro[indoline-3,3'-pyrrolidine]-1'-carboxylate and 2-amino-6-chloropyrazine

Example 392

1'-Acetyl-N-(5-bromopyrazin-2-yl)-5-chlorospiro[indoline-3,3'-pyrrolidine]-1-carboxamide t-Butyl 5-chlorospiro[indoline-3,3'-pyrrolidine]-1'-carboxylate and 2-amino-5-bromopyrazine

Example 393

1'-Acetyl-5-chloro-N-(pyrazin-2-yl)spiro[indoline-3,3'-pyrrolidine]-1-carboxamide t-Butyl 5-chlorospiro[indoline-3,3'-pyrrolidine]-1'-carboxylate and 2-aminopyrazine

Example 394

1'-Acetyl-5-chloro-N-(5-methoxypyrazin-2-yl)spiro[indoline-3,3'-pyrrolidine]-1-carboxamide t-Butyl 5-chlorospiro[indoline-3,3'-pyrrolidine]-1'-carboxylate and 2-amino-5-methoxypyrazine

Example 395

1'-Acetyl-5-chloro-N-(5-chloropyrazin-2-yl)spiro[indoline-3,3'-pyrrolidine]-1-carboxamide t-Butyl 5-chlorospiro[indoline-3,3'-pyrrolidine]-1'-carboxylate and 2-amino-5-chloropyrazine

Example 396

1'-Acetyl-5-chloro-N-(pyridazin-3-yl)spiro[indoline-3,3'-pyrrolidine]-1-carboxamide t-Butyl 5-chlorospiro[indoline-3,3'-pyrrolidine]-1'-carboxylate and 3-aminopyridazine $^1$H-NMR (400 MHz, DMSO-d$_6$) δ: 1.92-2.35 (5H, m), 3.24-3.79 (4H, m), 4.17-4.35 (2H, m), 7.26-7.32 (1H, m), 7.43-7.48 (1H, m), 7.62-7.69 (1H, m), 7.87-7.95 (1H, m), 8.09-8.15 (1H, m), 8.92 (1H, br), 9.77-9.90 (1H, m).

Example 436

1'-Acetyl-N-(5-fluorothiazol-2-yl)-5-(trifluoromethyl)spiro[indoline-3,3'-pyrrolidine]-1-carboxamide tert-Butyl 5-(trifluoromethyl)spiro[indoline-3,3'-pyrrolidine]-1'-carboxylate and 2-amino-5-fluorothiazole hydrochloride

Example 437

1'-Acetyl-N-(5-methoxythiazol-2-yl)-5-(trifluoromethyl)spiro[indoline-3,3'-pyrrolidine]-1-carboxamide tert-Butyl 5-(trifluoromethyl)spiro[indoline-3,3'-pyrrolidine]-1'-carboxylate and 2-amino-5-methoxythiazole

Example 444

1'-Acetyl-N-(5-methylpyrazin-2-yl)-5-(trifluoromethyl)spiro[indoline-3,3'-pyrrolidine]-1-carboxamide tert-Butyl 5-(trifluoromethyl)spiro[indoline-3,3'-pyrrolidine]-1'-carboxylate and 2-amino-5-methylpyrazine

Example 456

1'-Acetyl-5-chloro-N-(5-cyanothiazol-2-yl)spiro[indoline-3,3'-pyrrolidine]-1-carboxamide t-Butyl 5-chlorospiro[indoline-3,3'-pyrrolidine]-1'-carboxylate and 2-amino-5-cyanothiazole ¹H-NMR (400 MHz, DMSO-d$_6$) δ: 1.95-2.22 (5H, m), 3.30 (2H, m), 3.60 (2H, m), 3.92 (2H, m), 7.18 (1H, m), 7.26 (1H, s), 7.87 (1H, s), 8.07 (1H, m).

Example 483

(R)-1'-Acetyl-5-cyano-N-(5-fluorothiazol-2-yl)spiro[indoline-3,3'-pyrrolidine]-1-carboxamide (S)-t-Butyl 5-cyanospiro[indoline-3,3'-pyrrolidine]-1'-carboxylate and 2-amino-5-fluorothiazole hydrochloride Example 486

(R)-1'-Acetyl-N-(5-methoxythiazol-2-yl)-5-(trifluoromethyl)spiro[indoline-3,3'-pyrrolidine]-1-carboxamide tert-Butyl(S)-5-(trifluoromethyl)spiro[indoline-3,3'-pyrrolidine]-1'-carboxylate and 2-amino-5-methoxythiazole Production of Examples 379, 449, 450, 457, 462, 468, 480, and 482

The below captioned compounds were all obtained in the form of a white solid by performing the same reactions and/or treatments as those in Examples 1, 2, and 3, with the exception that the below mentioned raw material compounds were used instead of t-butyl 5-bromospiro[indoline-3,3'-pyrrolidine]-1'-carboxylate and acetyl chloride.

Example 379

5-Chloro-N1-(5-chlorothiazol-2-yl)-N1'-ethylspiro[indoline-3,3'-pyrrolidine]-1,1'-dicarboxamide (t-Butyl 5-chlorospiro[indoline-3,3'-pyrrolidine]-1'-carboxylate and ethyl isocyanate)
The compounds in the parentheses that are described below the captioned compound are successively raw material compounds that were used instead of t-butyl 5-bromospiro[indoline-3,3'-pyrrolidine]-1'-carboxylate and acetyl chloride. The same shall apply hereafter.

Example 449

5-Chloro-N-(5-chlorothiazol-2-yl)-1'-(methylcarbamothioyl)spiro[indoline-3,3'-pyrrolidine]-1-carboxamide (t-Butyl 5-chlorospiro[indoline-3,3'-pyrrolidine]-1'-carboxylate and methyl isothiocyanate used instead of acetyl chloride)
¹H-NMR (400 MHz, CDCl$_3$) δ: 2.22 (1H, m), 2.38 (1H, m), 3.16 (3H, d, J=4.2 Hz), 3.70-4.05 (6H, m), 5.43 (1H, d, J=4.2 Hz), 7.11 (1H, s), 7.16 (1H, s), 7.26 (1H, d, J=8.6 Hz), 7.97 (1H, d, J=8.6 Hz).

Example 450

5-Chloro-N-(5-chlorothiazol-2-yl)-1'-(2-ethoxy-3,4-dioxocyclobut-1-en-1-yl)spiro[indoline-3,3'-pyrrolidine]-1-carboxamide t-Butyl 5-chlorospiro[indoline-3,3'-pyrrolidine]-1'-carboxylate and 3,4-diethoxy-3-cyclobutene-1,2-dione ¹H-NMR (400 MHz, CDCl$_3$) δ: 1.45 (3H, m), 2.25 (1H, m), 2.32 (1H, m), 3.65-4.23 (6H, m), 4.78 (2H, m), 7.10-7.15 (2H, m), 7.26 (1H, m), 8.01 (1H, m).

Example 457

Ethyl 2-(5-chloro-1-((5-chlorothiazol-2-yl)carbamoyl)spiro[indoline-3,3'-pyrrolidin]-1'-ylcarboxamido)acetate t-Butyl 5-chlorospiro[indoline-3,3'-pyrrolidine]-1'-carboxylate and ethyl isocyanatoacetate Example 462

Ethyl 3-(5-chloro-1-((5-chlorothiazol-2-yl)carbamoyl)spiro[indoline-3,3'-pyrrolidin]-1'-ylcarboxamido)propionate t-Butyl 5-chlorospiro[indoline-3,3'-pyrrolidine]-1'-carboxylate and ethyl 3-isocyanatopropionate Example 468

Ethyl 4-(5-chloro-1-((5-chlorothiazol-2-yl)carbamoyl)spiro[indoline-3,3'-pyrrolidin]-1'-ylcarboxamido)butanoate t-Butyl 5-chlorospiro[indoline-3,3'-pyrrolidine]-1'-carboxylate and ethyl 4-isocyanatobutanoate Example 480

5-Chloro-N1-(5-chlorothiazol-2-yl)-N1'-methoxyspiro[indoline-3,3'-pyrrolidine]-1,1'-dicarboxamide tert-Butyl 5-chlorospiro[indoline-3,3'-pyrrolidine]-1'-carboxylate and 4-nitrophenyl methoxycarbamate
¹H-NMR (400 MHz, DMSO-d$_6$) δ: 2.02 (1H, m), 2.20 (1H, m), 3.30 (2H, m), 3.45 (2H, m), 3.52 (3H, s), 4.06 (2H, m), 7.24 (1H, 1H, d, J=8.6 Hz), 7.36 (1H, br), 7.45 (1H, s), 7.89 (1H, d, J=8.6 Hz), 9.45 (1H, s).

Example 482

5-Chloro-N-(5-chlorothiazol-2-yl)-1'-(N-methylsulfamoyl)spiro[indoline-3,3'-pyrrolidine]-1-carboxamide tert-Butyl 5-chlorospiro[indoline-3,3'-pyrrolidine]-1'-carboxylate and methylsulfamoyl chloride
¹H-NMR (400 MHz, DMSO-d$_6$) δ: 2.10-2.19 (1H, m), 2.20-2.35 (1H, m), 2.61 (3H, d, J=4.9 Hz), 3.19-3.58 (4H, m), 4.08-4.25 (2H, m), 7.08-7.13 (1H, m), 7.25-7.34 (1H, m), 7.40-7.55 (2H, m), 7.88-7.98 (1H, m).

Production of Examples 365, 366, 368, 371, 435, and 441

The below captioned compounds were obtained in the form of a white solid by performing the same reactions and/or treatments as those in Examples 1, 2, and 17, with the exception that the below mentioned raw material compounds were used instead of t-butyl 5-bromospiro[indoline-3,3'-pyrrolidine]-1'-carboxylate and 2-amino-5-chlorothiazole hydrochloride.

Example 365

5-Cyano-N-(5-fluorothiazol-2-yl)-1'-(2-hydroxyacetyl)spiro[indoline-3,3'-pyrrolidine]-1-carboxamide t-Butyl 5-cyanospiro[indoline-3,3'-pyrrolidine]-1'-carboxylate and 2-amino-5-fluorothiazole The compounds in the parentheses that are described below the captioned compound are successively raw material compounds that were used instead of t-butyl 5-bromospiro[indoline-3,3'-pyrrolidine]-1'-carboxylate and 2-amino-5-chlorothiazole hydrochloride. The same shall apply hereafter.

Example 366

5-Chloro-1'-(2-hydroxyacetyl)-N-(5-methoxythiazol-2-yl)spiro[indoline-3,3'-pyrrolidine]-1-carboxamide t-Butyl 5-chlorospiro[indoline-3,3'-pyrrolidine]-1'-carboxylate and 2-amino-5-methoxythiazole

Example 368

5-Chloro-N-(5-fluorothiazol-2-yl)-1'-(2-hydroxyacetyl)spiro[indoline-3,3'-pyrrolidine]-1-carboxamide t-Butyl 5-chlorospiro[indoline-3,3'-pyrrolidine]-1'-carboxylate and 2-amino-5-fluorothiazole hydrochloride

Example 371

5-Cyano-1'-(2-hydroxyacetyl)-N-(5-methoxythiazol-2-yl)spiro[indoline-3,3'-pyrrolidine]-1-carboxamide t-Butyl 5-cyanospiro[indoline-3,3'-pyrrolidine]-1'-carboxylate and 2-amino-5-methoxythiazole

Example 435

1'-(2-Hydroxyacetyl)-N-(5-methylpyrazin-2-yl)-5-(trifluoromethyl)spiro[indoline-3,3'-pyrrolidine]-1-carboxamide tert-Butyl 5-(trifluoromethyl)spiro[indoline-3,3'-pyrrolidine]-1'-carboxylate and 2-amino-5-methylpyrazine

Example 441

1'-(2-Hydroxyacetyl)-N-(5-methoxythiazol-2-yl)-5-(trifluoromethyl)spiro[indoline-3,3'-pyrrolidine]-1-carboxamide tert-Butyl 5-(trifluoromethyl)spiro[indoline-3,3'-pyrrolidine]-1'-carboxylate and 2-amino-5-methoxythiazole

Production of Examples 367, 370, 372, 375, 440, 442, and 443

The below captioned compounds were obtained in the form of a white solid by performing the same reactions and/or treatments as those in Examples 1, 2, 3, and 45, with the exception that the below mentioned raw material compounds were used instead of t-butyl 5-bromospiro[indoline-3,3'-pyrrolidine]-1'-carboxylate, acetyl chloride, 2-amino-5-chlorothiazole hydrochloride, and a saturated solution of ammonia-methanol.

Example 367

5-Chloro-N-(5-fluorothiazol-2-yl)-1'-(2-(methylamino)-2-oxoacetyl)spiro[indoline-3,3'-pyrrolidine]-1-carboxamide (t-Butyl 5-chlorospiro[indoline-3,3'-pyrrolidine]-1'-carboxylate, ethyl chloroglyoxylate, 2-amino-5-fluorothiazole hydrochloride, a solution of methylamine-tetrahydrofuran)

The compounds in the parentheses that are described below the captioned compound are successively raw material compounds that were used instead of t-butyl 5-bromospiro[indoline-3,3'-pyrrolidine]-1'-carboxylate, acetyl chloride, 2-amino-5-chlorothiazole hydrochloride, and a saturated solution of ammonia-methanol. The same shall apply hereafter.

Example 370

5-Chloro-N-(5-methoxythiazol-2-yl)-1'-(2-(methylamino)-2-oxoacetyl)spiro[indoline-3,3'-pyrrolidine]-1-carboxamide (t-Butyl 5-chlorospiro[indoline-3,3'-pyrrolidine]-1'-carboxylate, ethyl chloroglyoxylate, 2-amino-5-methoxythiazole, and a solution of methylamine-tetrahydrofuran)

Example 372

5-Cyano-N-(5-methoxythiazol-2-yl)-1'-(2-(methylamino)-2-oxoacetyl)spiro[indoline-3,3'-pyrrolidine]-1-carboxamide (t-Butyl 5-cyanospiro[indoline-3,3'-pyrrolidine]-1'-carboxylate, ethyl chloroglyoxylate, 2-amino-5-methoxythiazole, and a solution of methylamine-tetrahydrofuran)

Example 375

5-Chloro-N-(5-fluorothiazol-2-yl)-1'-(2-(methylamino)-2-oxoacetyl)spiro[indoline-3,3'-pyrrolidine]-1-carboxamide (t-Butyl 5-cyanospiro[indoline-3,3'-pyrrolidine]-1'-carboxylate, ethyl chloroglyoxylate, 2-amino-5-fluorothiazole hydrochloride, and a solution of methylamine-tetrahydrofuran)

Example 440

1'-(2-(Methylamino)-2-oxoacetyl)-N-(5-methylpyrazin-2-yl)-5-(trifluoromethyl)spiro[indoline-3,3'-pyrrolidine]-1-carboxamide (tert-Butyl 5-(trifluoromethyl)spiro[indoline-3,3'-pyrrolidine]-1'-carboxylate, ethyl chloroglyoxylate, 2-amino-5-methylpyrazine, and a solution of methylamine-tetrahydrofuran)

Example 442

N-(5-Methoxythiazol-2-yl)-1'-(2-(methylamino)-2-oxoacetyl)-5-(trifluoromethyl)spiro[indoline-3,3'-pyrrolidine]-1-carboxamide (tert-Butyl 5-(trifluoromethyl)spiro[indoline-3,3'-pyrrolidine]-1'-carboxylate, ethyl chloroglyoxylate, 2-amino-5-methoxythiazole, and a solution of methylamine-tetrahydrofuran)

Example 443

N-(5-Chlorothiazol-2-yl)-1'-(2-(methylamino)-2-oxoacetyl)-5-(trifluoromethyl)spiro[indoline-3,3'-pyrrolidine]-1-carboxamide (tert-Butyl 5-(trifluoromethyl)spiro[indoline-3,3'-pyrrolidine]-1'-carboxylate, ethyl chloroglyoxylate, 2-amino-5-chlorothiazole hydrochloride, and a solution of methylamine-tetrahydrofuran)

Example 373

Production of 5-chloro-N1-(5-chlorothiazol-2-yl)-N1'-methylspiro[indoline-3,3'-pyrrolidine]-1,1'-dicarboxamide The 5-chloro-N-(5-chlorothiazol-2-yl)spiro[indoline-3,3'-pyrrolidine]-1-carboxamide (50.0 mg, 0.135 mmol) obtained as an intermediate of Example 39 was dissolved in tetrahydrofuran (1.0 mL). Thereafter, phenyl N-carbamate (22.5 mg, 0.15 mmol) and a 1 N aqueous solution of sodium hydroxide (150 µL, 0.15 mmol) were added to the above obtained solution under cooling on ice, and the thus obtained mixture was then stirred for 3 hours. Thereafter, the reaction solution was diluted with water, and was then extracted with ethyl acetate. The organic layer was washed with brine, and was then dried over anhydrous sodium sulfate, followed by concentration in vacuo. The obtained residue was purified by silica gel column chromatography (chloroform:methanol=10:1) to obtain the captioned compound (30.0 mg, 52%) in the form of a white solid.

$^1$H-NMR (400 MHz, CDCl$_3$) δ: 2.10-2.40 (2H, m), 2.82-2.88 (3H, m), 3.42-3.75 (4H, m), 3.98-4.06 (2H, m), 4.23 (1H, br), 7.08-7.14 (1H, m), 7.17-7.20 (1H, m), 7.22-7.26 (1H, m), 7.94-8.00 (1H, m).

Example 374

Production of (R)-5-chloro-N1-(5-fluorothiazol-2-yl)-N1'-methylspiro[indoline-3,3'-pyrrolidine]-1,1'-dicarboxamide The captioned compound was obtained in the form of a white solid by performing the same reactions and/or treatments as those in Example 373, with the exceptions that the (S)-5-chloro-N-(5-chlorothiazol-2-yl)spiro[indoline-3,3'-pyrrolidine]-1-carboxamide obtained as an intermediate of Example 52 was used instead of 5-chloro-N-(5-chlorothiazol-2-yl)spiro[indoline-3,3'-pyrrolidine]-1-carboxamide, and that 2-amino-5-fluorothiazole was used instead of 2-amino-5-chlorothiazole hydrochloride.

Production of Examples 376, 377, 380, 381, 382, 390, 432, 433, 434, 438, 439, 485, 487, 488, and 489

The below captioned compounds were obtained in the form of a white solid by performing the same reactions and/or treatments as those in Examples 1, 2, and 373, with the exception that the below mentioned raw material compounds were used instead of t-butyl 5-bromospiro[indoline-3,3'-pyrrolidine]-1'-carboxylate and 2-amino-5-chlorothiazole hydrochloride.

Example 376

(R)—N1-(5-Chlorothiazol-2-yl)-5-cyano-N1'-methylspiro[indoline-3,3'-pyrrolidine]-1,1'-dicarboxamide ((S)-t-Butyl 5-cyanospiro[indoline-3,3'-pyrrolidine]-1'-carboxylate synthesized by a method described in the known methods (International Publication WO2006/090261 etc.) or a method similar thereto, and 2-amino-5-chlorothiazole hydrochloride)

The compounds in the parentheses that are described below the captioned compound are successively raw material compounds that were used instead of t-butyl 5-bromospiro[indoline-3,3'-pyrrolidine]-1'-carboxylate and 2-amino-5-chlorothiazole hydrochloride. The same shall apply hereafter.

Example 377

(R)-5-Cyano-N1-(5-fluorothiazol-2-yl)-N1'-methylspiro[indoline-3,3'-pyrrolidine]-1,1'-dicarboxamide (S)-t-Butyl 5-cyanospiro[indoline-3,3'-pyrrolidine]-1'-carboxylate and 2-amino-5-fluorothiazole hydrochloride

Example 380

(R)-5-Chloro-N1-(5-methoxythiazol-2-yl)-N1'-methylspiro[indoline-3,3'-pyrrolidine]-1,1'-dicarboxamide (S)-t-Butyl 5-chlorospiro[indoline-3,3'-pyrrolidine]-1'-carboxylate and 2-amino-5-methoxythiazole

Example 381

(R)-5-Cyano-N1-(5-methoxythiazol-2-yl)-N1'-methylspiro[indoline-3,3'-pyrrolidine]-1,1'-dicarboxamide (S)-t-Butyl 5-cyanospiro[indoline-3,3'-pyrrolidine]-1'-carboxylate and 2-amino-5-methoxythiazole

Example 382

(R)-5-Chloro-N1'-methyl-N1-(5-methylthiazol-2-yl)spiro[indoline-3,3'-pyrrolidine]-1,1'-dicarboxamide (S)-t-Butyl 5-chlorospiro[indoline-3,3'-pyrrolidine]-1'-carboxylate and 2-amino-5-methylthiazole

Example 390

(R)-5-Chloro-N1'-methyl-N1-(5-methylpyrazin-2-yl)spiro[indoline-3,3'-pyrrolidine]-1,1'-dicarboxamide ((S)-t-Butyl 5-chlorospiro[indoline-3,3'-pyrrolidine]-1'-carboxylate synthesized by a method described in the known

Example 432

N1-(5-Chlorothiazol-2-yl)-N1'-methyl-5-(trifluoromethyl)spiro[indoline-3,3'-pyrrolidine]-1,1'-dicarboxamide (tert-Butyl 5-(trifluoromethyl)spiro[indoline-3,3'-pyrrolidine]-1'-carboxylate obtained in Step 2 of Example 431, and 2-amino-5-chlorothiazole hydrochloride)

Example 433

N1'-Methyl-N1-(5-methylthiazol-2-yl)-5-(trifluoromethyl)spiro[indoline-3,3'-pyrrolidine]-1,1'-dicarboxamide tert-Butyl 5-(trifluoromethyl)spiro[indoline-3,3'-pyrrolidine]-1'-carboxylate and 2-amino-5-methylthiazole

Example 434

N1'-Methyl-N1-(5-methylpyrazin-2-yl)-5-(trifluoromethyl)spiro[indoline-3,3'-pyrrolidine]-1,1'-dicarboxamide tert-Butyl 5-(trifluoromethyl)spiro[indoline-3,3'-pyrrolidine]-1'-carboxylate and 2-amino-5-methylpyrazine

Example 438

N1-(5-Fluorothiazol-2-yl)-N1'-methyl-5-(trifluoromethyl)spiro[indoline-3,3'-pyrrolidine]-1,1'-dicarboxamide tert-Butyl 5-(trifluoromethyl)spiro[indoline-3,3'-pyrrolidine]-1'-carboxylate and 2-amino-5-fluorothiazole hydrochloride

Example 439

N1-(5-Methoxythiazol-2-yl)-N1'-methyl-5-(trifluoromethyl)spiro[indoline-3,3'-pyrrolidine]-1,1'-dicarboxamide tert-Butyl 5-(trifluoromethyl)spiro[indoline-3,3'-pyrrolidine]-1'-carboxylate and 2-amino-5-methoxythiazole

Example 485

(R)—N1'-Methyl-N1-(5-methylpyrazin-2-yl)-5-(trifluoromethyl)spiro[indoline-3,3'-pyrrolidine]-1,1'-dicarboxamide tert-Butyl(S)-5-(trifluoromethyl)spiro[indoline-3,3'-pyrrolidine]-1'-carboxylate and 2-amino-5-methylpyrazine

Example 487

(R)—N1-(5-Fluorothiazol-2-yl)-N1'-methyl-5-(trifluoromethyl)spiro[indoline-3,3'-pyrrolidine]-1,1'-dicarboxamide tert-Butyl(S)-5-(trifluoromethyl)spiro[indoline-3,3'-pyrrolidine]-1'-carboxylate and 2-amino-5-fluorothiazole hydrochloride

Example 488

(S)—N1-(5-Methoxythiazol-2-yl)-N1'-methyl-5-(trifluoromethyl)spiro[indoline-3,3'-pyrrolidine]-1,1'-dicarboxamide tert-Butyl(R)-5-(trifluoromethyl)spiro[indoline-3,3'-pyrrolidine]-1'-carboxylate and 2-amino-5-methoxythiazole

Example 489

(R)—N1-(5-Methoxythiazol-2-yl)-N1'-methyl-5-(trifluoromethyl)spiro[indoline-3,3'-pyrrolidine]-1,1'-dicarboxamide tert-Butyl(S)-5-(trifluoromethyl)spiro[indoline-3,3'-pyrrolidine]-1'-carboxylate and 2-amino-5-methoxythiazole Production of Examples 378 and 385

The below captioned compounds were obtained in the form of a white solid by performing the same reactions and/or treatments as those in Example 19, with the exception that the below mentioned raw material compounds were used instead of 5-bromo-N-(5-chlorothiazol-2-yl)spiro[indoline-3,3'-pyrrolidine]-1-carboxamide and N-Boc glycine.

Example 378

5-Chloro-N-(5-chlorothiazol-2-yl)-1'-(2-oxopropanoyl)spiro[indoline-3,3'-pyrrolidine]-1-carboxamide 5-Chloro-N-(5-chlorothiazol-2-yl)spiro[indoline-3,3'-pyrrolidine]-1-carboxamide and pyruvic acid The compounds in the parentheses that are described below the captioned compound are successively raw material compounds that were used instead of 5-bromo-N-(5-chlorothiazol-2-yl)spiro[indoline-3,3'-pyrrolidine]-1-carboxamide and N-Boc glycine. The same shall apply hereafter.

$^1$H-NMR (400 MHz, DMSO-$d_6$) δ: 2.00-2.43 (5H, m), 3.39-4.26 (6H, m), 7.27-7.33 (1H, m), 7.40-7.53 (2H, m), 7.87-7.99 (1H, m).

Example 385

5-Chloro-N-(5-chlorothiazol-2-yl)-1'-(2,2-difluoroacetyl)spiro[indoline-3,3'-pyrrolidine]-1-carboxamide 5-Chloro-N-(5-chlorothiazol-2-yl)spiro[indoline-3,3'-pyrrolidine]-1-carboxamide and difluoroacetic acid $^1$H-NMR (400 MHz, CDCl$_3$) δ: 2.16-2.41 (2H, m), 3.65-4.10 (6H, m), 6.07 (1H, m), 7.10-7.27 (3H, m), 7.99 (1H, m)

Example 383

Production of N1-(5-chlorothiazol-2-yl)-N1'-methyl-5-(methylsulfonyl)spiro[indoline-3,3'-pyrrolidine]-1,1'-dicarboxamide Step 1: t-Butyl spiro[indoline-3,3'-pyrrolidine]-1'-carboxylate (10.0 g, 36.4 mmol) was dissolved in methylene chloride (73 mL). Thereafter, triethylamine (15.2 mL, 109 mmol) and N-[2-(trimethylsilyl)ethoxycarbonyloxy]succinimide (14.2 g, 54.8 mmol) were added to the above obtained solution under cooling on ice, and the thus obtained mixture was then stirred at room temperature for 22 hours. Thereafter, the reaction solution was diluted with water, and was then extracted with chloroform. The organic layer was washed with brine, and was then dried over anhydrous sodium sulfate, followed by concentration in vacuo. The obtained residue was purified by silica gel column chromatography (hexane:ethyl acetate=5:1) to obtain 1-(2-(trimethylsilyl)ethyl) 1'-tert-butyl spiro[indoline-3,3'-pyrrolidine]-1,1'-dicarboxylate (16.1 g, quant.) in the form of a light yellow oily product.

$^1$H-NMR (400 MHz, CDCl$_3$) δ: 0.70 (9H, s), 1.12 (2H, br), 1.56 (9H, br), 2.00 (1H, m), 2.17 (1H, m), 3.38-3.75 (4H, m), 3.90 (2H, m), 4.32 (2H, m), 7.00 (1H, t, J=8.0 Hz), 7.13 (1H, d, J=8.0 Hz), 7.25 (1H, d, J=8.0 Hz), 7.89 (1H, br).

Step 2: 1-(2-(Trimethylsilyl)ethyl) 1'-tert-butyl spiro[indoline-3,3'-pyrrolidine]-1,1'-dicarboxylate (15.2 g, 36.5 mmol) was dissolved in t-butanol (240 mL) and water (40 mL). Thereafter, N-bromosuccinimide (7.9 g, 44.4 mmol) was added to the above obtained solution at room temperature, and the thus obtained mixture was then stirred at 60° C. for 15 hours. Thereafter, an aqueous solution of sodium thiosulfate was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (hexane:ethyl acetate=3:1) to obtain 1-(2-(trimethylsilyl)ethyl) 1'-tert-butyl 5-bromospiro[indoline-3,3'-pyrrolidine]-1,1'-dicarboxylate (12.9 g, 71%) in the form of a white amorphous product.

$^1$H-NMR (400 MHz, CDCl$_3$) δ: 0.70 (9H, s), 1.12 (2H, br), 1.56 (9H, br), 2.00 (1H, m), 2.15 (1H, m), 3.38-3.75 (4H, m), 3.90 (2H, m), 4.31 (2H, m), 7.20 (1H, d, J=8.0 Hz), 7.31 (1H, d, J=8.0 Hz), 7.75 (1H, br).

Step 3: 1-(2-(Trimethylsilyl)ethyl) 1'-tert-butyl 5-bromospiro[indoline-3,3'-pyrrolidine]-1,1'-dicarboxylate (300 mg, 0.603 mmol) was dissolved in xylene (10 mL). Thereafter, sodium thiomethoxide (85 mg, 1.21 mmol), tris(dibenzylideneacetone)dipalladium(0) (100 mg, 0.11 mmol), and xantphos (87.0 mg, 0.15 mmol) were added to the above obtained solution at room temperature, and the thus obtained mixture was then stirred at 150° C. for 1 hour. Thereafter, the reaction solution was purified by silica gel column chromatography (hexane:ethyl acetate=3:1) to obtain 1-(2-(trimethylsilyl)ethyl) 1'-tert-butyl 5-(methylthio)spiro[indoline-3,3'-pyrrolidine]-1,1'-dicarboxylate (192 mg, 69%) in the form of a white amorphous product.

$^1$H-NMR (400 MHz, CDCl$_3$) δ: 0.55 (9H, s), 1.11 (2H, br), 1.48 (9H, br), 2.00 (1H, m), 2.15 (1H, m), 2.43 (3H, s), 3.40-3.73 (4H, m), 3.91 (2H, m), 4.33 (2H, m), 7.03 (1H, s), 7.15 (1H, d, J=8.1 Hz), 7.75 (1H, br).

Step 4: 1-(2-(Trimethylsilyl)ethyl) 1'-tert-butyl 5-(methylthio)spiro[indoline-3,3'-pyrrolidine]-1,1'-dicarboxylate (192 mg, 0.41 mmol) was dissolved in methylene chloride (5 mL). Thereafter, meta-chloroperbenzoic acid (350 mg, 2.03 mmol) was added to the above obtained solution under cooling on ice, and the thus obtained mixture was then stirred for 30 minutes. Thereafter, an aqueous solution of sodium thiosulfate was added to the reaction solution, and the mixed solution was then extracted with chloroform. The organic layer was washed with brine, and was then dried over anhydrous sodium sulfate, followed by concentration in vacuo. The obtained residue was purified by silica gel column chromatography (hexane:ethyl acetate=1:1) to obtain 1-(2-(trimethylsilyl)ethyl) 1'-tert-butyl 5-(methylsulfonyl)spiro[indoline-3,3'-pyrrolidine]-1,1'-dicarboxylate (133.2 mg, 65%) in the form of a white amorphous product.

$^1$H-NMR (400 MHz, CDCl$_3$) δ: 0.50 (9H, s), 1.10 (2H, br), 1.45 (9H, br), 2.01 (1H, m), 2.18 (1H, m), 2.98 (3H, s), 3.39-3.74 (4H, m), 3.94 (2H, m), 4.33 (2H, m), 7.60 (1H, s), 7.77 (1H, d, J=8.0 Hz), 7.99 (1H, br).

Step 5: 1-(2-(Trimethylsilyl)ethyl) 1'-tert-butyl 5-(methylsulfonyl)spiro[indoline-3,3'-pyrrolidine]-1,1'-dicarboxylate (133 mg, 0.27 mmol) was dissolved in tetrahydrofuran (3 mL). Thereafter, tetra-n-butylammonium fluoride (1 M tetrahydrofuran solution, 0.5 mL) was added to the above obtained solution at room temperature, and the thus obtained mixture was then stirred for 1 hour. Thereafter, water was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (hexane:ethyl acetate=1:4) to obtain tert-butyl 5-(methylsulfonyl)spiro[indoline-3,3'-pyrrolidine]-1'-carboxylate (102 mg, quant.) in the form of a white amorphous product.

$^1$H-NMR (400 MHz, CDCl$_3$) δ: 1.49 (9H, br), 2.04 (1H, m), 2.15 (1H, m), 3.02 (3H, s), 3.40-3.75 (6H, m), 6.65 (1H, d, J=8.4 Hz), 7.55 (1H, s), 7.66 (1H, d, J=8.4 Hz).

Step 6: The captioned compound was obtained in the form of a white solid by performing the same reactions and/or treatments as those in Examples 1, 2, and 373, with the exception that tert-butyl 5-(methylsulfonyl)spiro[indoline-3,3'-pyrrolidine]-1'-carboxylate was used instead of t-butyl 5-bromospiro[indoline-3,3'-pyrrolidine]-1'-carboxylate.

Example 384

Production of 5-chloro-N-(5-chlorothiazol-2-yl)-1'-(2-(dimethylamino)-2-oxoacetyl)spiro[indoline-3,3'-pyrrolidine]-1-carboxamide The captioned compound was obtained in the form of a white solid by performing the same reactions and/or treatments as those in Example 45, with the exception that dimethylamine was used instead of a saturated solution of ammonia-methanol.

Example 397

Production of ethyl 4-((1'-acetyl-1-((5-chlorothiazol-2-yl)carbamoyl)spiro[indoline-3,3'-pyrrolidin]-5-yl)oxy)butanoate The captioned compound was obtained in the form of a white solid by performing the same reactions and/or treatments as those in Example 224, with the exception that ethyl 4-bromobutanoate was used instead of iodoethane.

Production of Examples 398, 421, 422, 427, 458, 463, 469, and 474

The below captioned compounds were obtained in the form of a white solid by performing the same reactions and/or treatments as those in Example 29, with the exception that the below mentioned raw material compounds were used instead of 2-((2-(1'-acetyl-5-bromospiro[indoline-3,3'-pyrrolidin]-1-ylcarboxamido)thiazol-5-yl)thio)acetate.

Example 398

4-((1'-Acetyl-1-((5-chlorothiazol-2-yl)carbamoyl)spiro[indoline-3,3'-pyrrolidin]-5-yl)oxy)butanoic acid Ethyl 4-((1'-acetyl-1-((5-chlorothiazol-2-yl)carbamoyl)spiro[indoline-3,3'-pyrrolidin]-5-yl)oxy)butanoate The compound in the parentheses that is described below the captioned compound is a raw material compound that was used instead of 2-((2-(1'-acetyl-5-bromospiro[indoline-3,3'-pyrrolidin]-1-ylcarboxamido)thiazol-5-yl)thio)acetate. The same shall apply hereafter.

Example 421

4-(1'-Acetyl-1-((5-chlorothiazol-2-yl)carbamoyl)spiro[indoline-3,3'-pyrrolidin]-5-yl)butanoic acid Ethyl 4-(1'-acetyl-1-((5-chlorothiazol-2-yl)carbamoyl)spiro[indoline-3,3'-pyrrolidin]-5-yl)butanoate

Example 422

4-(1-((5-Chlorothiazol-2-yl)carbamoyl)-1'-(methylcarbamoyl)spiro[indoline-3,3'-pyrrolidin]-5-yl)butanoic acid Ethyl 4-(1-((5-chlorothiazol-2-yl)carbamoyl)-1'-(methylcarbamoyl)spiro[indoline-3,3'-pyrrolidin]-5-yl)butanoate

Example 427

5-(1'-Acetyl-1-((5-chlorothiazol-2-yl)carbamoyl)spiro[indoline-3,3'-pyrrolidin]-5-yl)pentanoic acid Ethyl 5-(1'-acetyl-1-((5-chlorothiazol-2-yl)carbamoyl)spiro[indoline-3,3'-pyrrolidin]-5-yl)pentanoate

Example 458

2-(5-Chloro-1-((5-chlorothiazol-2-yl)carbamoyl)spiro[indoline-3,3'-pyrrolidin]-1'-ylcarboxamido)acetic acid Ethyl 2-(5-chloro-1-((5-chlorothiazol-2-yl)carbamoyl)spiro[indoline-3,3'-pyrrolidin]-1'-ylcarboxamido)acetate

Example 463

3-(5-Chloro-1-((5-chlorothiazol-2-yl)carbamoyl)spiro[indoline-3,3'-pyrrolidin]-1'-ylcarboxamido)propanoic acid Ethyl 3-(5-chloro-1-((5-chlorothiazol-2-yl)carbamoyl)spiro[indoline-3,3'-pyrrolidin]-1'-ylcarboxamido)propanoate

Example 469

4-(5-Chloro-1-((5-chlorothiazol-2-yl)carbamoyl)spiro[indoline-3,3'-pyrrolidin]-1'-ylcarboxamido)butanoic acid Ethyl 4-(5-chloro-1-((5-chlorothiazol-2-yl)carbamoyl)spiro[indoline-3,3'-pyrrolidin]-1'-ylcarboxamido)butanoate

Example 474

1-(5-Chloro-1-((5-chlorothiazol-2-yl)carbamoyl)spiro[indoline-3,3'-pyrrolidin]-1'-ylcarboxamido)cyclopropanecarboxylic acid Ethyl 1-(5-chloro-1-((5-chlorothiazol-2-yl)carbamoyl)spiro[indoline-3,3'-pyrrolidin]-1'-ylcarboxamido)cyclopropanecarboxylate

Production of Examples 399, 400, 402, 409, 413, 423, 424, 428, 460, 461, 465, 466, 471, 472, and 475

The below captioned compounds were obtained in the form of a white solid by performing the same reactions and/or treatments as those in Example 85, with the exception that the below mentioned raw material compounds were used instead of 2-(5-chloro-1'-(methoxycarbonyl)spiro[indoline-3,3'-pyrrolidin]-1-ylcarboxamido)thiazole-4-carboxylic acid and dimethylamine hydrochloride.

Example 399

1'-Acetyl-5-(4-(azetidin-1-yl)-4-oxobutoxy)-N-(5-chlorothiazol-2-yl)spiro[indoline-3,3'-pyrrolidine]-1-carboxamide 4-((1'-Acetyl-1-((5-chlorothiazol-2-yl)carbamoyl)spiro[indoline-3,3'-pyrrolidin]-5-yl)oxy)butanoic acid and azetidine hydrochloride The compounds in the parentheses that are described below the captioned compound are successively raw material compounds that were used instead of 2-(5-chloro-1'-(methoxycarbonyl)spiro[indoline-3,3'-pyrrolidin]-1-ylcarboxamido)thiazole-4-carboxylic acid and dimethylamine hydrochloride. The same shall apply hereafter.

Example 400

1'-Acetyl-N-(5-chlorothiazol-2-yl)-5-(4-(methylamino)-4-oxobutoxy)spiro[indoline-3,3'-pyrrolidine]-1-carboxamide 4-((1'-Acetyl-1-((5-chlorothiazol-2-yl)carbamoyl)spiro[indoline-3,3'-pyrrolidin]-5-yl)oxy)butanoic acid and methylamine hydrochloride

Example 402

1'-Acetyl-N1-(5-chlorothiazol-2-yl)-N-5-methylspiro[indoline-3,3'-pyrrolidine]-1,5-dicarboxamide 1'-Acetyl-1-((5-chlorothiazol-2-yl)carbamoyl)spiro[indoline-3,3'-pyrrolidine]-5-carboxylic acid and methylamine hydrochloride $^1$H-NMR (400 MHz, CDCl$_3$) δ: 2.05-2.35 (5H, m), 3.00 (3H, m), 3.5-4.14 (6H, m), 6.52 (1H, m), 7.17 (1H, s), 7.62 (1H, m), 7.70 (1H, m), 8.02 (1H, m), 8.08 (1H, m).

Example 409

1'-Acetyl-5-(2-(azetidin-1-yl)-2-oxoethyl)-N-(5-chlorothiazol-2-yl)spiro[indoline-3,3'-pyrrolidine]-1-carboxamide(2-(1'-Acetyl-1-((5-chlorothiazol-2-yl)carbamoyl)spiro[indoline-3,3'-pyrrolidin]-5-yl)acetic acid and azetidine hydrochloride)

Example 413

1'-Acetyl-5-(3-(azetidin-1-yl)-3-oxopropyl)-N-(5-chlorothiazol-2-yl)spiro[indoline-3,3'-pyrrolidine]-1-carboxamide (3-(1'-Acetyl-1-((5-chlorothiazol-2-yl)carbamoyl)spiro[indoline-3,3'-pyrrolidin]-5-yl)propanoic acid and azetidine hydrochloride

Example 423

1'-Acetyl-5-(4-(azetidin-1-yl)-4-oxobutyl)-N-(5-chlorothiazol-2-yl)spiro[indoline-3,3'-pyrrolidine]-1-carboxamide 4-(1'-Acetyl-1-((5-chlorothiazol-2-yl)carbamoyl)spiro[indoline-3,3'-pyrrolidin]-5-yl)butanoic acid and azetidine hydrochloride

Example 424

5-(4-(Azetidin-1-yl)-4-oxobutyl)-N1-(5-chlorothiazol-2-yl)-N1'-methylspiro[indoline-3,3'-pyrrolidine]-1,1'-dicarboxamide(4-(1-((5-Chlorothiazol-2-yl)carbamoyl)-1'-(methylcarbamoyl)spiro[indoline-3,3'-pyrrolidin]-5-yl)butanoic acid and azetidine hydrochloride)

Example 428

1'-Acetyl-5-(5-(azetidin-1-yl)-5-oxopentyl)-N-(5-chlorothiazol-2-yl)spiro[indoline-3,3'-pyrrolidine]-1-carboxamide 5-(1'-Acetyl-1-((5-chlorothiazol-2-yl)carbamoyl)spiro[indoline-3,3'-pyrrolidin]-5-yl)pentanoic acid and azetidine hydrochloride

Example 460

N1'-(2-(Azetidin-1-yl)-2-oxoethyl)-5-chloro-N1-(5-chlorothiazol-2-yl)spiro[indoline-3,3'-pyrrolidine]-1,1'-dicarboxamide 2-(5-Chloro-1-((5-chlorothiazol-2-yl)carbamoyl)spiro[indoline-3,3'-pyrrolidin]-1'-ylcarboxamido)acetic acid and azetidine hydrochloride

Example 461

5-Chloro-N1-(5-chlorothiazol-2-yl)-N1'-(2-(methylamino)-2-oxoethyl)spiro[indoline-3,3'-pyrrolidine]-1,1'-dicarboxamide 2-(5-Chloro-1-((5-chlorothiazol-2-yl)carbamoyl)spiro[indoline-3,3'-pyrrolidin]-1'-ylcarboxamido)acetic acid and methylamine hydrochloride

Example 465

5-Chloro-N1-(5-chlorothiazol-2-yl)-N1'-(3-(methylamino)-3-oxopropyl)spiro[indoline-3,3'-pyrrolidine]-1,1'-dicarboxamide 3-(5-Chloro-1-((5-chlorothiazol-2-yl)carbamoyl)spiro[indoline-3,3'-pyrrolidin]-1'-ylcarboxamido)propanoic acid and methylamine hydrochloride

Example 466

N1'-(3-(Azetidin-1-yl)-3-oxopropyl)-5-chloro-N1-(5-chlorothiazol-2-yl)spiro[indoline-3,3'-pyrrolidine]-1,1'-dicarboxamide 3-(5-Chloro-1-((5-chlorothiazol-2-yl)carbamoyl)spiro[indoline-3,3'-pyrrolidin]-1'-ylcarboxamido)propanoic acid and azetidine hydrochloride

Example 471

N1'-(4-(Azetidin-1-yl)-4-oxobutyl)-5-chloro-N1-(5-chlorothiazol-2-yl)spiro[indoline-3,3'-pyrrolidine]-1,1'-dicarboxamide 4-(5-Chloro-1-((5-chlorothiazol-2-yl)carbamoyl)spiro[indoline-3,3'-pyrrolidin]-1'-ylcarboxamido)butane and azetidine hydrochloride

Example 472

5-Chloro-N1-(5-chlorothiazol-2-yl)-N1'-(4-(methylamino)-4-oxobutyl)spiro[indoline-3,3'-pyrrolidine]-1,1'-dicarboxamide 4-(5-Chloro-1-((5-chlorothiazol-2-yl)carbamoyl)spiro[indoline-3,3'-pyrrolidin]-1'-ylcarboxamido)butanoic acid and methylamine hydrochloride

Example 475

5-Chloro-N1-(5-chlorothiazol-2-yl)-N1'-(1-(methylcarbamoyl)cyclopropyl)spiro[indoline-3,3'-pyrrolidine]-1,1'-dicarboxamide 1-(5-Chloro-1-((5-chlorothiazol-2-yl)carbamoyl)spiro[indoline-3,3'-pyrrolidin]-1'-ylcarboxamido)cyclopropanecarboxylic acid and methylamine hydrochloride

Example 401

Production of 1'-acetyl-1-((5-chlorothiazol-2-yl)carbamoyl)spiro[indoline-3,3'-pyrrolidine]-5-carboxylic acid Step 1: The tert-butyl 1-((5-chlorothiazol-2-yl)carbamoyl)-5-cyanospiro[indoline-3,3'-pyrrolidine]-1'-carboxylate (0.10 g, 0.217 mmol) obtained as an intermediate of Example 196 was dissolved in methylene chloride (4.3 mL). Thereafter, diisobutylaluminum hydride (1.1 mL, 1.09 mmol) was added to the above obtained solution under cooling on ice, and the thus obtained mixture was then stirred at room temperature for 1 hour. Thereafter, the reaction was terminated with a saturated aqueous solution of ammonium chloride, and Rochelle salt and water were then added to the reaction solution, followed by stirring the mixture. The reaction solution was filtered through a pad of celite, and was then extracted with chloroform methanol=10:1. The organic layer was dried over anhydrous sodium sulfate, and was then concentrated in vacuo. The obtained residue was purified by silica gel column chromatography (chloroform:methanol=30:1) to obtain tert-butyl 1-((5-chlorothiazol-2-yl)carbamoyl)-5-formylspiro[indoline-3,3'-pyrrolidine]-1'-carboxylate (35.6 mg, 35%) in the form of a yellow solid.

$^1$H-NMR (400 MHz, CDCl$_3$) δ: 1.47 (9H, br), 2.20-2.14 (1H, m), 2.25-2.40 (1H, m), 3.40-3.84 (4H, m), 3.94-4.12 (2H, m), 7.19 (1H, s), 7.74 (1H, br), 7.81 (1H, dd, J=1.6, 8.4 Hz), 8.22 (1H, d, J=8.4 Hz), 9.91 (1H, s).

Step 2: 1'-Acetyl-N-(5-chlorothiazol-2-yl)-5-formylspiro[indoline-3,3'-pyrrolidine]-1-carboxamide was obtained in the form of a yellow oily product by performing the same reactions and/or treatments as those in Examples 2 and 3, with the exception that tert-butyl 1-((5-chlorothiazol-2-yl)carbamoyl)-5-formylspiro[indoline-3,3'-pyrrolidine]-1'-carboxylate was used instead of t-butyl 5-bromo-1-((5-chlorothiazol-2-yl)carbamoyl)spiro[indoline-3,3'-pyrrolidine]-1'-carboxylate.

$^1$H-NMR (400 MHz, CDCl$_3$) δ: 2.08-2.46 (5H, m), 3.50-4.00 (4H, m), 4.02-4.24 (2H, m), 7.17 (1H, d, J=4.4 Hz), 7.73 (1H, dd, J=1.2, 13.6 Hz), 7.78-7.84 (1H, m), 8.25 (1H, d, J=8.4, 19.6 Hz), 9.91 (1H, d, J=4.4 Hz).

Step 3: 1'-Acetyl-N-(5-chlorothiazol-2-yl)-5-formylspiro[indoline-3,3'-pyrrolidine]-1-carboxamide (7.6 mg, 0.0188 mmol) was dissolved in t-butanol (1.5 mL) and water (0.5 mL). Thereafter, 2-methyl-2-butene (52 μL, 0.50 mmol), sodium dihydrogen phosphate (14 mg, 0.113 mmol) and sodium chlorite (15 mg, 0.169 mmol) were added to the above obtained solution, and the thus obtained mixture was then stirred at room temperature for 3.3 hours. Thereafter, a saturated aqueous solution of ammonium chloride was added to the reaction solution, and the mixed solution was then extracted with chloroform:methanol=5:1. The organic layer was dried over anhydrous sodium sulfate, and was then concentrated in vacuo. The obtained residue was purified by silica gel column chromatography (chloroform:methanol=5:1) to obtain the captioned compound (6.9 mg, 87%) in the form of a white solid.

$^1$H-NMR (400 MHz, CDCl$_3$) δ: 2.05-2.45 (5H, m), 3.50-3.94 (4H, m), 4.04-4.18 (2H, m), 7.17 (1H, d, J=2.4 Hz), 7.87 (1H, dd, J=2.0, 10.8 Hz), 8.00-8.08 (1H, m), 8.10-8.16 (1H, m).

Example 403

Production of 3-(N-benzyl-1-((5-chlorothiazol-2-yl)carbamoyl)-1'-(methylcarbamoyl)spiro[indoline-3,3'-pyrrolidin]-5-ylcarboxamido)propanoic acid The captioned compound was obtained in the form of a white solid by performing the same reactions and/or treatments as those in Examples 85 and 2, with the exceptions that the 1'-acetyl-1-((5-chlorothiazol-2-yl)carbamoyl)spiro[indoline-3,3'-pyrrolidine]-5-carboxylic acid obtained in Example 401 was used instead of 2-(5-chloro-1'-(methoxycarbonyl)spiro[indoline-3,3'-pyrrolidin]-1-ylcarboxamido)thiazole-4-carboxylic acid, and that t-butyl 3-(benzylamino)propanoate was used instead of dimethylamine hydrochloride.

$^1$H-NMR (400 MHz, CD$_3$OD) δ: 2.01-2.60 (7H, m), 3.30-3.75 (7H, m), 4.15 (2H, m), 4.70 (1H, m), 7.05-7.45 (8H, m), 8.05 (1H, m).

Example 404

Production of 1'-acetyl-N-(5-chlorothiazol-2-yl)-5-(hydroxymethyl)spiro[indoline-3,3'-pyrrolidine]-1-carboxamide The 1'-acetyl-N-(5-chlorothiazol-2-yl)-5-formylspiro[indoline-3,3'-pyrrolidine]-1-carboxamide (30.6 mg, 0.076 mmol) obtained in Step 2 of Example 401 was dissolved in methanol (1 mL). Thereafter, sodium borohydride (3.0 mg, 0.091 mmol) was added to the above obtained solution under cooling on ice, and the thus obtained mixture was then stirred at room temperature for 1 hour. Thereafter, the reaction solution was concentrated in vacuo, and the obtained residue was then purified by silica gel column chromatography (chloroform:methanol=10:1) to obtain the captioned compound (30.4 mg, 99%) in the form of a white solid.

$^1$H-NMR (400 MHz, CDCl$_3$) δ: 2.06-2.35 (5H, m), 3.53-4.38 (6H, m), 4.66 (2H, d, J=6.0 Hz), 7.18 (2H, m), 7.26 (1H, s), 7.98 (1H, m).

Example 405

Production of 1'-acetyl-N-(5-chlorothiazol-2-yl)-5-(1-hydroxyethyl)spiro[indoline-3,3'-pyrrolidine]-1-carboxamide The 1'-acetyl-N-(5-chlorothiazol-2-yl)-5-formylspiro[indoline-3,3'-pyrrolidine]-1-carboxamide (30.0 mg, 0.074 mmol) obtained in Step 2 of Example 401 was dissolved in tetrahydrofuran (1.4 mL). Thereafter, methyl magnesium bromide (1 M tetrahydrofuran solution, 224 μL) was added to the above obtained solution under cooling on ice, and the thus obtained mixture was then stirred at the same temperature as above for 1 hour. Thereafter, the reaction solution was diluted with a saturated aqueous solution of ammonium chloride, and was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain the captioned compound (28.1 mg, 91%) in the form of a white solid.

Example 406

Production of 1',5-diacetyl-N-(5-chlorothiazol-2-yl)spiro[indoline-3,3'-pyrrolidine]-1-carboxamide The 1'-acetyl-N-(5-chlorothiazol-2-yl)-5-(1-hydroxyethyl)spiro[indoline-3,3'-pyrrolidine]-1-carboxamide (22.3 mg, 0.053 mmol) obtained in Step 2 of Example 401 was dissolved in methylene chloride (0.5 mL). Thereafter, Dess-martin periodinane (27.0 mg, 0.0635 mmol) was added to the above obtained solution at room temperature, and the thus obtained mixture was then stirred at the same temperature as above for 1 hour. Thereafter, an aqueous solution of sodium sulfite was added to the reaction solution, and the mixed solution was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain the captioned compound (21.7 mg, 99%) in the form of a white solid.

$^1$H-NMR (400 MHz, CDCl$_3$) δ: 2.04-2.38 (5H, m), 2.59 (3H, m), 3.40-4.15 (6H, m), 7.17 (1H, m), 7.82 (1H, m), 7.92 (1H, m), 8.11 (1H, m).

Example 407

Production of 1'-acetyl-N-(5-chlorothiazol-2-yl)-5-(2-hydroxypropan-2-yl)spiro[indoline-3,3'-pyrrolidine]-1-carboxamide The captioned compound was obtained in the form of a white solid by performing the same reactions and/or treatments as those in Example 405, with the exception that 1',5-diacetyl-N-(5-chlorothiazol-2-yl)spiro[indoline-3,3'-pyrrolidine]-1-carboxamide was used instead of the 1'-acetyl-N-(5-chlorothiazol-2-yl)-5-formylspiro[indoline-3,3'-pyrrolidine]-1-carboxamide obtained in Step 2 of Example 401.

Example 408

Production of 2-(1'-acetyl-1-((5-chlorothiazol-2-yl)carbamoyl)spiro[indoline-3,3'-pyrrolidin]-5-yl)acetic acid Step 1: (Methoxymethyl)triphenylphosphonium chloride (0.63 g, 1.85 mmol) was dissolved in tetrahydrofuran (4 mL). Thereafter, potassium tert-butoxide (0.21 g, 1.85 mmol) was added to the above obtained solution under cooling on ice, and the thus obtained mixture was then stirred for 10 minutes. Thereafter, a tetrahydrofuran solution (3 mL) of the 1'-acetyl-N-(5-chlorothiazol-2-yl)-5-formylspiro[indoline-3,3'-pyrrolidine]-1-carboxamide (100 mg, 0.247 mmol) obtained in Step 2 of Example 401 was added to the reaction solution, and the thus obtained mixture was then stirred at room temperature for 1 hour. Thereafter, a saturated aqueous solution of ammonium chloride and water were added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (chloroform:methanol=30:1) to obtain 1'-acetyl-N-(5-chlorothiazol-2-yl)-5-(2-methoxyvinyl)spiro[indoline-3,3'-pyrrolidine]-1-carboxamide (83 mg, 78%) in the form of a yellow amorphous product.

Step 2: 1'-Acetyl-N-(5-chlorothiazol-2-yl)-5-(2-methoxyvinyl)spiro[indoline-3,3'-pyrrolidine]-1-carboxamide (83 mg, 0.192 mmol) was dissolved in acetone (3 mL). Thereafter, 6 N hydrochloric acid (1.5 mL) was added to the above obtained solution, and the thus obtained mixture was then stirred at 50° C. for 2 hours. Thereafter, saturated sodium hydrogen carbonate and water were added to the reaction solution, and the mixed solution was then extracted with ethyl acetate. The organic layer was washed with brine, and was then dried over anhydrous sodium sulfate, followed by concentration in vacuo, to obtain 1'-acetyl-N-(5-chlorothiazol-2-yl)-5-(2-oxoethyl)spiro[indoline-3,3'-pyrrolidine]-1-carboxamide (66.1 mg, 82%) in the form of a yellow solid.

$^1$H-NMR (400 MHz, CDCl$_3$) δ: 2.04-2.40 (5H, m), 3.50-4.12 (8H, m), 6.98-7.03 (1H, m), 7.14-7.22 (2H, m), 7.96-8.04 (1H, m), 9.74-9.77 (1H, m).

Step 3: The captioned compound was obtained in the form of a white solid by performing the same reactions and/or treatments as those in Step 3 of Example 401, with the exception that 1'-acetyl-N-(5-chlorothiazol-2-yl)-5-(2-oxoethyl)spiro[indoline-3,3'-pyrrolidine]-1-carboxamide was used instead of 1'-acetyl-N-(5-chlorothiazol-2-yl)-5-formylspiro[indoline-3,3'-pyrrolidine]-1-carboxamide.

Example 410

Production of (E)-ethyl 3-(1'-acetyl-1-((5-chlorothiazol-2-yl)carbamoyl)spiro[indoline-3,3'-pyrrolidin]-5-yl)acrylate Step 1: The 1-(2-(trimethylsilyl)ethyl) 1'-tert-butyl 5-bromospiro[indoline-3,3'-pyrrolidine]-1,1'-dicarboxylate (1.39 g, 2.79 mmol) obtained in Step 2 of Example 383 was dissolved in acetonitrile (28 mL). Thereafter, palladium diacetate (0.13 g, 0.558 mmol), tri(o-tolyl)phosphine (0.34 g, 1.12 mmol), N,N-diisopropylethylamine (0.97 mL, 5.58 mmol), and ethyl acrylate (1.2 mL, 11.16 mmol) were added to the above obtained solution at room temperature, and the thus obtained mixture was then stirred at 100° C. for 2 hours. Thereafter, the reaction solution was concentrated in vacuo, and the obtained residue was then purified by silica gel column chromatography (hexane:ethyl acetate=5:1) to obtain 1-(2-(trimethylsilyl)ethyl)(E)-1'-tert-butyl 5-(3-ethoxy-3-oxoprop-1-en-1-yl)spiro[indoline-3,3'-pyrrolidine]-1,1'-dicarboxylate (630 mg, 44%) in the form of a yellow oily product.

$^1$H-NMR (400 MHz, CDCl$_3$) δ: 0.08 (9H, s), 1.08-1.20 (2H, m), 1.33 (3H, t, J=7.2 Hz), 1.47-1.51 (9H, m), 1.98-2.26 (2H, m), 3.40-3.78 (4H, m), 3.86-4.00 (2H, m), 4.26 (2H, q, J=7.2 Hz), 4.30-4.40 (2H, m), 6.33 (1H, d, J=8.0 Hz), 7.31 (1H, br), 7.40-7.46 (1H, m), 7.63 (1H, d, J=8.0 Hz).

Step 2: The captioned compound was obtained in the form of a white solid by performing the same reactions and/or treatments as those in Step 5 of Example 21, and Examples 1, 2, and 3, with the exception that 1-(2-(trimethylsilyl)ethyl) (E)-1'-tert-butyl 5-(3-ethoxy-3-oxoprop-1-en-1-yl)spiro[indoline-3,3'-pyrrolidine]-1,1'-dicarboxylate was used instead of 1-(2-(trimethylsilyl)ethyl) 1'-tert-butyl 5-(methylsulfonyl)spiro[indoline-3,3'-pyrrolidine]-1,1'-dicarboxylate.

$^1$H-NMR (400 MHz, DMSO-d$_6$) δ: 1.25 (3H, t, J=7.1 Hz), 2.00 (3H, m), 2.03-2.32 (2H, m), 3.42-3.67 (3H, m), 3.78 (1H, m), 4.15 (2H, m), 4.17 (2H, q, J=7.1 Hz), 6.60 (1H, m), 7.50-6.62 (3H, m), 7.80-7.95 (2H, m)

Example 411

Production of (E)-1'-acetyl-5-(3-(azetidin-1-yl)-3-oxoprop-1-en-1-yl)-N-(5-chlorothiazol-2-yl)spiro[indoline-3,3'-pyrrolidine]-1-carboxamide Step 1: (E)-3-(1'-Acetyl-1-((5-chlorothiazol-2-yl)carbamoyl)spiro[indoline-3,3'-pyrrolidin]-5-yl)acrylic acid was obtained in the form of a white solid by performing the same reactions and/or treatments as those in Example 29, with the exception that the (E)-ethyl 3-(1'-acetyl-1-((5-chlorothiazol-2-yl)carbamoyl)spiro[indoline-3,3'-pyrrolidin]-5-yl)acrylate obtained in Example 410 was used instead of 2-((2-(1'-acetyl-5-bromospiro[indoline-3,3'-pyrrolidin]-1-ylcarboxamido)thiazol-5-yl)thio)acetate.

$^1$H-NMR (400 MHz, DMSO-d$_6$) δ: 1.94-2.32 (5H, m), 3.40-3.84 (4H, m), 4.02-4.26 (2H, m), 6.47 (1H, dd, J=2.0, 13.6 Hz), 7.48-7.60 (3H, m), 7.74-7.82 (1H, m), 7.90-8.00 (1H, m).

Step 2: The captioned compound was obtained in the form of a white solid by performing the same reactions and/or treatments as those in Example 85, with the exceptions that (E)-3-(1'-acetyl-1-((5-chlorothiazol-2-yl)carbamoyl)spiro[indoline-3,3'-pyrrolidin]-5-yl)acrylic acid was used instead of 2-(5-chloro-1'-(methoxycarbonyl)spiro[indoline-3,3'-pyrrolidin]-1-ylcarboxamido)thiazole-4-carboxylic acid, and that azetidine hydrochloride was used instead of dimethylamine hydrochloride.

$^1$H-NMR (400 MHz, DMSO-$d_6$) δ: 1.92-2.28 (5H, m), 3.40-3.84 (4H, m), 3.86-4.36 (6H, m), 6.58-6.70 (1H, m), 7.34-7.42 (1H, m), 7.45-7.60 (2H, m), 7.66-7.80 (1H, m), 7.86-8.00 (1H, m).

Example 412

Production of 3-(1'-acetyl-1-((5-chlorothiazol-2-yl) carbamoyl)spiro[indoline-3,3'-pyrrolidin]-5-yl)propanoic acid Step 1: 1-(2-(Trimethylsilyl)ethyl)(E)-1'-tert-butyl 5-(3-ethoxy-3-oxoprop-1-en-1-yl)spiro[indoline-3,3'-pyrrolidine]-1,1'-dicarboxylate (1.12 g, 2.20 mmol) was dissolved in methanol (125 mL). Thereafter, palladium-carbon (cat.) was added to the above obtained solution, and the thus obtained mixture was then stirred under a hydrogen atmosphere at room temperature for 21 hours. Thereafter, the reaction solution was filtered through a pad of celite, and the filtrate was then concentrated in vacuo. The obtained residue was purified by silica gel column chromatography (ethyl acetate) to obtain 1-(2-(trimethylsilyl)ethyl) 1'-tert-butyl 5-(3-ethoxy-3-oxopropyl)spiro[indoline-3,3'-pyrrolidine]-1,1'-dicarboxylate (860 mg, 75%) in the form of a white solid.

$^1$H-NMR (400 MHz, CDCl$_3$) δ: 0.05 (9H, s), 1.11 (2H, br), 1.23 (3H, t, J=6.9 Hz), 1.56 (9H, br), 2.01 (1H, m), 2.18 (1H, m), 2.70 (2H, t, J=7.8 Hz), 2.91 (2H, t, J=7.8 Hz), 3.40-3.93 (6H, m), 4.12 (2H, q, J=6.8 Hz), 4.33 (2H, br), 6.96 (1H, s,), 7.05 (1H, br), 7.79 (1H, br)

Step 2: The captioned compound was obtained in the form of a white solid by performing the same reactions and/or treatments as those in Step 5 of Example 383, and Examples 1, 2, 3, and 29, with the exception that 1-(2-(trimethylsilyl) ethyl) 1'-tert-butyl 5-(3-ethoxy-3-oxopropyl)spiro[indoline-3,3'-pyrrolidine]-1,1'-dicarboxylate was used instead of 1-(2-(trimethylsilyl)ethyl) 1'-tert-butyl 5-(methylsulfonyl)spiro [indoline-3,3'-pyrrolidine]-1,1'-dicarboxylate.

Example 414

Production of 5-(3-(azetidin-1-yl)-3-oxopropyl)-1'-(2-hydroxyacetyl)-N-(5-methoxythiazol-2-yl)spiro [indoline-3,3'-pyrrolidine]-1-carboxamide The captioned compound was obtained in the form of a white solid by performing the same reactions and/or treatments as those in Step 5 of Example 383, and Examples 1, 2, 3, 29, and 85, with the exceptions that the 1-(2-(trimethylsilyl)ethyl) 1'-tert-butyl 5-(3-ethoxy-3-oxopropyl)spiro[indoline-3,3'-pyrrolidine]-1,1'-dicarboxylate obtained in Step 1 of Example 412 was used instead of 1-(2-(trimethylsilyl)ethyl) 1'-tert-butyl 5-(methylsulfonyl)spiro[indoline-3,3'-pyrrolidine]-1,1'-dicarboxylate, that 2-amino-5-methoxythiazole was used instead of 2-amino-5-chlorothiazole hydrochloride, that acetoxyacetyl chloride was used instead of acetyl chloride, and that azetidine hydrochloride was used instead of dimethylamine hydrochloride.

Example 415

Production of 5-(3-(azetidin-1-yl)-3-oxopropyl)-1'-(2-hydroxyacetyl)-N-(5-methylthiazol-2-yl)spiro [indoline-3,3'-pyrrolidine]-1-carboxamide The captioned compound was obtained in the form of a white solid by performing the same reactions and/or treatments as those in Step 5 of Example 383, and Examples 1, 2, 3, 29, and 85, with the exceptions that 1-(2-(trimethylsilyl) ethyl) 1'-tert-butyl 5-(3-ethoxy-3-oxopropyl)spiro[indoline-3,3'-pyrrolidine]-1,1'-dicarboxylate was used instead of 1-(2-(trimethylsilyl)ethyl) 1'-tert-butyl 5-(methylsulfonyl)spiro [indoline-3,3'-pyrrolidine]-1,1'-dicarboxylate, that 2-amino-5-methylthiazole was used instead of 2-amino-5-chlorothiazole hydrochloride, that acetoxyacetyl chloride was used instead of acetyl chloride, and that azetidine hydrochloride was used instead of dimethylamine hydrochloride.

Example 416

Production of 5-(3-(azetidin-1-yl)-3-oxopropyl)-N1-(5-chlorothiazol-2-yl)-N1'-methylspiro[indoline-3,3'-pyrrolidine]-1,1'-dicarboxamide The captioned compound was obtained in the form of a white solid by performing the same reactions and/or treatments as those in Step 5 of Example 383, and Examples 1, 2, 373, 29, and 85, with the exceptions that 1-(2-(trimethylsilyl) ethyl) 1'-tert-butyl 5-(3-ethoxy-3-oxopropyl)spiro[indoline-3,3'-pyrrolidine]-1,1'-dicarboxylate was used instead of 1-(2-(trimethylsilyl)ethyl) 1'-tert-butyl 5-(methylsulfonyl)spiro [indoline-3,3'-pyrrolidine]-1,1'-dicarboxylate, and that azetidine hydrochloride was used instead of dimethylamine hydrochloride.

Example 417

Production of 5-(3-(azetidin-1-yl)-3-oxopropyl)-N1-(5-methoxythiazol-2-yl)-N1'-methylspiro[indoline-3,3'-pyrrolidine]-1,1'-dicarboxamide The captioned compound was obtained in the form of a white solid by performing the same reactions and/or treatments as those in Step 5 of Example 383, and Examples 1, 2, 373, 29, and 85, with the exceptions that 1-(2-(trimethylsilyl) ethyl) 1'-tert-butyl 5-(3-ethoxy-3-oxopropyl)spiro[indoline-3,3'-pyrrolidine]-1,1'-dicarboxylate was used instead of 1-(2-(trimethylsilyl)ethyl) 1'-tert-butyl 5-(methylsulfonyl)spiro [indoline-3,3'-pyrrolidine]-1,1'-dicarboxylate, that 2-amino-5-methoxythiazole was used instead of 2-amino-5-chlorothiazole hydrochloride, and that azetidine hydrochloride was used instead of dimethylamine hydrochloride.

Example 418

Production of ethyl 4-(1'-acetyl-1-((5-chlorothiazol-2-yl)carbamoyl)spiro[indoline-3,3'-pyrrolidin]-5-yl) butanoate Step 1: The 1-(2-(trimethylsilyl)ethyl) 1'-tert-butyl 5-bromospiro[indoline-3,3'-pyrrolidine]-1,1'-dicarboxylate (100 mg, 0.201 mmol) obtained in Step 2 of Example 383 was dissolved in tetrahydrofuran (1.5 mL). Thereafter, palladium diacetate (10.0 mg, 0.045 mmol), S-Phos (33.0 mg, 0.080 mmol), and 4-ethoxy-4-oxobutylzinc bromide (0.5 M tetrahydrofuran solution, 0.5 mL) were added to the above obtained solution at room temperature, and the thus obtained mixture was then stirred at room temperature for 14 hours. Thereafter, a saturated aqueous solution of ammonium chloride was added to the reaction solution, and the mixed solution was then extracted with chloroform. The organic layer was washed with brine, and was then dried over anhydrous sodium sulfate, followed by concentration in vacuo. The obtained residue was purified by silica gel column chromatography (hexane ethyl acetate=10:1) to obtain 1-(2-(trimethylsilyl)ethyl) 1'-tert-butyl 5-(4-ethoxy-4-oxobutyl)spiro[indoline-3,3'-pyrrolidine]-1,1'-dicarboxylate (75.2 mg, 70%) in the form of a white solid.

$^1$H-NMR (400 MHz, CDCl$_3$) δ: 0.07 (9H, s), 1.26 (3H, t, J=7.2 Hz), 1.44-1.52 (9H, m), 1.86-2.64 (6H, m), 2.61 (2H, t, J=7.6 Hz), 3.38-3.75 (4H, m), 3.80-3.96 (2H, m), 4.09-4.17 (2H, m), 4.25-4.40 (2H, m), 6.95 (1H, s), 7.05 (1H, d, J=8.8 Hz).

Step 2: The captioned compound was obtained in the form of a white solid by performing the same reactions and/or treatments as those in Step 5 of Example 21, and Examples 1, 2, and 3, with the exception that 1-(2-(trimethylsilyl)ethyl) 1'-tert-butyl 5-(4-ethoxy-4-oxobutyl)spiro[indoline-3,3'-pyrrolidine]-1,1'-dicarboxylate was used instead of 1-(2-(trimethylsilyl)ethyl) 1'-tert-butyl 5-(methylsulfonyl)spiro[indoline-3,3'-pyrrolidine]-1,1'-dicarboxylate.

Example 419

Production of ethyl 4-(1-((5-chlorothiazol-2-yl)carbamoyl)-1'-(methylcarbamoyl)spiro[indoline-3,3'-pyrrolidin]-5-yl)butanoate The captioned compound was obtained in the form of a white solid by performing the same reactions and/or treatments as those in Step 5 of Example 21, and Examples 1, 2, and 373, with the exception that the 1-(2-(trimethylsilyl)ethyl) 1'-tert-butyl 5-(4-ethoxy-4-oxobutyl)spiro[indoline-3,3'-pyrrolidine]-1,1'-dicarboxylate obtained in Step 1 of Example 418 was used instead of 1-(2-(trimethylsilyl)ethyl) 1'-tert-butyl 5-(methylsulfonyl)spiro[indoline-3,3'-pyrrolidine]-1,1'-dicarboxylate.

Example 420

Production of ethyl 4-(1'-(methylcarbamoyl)-1-((5-methylpyrazin-2-yl)carbamoyl)spiro[indoline-3,3'-pyrrolidin]-5-yl)butanoate The captioned compound was obtained in the form of a white solid by performing the same reactions and/or treatments as those in Step 5 of Example 21, and Examples 1, 2, and 373, with the exceptions that the 1-(2-(trimethylsilyl)ethyl) 1'-tert-butyl 5-(4-ethoxy-4-oxobutyl)spiro[indoline-3,3'-pyrrolidine]-1,1'-dicarboxylate obtained in Step 1 of Example 418 was used instead of 1-(2-(trimethylsilyl)ethyl) 1'-tert-butyl 5-(methylsulfonyl)spiro[indoline-3,3'-pyrrolidine]-1,1'-dicarboxylate, and that 2-amino-5-methylpyrazine was used instead of 2-amino-5-chlorothiazole hydrochloride.

Example 425

Production of 5-(4-(azetidin-1-yl)-4-oxobutyl)-N1'-methyl-N1-(5-methylpyrazin-2-yl)spiro[indoline-3,3'-pyrrolidine]-1,1'-dicarboxamide The captioned compound was obtained in the form of a white solid by performing the same reactions and/or treatments as those in Examples 29 and 85, with the exceptions that the ethyl 4-(1'-(methylcarbamoyl)-1-((5-methylpyrazin-2-yl)carbamoyl)spiro[indoline-3,3'-pyrrolidin]-5-yl)butanoate obtained in Example 420 was used instead of 2-((2-(1'-acetyl-5-bromospiro[indoline-3,3'-pyrrolidin]-1-ylcarboxamido)thiazol-5-yl)thio)acetate, and that azetidine hydrochloride was used instead of dimethylamine hydrochloride.

Example 426

Production of ethyl 5-(1'-acetyl-1-((5-chlorothiazol-2-yl)carbamoyl)spiro[indoline-3,3'-pyrrolidin]-5-yl)pentanoate The captioned compound was obtained in the form of a white solid by performing the same reactions and/or treatments as those in Example 418, with the exception that 5-ethoxy-5-oxopentylzinc bromide was used instead of 4-ethoxy-4-oxobutylzinc bromide.

Example 429

Production of 1'-acetyl-N-(5-chlorothiazol-2-yl)-5-(4-(methylsulfonyl)butyl)spiro[indoline-3,3'-pyrrolidine]-1-carboxamide Step 1: 1-(2-(Trimethylsilyl)ethyl) 1'-tert-butyl 5-(4-hydroxybutyl)spiro[indoline-3,3'-pyrrolidine]-1,1'-dicarboxylate was obtained in the form of a yellow oily product by performing the same reactions and/or treatments as those in Step 1 of Example 401, with the exception that the 1-(2-(trimethylsilyl)ethyl) 1'-tert-butyl 5-(4-ethoxy-4-oxobutyl)spiro[indoline-3,3'-pyrrolidine]-1,1'-dicarboxylate obtained in Step 1 of Example 418 was used instead of tert-butyl 1-((5-chlorothiazol-2-yl)carbamoyl)-5-cyanospiro[indoline-3,3'-pyrrolidine]-1'-carboxylate.

$^1$H-NMR (400 MHz, CDCl$_3$) δ: 0.07 (9H, s), 1.04-1.26 (2H, m), 1.44-1.52 (9H, m), 1.58-1.72 (4H, m), 1.96-2.03 (1H, m), 2.20-2.24 (1H, m), 2.60 (2H, t, J=7.6 Hz), 3.38-3.76 (6H, m), 3.80-4.00 (2H, m), 4.26-4.38 (2H, m), 6.95 (1H, s), 7.06 (1H, d, J=7.6 Hz).

Step 2: 1-(2-(Trimethylsilyl)ethyl) 1'-tert-butyl 5-(4-hydroxybutyl)spiro[indoline-3,3'-pyrrolidine]-1,1'-dicarboxylate (120.7 mg, 0.246 mmol) was dissolved in tetrahydrofuran (2.5 mL). Thereafter, triethylamine (46 μL, 0.32 mmol) and methanesulfonyl chloride (21 μL, 0.27 mmol) were added to the above obtained solution under cooling on ice, and the thus obtained mixture was then stirred at room temperature for 1 hour. Thereafter, insoluble matters were filtered, and the filtrate was then concentrated in vacuo. The residue was dissolved in N,N-dimethylformamide (2.4 mL), and S-potassium thioacetate (62 mg, 0.54 mmol) was then added to the above solution. The thus obtained mixture was stirred at room temperature for 15 hours. Thereafter, water was added to the reaction solution, and the mixed solution was then extracted with ethyl acetate. The organic layer was washed with water and brine, and was then dried over anhydrous sodium sulfate, followed by concentration in vacuo. The obtained residue was purified by silica gel column chromatography (hexane ethyl acetate=5:1) to obtain 1-(2-(trimethylsilyl)ethyl) 1'-tert-butyl 5-(4-(acetylthio)butyl)spiro[indoline-3,3'-pyrrolidine]-1,1'-dicarboxylate (89.2 mg, 66%) in the form of a brown oily product.

$^1$H-NMR (400 MHz, CDCl$_3$) δ: 0.07 (9H, s), 1.04-1.20 (2H, m), 1.42-1.54 (9H, m), 1.58-1.72 (4H, m), 1.95-2.08 (1H, m), 2.10-2.25 (1H, m), 2.32 (3H, s), 2.58 (2H, t, J=7.2 Hz), 2.88 (2H, t, J=7.2 Hz), 3.38-3.95 (6H, m), 4.24-4.42 (2H, m), 6.94 (1H, s), 7.04 (1H, d, J=7.6 Hz).

Step 3: 1-(2-(Trimethylsilyl)ethyl) 1'-tert-butyl 5-(4-(acetylthio)butyl)spiro[indoline-3,3'-pyrrolidine]-1,1'-dicarboxylate (89.2 mg, 0.163 mmol) was dissolved in methanol (1.5 mL) and tetrahydrofuran (1.5 mL). Thereafter, a 4 N aqueous solution of sodium hydroxide (0.4 mL, 1.6 mmol) and iodomethane (51 µL, 0.815 mmol) were added to the above obtained solution, and the thus obtained mixture was then stirred at room temperature for 1 hour. Thereafter, water was added to the reaction solution, and the mixed solution was then extracted with ethyl acetate. The organic layer was washed with brine, and was then dried over anhydrous sodium sulfate, followed by concentration in vacuo, to obtain 1-(2-(trimethylsilyl)ethyl) 1'-tert-butyl 5-(4-(methylthio)butyl)spiro[indoline-3,3'-pyrrolidine]-1,1'-dicarboxylate (85 mg, quant.) in the form of a brown oily product.

$^1$H-NMR (400 MHz, CDCl$_3$) δ: 0.07 (9H, s), 1.06-1.20 (2H, m), 1.42-1.52 (9H, m), 1.60-1.74 (4H, m), 1.96-2.04 (1H, m), 2.08 (3H, s), 2.12-2.24 (1H, m), 2.51 (2H, t, J=7.2 Hz), 2.59 (2H, t, J=7.2 Hz), 3.26-3.98 (6H, m), 4.24-4.42 (2H, m), 6.94 (1H, s), 7.05 (1H, d, J=7.6 Hz).

Step 4: The captioned compound was obtained in the form of a light brown solid by performing the same reactions and/or treatments as those in Steps 4 and 5 of Example 21, and Examples 1, 2, and 3, with the exception that 1-(2-(trimethylsilyl)ethyl) 1'-tert-butyl 5-(4-(methylthio)butyl)spiro[indoline-3,3'-pyrrolidine]-1,1'-dicarboxylate was used instead of 1-(2-(trimethylsilyl)ethyl) 1'-tert-butyl 5-(methylthio)spiro[indoline-3,3'-pyrrolidine]-1,1'-dicarboxylate.

$^1$H-NMR (400 MHz, CDCl$_3$) δ: 1.70-1.94 (4H, m), 2.06-2.36 (5H, m), 2.60-2.70 (2H, m), 2.89 (3H, d, J=2.4 Hz), 2.98-3.06 (2H, m), 3.52-4.08 (6H, m), 6.94-6.99 (1H, m), 7.08-7.14 (1H, m), 7.18 (1H, s), 7.86-7.95 (1H, m).

Example 430

Production of 1'-acetyl-5-((3-(azetidine-1-carbonyl)cyclobutyl)methyl)-N-(5-chlorothiazol-2-yl)spiro[indoline-3,3'-pyrrolidine]-1-carboxamide Step 1: The 1-(2-(trimethylsilyl)ethyl) 1'-tert-butyl 5-bromospiro[indoline-3,3'-pyrrolidine]-1,1'-dicarboxylate (1.00 g, 2.01 mmol) obtained in Step 2 of Example 383 was dissolved in tetrahydrofuran (20 mL). Thereafter, tributyl(vinyl)tin (1.40 mL, 4.79 mmol), tetrakistriphenylphosphine palladium (240 mg, 0.21 mmol), and lithium chloride (260 mg, 6.13 mmol) were added to the above obtained solution at room temperature, and the thus obtained mixture was then stirred for 21 hours while heating under reflux. Thereafter, the reaction solution was purified by silica gel column chromatography (hexane:ethyl acetate=10:1) to obtain 1-(2-(trimethylsilyl)ethyl) 1'-tert-butyl 5-vinylspiro[indoline-3,3'-pyrrolidine]-1,1'-dicarboxylate (723 mg, 81%) in the form of a light yellow solid.

$^1$H-NMR (400 MHz, CDCl$_3$) δ: 0.08 (9H, s), 1.11 (2H, br), 1.48 (9H, s), 2.02 (1H, m), 2.20 (1H, m), 3.43-3.74 (4H, m), 3.92 (2H, m), 4.33 (2H, br), 5.15 (1H, d, J=11.0 Hz), 5.63 (1H, d, J=17.6 Hz), 6.66 (1H, dd, J=11.0, 17.6 Hz), 7.20 (1H, s), 7.26 (1H, br), 7.84 (1H, br).

Step 2: 1-(2-(Trimethylsilyl)ethyl) 1'-tert-butyl 5-vinylspiro[indoline-3,3'-pyrrolidine]-1,1'-dicarboxylate (674 mg, 1.52 mmol) was dissolved in dioxane (15 mL). Thereafter, sodium periodate (1.30 g, 6.08 mmol), water (5 mL), 2,6-lutidine (0.35 mL, 3.01 mmol), and osmium tetroxide (1% t-butanol aqueous solution, 1 mL) were added to the above obtained solution under cooling on ice, and the thus obtained mixture was then stirred at the same temperature as above for 3 hours. Thereafter, an aqueous solution of sodium sulfite was added to the reaction solution, and the mixture was then extracted with chloroform. The organic layer was washed with brine, and was then dried over anhydrous sodium sulfate, followed by concentration in vacuo. The obtained residue was purified by silica gel column chromatography (hexane ethyl acetate=5:1) to obtain 1-(2-(trimethylsilyl)ethyl) 1'-tert-butyl 5-formylspiro[indoline-3,3'-pyrrolidine]-1,1'-dicarboxylate (553 mg, 82%) in the form of a light yellow solid.

$^1$H-NMR (400 MHz, CDCl$_3$) δ: 0.08 (9H, s), 1.14 (2H, br), 1.47 (9H, br), 2.05 (1H, m), 2.24 (1H, m), 3.45-3.81 (4H, m), 3.99 (2H, m), 4.37 (2H, m), 7.70 (1H, s), 7.77 (1H, d, J=8.6 Hz), 8.01 (1H, br), 9.88 (1H, s).

Step 3: 1-(2-(Trimethylsilyl)ethyl) 1'-tert-butyl 5-formylspiro[indoline-3,3'-pyrrolidine]-1,1'-dicarboxylate (553 mg, 1.24 mmol) was dissolved in ethanol (12 mL). Thereafter, sodium borohydride (76.0 mg, 2.01 mmol) was added to the above obtained solution under cooling on ice, and the thus obtained mixture was then stirred at the same temperature as above for 30 minutes. Thereafter, water was added to the reaction solution, and the mixed solution was then extracted with chloroform. The organic layer was washed with brine, and was then dried over anhydrous sodium sulfate, followed by concentration in vacuo. The obtained residue was purified by silica gel column chromatography (hexane:ethyl acetate=5:1) to obtain 1-(2-(trimethylsilyl)ethyl) 1'-tert-butyl 5-(hydroxymethyl)spiro[indoline-3,3'-pyrrolidine]-1,1'-dicarboxylate (473 mg, 85%) in the form of a light yellow solid.

$^1$H-NMR (400 MHz, CDCl$_3$) δ: 0.08 (9H, s), 0.111 (2H, br), 1.47 (9 h, br), 2.01 (1H, m), 2.20 (1H, m), 3.42-3.72 (4H, m), 3.90 (2H, m), 4.33 (2H, br), 4.64 (2H, m), 4.64 (1H, s), 7.20 (1H, d, J=8.6 Hz), 7.87 (1H, br).

Step 4: 1-(2-(Trimethylsilyl)ethyl) 1'-tert-butyl 5-(hydroxymethyl)spiro[indoline-3,3'-pyrrolidine]-1,1'-dicarboxylate (441 mg, 0.98 mmol) was dissolved in methylene chloride (10 mL). Thereafter, carbon tetrabromide (359 mg, 1.08 mmol) and triphenylphosphine (310 mg, 1.18 mmol) were added to the above obtained solution under cooling on ice, and the thus obtained mixture was then stirred at the same temperature as above for 2.5 hours. Thereafter, the reaction solution was concentrated in vacuo, and the obtained residue was then purified by silica gel column chromatography (hexane:ethyl acetate=10:1) to obtain 1-(2-(trimethylsilyl)ethyl) 1'-tert-butyl 5-(bromomethyl)spiro[indoline-3,3'-pyrrolidine]-1,1'-dicarboxylate (390 mg, 77%) in the form of a colorless amorphous product.

$^1$H-NMR (400 MHz, CDCl$_3$) δ: 0.07 (9H, s), 1.11 (2H, br), 1.47 (9H, br), 2.02 (1H, m), 2.17 (1H, m), 3.42-3.74 (4H, m), 3.90 (2H, m), 4.33 (2H, br), 4.50 (2H, s), 7.16 (1H, s), 7.27 (1H, d, J=8.6 Hz), 7.85 (1H, br)

Step 5: Diethyl malonate (183 mg, 1.14 mmol) was dissolved in ethanol (2 mL). Thereafter, sodium ethoxide (78.0 mg, 1.15 mmol) and an ethanol (2 mL) solution of 1-(2-(trimethylsilyl)ethyl) 1'-tert-butyl 5-(bromomethyl)spiro[indoline-3,3'-pyrrolidine]-1,1'-dicarboxylate (390 mg, 0.76 mmol) were added to the above obtained solution under cooling on ice, and the thus obtained mixture was then stirred at the same temperature as above for 1.5 hours. Thereafter, water was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (hexane:ethyl acetate=3:1) to obtain 1-(2-(trimethylsilyl)ethyl) 1'-tert-butyl 5-(3-ethoxy-2-(ethoxycarbonyl)-3-oxopropyl)spiro[indoline-3,3'-pyrrolidine]-1,1'-dicarboxylate (300 mg, 67%) in the form of a colorless amorphous product.

¹H-NMR (400 MHz, CDCl₃) δ: 0.07 (9H, s), 1.10 (2H, br), 1.22 (6H, m), 1.47 (9H, br), 2.00 (1H, m), 2.14 (1H, m), 3.16 (2H, d, J=7.8 Hz), 3.36-3.72 (5H, m), 3.87 (2H, m), 4.15 (4H, m), 4.31 (2H, br), 6.98 (1H, s), 7.08 (1H, d, J=8.6 Hz), 7.79 (1H, br)

Step 6: Lithium aluminum hydride (39.0 mg, 1.03 mmol) was dissolved in diethyl ether (5 mL). Thereafter, a diethyl ether (5 mL) solution of 1-(2-(trimethylsilyl)ethyl) 1'-tert-butyl 5-(3-ethoxy-2-(ethoxycarbonyl)-3-oxopropyl)spiro[indoline-3,3'-pyrrolidine]-1,1'-dicarboxylate (300 mg, 0.51 mmol) was added to the above obtained solution under cooling on ice, and the thus obtained mixture was then stirred at the same temperature as above for 1 hour. Thereafter, a saturated aqueous solution of sodium sulfate was added to the reaction solution, and the mixed solution was then filtered through a pad of celite, followed by washing with chloroform. The filtrate was concentrated in vacuo, and the obtained residue was then purified by silica gel column chromatography (chloroform:methanol=10:1) to obtain 1-(2-(trimethylsilyl)ethyl) 1'-tert-butyl 5-(3-hydroxy-2-(hydroxymethyl)propyl)spiro[indoline-3,3'-pyrrolidine]-1,1'-dicarboxylate (58.7 mg, 23%) in the form of a light red amorphous product.

¹H-NMR (400 MHz, CDCl₃) δ: 0.07 (9H, s), 1.10 (2H, br), 1.22 (6H, m), 1.47 (9H, br), 2.00 (1H, m), 2.19 (2H, m), 2.60 (2H, d, J=7.3 Hz), 3.35-3.93 (10H, m), 4.32 (2H, br), 6.97 (1H, s), 7.06 (1H, d, J=8.6 Hz), 7.80 (1H, br)

Step 7: 1-(2-(Trimethylsilyl)ethyl) 1'-tert-butyl 5-(3-hydroxy-2-(hydroxymethyl)propyl)spiro[indoline-3,3'-pyrrolidine]-1,1'-dicarboxylate (58.7 mg, 0.12 mmol) was dissolved in methylene chloride (1.2 mL). Thereafter, carbon tetrabromide (81.0 mg, 0.24 mmol) and triphenylphosphine (67.0 mg, 0.26 mmol) were added to the above obtained solution under cooling on ice, and the thus obtained mixture was then stirred at the same temperature as above for 3 hours. Thereafter, the reaction solution was concentrated in vacuo, and the obtained residue was then purified by silica gel column chromatography (hexane ethyl acetate=5:1) to obtain 1-(2-(trimethylsilyl)ethyl) 1'-tert-butyl 5-(3-bromo-2-(bromomethyl)propyl)spiro[indoline-3,3'-pyrrolidine]-1,1'-dicarboxylate (47.1 mg, 64%) in the form of a colorless oily product.

¹H-NMR (400 MHz, CDCl₃) δ: 0.07 (9H, s), 1.11 (2H, br), 1.47 (9H, br), 2.02 (1H, m), 2.19 (2H, m), 2.72 (2H, d, J=6.8 Hz), 3.40-3.71 (8H, m), 3.88 (2H, m), 4.32 (2H, m), 6.99 (1H, s), 7.09 (1H, d, J=8.6 Hz), 7.83 (1H, br).

Step 8: Sodium hydride (10.0 mg, 0.21 mmol) was dissolved in N,N-dimethylformamide (1 mL). Thereafter, diethyl malonate (13.0 μL, 0.086 mmol) was added to the above obtained solution under cooling on ice, and the thus obtained mixture was then stirred at 100° C. for 30 minutes. Thereafter, an N,N-dimethylformamide (0.5 mL) solution of 1-(2-(trimethylsilyl)ethyl) 1'-tert-butyl 5-(3-bromo-2-(bromomethyl)propyl)spiro[indoline-3,3'-pyrrolidine]-1,1'-dicarboxylate (51.1 mg, 0.080 mmol) was further added to the reaction solution under cooling on ice, and the thus obtained mixture was then stirred at 100° C. for 2 hours. Thereafter, water was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (hexane ethyl acetate=5:1) to obtain 1-(2-(trimethylsilyl)ethyl) 1'-tert-butyl 5-((3,3-bis(ethoxycarbonyl)cyclobutyl)methyl)spiro[indoline-3,3'-pyrrolidine]-1,1'-dicarboxylate (20.8 mg, 41%) in the form of a colorless oily product.

¹H-NMR (400 MHz, CDCl₃) δ: 0.07 (9H, s), 1.10 (2H, br), 1.26 (6H, m), 1.50 (9H, br), 2.00 (1H, m), 2.15 (1H, m), 2.27 (2H, m), 2.55-2.68 (5H, m), 3.39-3.70 (4H, m), 3.88 (2H, m), 4.19 (4H, m), 4.31 (2H, br), 6.89 (1H, m), 7.00 (1H, d, J=8.6 Hz), 7.77 (1H, m).

Step 9: 1-(2-(Trimethylsilyl)ethyl) 1'-tert-butyl 5-((3,3-bis(ethoxycarbonyl)cyclobutyl)methyl)spiro[indoline-3,3'-pyrrolidine]-1,1'-dicarboxylate (20.8 mg, 0.033 mmol) was dissolved in ethanol (1 mL). Thereafter, an 8 N aqueous solution of sodium hydroxide (0.5 mL) was added to the above obtained solution under cooling on ice, and the thus obtained mixture was then stirred at room temperature for 4 hours. Thereafter, a 1 N aqueous solution of hydrochloric acid was added to the reaction solution, and the thus obtained mixture was neutralized and was then extracted with chloroform. The organic layer was washed with brine, and was then dried over anhydrous sodium sulfate, followed by concentration in vacuo, to obtain 3-((1'-(tert-butoxycarbonyl)-1-((2-(trimethylsilyl)ethoxy) carbonyl)spiro[indoline-3,3'-pyrrolidin]-5-yl)methyl)cyclobutane-1,1-dicarboxylic acid (19.3 mg, quant.) in the form of a colorless oily product.

¹H-NMR (400 MHz, CDCl₃) δ: 0.07 (9H, s), 1.10 (2H, br), 1.50 (9H, br), 2.00 (1H, m), 2.15 (1H, m), 2.29 (2H, m), 2.54-2.68 (5H, m), 3.38-3.71 (4H, m), 3.90 (2H, m), 4.31 (2H, br), 6.89 (1H, m), 7.00 (1H, d, J=8.6 Hz), 7.76 (1H, m).

Step 10: 3-((1'-(tert-Butoxycarbonyl)-1-((2-(trimethylsilyl)ethoxy)carbonyl)spiro[indoline-3,3'-pyrrolidin]-5-yl)methyl)cyclobutane-1,1-dicarboxylic acid (19.0 mg, 0.033 mmol) was dissolved in tetrahydrofuran (1 mL). Thereafter, carbonyldiimidazole (6.0 mg, 0.037 mmol) was added to the above obtained solution at room temperature, and the thus obtained mixture was then stirred for 1.5 hours. Thereafter, the reaction solution was concentrated in vacuo, and the obtained reaction mixture was then dissolved in ethanol (1 mL). Subsequently, an 8 N aqueous solution of sodium hydroxide (0.5 mL) was added to the above obtained solution under cooling on ice, and the thus obtained mixture was then stirred at room temperature for 18 hours. Thereafter, a 1 N aqueous solution of hydrochloric acid was added to the reaction solution. The thus obtained mixture was neutralized, and was then extracted with chloroform. The organic layer was washed with brine, and was then dried over anhydrous sodium sulfate, followed by concentration in vacuo, so as to obtain 3-((1'-(tert-butoxycarbonyl)-1-((2-(trimethylsilyl)ethoxy)carbonyl)spiro[indoline-3,3'-pyrrolidin]-5-yl)methyl)cyclobutanecarboxylic acid (17.3 mg, 99%) in the form of a brown oily product.

¹H-NMR (400 MHz, CDCl₃) δ: 0.07 (9H, m), 1.10 (2H, br), 1.50 (9H, br), 1.99-2.78 (10H, m), 3.38-3.71 (4H, m), 3.90 (2H, m), 4.31 (2H, br), 6.89-7.02 (2H, m), 7.78 (1H, br).

Step 11: 3-((1'-(tert-Butoxycarbonyl)-1-((2-(trimethylsilyl)ethoxy)carbonyl)spiro[indoline-3,3'-pyrrolidin]-5-yl)methyl)cyclobutanecarboxylic acid (17.5 mg, 0.033 mmol) was dissolved in methylene chloride (1 mL) Thereafter, azetidine hydrochloride (6.0 mg, 0.064 mmol), triethylamine (9.0 μL, 0.065 mmol), and PyBOP (34.0 mg, 0.065 mmol) were added to the above obtained solution at room temperature, and the thus obtained mixture was then stirred for 15 hours. Thereafter, water was added to the reaction solution, and the mixed solution was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain 1-(2-(trimethylsilyl)ethyl) 1'-tert-butyl 5-((3-(azetidine-1-carbonyl)cyclobutyl)methyl)spiro[indoline-3,3'-pyrrolidine]-1,1'-dicarboxylate (11.2 mg, 60%) in the form of a light brown oily product.

¹H-NMR (400 MHz, CDCl₃) δ: 0.07 (9H, m), 1.10 (2H, br), 1.50 (9H, br), 1.99-2.78 (12H, m), 3.38-3.71 (4H, m), 3.88-4.12 (6H, m), 4.30 (2H, br), 6.88-7.02 (2H, m), 7.77 (1H, br)

Step 12: The captioned compound was obtained in the form of a white solid by performing the same reactions and/or treatments as those in Step 5 of Example 21, and Examples 1, 2, and 3, with the exception that 1-(2-(trimethylsilyl)ethyl) 1'-tert-butyl 5-((3-(azetidine-1-carbonyl)cyclobutyl)methyl)spiro[indoline-3,3'-pyrrolidine]-1,1'-dicarboxylate was used instead of 1-(2-(trimethylsilyl)ethyl) 1'-tert-butyl 5-(methylsulfonyl)spiro[indoline-3,3'-pyrrolidine]-1,1'-dicarboxylate.

Example 431

Production of 1'-acetyl-N-(5-chlorothiazol-2-yl)-5-(trifluoromethyl)spiro[indoline-3,3'-pyrrolidine]-1-carboxamide Step 1: 4-Amino-3-bromobenzotrifluoride (15.0 g, 62.5 mmol) was dissolved in N,N-dimethylformamide (400 mL). Thereafter, sodium hydride (5.0 g, 126 mmol) was added to the above obtained solution under cooling on ice, and the thus obtained mixture was then stirred at room temperature for 2 hours. Thereafter, an N,N-dimethylformamide (30 mL) solution of the tert-butyl 3-(chloromethyl)-2,5-dihydro-1H-pyrrole-1-carboxylate (9.20 g, 42.0 mmol) synthesized by a method described in the known methods (European Journal of Organic Chemistry, 4264-4276; 2008 etc.) or a method similar thereto was further added to the reaction solution under cooling on ice, and the thus obtained mixture was then stirred at room temperature for 3 hours. Subsequently, water was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (hexane ethyl acetate=3:1) to obtain tert-butyl 3-(((2-bromo-4-(trifluoromethyl)phenyl)amino)methyl)-2,5-dihydro-1H-pyrrole-1-carboxylate (6.46 g, 37%) in the form of a colorless amorphous product.

¹H-NMR (400 MHz, CDCl₃) δ: 1.46 (9H, s), 3.93 (2H, m), 4.13 (4H, m), 4.88 (1H, m), 5.64 (1H, m), 6.61 (1H, m), 7.39 (1H, m), 7.67 (1H, s).

Step 2: tert-Butyl 3-(((2-bromo-4-(trifluoromethyl)phenyl)amino)methyl)-2,5-dihydro-1H-pyrrole-1-carboxylate (6.46 g, 15.3 mmol) was dissolved in benzene (300 mL). Thereafter, tributyltin hydride (6.02 mL, 23.0 mmol) and azobisisobutyronitrile (380 mg, 2.31 mmol) were added to the above obtained solution at room temperature, and the thus obtained mixture was then stirred for 15 hours while heating under reflux. Thereafter, the reaction solution was concentrated in vacuo, and the obtained residue was then purified by silica gel column chromatography (hexane:ethyl acetate=3:1) to obtain tert-butyl 5-(trifluoromethyl)spiro[indoline-3,3'-pyrrolidine]-1'-carboxylate (2.21 g, 42%) in the form of a colorless amorphous product.

¹H-NMR (400 MHz, CDCl₃) δ: 1.46 (9H, s), 2.13 (2H, m), 3.39-3.60 (6H, m), 4.04 (1H, s), 6.61 (1H, d, J=8.6 Hz), 7.24 (1H, s), 7.32 (1H, d, J=8.6 Hz).

Step 3: The captioned compound was obtained in the form of a white solid by performing the same reactions and/or treatments as those in Examples 1, 2, and 3, with the exception that tert-butyl 5-(trifluoromethyl)spiro[indoline-3,3'-pyrrolidine]-1'-carboxylate was used instead of t-butyl 5-bromospiro[indoline-3,3'-pyrrolidine]-1'-carboxylate.

¹H-NMR (400 MHz, CDCl₃) δ: 2.03-2.43 (5H, m), 3.51-4.18 (6H, m), 7.16-7.22 (1H, m), 7.36-7.43 (1H, m), 7.53-7.62 (1H, m), 8.14-8.24 (1H, m).

Example 445

Production of N1'-((1-acetylazetidin-3-yl)methyl)-N1-(5-chlorothiazol-2-yl)-5-(trifluoromethyl)spiro[indoline-3,3'-pyrrolidine]-1,1'-dicarboxamide Step 1: tert-Butyl 3-(aminomethyl)azetidine-1-carboxylate (1.10 g, 5.91 mmol) was dissolved in methylene chloride (50 mL). Thereafter, 4-nitrophenyl chloroformate (1.19 g, 5.91 mmol) and pyridine (0.47 g, 5.91 mmol) were added to the above obtained solution, and the thus obtained mixture was then stirred for 16 hours. Thereafter, the reaction solution was concentrated in vacuo to obtain tert-butyl 3-((((4-nitrophenoxy)carbonyl)amino)methyl)azetidine-1-carboxylate (2.52 g, >100%) in the form of a white solid.

¹H-NMR (CDCl₃) δ: 1.45 (9H, s), 2.80 (1H, m), 3.52 (2H, m), 3.69 (2H, m), 4.06 (2H, m) 7.32 (2H, d, J=9.0 Hz), 8.25 (2H, d, J=9.0 Hz).

Step 2: tert-Butyl 3-((1-((5-chlorothiazol-2-yl)carbamoyl)-5-(trifluoromethyl)spiro[indoline-3,3'-pyrrolidin]-1'-ylcarboxamido)methyl)azetidine-1-carboxylate was obtained in the form of a white solid by performing the same reactions and/or treatments as those in Examples 1, 2, and 3, with the exceptions that the tert-butyl 5-(trifluoromethyl)spiro[indoline-3,3'-pyrrolidine]-1'-carboxylate obtained in Step 2 of Example 431 was used instead of t-butyl 5-bromospiro[indoline-3,3'-pyrrolidine]-1'-carboxylate, and that tert-butyl 3-((((4-nitrophenoxy)carbonyl)amino)methyl)azetidine-1-carboxylate was used instead of acetyl chloride.

¹H-NMR (400 MHz, CDCl₃) δ: 1.42 (9H, s), 2.11-2.23 (1H, m), 2.30-2.46 (1H, m), 2.63-2.80 (1H, m), 3.27-4.19 (12H, m), 4.59-4.85 (1H, m), 7.15 (1H, s), 7.39 (1H, s), 7.56 (1H, d, J=8.3 Hz), 8.19 (1H, d, J=8.3 Hz).

Step 3: The captioned compound was obtained in the form of a white solid by performing the same reactions and/or treatments as those in Examples 2 and 3, with the exception that tert-butyl 3-((1-((5-chlorothiazol-2-yl)carbamoyl)-5-(trifluoromethyl)spiro[indoline-3,3'-pyrrolidin]-1'-ylcarboxamido)methyl)azetidine-1-carboxylate was used instead of t-butyl 5-bromo-1-((5-chlorothiazol-2-yl)carbamoyl)spiro[indoline-3,3'-pyrrolidine]-1'-carboxylate.

¹H-NMR (400 MHz, CDCl₃) δ: 1.82-1.94 (3H, m), 2.12-2.22 (1H, m), 2.29-2.45 (1H, m), 2.61-2.84 (1H, m), 3.36-4.19 (12H, m), 4.66-4.75 (1H, m), 7.12-7.19 (1H, m), 7.38 (1H, s), 7.56 (1H, d, J=8.3 Hz), 8.20 (1H, d, J=8.3 Hz).

Example 446

Production of N1'-((1-acetylazetidin-3-yl)methyl)-N1-(5-fluorothiazol-2-yl)-5-(trifluoromethyl)spiro[indoline-3,3'-pyrrolidine]-1,1'-dicarboxamide The captioned compound was obtained in the form of a white solid by performing the same reactions and/or treatments as those in Examples 1, 2, 373, 2, and 3, with the exceptions that the tert-butyl 5-(trifluoromethyl)spiro[indoline-3,3'-pyrrolidine]-1'-carboxylate obtained in Step 2 of Example 431 was used instead of t-butyl 5-bromospiro[indoline-3,3'-pyrrolidine]-1'-carboxylate, that 2-amino-5-fluorothiazole hydrochloride was used instead of 2-amino-5-chlorothiazole hydrochloride, and that the tert-butyl 3-((((4-nitrophenoxy)carbonyl)amino)methyl)azetidine-1- carboxylate obtained in Step 1 of Example 445 was used instead of phenyl N-carbamate.

Example 447

Production of N1'-((1-acetylazetidin-3-yl)methyl)-N1-(5-methoxythiazol-2-yl)-5-(trifluoromethyl)spiro[indoline-3,3'-pyrrolidine]-1,1'-dicarboxamide The captioned compound was obtained in the form of a white solid by performing the same reactions and/or treatments as those in Examples 1, 2, 373, 2, and 3, with the exceptions that the tert-butyl 5-(trifluoromethyl)spiro[indoline-3,3'-pyrrolidine]-1'-carboxylate obtained in Step 2 of Example 431 was used instead of t-butyl 5-bromospiro[indoline-3,3'-pyrrolidine]-1'-carboxylate, that 2-amino-5-methoxythiazole was used instead of 2-amino-5-chlorothiazole hydrochloride, and that the tert-butyl 3-((((4-nitrophenoxy)carbonyl)amino)methyl)azetidine-1-carboxylate obtained in Step 1 of Example 445 was used instead of phenyl N-carbamate.

Example 448

Production of N1'-((1-acetylazetidin-3-yl)methyl)-N1-(5-methylpyrazin-2-yl)-5-(trifluoromethyl)spiro[indoline-3,3'-pyrrolidine]-1,1'-dicarboxamide The captioned compound was obtained in the form of a white solid by performing the same reactions and/or treatments as those in Examples 1, 2, 373, 2, and 3, with the exceptions that the tert-butyl 5-(trifluoromethyl)spiro[indoline-3,3'-pyrrolidine]-1'-carboxylate obtained in Step 2 of Example 431 was used instead of t-butyl 5-bromospiro[indoline-3,3'-pyrrolidine]-1'-carboxylate, that 2-amino-5-methylpyrazine was used instead of 2-amino-5-chlorothiazole hydrochloride, and that the tert-butyl 3-((((4-nitrophenoxy)carbonyl)amino)methyl)azetidine-1-carboxylate obtained in Step 1 of Example 445 was used instead of phenyl N-carbamate.

Example 451

Production of 5-chloro-N-(5-chlorothiazol-2-yl)-1'-(2-(methylamino)-3,4-dioxocyclobut-1-en-1-yl)spiro[indoline-3,3'-pyrrolidine]-1-carboxamide The captioned compound was obtained in the form of a white solid by performing the same reactions and/or treatments as those in Example 45, with the exceptions that the 5-chloro-N-(5-chlorothiazol-2-yl)-1'-(2-ethoxy-3,4-dioxocyclobut-1-en-1-yl)spiro[indoline-3,3'-pyrrolidine]-1-carboxamide obtained in Example 450 was used instead of ethyl 2-(5-chloro-1-((5-chlorothiazol-2-yl)carbamoyl)spiro[indoline-3,3'-pyrrolidin]-1'-yl)-2-oxoacetate, and that a solution of methylamine-tetrahydrofuran was used instead of a saturated solution of ammonia-methanol.
$^1$H-NMR (400 MHz, DMSO-$d_6$) δ: 2.12 (1H, m), 2.28 (1H, m), 3.10 (3H, s), 3.72-3.81 (2H, m), 3.89-4.06 (4H, m), 7.09 (1H, s), 7.18 (1H, d, J=8.6 Hz), 7.32 (1H, s), 7.57 (1H, br), 8.02 (1H, d, J=8.6 Hz).

Example 452

Production of 1'-acetyl-N-(5-((3-aminopropyl)thio)thiazol-2-yl)-5-chlorospiro[indoline-3,3'-pyrrolidine]-1-carboxamide Step 1: 1'-Acetyl-5-chloro-N-(5-((3-(1,3-dioxoisoindolin-2-yl)propyl)thio)thiazol-2-yl)spiro[indoline-3,3'-pyrrolidine]-1-carboxamide was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that the 2-(3-((2-aminothiazol-5-yl)thio)propyl)isoindoline-1,3-dione synthesized by a method described in the known methods (International Publication WO2005/066145 etc.) or a method similar thereto was used instead of 2-amino-5-chlorothiazole hydrochloride.
$^1$H-NMR (400 MHz, CDCl$_3$) δ: 1.90-2.01 (1H, m), 2.01-2.37 (5H, m), 2.75 (2H, t, J=7.1 Hz), 3.48-3.28 (2H, m), 3.72-4.18 (6H, m), 7.07-7.17 (1H, m), 7.21-7.30 (1H, m), 7.34-7.40 (1H, m), 7.68-7.77 (2H, m), 7.77-7.88 (2H, m), 7.96-8.06 (1H, m).

Step 2: 1'-Acetyl-5-chloro-N-(5-((3-(1,3-dioxoisoindolin-2-yl)propyl)thio)thiazol-2-yl)spiro[indoline-3,3'-pyrrolidine]-1-carboxamide (0.93 g, 1.57 mmol) was dissolved in ethanol (30 mL). Thereafter, a hydrazine hydrate (0.12 g, 2.36 mmol) was added to the above obtained solution at room temperature, and the thus obtained mixture was then stirred at 90° C. for 3.5 hours. Thereafter, the reaction solution was concentrated in vacuo, and the obtained residue was then purified by silica gel column chromatography (chloroform:methanol=4:1) to obtain the captioned compound (0.56 g, 77%) in the form of a colorless solid.

Example 453

Production of N-(5-((3-acetamidopropyl)thio)thiazol-2-yl)-1'-acetyl-5-chlorospiro[indoline-3,3'-pyrrolidine]-1-carboxamide The captioned compound was obtained in the form of a white solid by performing the same reactions and/or treatments as those in Example 3, with the exception that the 1'-acetyl-N-(5-((3-aminopropyl)thio)thiazol-2-yl)-5-chlorospiro[indoline-3,3'-pyrrolidine]-1-carboxamide obtained in Example 452 was used instead of 5-bromo-N-(5-chlorothiazol-2-yl)spiro[indoline-3,3'-pyrrolidine]-1-carboxamide.

Example 454

Production of methyl 5-chloro-1-((5-((3-(cyclopropanecarboxamido)propyl)thio)thiazol-2-yl)carbamoyl)spiro[indoline-3,3'-pyrrolidine]-1'-carboxylate Step 1: Methyl 1-((5-((3-aminopropyl)thio)thiazol-2-yl)carbamoyl)-5-chlorospiro[indoline-3,3'-pyrrolidine]-1'-carboxylate was obtained in the form of a white solid by performing the same reactions and/or treatments as those in Examples 1, 2, and 3, and Step 2 of Example 452, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, that the 2-(3-((2-aminothiazol-5-yl)thio)propyl)isoindoline-1,3-dione synthesized by a method described in the known methods (International Publication WO2005/066145 etc.) or a method similar thereto was used instead of 2-amino-5-chlorothiazole hydrochloride, and that methyl chloroformate was used instead of acetyl chloride.
$^1$H-NMR (400 MHz, DMSO-$d_6$) δ: 1.68-1.79 (2H, m), 1.95-2.17 (1H, m), 2.19-2.24 (1H, m), 2.64 (2H, t, J=7.3 Hz), 2.81 (2H, t, J=7.3 Hz), 3.35-3.66 (7H, m), 3.92 (2H, br), 7.15 (1H, dd, J=2.2, 8.5 Hz), 7.19 (1H, s), 7.24 (1H, d, J=2.2 Hz), 8.03 (1H, d, J=8.5 Hz).

Step 2: The captioned compound was obtained in the form of a white solid by performing the same reactions and/or treatments as those in Example 3, with the exceptions that methyl 1-((5-((3-aminopropyl)thio)thiazol-2-yl)carbamoyl)-5-chlorospiro[indoline-3,3'-pyrrolidine]-1'-carboxylate was used instead of 5-bromo-N-(5-chlorothiazol-2-yl)spiro[indoline-3,3'-pyrrolidine]-1-carboxamide, and that cyclopropanecarbonyl chloride was used instead of acetyl chloride.

Example 455

Production of methyl 5-chloro-1-((5-((3-((methoxycarbonyl)amino)propyl)thio)thiazol-2-yl)carbamoyl) spiro[indoline-3,3'-pyrrolidine]-1'-carboxylate The captioned compound was obtained in the form of a white solid by performing the same reactions and/or treatments as those in Example 3, with the exceptions that the methyl 1-((5-((3-aminopropyl)thio)thiazol-2-yl)carbamoyl)-5-chlorospiro[indoline-3,3'-pyrrolidine]-1'-carboxylate obtained in Step 1 of Example 454 was used instead of 5-bromo-N-(5-chlorothiazol-2-yl)spiro[indoline-3,3'-pyrrolidine]-1-carboxamide, and that methyl chloroformate was used instead of acetyl chloride.

Example 459

Production of 5-chloro-N1-(5-chlorothiazol-2-yl)-N1'-(2-hydroxyethyl)spiro[indoline-3,3'-pyrrolidine]-1,1'-dicarboxamide The captioned compound was obtained in the form of a white solid by performing the same reactions and/or treatments as those in Step 1 of Example 401, with the exception that the ethyl 2-(5-chloro-1-((5-chlorothiazol-2-yl)carbamoyl)spiro[indoline-3,3'-pyrrolidin]-1'-ylcarboxamido)acetate obtained in Example 457 was used instead of tert-butyl 1-((5-chlorothiazol-2-yl)carbamoyl)-5-cyanospiro[indoline-3,3'-pyrrolidine]-1'-carboxylate.

Example 464

Production of 5-chloro-N1-(5-chlorothiazol-2-yl)-N1'-(3-hydroxypropyl)spiro[indoline-3,3'-pyrrolidine]-1,1'-dicarboxamide The captioned compound was obtained in the form of a white solid by performing the same reactions and/or treatments as those in Step 1 of Example 401, with the exception that the ethyl 3-(5-chloro-1-((5-chlorothiazol-2-yl)carbamoyl)spiro[indoline-3,3'-pyrrolidin]-1'-ylcarboxamido)propanoate obtained in Example 462 was used instead of tert-butyl 1-((5-chlorothiazol-2-yl)carbamoyl)-5-cyanospiro[indoline-3,3'-pyrrolidine]-1'-carboxylate.

Example 467

Production of 5-chloro-N1-(5-chlorothiazol-2-yl)-N1'-(2-(methylsulfonyl)ethyl)spiro[indoline-3,3'-pyrrolidine]-1,1'-dicarboxamide Step 1: 4-Nitrophenyl (2-(methylsulfonyl)ethyl)carbamate was obtained in the form of a yellow solid by performing the same reactions and/or treatments as those in Step 1 of Example 445, with the exception that 2-(methylsulfonyl) ethanamine was used instead of tert-butyl 3-(aminomethyl) azetidine-1-carboxylate.

$^1$H-NMR (400 MHz, CDCl$_3$) δ: 3.03 (3H, s), 3.33 (2H, m), 3.86 (2H, m), 5.92 (1H, m), 7.33 (2H, d, J=9.0 Hz), 8.26 (2H, d, J=9.0 Hz).

Step 2: The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that 4-nitrophenyl (2-(methylsulfonyl)ethyl)carbamate was used instead of acetyl chloride.

$^1$H-NMR (400 MHz, DMSO-d$_6$) δ: 2.09 (1H, m), 2.24 (1H, m), 3.01 (3H, s), 3.24 (2H, m), 3.32 (2H, m), 3.45 (2H, m), 3.52 (2H, m), 4.10 (2H, m), 6.51 (1H, br), 7.29 (1H, d, J=8.6 Hz), 7.43 (1H, s), 7.49 (1H, s), 7.92 (1H, d, J=8.6 Hz).

Example 470

Production of 5-chloro-N1-(5-chlorothiazol-2-yl)-N1'-(4-hydroxybutyl)spiro[indoline-3,3'-pyrrolidine]-1,1'-dicarboxamide The captioned compound was obtained in the form of a white solid by performing the same reactions and/or treatments as those in Step 1 of Example 401, with the exception that the ethyl 4-(5-chloro-1-((5-chlorothiazol-2-yl)carbamoyl)spiro[indoline-3,3'-pyrrolidin]-1'-ylcarboxamido)butanoate obtained in Example 468 was used instead of tert-butyl 1-((5-chlorothiazol-2-yl)carbamoyl)-5-cyanospiro[indoline-3,3'-pyrrolidine]-1'-carboxylate.

Example 473

Production of ethyl 1-(5-chloro-1-((5-chlorothiazol-2-yl)carbamoyl)spiro[indoline-3,3'-pyrrolidin]-1'-ylcarboxamido)cyclopropanecarboxylate Step 1: Ethyl 1-(((4-nitrophenoxy)carbonyl)amino)cyclopropanecarboxylate was obtained in the form of a yellow solid by performing the same reactions and/or treatments as those in Step 1 of Example 445, with the exception that ethyl 1-aminocyclopropanecarboxylate was used instead of tert-butyl 3-(aminomethyl)azetidine-1-carboxylate.

$^1$H-NMR (400 MHz, CDCl$_3$) δ: 1.22 (3H, t, J=7.1 Hz), 1.27 (2H, m), 1.65 (2H, m), 4.19 (2H, q, J=7.1 Hz), 5.79 (1H, s), 7.33 (2H, d, J=9.0 Hz), 8.24 (2H, d, J=9.0 Hz).

Step 2: The captioned compound was obtained in the form of a white solid by performing the same reactions and/or treatments as those in Examples 1, 2, and 3, with the exceptions that t-butyl 5-chlorospiro[indoline-3,3'-pyrrolidine]-1'-carboxylate was used instead of t-butyl 5-bromospiro[indoline-3,3'-pyrrolidine]-1'-carboxylate, and that ethyl 1-(((4-nitrophenoxy)carbonyl)amino)cyclopropanecarboxylate was used instead of acetyl chloride.

$^1$H-NMR (400 MHz, DMSO-d$_6$) δ: 1.04 (2H, m), 1.15 (3H, t, J=7.1 Hz), 1.34 (2H, m), 2.08 (1H, m), 2.22 (1H, m), 3.34 (2H, m), 3.52 (2H, m), 4.05 (2H, q, J=7.1 Hz), 4.11 (2H, m), 6.99 (1H, s), 7.28 (1H, d, J=8.6 Hz), 7.42 (1H, s), 7.49 (1H, s), 7.93 (1H, d, J=8.6 Hz).

Example 476

Production of N1'-((1-acetylazetidin-3-yl)methyl)-5-chloro-N1-(5-chlorothiazol-2-yl)spiro[indoline-3,3'-pyrrolidine]-1,1'-dicarboxamide Step 1: tert-Butyl 3-((5-chloro-1-((5-chlorothiazol-2-yl) carbamoyl)spiro[indoline-3,3'-pyrrolidin]-1'-ylcarboxamido)methyl)azetidine-1-carboxylate was obtained in the form of a white solid by performing the same reactions and/or treatments as those in Examples 1, 2, and 3, with the exceptions that tert-butyl 5-chlorospiro[indoline-3,3'-pyrrolidine]-1'-carboxylate was used instead of t-butyl 5-bromospiro[indoline-3,3'-pyrrolidine]-1'-carboxylate, and that the tert-butyl 3-((((4-nitrophenoxy)carbonyl)amino)methyl)azetidine-1-carboxylate obtained in Step 1 of Example 445 was used instead of acetyl chloride.

$^1$H-NMR (CDCl$_3$) δ: 1.42 (9H, s), 2.09-2.18 (1H, m), 2.26-2.37 (1H, m), 2.64-2.79 (1H, m), 3.32-4.08 (12H, m), 4.55-4.63 (1H, m), 7.10-7.14 (1H, m), 7.16 (1H, s), 7.22-7.28 (1H, m), 8.00 (1H, d, J=8.8 Hz).

Step 2: The captioned compound was obtained in the form of a white solid by performing the same reactions and/or treatments as those in Examples 2 and 3, with the exception that tert-butyl 3-((5-chloro-1-((5-chlorothiazol-2-yl)carbamoyl)spiro[indoline-3,3'-pyrrolidin]-1'-ylcarboxamido)methyl)azetidine-1-carboxylate was used instead of t-butyl 5-bromo-1-((5-chlorothiazol-2-yl)carbamoyl)spiro[indoline-3,3'-pyrrolidine]-1'-carboxylate.

Example 477

Production of 5-chloro-N-(5-chlorothiazol-2-yl)-1'-((S)-2,3-dihydroxypropanoyl)spiro[indoline-3,3'-pyrrolidine]-1-carboxamide Step 1: 5-Chloro-N-(5-chlorothiazol-2-yl)-1'-((S)-2,2-dimethyl-1,3-dioxolane-4-carbonyl)spiro[indoline-3,3'-pyrrolidine]-1-carboxamide was obtained in the form of a white solid by performing the same reactions and/or treatments as those in Example 19, with the exceptions that the 5-chloro-N-(5-chlorothiazol-2-yl)spiro[indoline-3,3'-pyrrolidine]-1-carboxamide obtained as an intermediate of Example 39 was used instead of 5-bromo-N-(5-chlorothiazol-2-yl)spiro[indoline-3,3'-pyrrolidine]-1-carboxamide, and that (S)-2,2-dimethyl-1,3-dioxolane-4-carboxylic acid was used instead of N-Boc glycine.

$^1$H-NMR (CDCl$_3$) δ: 1.45-1.50 (6H, m), 2.10-2.32 (2H, m), 3.61-4.22 (7H, m), 4.41 (1H, m), 4.63 (1H, m), 7.04-7.13 (2H, m), 8.27 (1H, m), 7.96 (1H, m).

Step 2: 5-Chloro-N-(5-chlorothiazol-2-yl)-1'-((S)-2,2-dimethyl-1,3-dioxolane-4-carbonyl)spiro[indoline-3,3'-pyrrolidine]-1-carboxamide (116 mg, 0.233 mmol) was dissolved in tetrahydrofuran (1 mL) and methanol (1 mL) Thereafter, a 1 N aqueous solution of hydrochloric acid (1 mL) was added to the above obtained solution at room temperature, and the thus obtained mixture was then stirred at 50° C. for 20 minutes. Thereafter, the reaction solution was diluted with water, and was then extracted with chloroform. The organic layer was washed with brine, and was then dried over anhydrous sodium sulfate, followed by concentration in vacuo. The obtained residue was purified by silica gel column chromatography (chloroform:methanol=10:1) to obtain the captioned compound (43.4 mg, 41%) in the form of a colorless amorphous product.

Example 478

Production of 5-chloro-N-(5-chlorothiazol-2-yl)-1'-((R)-2,3-dihydroxypropanoyl)spiro[indoline-3,3'-pyrrolidine]-1-carboxamide The captioned compound was obtained in the form of a white solid by performing the same reactions and/or treatments as those in Example 19 and Step 2 of Example 117, with the exceptions that the 5-chloro-N-(5-chlorothiazol-2-yl)spiro[indoline-3,3'-pyrrolidine]-1-carboxamide obtained as an intermediate of Example 39 was used instead of 5-bromo-N-(5-chlorothiazol-2-yl)spiro[indoline-3,3'-pyrrolidine]-1-carboxamide, and that (R)-2,2-dimethyl-1,3-dioxolane-4-carboxylic acid was used instead of N-Boc glycine.

Example 479

Production of 5-chloro-N-(5-chlorothiazol-2-yl)-1'-(3-hydroxypropanoyl)spiro[indoline-3,3'-pyrrolidine]-1-carboxamide Step 1: Ethyl 3-(5-chloro-1-((5-chlorothiazol-2-yl)carbamoyl)spiro[indoline-3,3'-pyrrolidin]-1'-yl)-3-oxopropanoate was obtained in the form of a white solid by performing the same reactions and/or treatments as those in Example 19, with the exceptions that the 5-chloro-N-(5-chlorothiazol-2-yl)spiro[indoline-3,3'-pyrrolidine]-1-carboxamide obtained as an intermediate of Example 39 was used instead of 5-bromo-N-(5-chlorothiazol-2-yl)spiro[indoline-3,3'-pyrrolidine]-1-carboxamide, and that monoethyl malonate was used instead of N-Boc glycine.

$^1$H-NMR (CDCl$_3$) δ: 1.21 (3H, m), 2.11-2.30 (2H, m), 3.48-4.38 (10H, m), 7.15 (1H, m), 7.17 (1H, m), 7.26 (1H, m), 8.02 (1H, m).

Step 2: Ethyl 3-(5-chloro-1-((5-chlorothiazol-2-yl)carbamoyl)spiro[indoline-3,3'-pyrrolidin]-1'-yl)-3-oxopropanoate (62.1 mg, 0.128 mmol) was dissolved in tetrahydrofuran (5 mL) and methanol (5 mL). Thereafter, sodium borohydride (150 mg, 3.97 mmol) was added to the above obtained solution at room temperature, and the thus obtained mixture was then stirred for 2 hours while heating under reflux. Thereafter, a saturated aqueous solution of ammonium chloride was added to the reaction solution, and the mixed solution was then extracted with ethyl acetate. The organic layer was washed with brine, and was then dried over anhydrous sodium sulfate, followed by concentration in vacuo. The obtained residue was purified by silica gel column chromatography (chloroform:methanol=10:1) to obtain the captioned compound (28.2 mg, 49%) in the form of a white amorphous product.

Example 481

Production of 5-chloro-N1-(5-chlorothiazol-2-yl)-N1'-hydroxyspiro[indoline-3,3'-pyrrolidine]-1,1'-dicarboxamide The captioned compound was obtained in the form of a white solid by performing the same reactions and/or treatments as those in Example 373, with the exception that phenyl hydroxycarbamate was used instead of phenyl N-carbamate.

$^1$H-NMR (400 MHz, DMSO-d$_6$) δ: 2.02 (1H, m), 2.20 (1H, m), 3.30 (2H, m), 3.47 (2H, m), 4.03 (2H, m), 7.22 (1H, d, J=8.6 Hz), 7.32 (1H, s), 7.42 (1H, s), 7.90 (1H, d, J=8.6 Hz), 8.11 (1H, d, J=1.8 Hz), 8.74 (1H, d, J=1.8 Hz).

Example 484

Production of (R)-5-chloro-N1-(5-chlorothiazol-2-yl)-N1'-methylspiro[indoline-3,3'-pyrrolidine]-1,1'-dicarboxamide The captioned compound was obtained in the form of a white solid by performing the same reactions and/or treatments as those in Example 373, with the exception that the (S)-5-chloro-N-(5-chlorothiazol-2-yl)spiro[indoline-3,3'-pyrrolidine]-1-carboxamide obtained as an intermediate of Example 52 was used instead of 5-chloro-N-(5-chlorothiazol-2-yl)spiro[indoline-3,3'-pyrrolidine]-1-carboxamide.

The chemical structures and instrumental data of some compounds included in the present invention are shown in the following Table 1-1 to Table 1-31.

TABLE 1-1-continued

| Example | Structural formula |
|---|---|
| 10 | (cyclopentylcarbonyl-spiropyrrolidine-bromoindoline-N-(5-chlorothiazol-2-yl)urea) |
| 11 | (cyclohexylcarbonyl-spiropyrrolidine-bromoindoline-N-(5-chlorothiazol-2-yl)urea) |
| 12 | (benzoyl-spiropyrrolidine-bromoindoline-N-(5-chlorothiazol-2-yl)urea) |
| 13 | (methoxycarbonyl-spiropyrrolidine-bromoindoline-N-(5-chlorothiazol-2-yl)urea) |
| 14 | (trifluoroacetyl-spiropyrrolidine-bromoindoline-N-(5-chlorothiazol-2-yl)urea) |

TABLE 1-1-continued

| Example | Structural formula |
|---|---|
| 15 | (N,N-dimethylcarbamoyl-spiropyrrolidine-bromoindoline-N-(5-chlorothiazol-2-yl)urea) |
| 16 | (carbamoyl-spiropyrrolidine-bromoindoline-N-(5-chlorothiazol-2-yl)urea) |

TABLE 1-2

| Example | Structural formula |
|---|---|
| 17 | (hydroxyacetyl-spiropyrrolidine-bromoindoline-N-(5-chlorothiazol-2-yl)urea) |
| 18 | (methoxyacetyl-spiropyrrolidine-bromoindoline-N-(5-chlorothiazol-2-yl)urea) |

TABLE 1-2-continued
| Example | Structural formula |
|---|---|
| 19 | 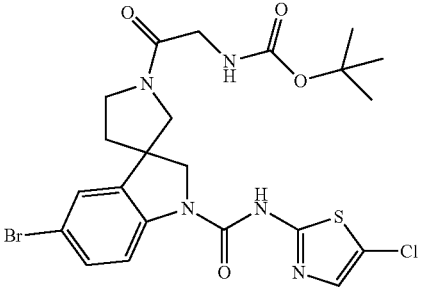 [SMILES: CC(C)(C)OC(=O)NCC(=O)N1CCC2(C1)CN(C(=O)Nc1ncc(Cl)s1)c1ccc(Br)cc12] |
| 20 | 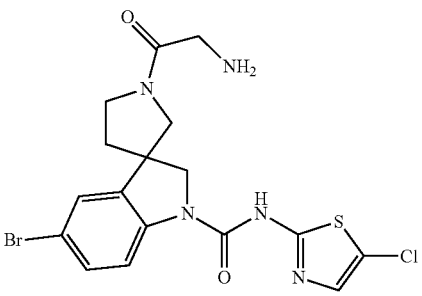 [SMILES: NCC(=O)N1CCC2(C1)CN(C(=O)Nc1ncc(Cl)s1)c1ccc(Br)cc12] |
| 21 | 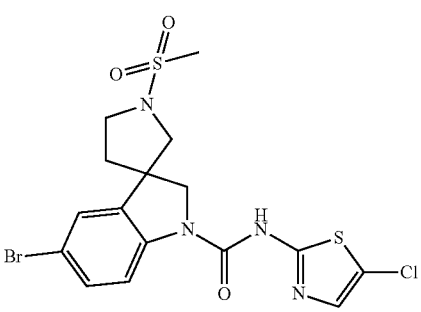 [SMILES: CS(=O)(=O)N1CCC2(CN(C(=O)Nc3ncc(Cl)s3)c3ccc(Br)cc32)C1] |
| 22 | 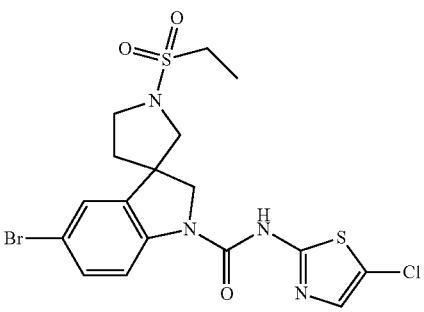 [SMILES: CCS(=O)(=O)N1CCC2(CN(C(=O)Nc3ncc(Cl)s3)c3ccc(Br)cc32)C1] |
| 23 | 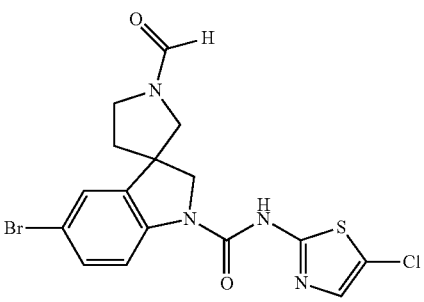 [SMILES: O=CN1CCC2(C1)CN(C(=O)Nc1ncc(Cl)s1)c1ccc(Br)cc12] |
TABLE 1-2-continued
| Example | Structural formula |
|---|---|
| 24 | 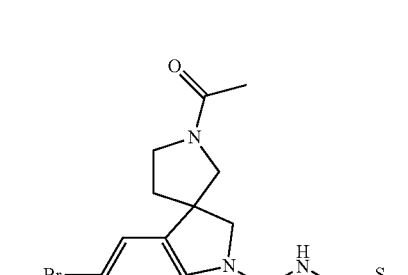 |
| 25 |  |
| 26 | 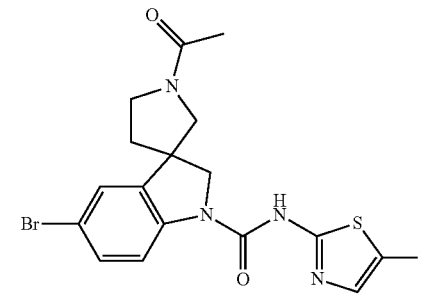 |
| 27 | 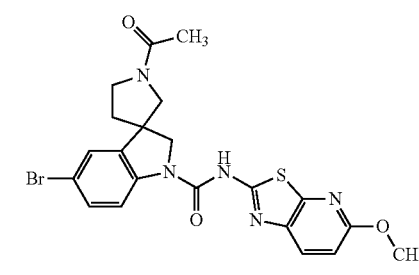 |
| 28 | 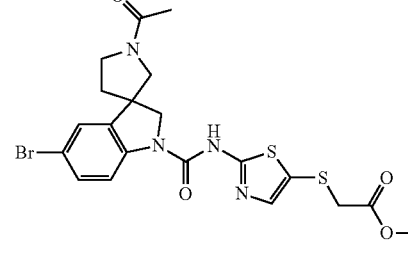 |

TABLE 1-2-continued
| Example | Structural formula |
|---|---|
| 29 | 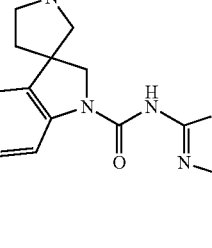 |
| 30 | 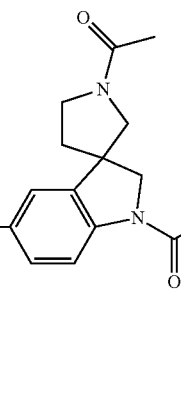 |
| 31 | 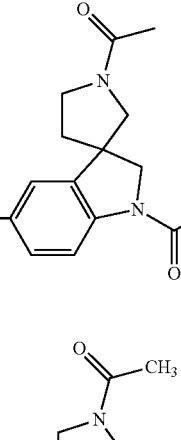 |
| 32 | 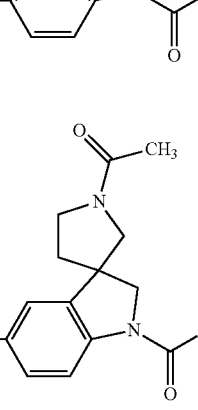 |
TABLE 1-3
| Example | Structural formula |
|---|---|
| 33 | 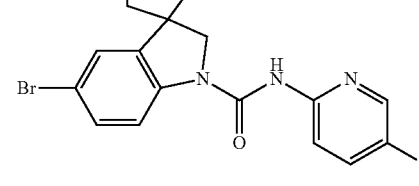 |
| 34 | 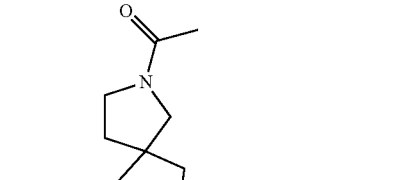 |
| 35 | 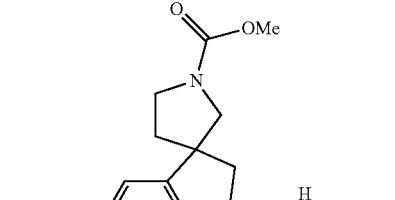 |
| 36 | 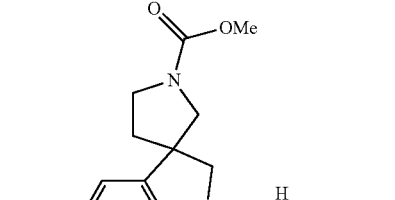 |
| 37 | 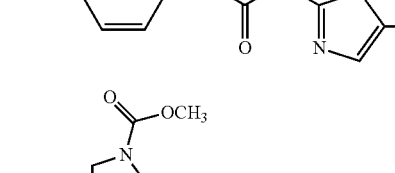 |

TABLE 1-3-continued

| Example | Structural formula |
|---|---|
| 38 | (5-bromo-spiro[indoline-3,3'-pyrrolidine] with N-methyl carbamate, N-(thiazol-2-yl)carboxamide with S-CH2COOH substituent) |
| 39 | (5-chloro-spiro[indoline-3,3'-pyrrolidine] with N-acetyl, N-(5-chlorothiazol-2-yl)carboxamide) |
| 40 | (5-chloro-spiro[indoline-3,3'-pyrrolidine] with N-formyl, N-(5-chlorothiazol-2-yl)carboxamide) |
| 41 | (5-chloro-spiro[indoline-3,3'-pyrrolidine] with N-CO-OMe, N-(5-chlorothiazol-2-yl)carboxamide) |
| 42 | (5-chloro-spiro[indoline-3,3'-pyrrolidine] with N-SO2Me, N-(5-chlorothiazol-2-yl)carboxamide) |
| 43 | (5-chloro-spiro[indoline-3,3'-pyrrolidine] with N-CO-COOEt, N-(5-chlorothiazol-2-yl)carboxamide) |
| 44 | (5-chloro-spiro[indoline-3,3'-pyrrolidine] with N-CO-COOH, N-(5-chlorothiazol-2-yl)carboxamide) |
| 45 | (5-chloro-spiro[indoline-3,3'-pyrrolidine] with N-CO-CONH2, N-(5-chlorothiazol-2-yl)carboxamide) |
| 46 | (5-chloro-spiro[indoline-3,3'-pyrrolidine] with N-CO-CONHMe, N-(5-chlorothiazol-2-yl)carboxamide) |
| 47 | (5-chloro-spiro[indoline-3,3'-pyrrolidine] with N-CO-CH2NH2, N-(5-chlorothiazol-2-yl)carboxamide) |

TABLE 1-3-continued

| Example | Structural formula |
|---|---|
| 48 | (structure) |

TABLE 1-4

| Example | Structural formula |
|---|---|
| 49 | (structure) |
| 50 | (structure) |
| 51 | (structure) |

TABLE 1-4-continued

| Example | Structural formula |
|---|---|
| 52 | (structure) |
| 53 | (structure) |
| 54 | (structure) |
| 55 | (structure) |
| 56 | (structure) |

TABLE 1-4-continued

| Example | Structural formula |
|---|---|
| 57 | (structure) |
| 58 | (structure) |
| 59 | (structure) |
| 60 | (structure) |
| 61 | (structure) |

TABLE 1-4-continued

| Example | Structural formula |
|---|---|
| 62 | (structure) |
| 63 | (structure) |
| 64 | (structure) |

TABLE 1-5

| Example | Structural formula |
|---|---|
| 65 | (structure) |
| 66 | (structure) |

TABLE 1-5-continued

| Example | Structural formula |
|---------|-------------------|
| 67 | |
| 68 | |
| 69 | |
| 70 | |
| 71 | |

TABLE 1-5-continued

| Example | Structural formula |
|---------|-------------------|
| 72 | |
| 73 | |
| 74 | |
| 75 | |
| 76 | |

TABLE 1-5-continued

| Example | Structural formula |
|---|---|
| 77 | |
| 78 | |
| 79 | |
| 80 | |

TABLE 1-6

| Example | Structural formula |
|---|---|
| 81 | |

TABLE 1-6-continued

| Example | Structural formula |
|---|---|
| 82 | |
| 83 | |
| 84 | |
| 85 | |

TABLE 1-6-continued
| Example | Structural formula |
|---|---|
| 86 | 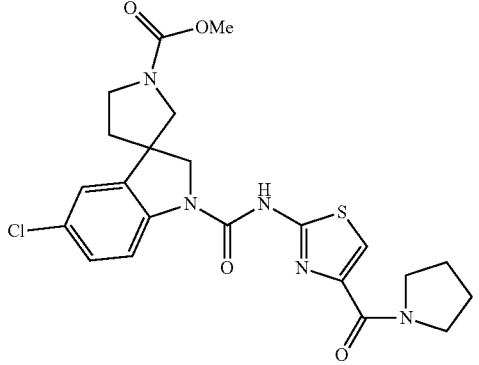 [SMILES: COC(=O)N1CCC2(C1)CN(C(=O)Nc1nc(C(=O)N3CCCC3)cs1)c1ccc(Cl)cc12] |
| 87 | 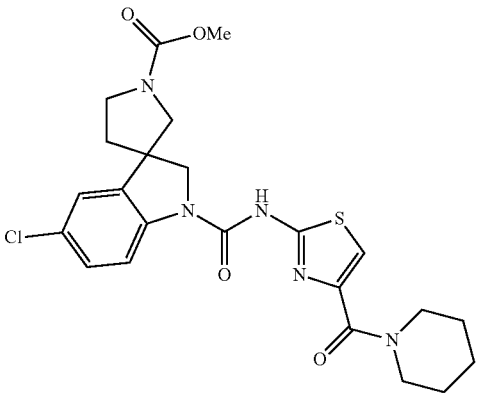 [SMILES: COC(=O)N1CCC2(C1)CN(C(=O)Nc1nc(C(=O)N3CCCCC3)cs1)c1ccc(Cl)cc12] |
| 88 | 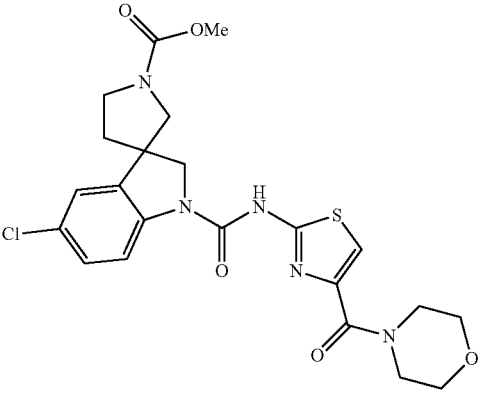 [SMILES: COC(=O)N1CCC2(C1)CN(C(=O)Nc1nc(C(=O)N3CCOCC3)cs1)c1ccc(Cl)cc12] |
| 89 | 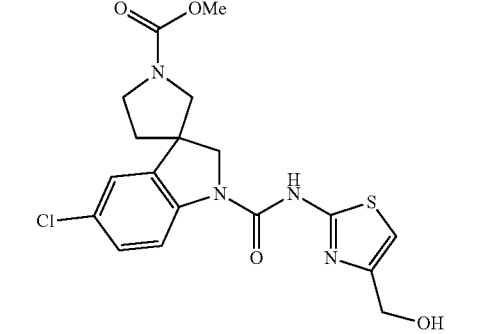 [SMILES: COC(=O)N1CCC2(C1)CN(C(=O)Nc1nc(CO)cs1)c1ccc(Cl)cc12] |
| 90 | 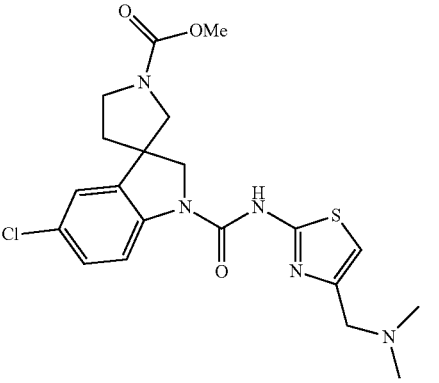 [SMILES: COC(=O)N1CCC2(C1)CN(C(=O)Nc1nc(CN(C)C)cs1)c1ccc(Cl)cc12] |
| 91 | 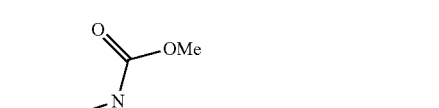 |
| 92 | 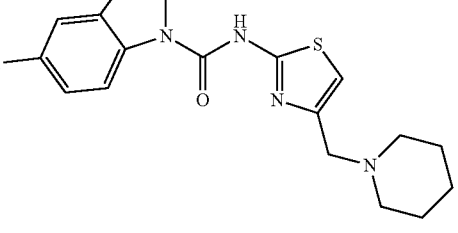 |
| 93 | 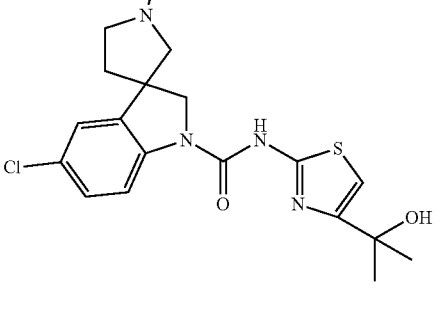 |

TABLE 1-6-continued

| Example | Structural formula |
|---|---|
| 94 | (structure) |
| 95 | (structure) |
| 96 | (structure) |

TABLE 1-7

| Example | Structural formula |
|---|---|
| 97 | (structure) |
| 98 | (structure) |
| 99 | (structure) |

TABLE 1-7-continued
| Example | Structural formula |
|---|---|
| 100 | 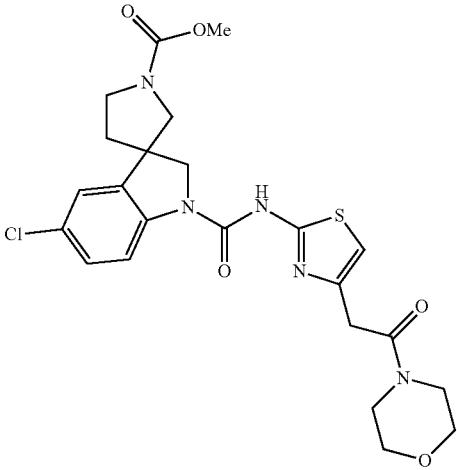 [SMILES: COC(=O)N1CCC2(C1)CN(C(=O)Nc1nc(CC(=O)N3CCOCC3)cs1)c1ccc(Cl)cc12] |
| 101 | 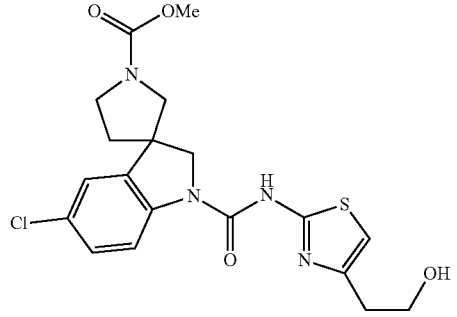 [SMILES: COC(=O)N1CCC2(C1)CN(C(=O)Nc1nc(CCO)cs1)c1ccc(Cl)cc12] |
| 102 | 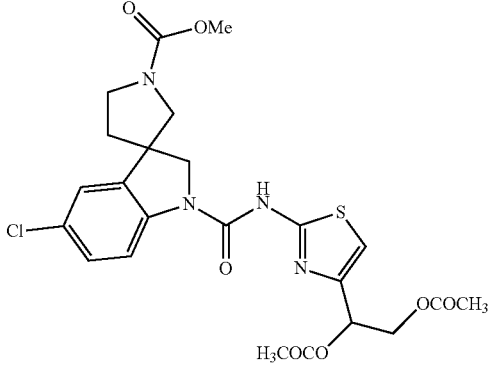 |
| 103 | 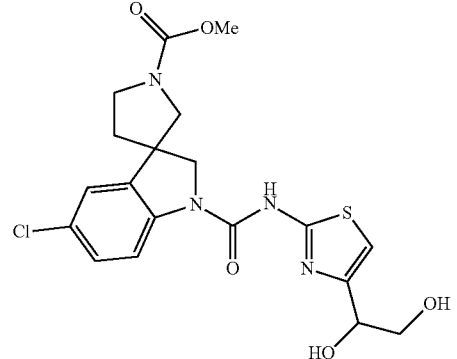 [SMILES: COC(=O)N1CCC2(C1)CN(C(=O)Nc1nc(C(O)CO)cs1)c1ccc(Cl)cc12] |
| 104 | 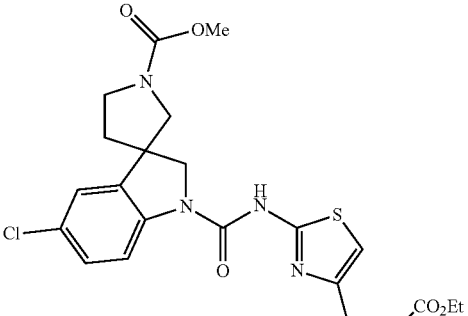 |
| 105 | 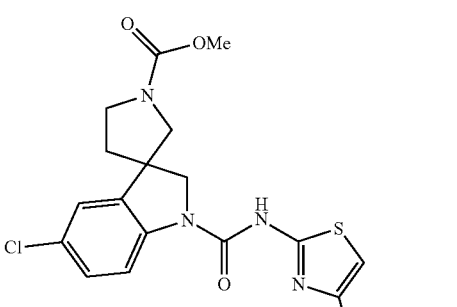 |
| 106 | 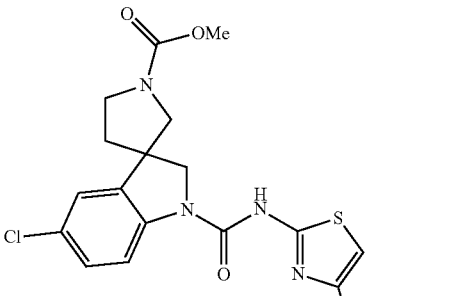 |
| 107 | 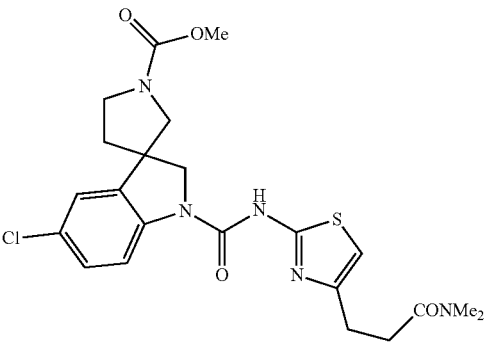 |

TABLE 1-7-continued

| Example | Structural formula |
|---|---|
| 108 | (structure: 5-chloro-spiro[pyrrolidine-3,3'-indoline]-1-carboxylic acid methyl ester, N-acyl urea linked to 4-butylthiazol-2-yl) |
| 109 | (structure with thiazole bearing CO₂Et at 5-position) |
| 110 | (structure with thiazole bearing CO₂H at 5-position) |
| 111 | (structure with thiazole bearing CONH₂ at 5-position) |
| 112 | (structure with thiazole bearing C(O)N(Me)₂ at 5-position) |

TABLE 1-8

| Example | Structural formula |
|---|---|
| 113 | (structure with thiazole bearing azetidine-1-carbonyl at 5-position) |
| 114 | (structure with thiazole bearing pyrrolidine-1-carbonyl at 5-position) |
| 115 | (structure with thiazole bearing piperidine-1-carbonyl at 5-position) |
| 116 | (structure with thiazole bearing morpholine-4-carbonyl at 5-position) |

TABLE 1-8-continued

| Example | Structural formula |
|---|---|
| 117 | |
| 118 | |
| 119 | |
| 120 | |
| 121 | |
| 122 | |
| 123 | |
| 124 | |
| 125 | |
| 126 | |

TABLE 1-8-continued

| Example | Structural formula |
|---|---|
| 127 | (5-chloro-spiro[indoline-3,3'-pyrrolidine]-1'-carboxylic acid methyl ester; N-(5-methylthio-thiazol-2-yl)carboxamide at N1) |
| 128 | (5-chloro-spiro[indoline-3,3'-pyrrolidine]-1'-carboxylic acid methyl ester; N-(5-methylsulfonyl-thiazol-2-yl)carboxamide at N1) |

TABLE 1-9

| Example | Structural formula |
|---|---|
| 129 | (5-chloro-spiro[indoline-3,3'-pyrrolidine]-1'-carboxylic acid methyl ester; N-(5-((methoxycarbonylmethyl)thio)thiazol-2-yl)carboxamide) |
| 130 | (5-chloro-spiro[indoline-3,3'-pyrrolidine]-1'-carboxylic acid methyl ester; N-(5-((carboxymethyl)thio)thiazol-2-yl)carboxamide) |

TABLE 1-9-continued

| Example | Structural formula |
|---|---|
| 131 | (5-chloro-spiro[indoline-3,3'-pyrrolidine]-1'-carboxylic acid methyl ester; N-(5-((N,N-dimethylcarbamoylmethyl)thio)thiazol-2-yl)carboxamide) |
| 132 | (5-chloro-spiro[indoline-3,3'-pyrrolidine]-1'-carboxylic acid methyl ester; N-(5-((carbamoylmethyl)thio)thiazol-2-yl)carboxamide) |
| 133 | (5-chloro-spiro[indoline-3,3'-pyrrolidine]-1'-carboxylic acid methyl ester; N-(5-((N-methylcarbamoylmethyl)thio)thiazol-2-yl)carboxamide) |

TABLE 1-9-continued
| Example | Structural formula |
|---|---|
| 134 | 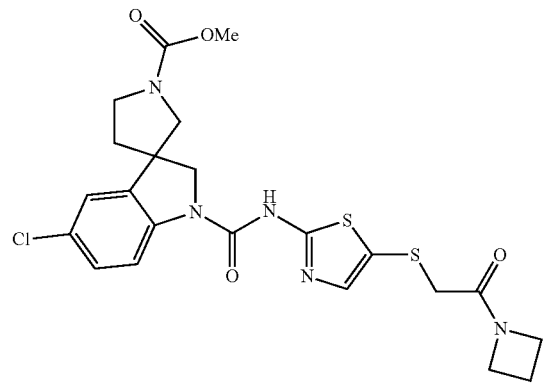 [SMILES: COC(=O)N1CCC2(C1)CN(C(=O)Nc1ncc(SCC(=O)N3CCC3)s1)c1ccc(Cl)cc12] |
| 135 | 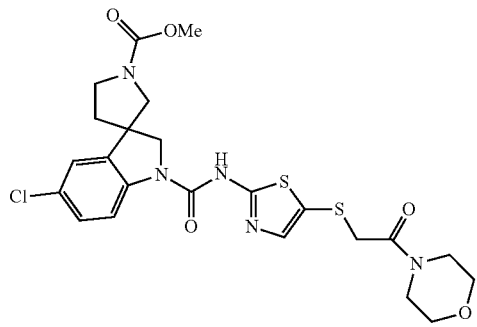 [SMILES: COC(=O)N1CCC2(C1)CN(C(=O)Nc1ncc(SCC(=O)N3CCOCC3)s1)c1ccc(Cl)cc12] |
| 136 | 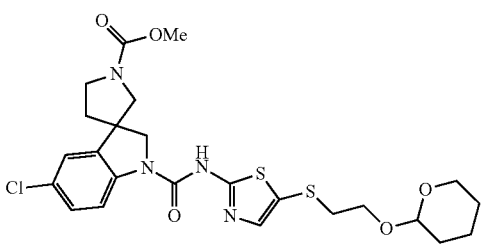 [SMILES: COC(=O)N1CCC2(C1)CN(C(=O)Nc1ncc(SCCOC3CCCCO3)s1)c1ccc(Cl)cc12] |
| 137 | 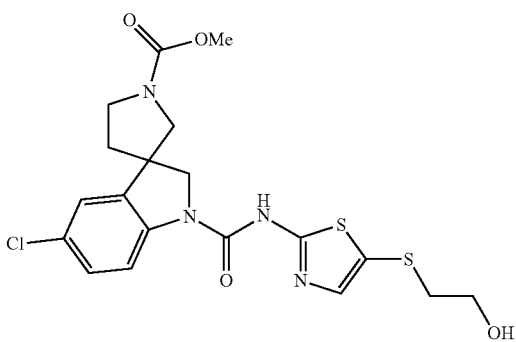 [SMILES: COC(=O)N1CCC2(C1)CN(C(=O)Nc1ncc(SCCO)s1)c1ccc(Cl)cc12] |
TABLE 1-9-continued
| Example | Structural formula |
|---|---|
| 138 | 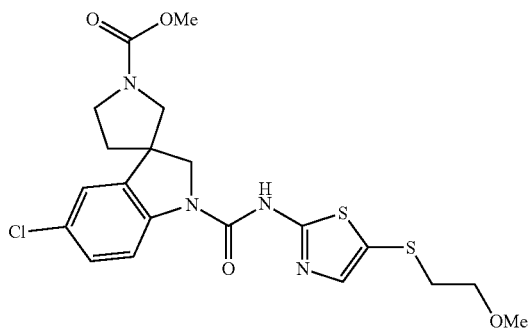 [SMILES: COCCSc1cnc(NC(=O)N2CC3(CCN(C(=O)OC)C3)c3cc(Cl)ccc32)s1] |
| 139 | 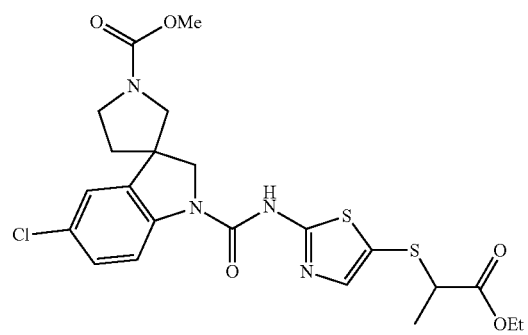 [SMILES: CCOC(=O)C(C)Sc1cnc(NC(=O)N2CC3(CCN(C(=O)OC)C3)c3cc(Cl)ccc32)s1] |
| 140 | 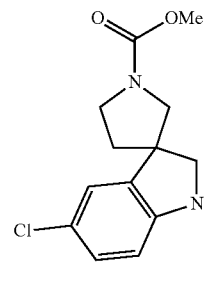 |

TABLE 1-9-continued
| Example | Structural formula |
|---|---|
| 141 | 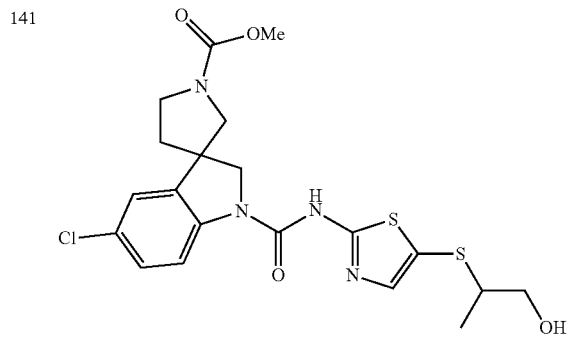 |
| 142 | 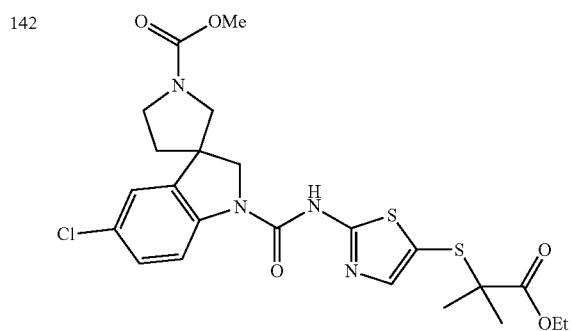 |
| 143 | 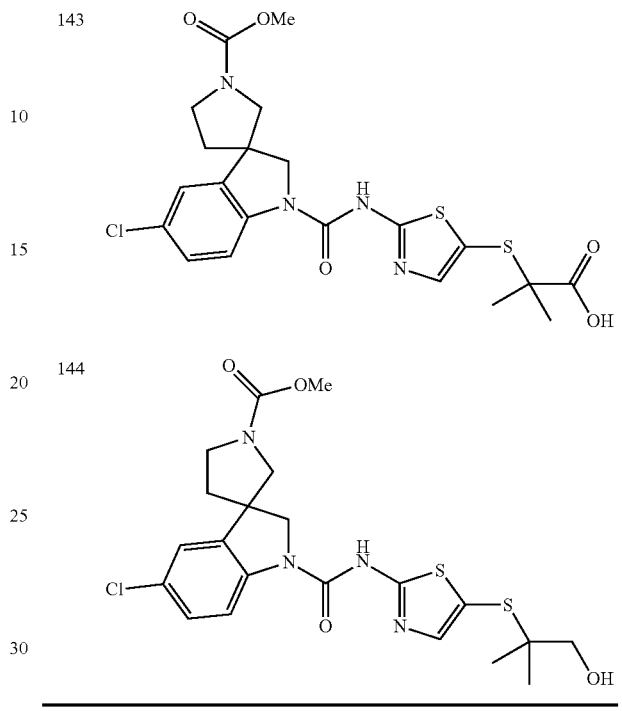 |
| 144 | |
TABLE 1-10
| Example | Structural formula |
|---|---|
| 145 | 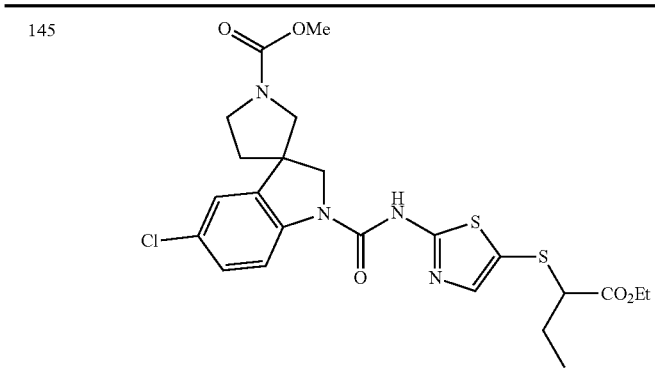 |
| 146 | 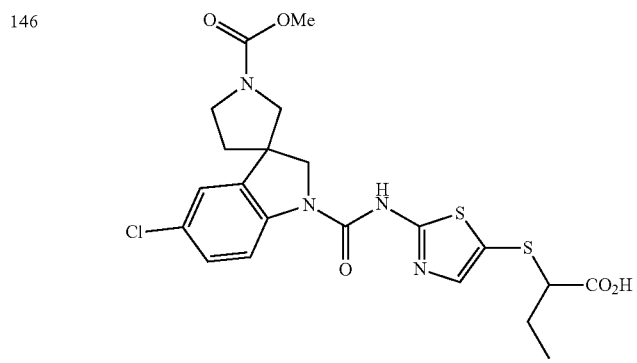 |

TABLE 1-10-continued
| Example | Structural formula |
| --- | --- |
| 147 | 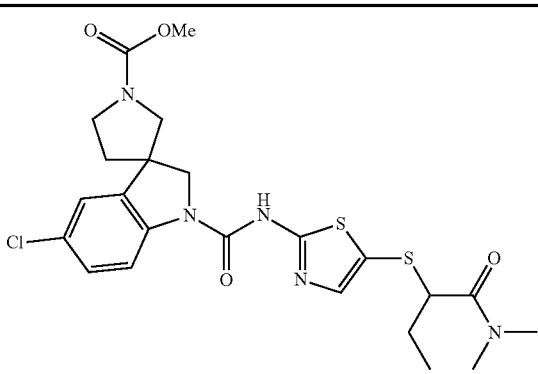 |
| 148 | 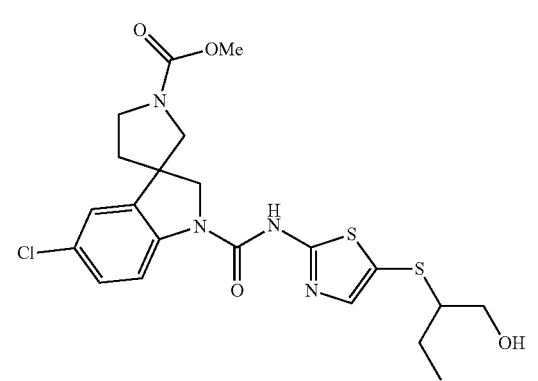 [SMILES: CCC(CO)Sc1cnc(NC(=O)N2CC3(CCN(C(=O)OC)C3)c3cc(Cl)ccc32)s1] |
| 149 | 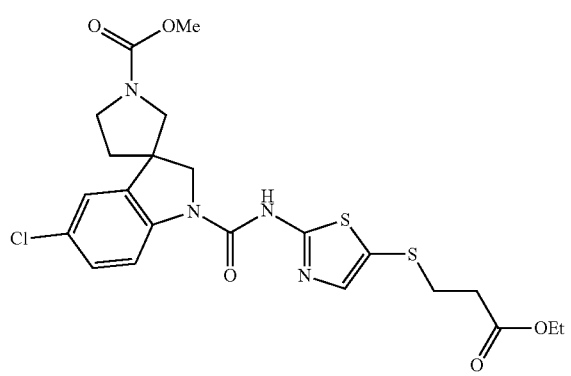 [SMILES: CCOC(=O)CCSc1cnc(NC(=O)N2CC3(CCN(C(=O)OC)C3)c3cc(Cl)ccc32)s1] |
| 150 | 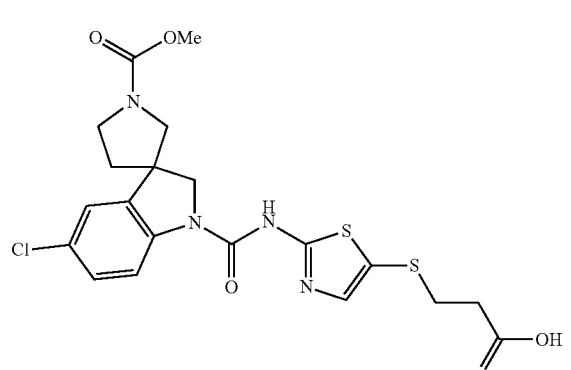 |

TABLE 1-10-continued

| Example | Structural formula |
|---------|--------------------|
| 151 | |
| 152 | |
| 153 | |
| 154 | |

TABLE 1-10-continued

| Example | Structural formula |
|---------|-------------------|
| 155 | |
| 156 | |
| 157 | |
| 158 | |

TABLE 1-10-continued

| Example | Structural formula |
|---|---|
| 159 | (5-chloro-spiro[indoline-3,3'-pyrrolidine] with N-methoxycarbonyl on pyrrolidine, N-carboxamide linked to thiazole-5-yl-S-(CH₂)₃-CO₂Et) |
| 160 | (same core; thiazole-5-yl-S-(CH₂)₃-CO₂H) |

TABLE 1-11

| Example | Structural formula |
|---|---|
| 161 | (same core; thiazole-5-yl-S-(CH₂)₃-OH) |
| 162 | (same core; thiazole-5-yl-S-(CH₂)₃-OMe) |

TABLE 1-11-continued

| Example | Structural formula |
|---------|--------------------|
| 163 | |
| 164 | |
| 165 | |
| 166 | |

TABLE 1-11-continued
| Example | Structural formula |
|---------|---------------------|
| 167 | 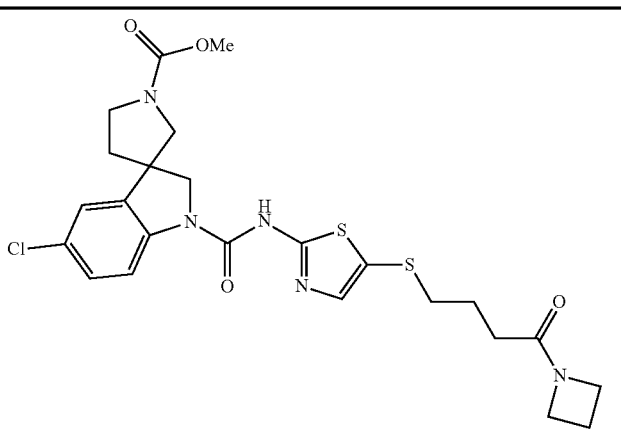 |
| 168 | 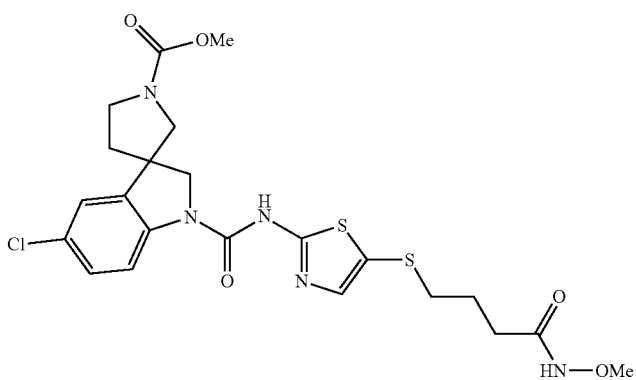 [SMILES: CONC(=O)CCCSc1cnc(NC(=O)N2CC3(CCN(C(=O)OC)C3)c3cc(Cl)ccc32)s1] |
| 169 | 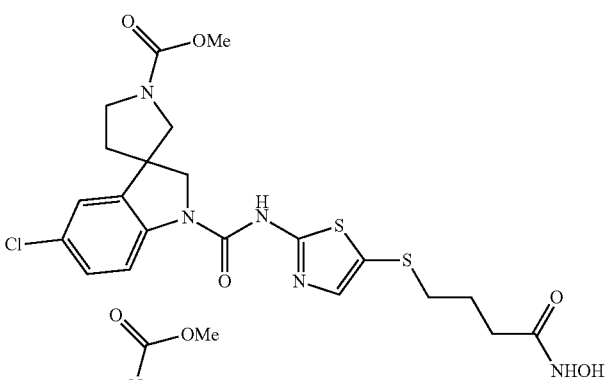 |
| 170 | 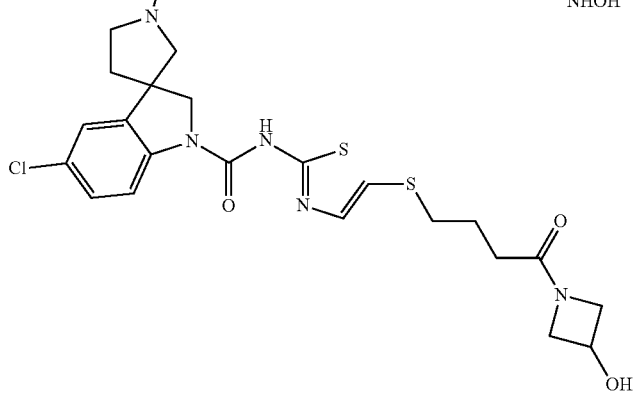 |

TABLE 1-11-continued
| Example | Structural formula |
|---|---|
| 171 | 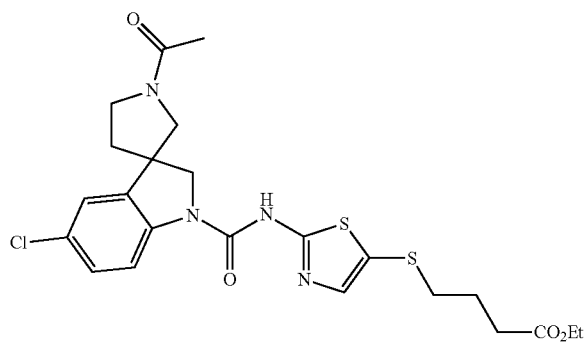 [SMILES: CCOC(=O)CCCSc1cnc(NC(=O)N2CC3(CCN(C(C)=O)C3)c3cc(Cl)ccc32)s1] |
| 172 | 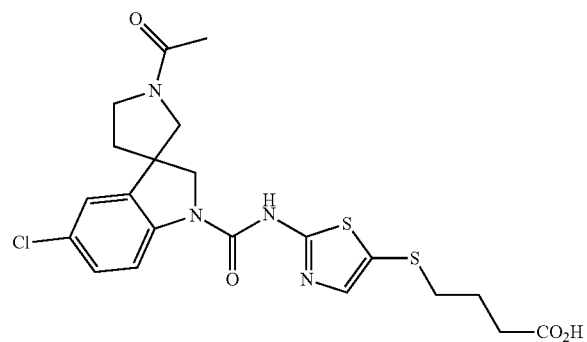 [SMILES: CC(=O)N1CCC2(C1)CN(C(=O)Nc1ncc(SCCCC(=O)O)s1)c1ccc(Cl)cc12] |
| 173 | 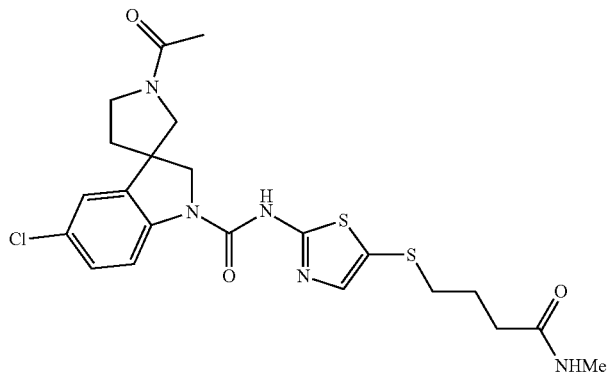 [SMILES: CNC(=O)CCCSc1cnc(NC(=O)N2CC3(CCN(C(C)=O)C3)c3cc(Cl)ccc32)s1] |
| 174 | 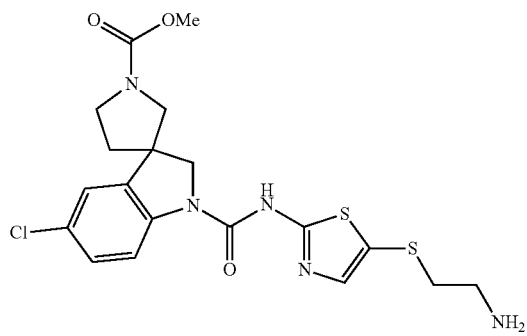 [SMILES: COC(=O)N1CCC2(C1)CN(C(=O)Nc1ncc(SCCN)s1)c1ccc(Cl)cc12] |

TABLE 1-11-continued
| Example | Structural formula |
|---|---|
| 175 | 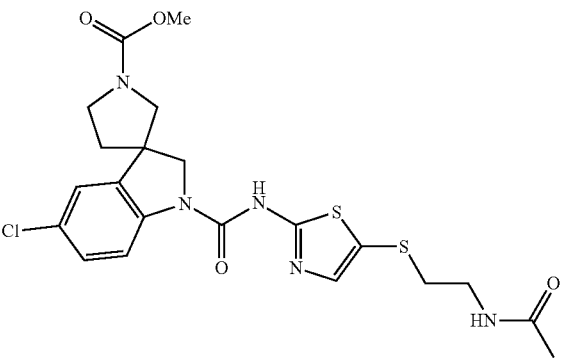 [SMILES: COC(=O)N1CCC2(C1)CN(C(=O)Nc1ncc(SCCNC(C)=O)s1)c1ccc(Cl)cc12] |
| 176 | 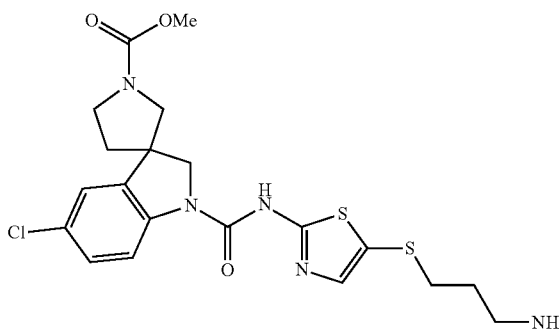 |
TABLE 1-12
| Example | Structural formula |
|---|---|
| 177 | 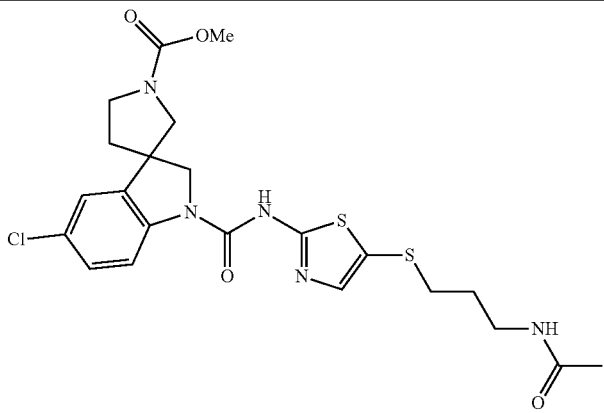 |
| 178 | 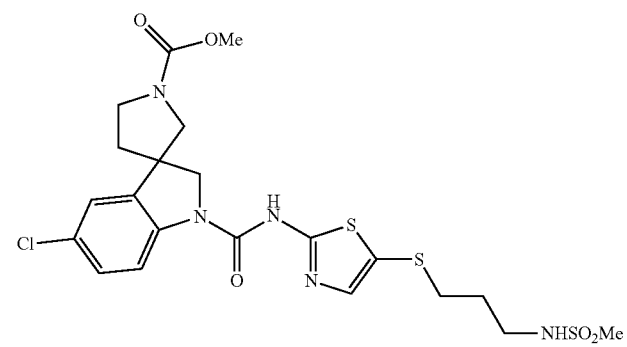 |

TABLE 1-12-continued

| Example | Structural formula |
|---|---|
| 179 | (chemical structure: 5-chloro-spiro[indoline-3,3'-pyrrolidine]-1'-carboxylic acid methyl ester, N-[5-({3-[(cyclopropylsulfonyl)amino]propyl}thio)thiazol-2-yl]-1-carboxamide) |
| 180 | (chemical structure: 5-chloro-spiro[indoline-3,3'-pyrrolidine]-1'-carboxylic acid methyl ester, N-{5-[(3-(dimethylamino)propyl)thio]thiazol-2-yl}-1-carboxamide) |
| 181 | (chemical structure: 5-chloro-spiro[indoline-3,3'-pyrrolidine]-1'-carboxylic acid methyl ester, N-(5-methoxythiazol-2-yl)-1-carboxamide) |
| 182 | (chemical structure: 1'-acetyl-5-chloro-spiro[indoline-3,3'-pyrrolidine], N-(5-methoxythiazol-2-yl)-1-carboxamide) |

TABLE 1-12-continued

| Example | Structural formula |
|---------|-------------------|
| 183 | |
| 184 | |
| 185 | |
| 186 | |
| 187 | |

TABLE 1-12-continued

| Example | Structural formula |
|---------|-------------------|
| 188 | |
| 189 | |
| 190 | |
| 191 | |
| 192 | |

TABLE 1-13
| Example | Structural formula |
|---|---|
| 193 | 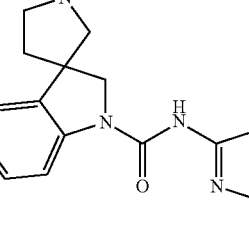 |
| 194 | 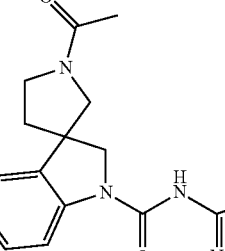 |
| 195 | 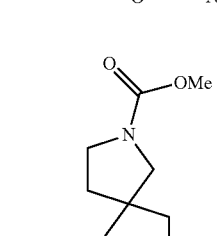 |
| 196 | 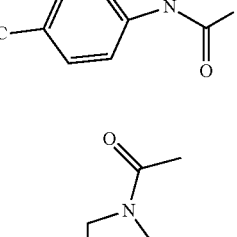 |
| 197 | 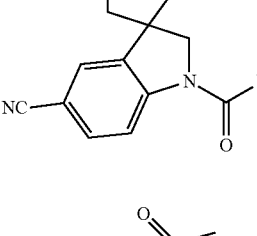 |

TABLE 1-13-continued
| Example | Structural formula |
|---|---|
| 198 | 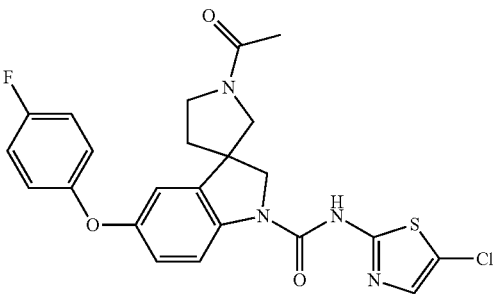 [SMILES: CC(=O)N1CCC2(C1)CN(C(=O)Nc1ncc(Cl)s1)c1ccc(Oc3ccc(F)cc3)cc12] |
| 199 | 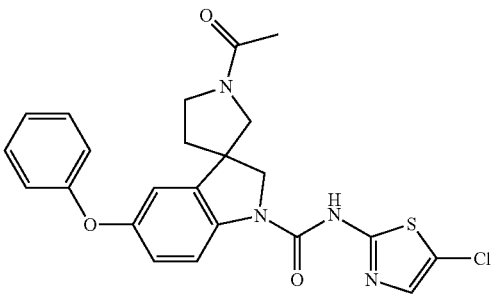 [SMILES: CC(=O)N1CCC2(C1)CN(C(=O)Nc1ncc(Cl)s1)c1ccc(Oc3ccccc3)cc12] |
| 200 | 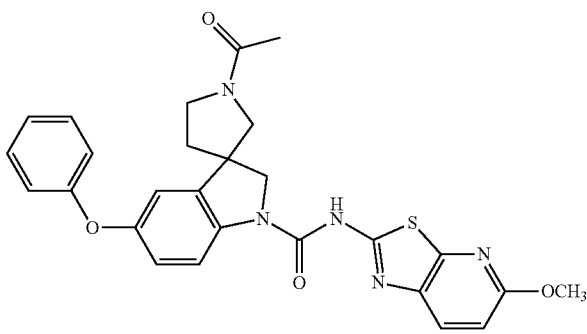 [SMILES: COc1ccc2nc(NC(=O)N3CC4(CCN(C(C)=O)C4)c4cc(Oc5ccccc5)ccc43)sc2n1] |
| 201 | 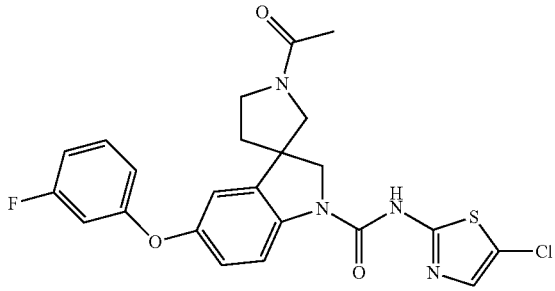 [SMILES: CC(=O)N1CCC2(C1)CN(C(=O)Nc1ncc(Cl)s1)c1ccc(Oc3cccc(F)c3)cc12] |
| 202 | 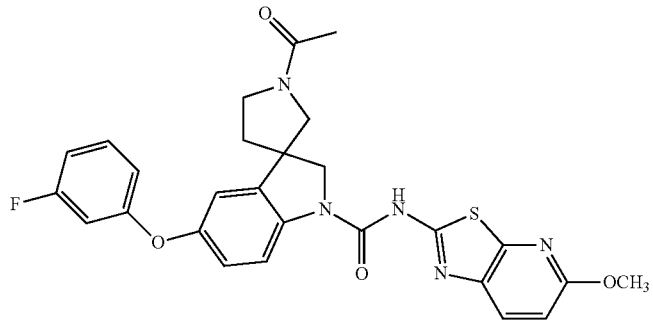 [SMILES: COc1ccc2nc(NC(=O)N3CC4(CCN(C(C)=O)C4)c4cc(Oc5cccc(F)c5)ccc43)sc2n1] |

TABLE 1-13-continued
| Example | Structural formula |
|---|---|
| 203 | 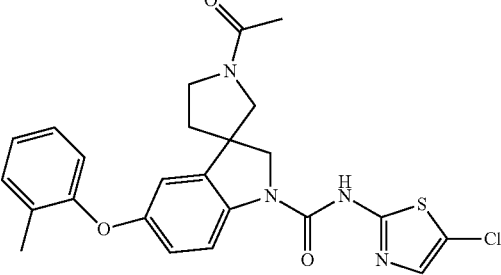 |
| 204 | 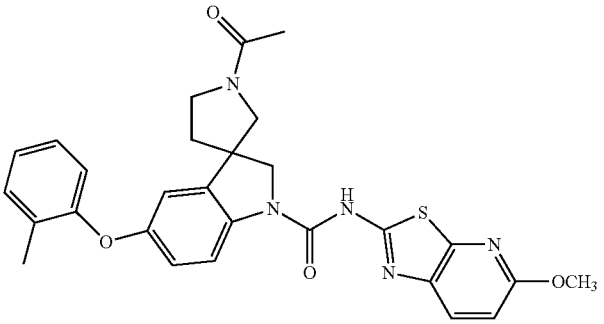 [SMILES: COc1ccc2nc(NC(=O)N3CC4(CCN(C(C)=O)C4)c4cc(Oc5ccccc5C)ccc43)sc2n1] |
| 205 | 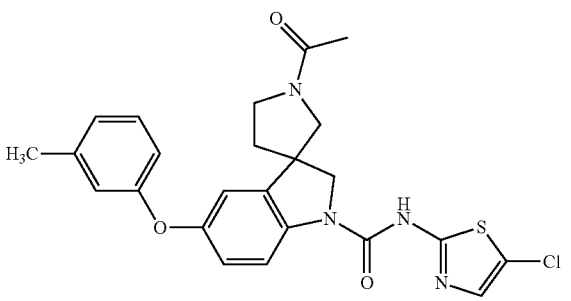 [SMILES: CC(=O)N1CCC2(C1)CN(C(=O)Nc1ncc(Cl)s1)c1ccc(Oc3cccc(C)c3)cc12] |
| 206 | 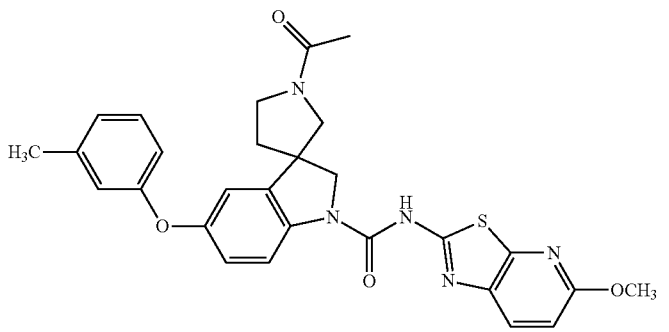 [SMILES: COc1ccc2nc(NC(=O)N3CC4(CCN(C(C)=O)C4)c4cc(Oc5cccc(C)c5)ccc43)sc2n1] |
| 207 | 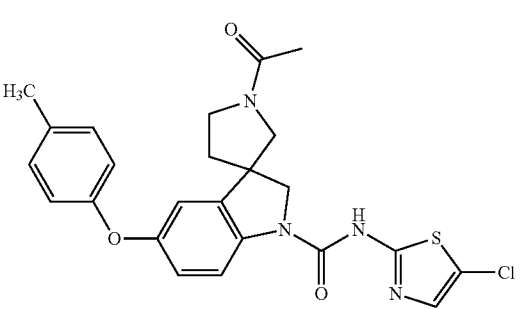 [SMILES: CC(=O)N1CCC2(C1)CN(C(=O)Nc1ncc(Cl)s1)c1ccc(Oc3ccc(C)cc3)cc12] |

TABLE 1-13-continued
| Example | Structural formula |
| --- | --- |
| 208 | 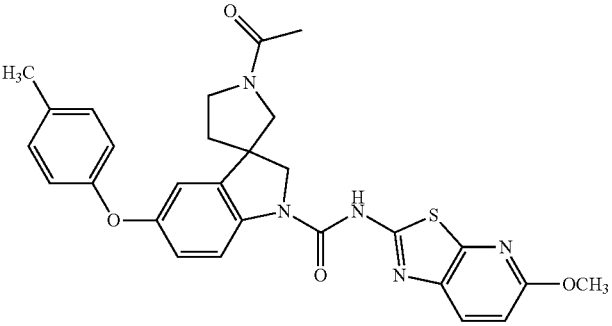 |
TABLE 1-14
| Example | Structural formula |
| --- | --- |
| 209 | 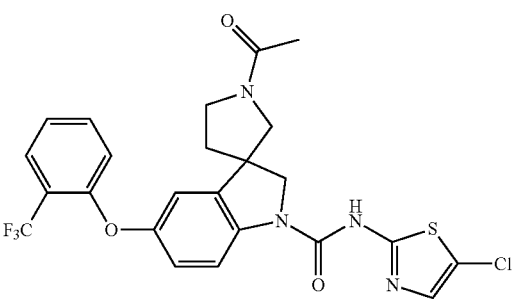 [SMILES: CC(=O)N1CCC2(C1)CN(C(=O)Nc1ncc(Cl)s1)c1ccc(Oc3ccccc3C(F)(F)F)cc12] |
| 210 | 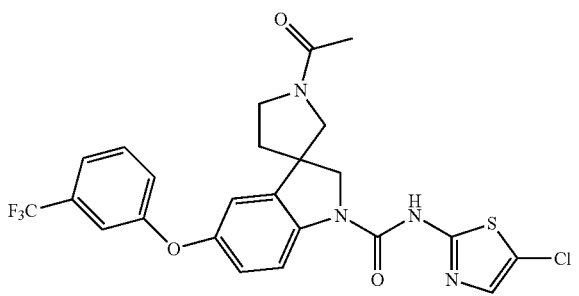 [SMILES: CC(=O)N1CCC2(C1)CN(C(=O)Nc1ncc(Cl)s1)c1ccc(Oc3cccc(C(F)(F)F)c3)cc12] |
| 211 | 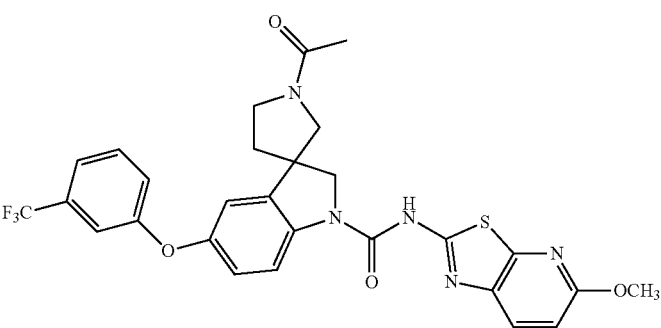 [SMILES: COc1ccc2nc(NC(=O)N3CC4(CCN(C(C)=O)C4)c4cc(Oc5cccc(C(F)(F)F)c5)ccc43)sc2n1] |

TABLE 1-14-continued

| Example | Structural formula |
|---|---|
| 212 | |
| 213 | |
| 214 | |
| 215 | |
| 216 | |

TABLE 1-14-continued
| Example | Structural formula |
|---|---|
| 217 | 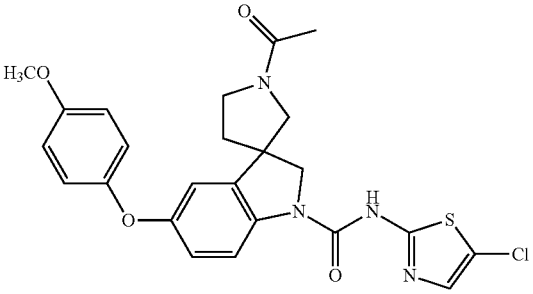 [SMILES: COc1ccc(Oc2ccc3c(c2)C2(CCN(C(C)=O)C2)CN3C(=O)Nc2ncc(Cl)s2)cc1] |
| 218 | 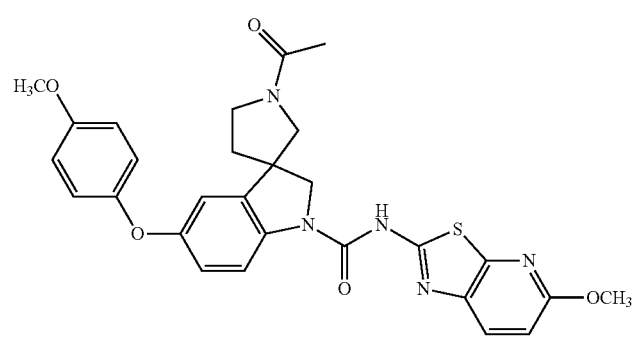 [SMILES: COc1ccc(Oc2ccc3c(c2)C2(CCN(C(C)=O)C2)CN3C(=O)Nc2nc3ccc(OC)nc3s2)cc1] |
| 219 | 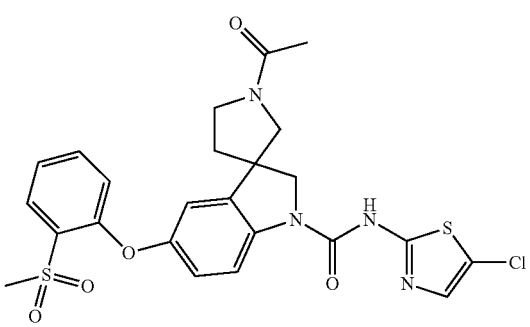 [SMILES: CC(=O)N1CCC2(C1)CN(C(=O)Nc1ncc(Cl)s1)c1ccc(Oc3ccccc3S(C)(=O)=O)cc12] |
| 220 | 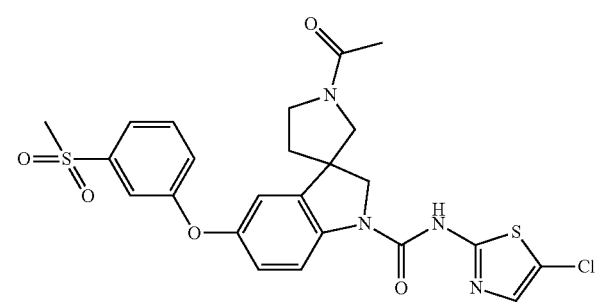 [SMILES: CC(=O)N1CCC2(C1)CN(C(=O)Nc1ncc(Cl)s1)c1ccc(Oc3cccc(S(C)(=O)=O)c3)cc12] |
| 221 | 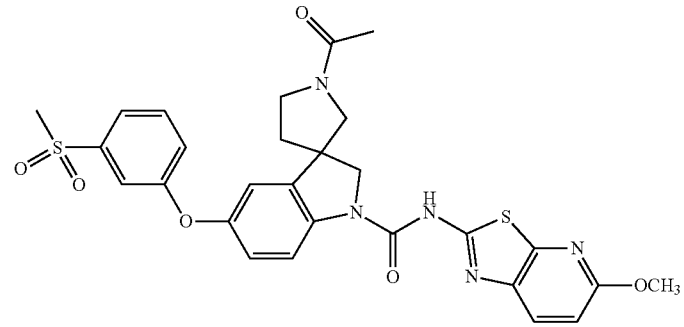 [SMILES: COc1ccc2nc(NC(=O)N3CC4(CCN(C(C)=O)C4)c4cc(Oc5cccc(S(C)(=O)=O)c5)ccc43)sc2n1] |

TABLE 1-14-continued
| Example | Structural formula |
|---|---|
| 222 | 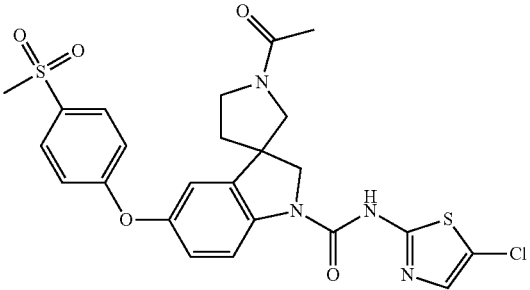 [SMILES: CC(=O)N1CCC2(C1)CN(C(=O)Nc1ncc(Cl)s1)c1ccc(Oc3ccc(S(C)(=O)=O)cc3)cc12] |
| 223 | 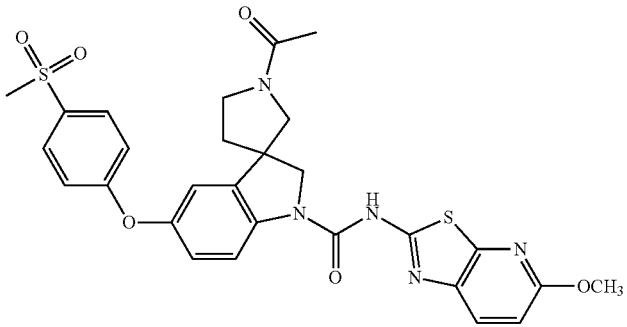 [SMILES: COc1ccc2nc(NC(=O)N3CC4(CCN(C(C)=O)C4)c4cc(Oc5ccc(S(C)(=O)=O)cc5)ccc43)sc2n1] |
| 224 | 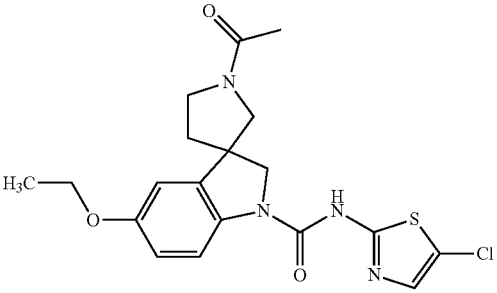 [SMILES: CCOc1ccc2c(c1)C1(CCN(C(C)=O)C1)CN2C(=O)Nc1ncc(Cl)s1] |
TABLE 1-15
| Example | Structural formula |
|---|---|
| 225 | 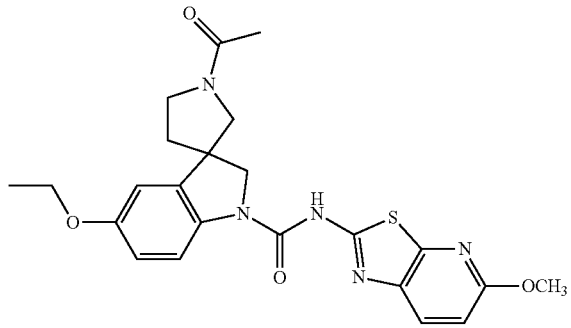 [SMILES: CCOc1ccc2c(c1)C1(CCN(C(C)=O)C1)CN2C(=O)Nc1nc2ccc(OC)nc2s1] |

TABLE 1-15-continued
| Example | Structural formula |
|---|---|
| 226 | 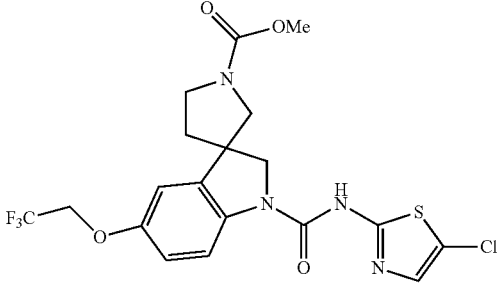 [SMILES: COC(=O)N1CCC2(C1)CN(C(=O)Nc1ncc(Cl)s1)c1ccc(OCC(F)(F)F)cc12] |
| 227 | 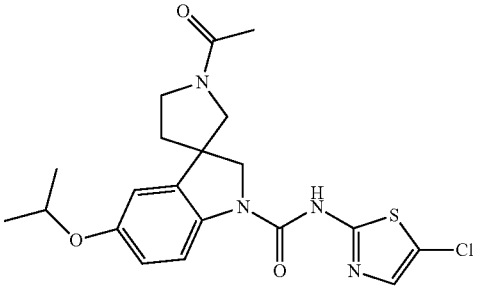 [SMILES: CC(=O)N1CCC2(C1)CN(C(=O)Nc1ncc(Cl)s1)c1ccc(OC(C)C)cc12] |
| 228 | 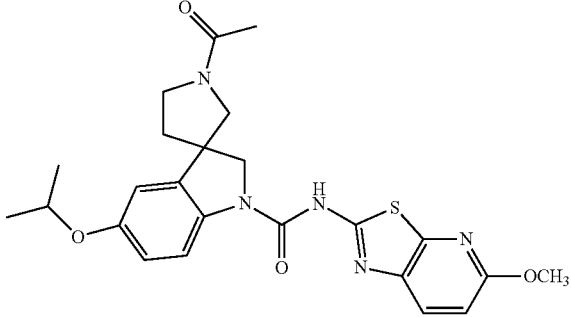 [SMILES: COc1ccc2nc(NC(=O)N3CC4(CCN(C(C)=O)C4)c4cc(OC(C)C)ccc43)sc2n1] |
| 229 | 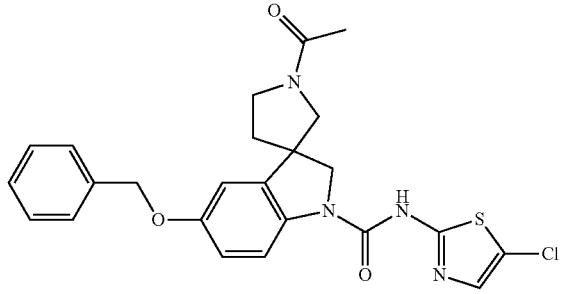 [SMILES: CC(=O)N1CCC2(C1)CN(C(=O)Nc1ncc(Cl)s1)c1ccc(OCc3ccccc3)cc12] |
| 230 | 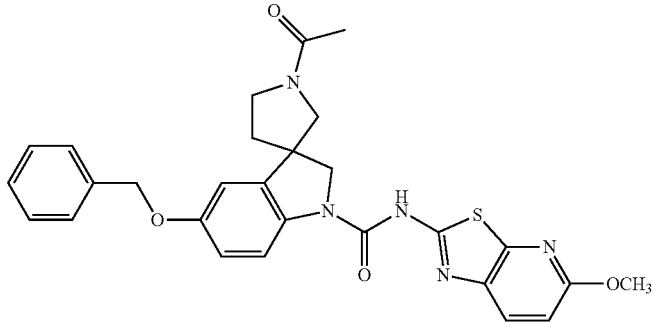 [SMILES: COc1ccc2nc(NC(=O)N3CC4(CCN(C(C)=O)C4)c4cc(OCc5ccccc5)ccc43)sc2n1] |

TABLE 1-15-continued

| Example | Structural formula |
|---------|-------------------|
| 231 | |
| 232 | |
| 233 | |
| 234 | |
| 235 | |

TABLE 1-15-continued
| Example | Structural formula |
|---|---|
| 236 | 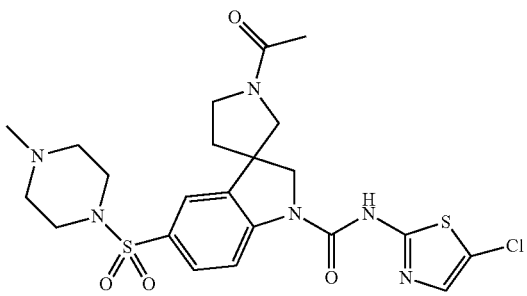 [SMILES: CC(=O)N1CCC2(C1)CN(C(=O)Nc1ncc(Cl)s1)c1ccc(S(=O)(=O)N3CCN(C)CC3)cc12] |
| 237 | 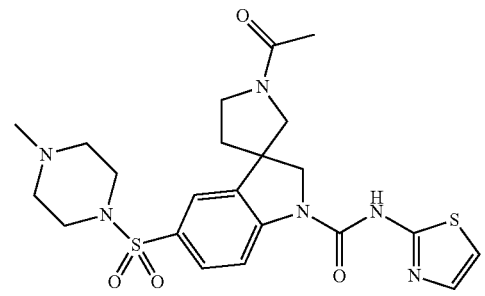 [SMILES: CC(=O)N1CCC2(C1)CN(C(=O)Nc1nccs1)c1ccc(S(=O)(=O)N3CCN(C)CC3)cc12] |
| 238 | 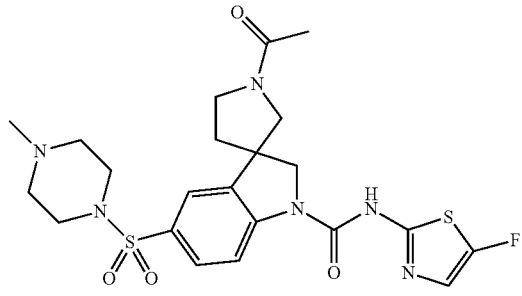 [SMILES: CC(=O)N1CCC2(C1)CN(C(=O)Nc1ncc(F)s1)c1ccc(S(=O)(=O)N3CCN(C)CC3)cc12] |
| 239 | 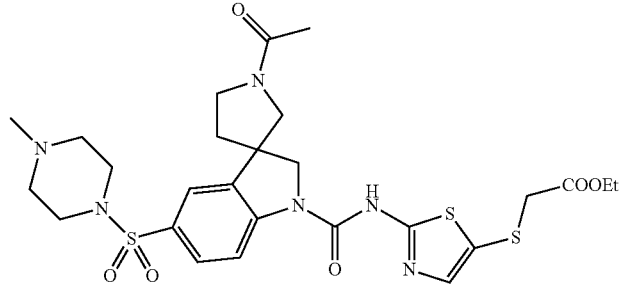 [SMILES: CCOC(=O)CSc1cnc(NC(=O)N2CC3(CCN(C(C)=O)C3)c3cc(S(=O)(=O)N4CCN(C)CC4)ccc32)s1] |
| 240 | 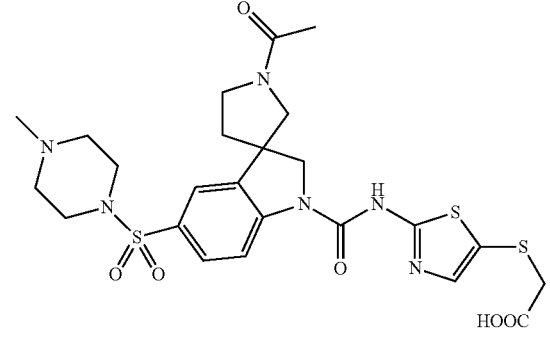 [SMILES: CC(=O)N1CCC2(C1)CN(C(=O)Nc1ncc(SCC(=O)O)s1)c1ccc(S(=O)(=O)N3CCN(C)CC3)cc12] |

TABLE 1-16

| Example | Structural formula |
|---|---|
| 241 | (structure) |
| 242 | (structure) |
| 243 | (structure) |
| 244 | (structure) |
| 245 | (structure) |

TABLE 1-16-continued

| Example | Structural formula |
|---|---|
| 246 | (structure) |
| 247 | (structure) |
| 248 | (structure) |
| 249 | (structure) |
| 250 | (structure) |
| 251 | (structure) |

TABLE 1-16-continued

| Example | Structural formula |
|---|---|
| 252 | |
| 253 | |
| 254 | |

TABLE 1-16-continued

| Example | Structural formula |
|---|---|
| 255 | |
| 256 | |

TABLE 1-17

| Example | Structural formula |
|---|---|
| 257 | |
| 258 | |

TABLE 1-17-continued

| Example | Structural formula |
|---------|-------------------|
| 259 | |
| 260 | |
| 261 | |
| 262 | |
| 263 | |

TABLE 1-17-continued
| Example | Structural formula |
|---|---|
| 264 | 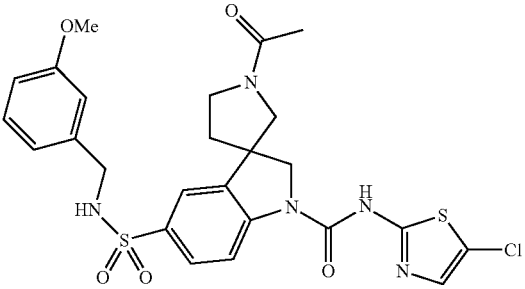 [SMILES: COc1cccc(CNS(=O)(=O)c2ccc3c(c2)C2(CCN(C(C)=O)C2)CN3C(=O)Nc2ncc(Cl)s2)c1] |
| 265 | 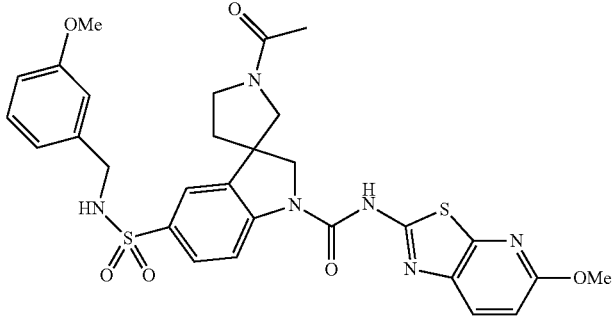 [SMILES: COc1cccc(CNS(=O)(=O)c2ccc3c(c2)C2(CCN(C(C)=O)C2)CN3C(=O)Nc2nc3ccc(OC)nc3s2)c1] |
| 266 | 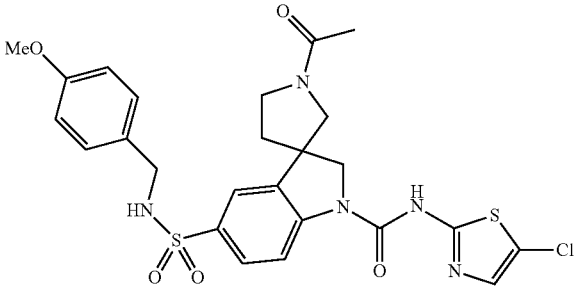 [SMILES: COc1ccc(CNS(=O)(=O)c2ccc3c(c2)C2(CCN(C(C)=O)C2)CN3C(=O)Nc2ncc(Cl)s2)cc1] |
| 267 | 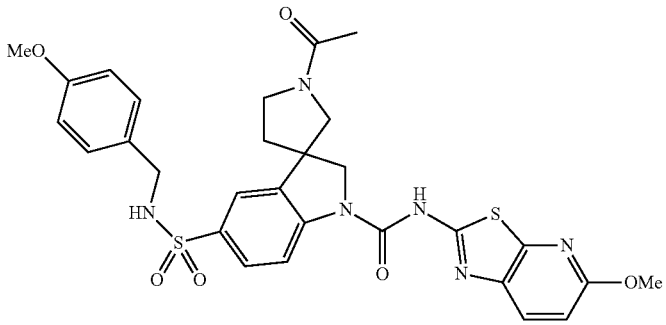 [SMILES: COc1ccc(CNS(=O)(=O)c2ccc3c(c2)C2(CCN(C(C)=O)C2)CN3C(=O)Nc2nc3ccc(OC)nc3s2)cc1] |
| 268 | 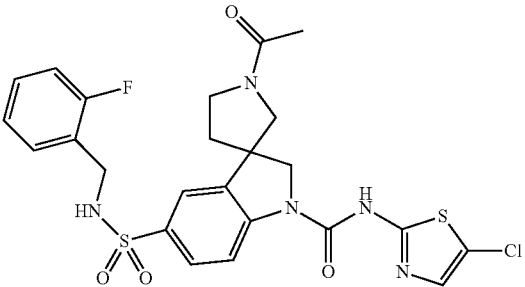 [SMILES: CC(=O)N1CCC2(C1)CN(C(=O)Nc1ncc(Cl)s1)c1ccc(S(=O)(=O)NCc3ccccc3F)cc12] |

TABLE 1-17-continued
| Example | Structural formula |
|---|---|
| 269 | 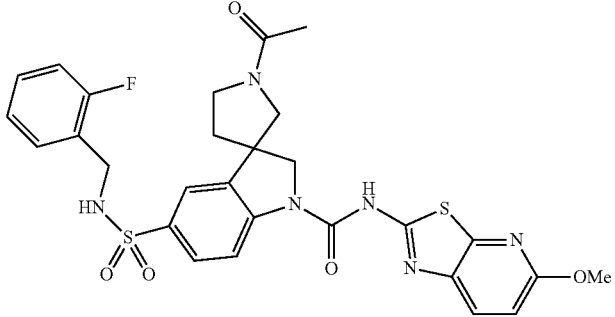 [SMILES: COc1ccc2nc(NC(=O)N3CC4(CCN(C(C)=O)C4)c4cc(S(=O)(=O)NCc5ccccc5F)ccc43)sc2n1] |
| 270 | 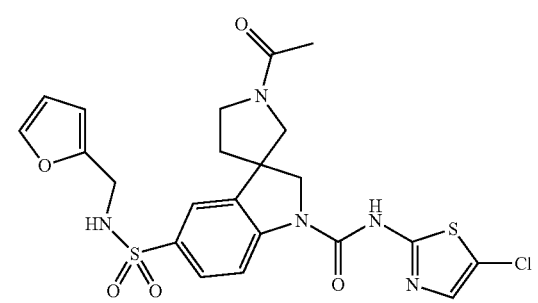 [SMILES: CC(=O)N1CCC2(C1)CN(C(=O)Nc1ncc(Cl)s1)c1ccc(S(=O)(=O)NCc3cccs3)cc12] |
| 271 | 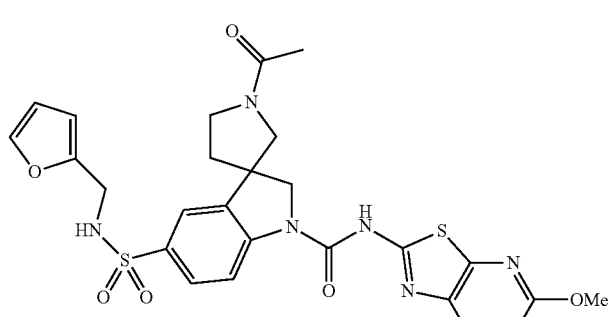 |
| 272 | 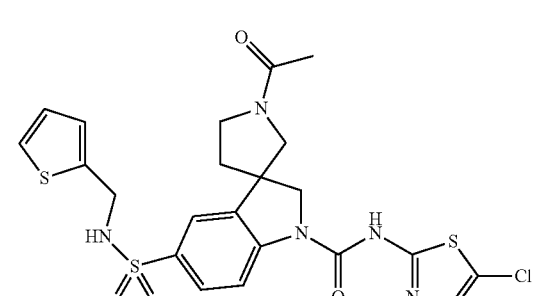 |

TABLE 1-18
| Example | Structural formula |
|---|---|
| 273 | 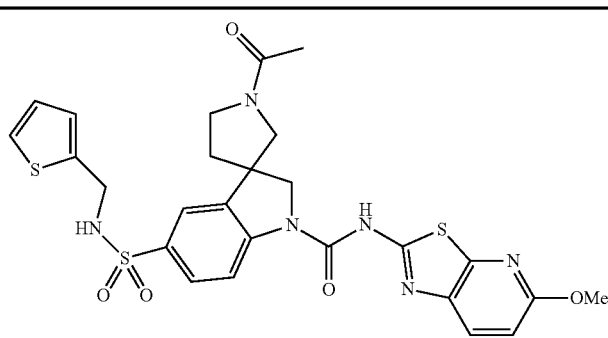 |
| 274 | 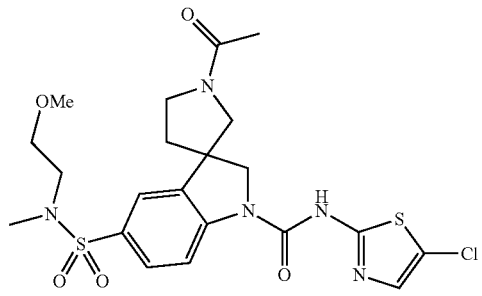 [SMILES: COCCN(C)S(=O)(=O)c1ccc2c(c1)C1(CCN(C(C)=O)C1)CN2C(=O)Nc1ncc(Cl)s1] |
| 275 | 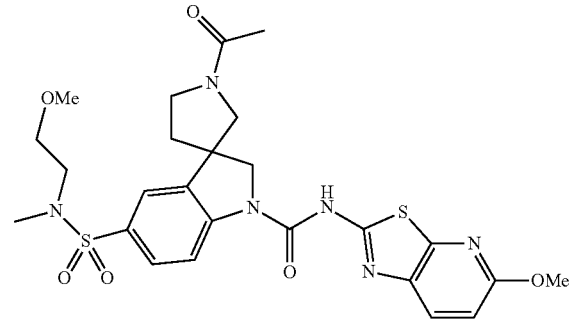 [SMILES: COCCN(C)S(=O)(=O)c1ccc2c(c1)C1(CCN(C(C)=O)C1)CN2C(=O)Nc1nc2ccc(OC)nc2s1] |
| 276 | 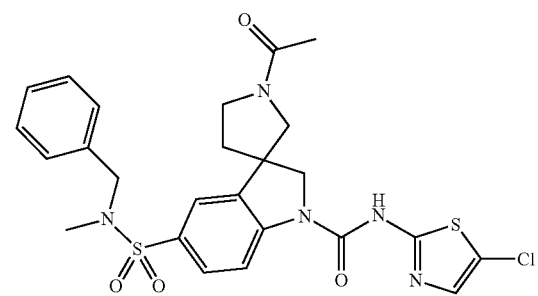 [SMILES: CC(=O)N1CCC2(C1)CN(C(=O)Nc1ncc(Cl)s1)c1ccc(S(=O)(=O)N(C)Cc3ccccc3)cc12] |
| 277 | 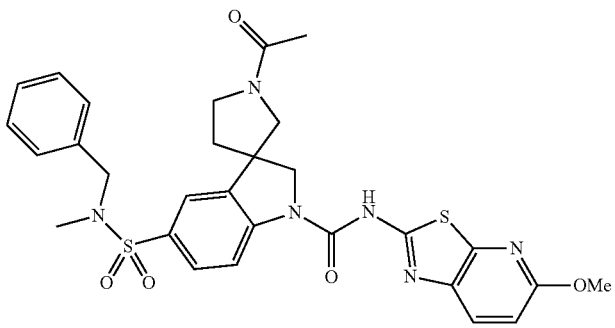 [SMILES: COc1ccc2nc(NC(=O)N3CC4(CCN(C(C)=O)C4)c4cc(S(=O)(=O)N(C)Cc5ccccc5)ccc43)sc2n1] |

TABLE 1-18-continued

| Example | Structural formula |
|---|---|
| 278 | |
| 279 | |
| 280 | |
| 281 | |
| 282 | |

TABLE 1-18-continued

| Example | Structural formula |
|---------|--------------------|
| 283 | |
| 284 | |
| 285 | |
| 286 | |
| 287 | |

TABLE 1-18-continued

| Example | Structural formula |
|---|---|
| 288 | |

TABLE 1-19

| Example | Structural formula |
|---|---|
| 289 | |
| 290 | |
| 291 | |

TABLE 1-19-continued

| Example | Structural formula |
|---|---|
| 292 | |
| 293 | |
| 294 | |
| 295 | |

TABLE 1-19-continued
| Example | Structural formula |
|---|---|
| 296 | 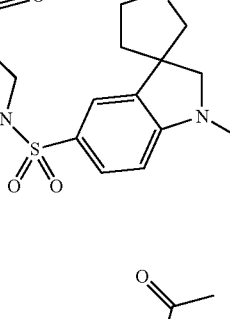 |
| 297 | 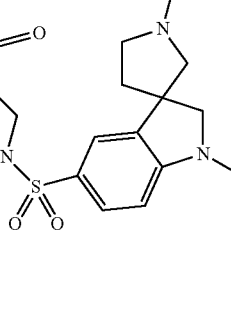 |
| 298 | 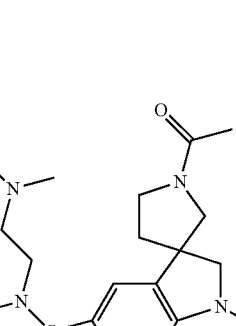 |
| 299 | 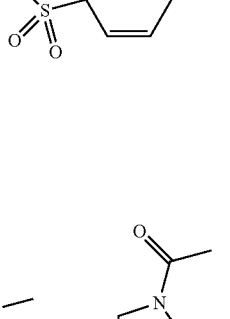 |

TABLE 1-19-continued

| Example | Structural formula |
|---------|-------------------|
| 300 | |
| 301 | |
| 302 | |
| 303 | |

TABLE 1-19-continued
| Example | Structural formula |
|---|---|
| 304 | 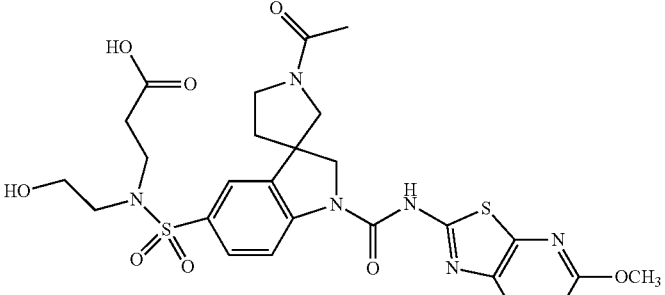 |
TABLE 1-20
| Example | Structural formula |
|---|---|
| 305 | 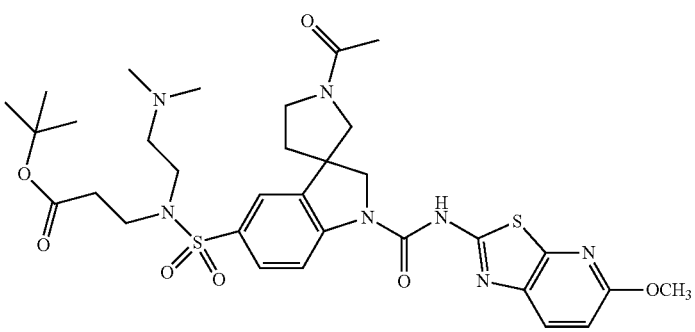 [SMILES: COc1ccc2nc(NC(=O)N3CC4(CCN(C(C)=O)C4)c4cc(S(=O)(=O)N(CCC(=O)OC(C)(C)C)CCN(C)C)ccc43)sc2n1] |
| 306 | 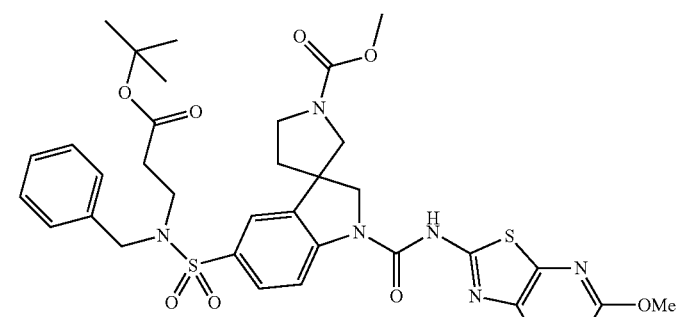 |
| 307 | 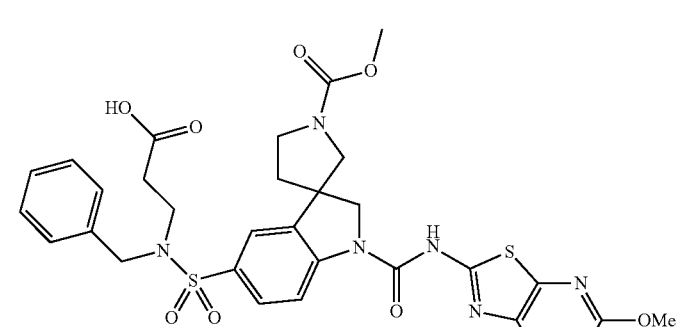 |

TABLE 1-20-continued

| Example | Structural formula |
| --- | --- |
| 308 | |
| 309 | |
| 310 | |
| 311 | |
| 312 | |

TABLE 1-20-continued

| Example | Structural formula |
|---|---|
| 313 | |
| 314 | |
| 315 | |
| 316 | |
| 317 | |

TABLE 1-20-continued

| Example | Structural formula |
|---|---|
| 318 | |
| 319 | |
| 320 | |

TABLE 1-21

| Example | Structural formula |
|---|---|
| 321 | |

TABLE 1-21-continued

| Example | Structural formula |
|---------|--------------------|
| 322 | |
| 323 | |
| 324 | |
| 325 | |

TABLE 1-21-continued

| Example | Structural formula |
|---|---|
| 326 | |
| 327 | |
| 328 | |
| 329 | |
| 330 | |

TABLE 1-21-continued

| Example | Structural formula |
|---|---|
| 331 | |
| 332 | |
| 333 | |
| 334 | |
| 335 | |

TABLE 1-21-continued
| Example | Structural formula |
| --- | --- |
| 336 | 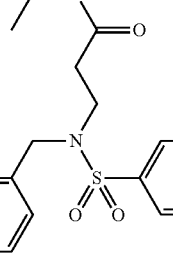 |
TABLE 1-22
| Example | Structural formula |
| --- | --- |
| 337 | 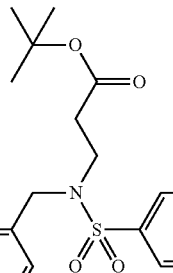 |
| 338 | |
| 339 | 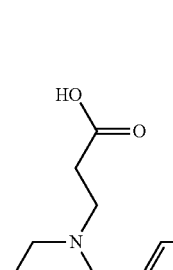 |

TABLE 1-22-continued

| Example | Structural formula |
|---|---|
| 340 | |
| 341 | |
| 342 | |
| 343 | |

TABLE 1-22-continued

| Example | Structural formula |
|---------|--------------------|
| 344 | |
| 345 | |
| 346 | |
| 347 | |

TABLE 1-22-continued
| Example | Structural formula |
|---|---|
| 348 | 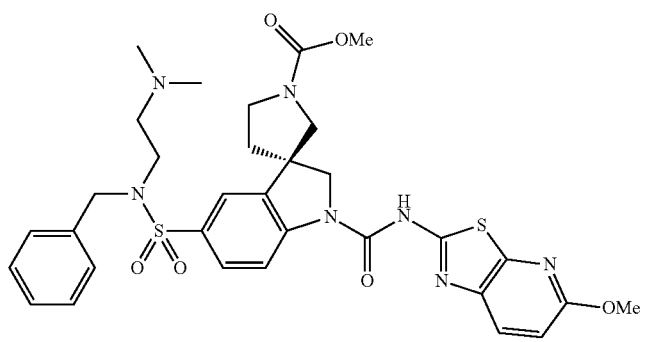 [SMILES: COC(=O)N1CC[C@]2(C1)CN(C(=O)Nc1nc3ccc(OC)nc3s1)c1ccc(S(=O)(=O)N(CCN(C)C)Cc3ccccc3)cc12] |
| 349 | 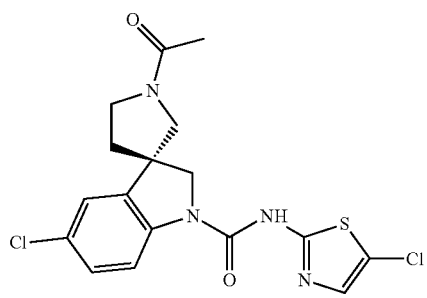 [SMILES: CC(=O)N1CC[C@@]2(C1)CN(C(=O)Nc1ncc(Cl)s1)c1ccc(Cl)cc12] |
| 350 | 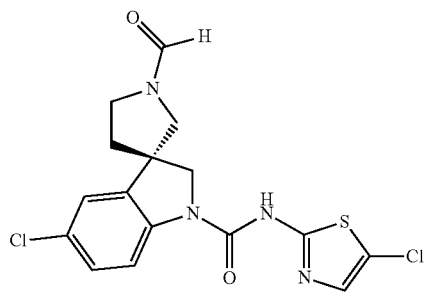 [SMILES: O=CN1CC[C@@]2(C1)CN(C(=O)Nc1ncc(Cl)s1)c1ccc(Cl)cc12] |
| 351 | 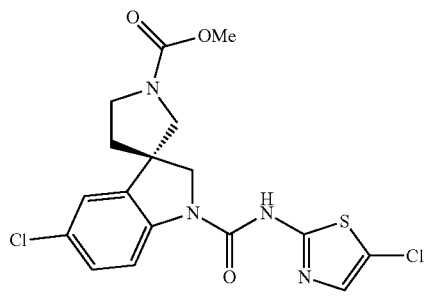 [SMILES: COC(=O)N1CC[C@@]2(C1)CN(C(=O)Nc1ncc(Cl)s1)c1ccc(Cl)cc12] |
| 352 | 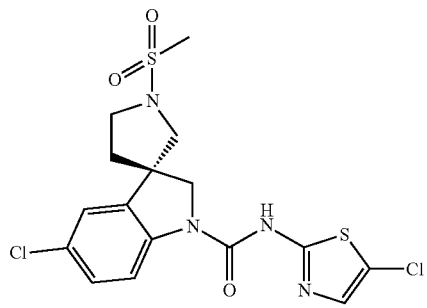 [SMILES: CS(=O)(=O)N1CC[C@]2(CN(C(=O)Nc3ncc(Cl)s3)c3ccc(Cl)cc32)C1] |

TABLE 1-23

| Example | Structural formula |
|---|---|
| 353 | |
| 354 | |
| 355 | |
| 356 | |
| 357 | |

TABLE 1-23-continued
| Example | Structural formula |
|---|---|
| 358 | 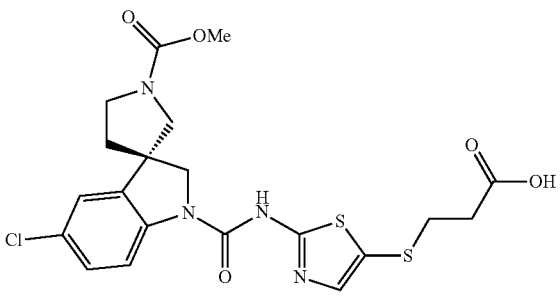 [SMILES: COC(=O)N1CC[C@@]2(C1)CN(C(=O)Nc1ncc(SCCC(=O)O)s1)c1ccc(Cl)cc12] |
| 359 | 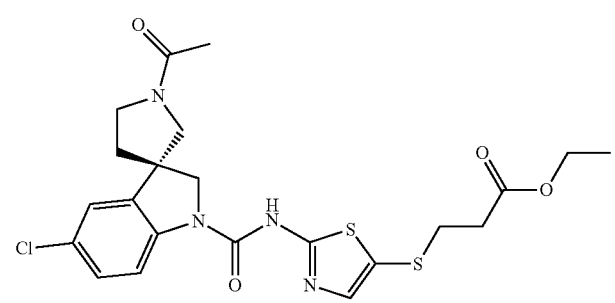 [SMILES: CCOC(=O)CCSc1cnc(NC(=O)N2C[C@]3(CCN(C(C)=O)C3)c3cc(Cl)ccc32)s1] |
| 360 | 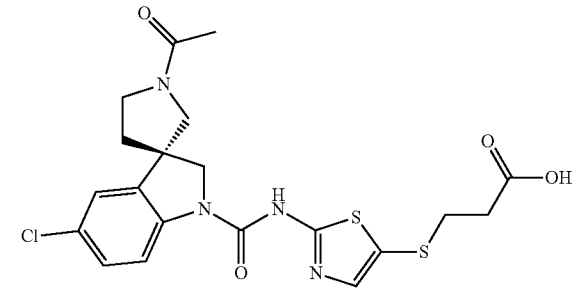 [SMILES: CC(=O)N1CC[C@@]2(C1)CN(C(=O)Nc1ncc(SCCC(=O)O)s1)c1ccc(Cl)cc12] |
| 361 | 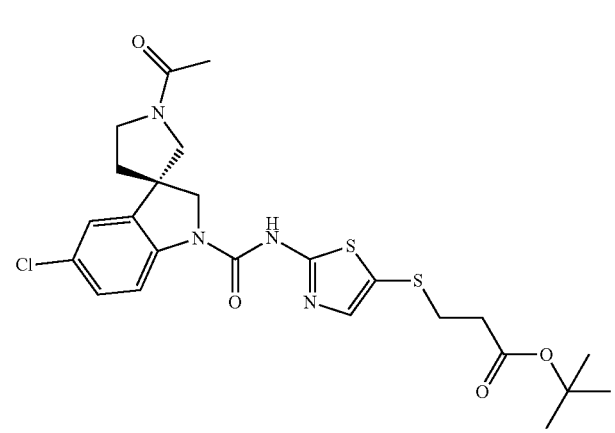 [SMILES: CC(=O)N1CC[C@@]2(C1)CN(C(=O)Nc1ncc(SCCC(=O)OC(C)(C)C)s1)c1ccc(Cl)cc12] |

TABLE 1-23-continued

| Example | Structural formula |
|---------|--------------------|
| 362 | |
| 363 | |
| 364 | |
| 365 | |
| 366 | |

TABLE 1-23-continued
| Example | Structural formula |
|---|---|
| 367 | 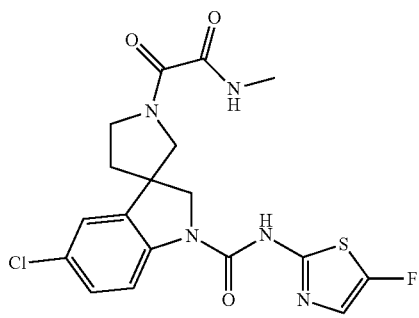 [SMILES: CNC(=O)C(=O)N1CCC2(C1)CN(C(=O)Nc1ncc(F)s1)c1ccc(Cl)cc12] |
| 368 | 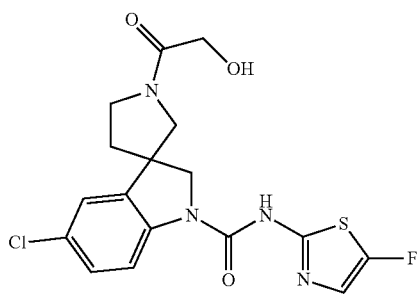 [SMILES: O=C(CO)N1CCC2(C1)CN(C(=O)Nc1ncc(F)s1)c1ccc(Cl)cc12] |
TABLE 1-24
| Example | Structural formula |
|---|---|
| 369 | 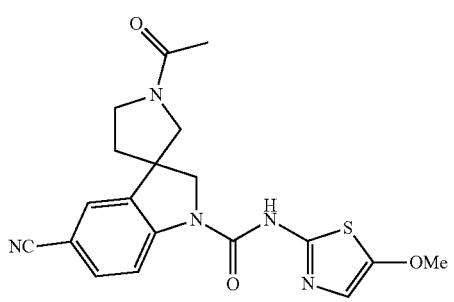 [SMILES: COc1cnc(NC(=O)N2CC3(CCN(C(C)=O)C3)c3cc(C#N)ccc32)s1] |
| 370 | 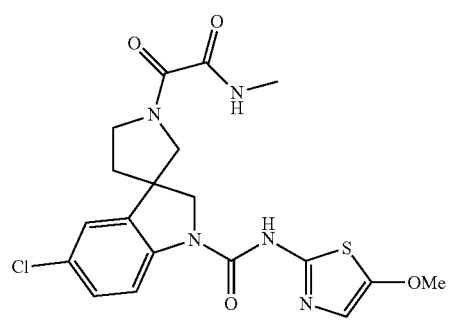 [SMILES: CNC(=O)C(=O)N1CCC2(C1)CN(C(=O)Nc1ncc(OC)s1)c1ccc(Cl)cc12] |
TABLE 1-24-continued
| Example | Structural formula |
|---|---|
| 371 | 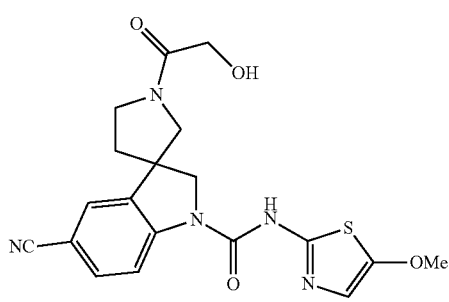 [SMILES: COc1cnc(NC(=O)N2CC3(CCN(C(=O)CO)C3)c3cc(C#N)ccc32)s1] |
| 372 | 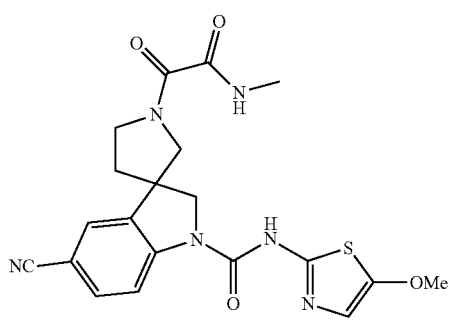 [SMILES: CNC(=O)C(=O)N1CCC2(C1)CN(C(=O)Nc1ncc(OC)s1)c1ccc(C#N)cc12] |

TABLE 1-24-continued

| Example | Structural formula |
|---|---|
| 373 | |
| 374 | |
| 375 | |
| 376 | |
| 377 | |

TABLE 1-24-continued

| Example | Structural formula |
|---|---|
| 378 | |
| 379 | |
| 380 | |
| 381 | |
| 382 | |

TABLE 1-24-continued
| Example | Structural formula |
|---|---|
| 383 | 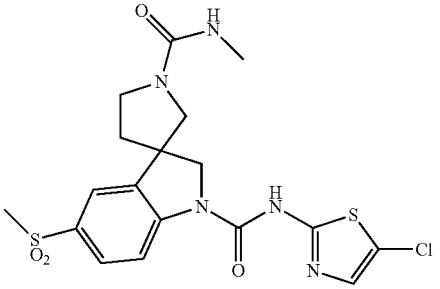 [SMILES: CNC(=O)N1CCC2(C1)CN(C(=O)Nc1ncc(Cl)s1)c1ccc(S(C)(=O)=O)cc12] |
| 384 | 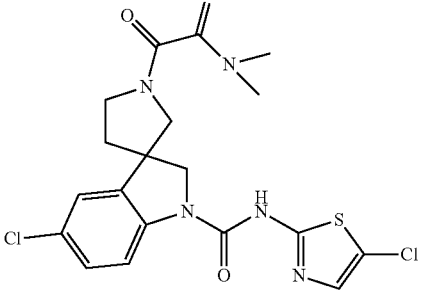 |
TABLE 1-25
| Example | Structural formula |
|---|---|
| 385 | 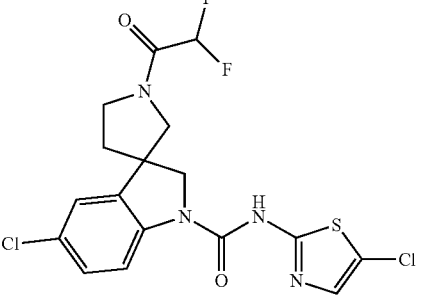 |
| 386 | 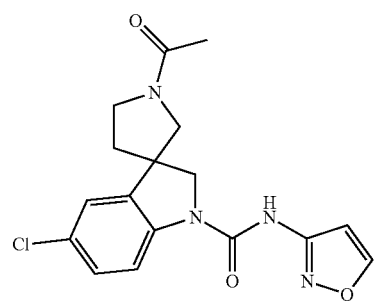 [SMILES: CC(=O)N1CCC2(C1)CN(C(=O)Nc1ccon1)c1ccc(Cl)cc12] |
| 387 | 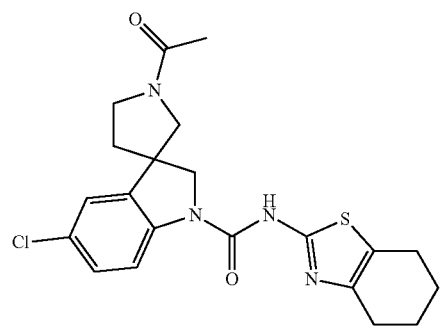 [SMILES: CC(=O)N1CCC2(C1)CN(C(=O)Nc1nc3c(s1)CCCC3)c1ccc(Cl)cc12] |

TABLE 1-25-continued

| Example | Structural formula |
|---------|-------------------|
| 388 | |
| 389 | |
| 390 | |
| 391 | |
| 392 | |

TABLE 1-25-continued

| Example | Structural formula |
| --- | --- |
| 393 | |
| 394 | |
| 395 | |
| 396 | |
| 397 | |

TABLE 1-25-continued

| Example | Structural formula |
|---|---|
| 398 | |
| 399 | |
| 400 | |

TABLE 1-26

| Example | Structural formula |
|---|---|
| 401 | |
| 402 | |

TABLE 1-26-continued
| Example | Structural formula |
|---|---|
| 403 | 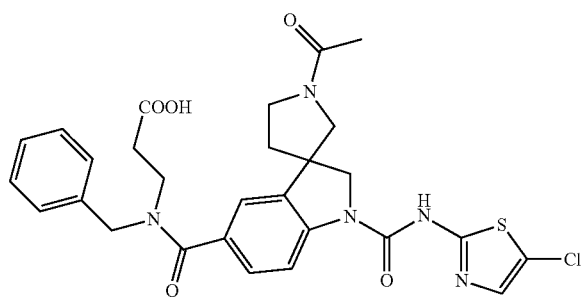 [SMILES: CC(=O)N1CCC2(C1)CN(C(=O)Nc1ncc(Cl)s1)c1ccc(C(=O)N(CCC(=O)O)Cc3ccccc3)cc12] |
| 404 | 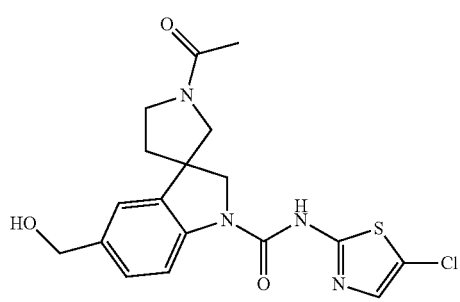 [SMILES: CC(=O)N1CCC2(C1)CN(C(=O)Nc1ncc(Cl)s1)c1ccc(CO)cc12] |
| 405 | 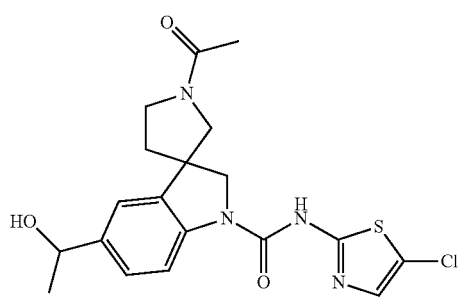 [SMILES: CC(=O)N1CCC2(C1)CN(C(=O)Nc1ncc(Cl)s1)c1ccc(C(C)O)cc12] |
| 406 | 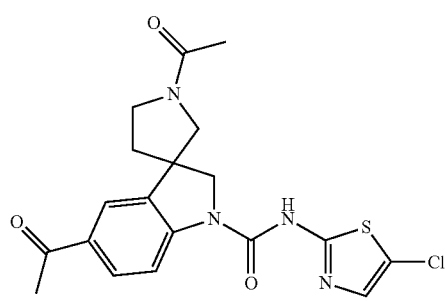 [SMILES: CC(=O)c1ccc2c(c1)C1(CCN(C(C)=O)C1)CN2C(=O)Nc1ncc(Cl)s1] |
| 407 | 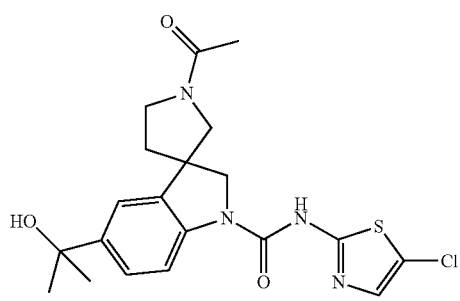 [SMILES: CC(=O)N1CCC2(C1)CN(C(=O)Nc1ncc(Cl)s1)c1ccc(C(C)(C)O)cc12] |

TABLE 1-26-continued

| Example | Structural formula |
|---------|-------------------|
| 408 | |
| 409 | |
| 410 | |
| 411 | |
| 412 | |

TABLE 1-26-continued
| Example | Structural formula |
|---------|-------------------|
| 413 | 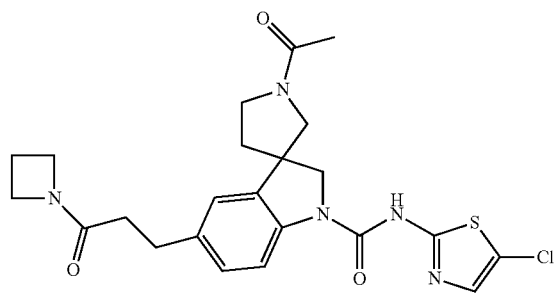 [SMILES: CC(=O)N1CCC2(C1)CN(C(=O)Nc1ncc(Cl)s1)c1ccc(CCC(=O)N3CCC3)cc12] |
| 414 | 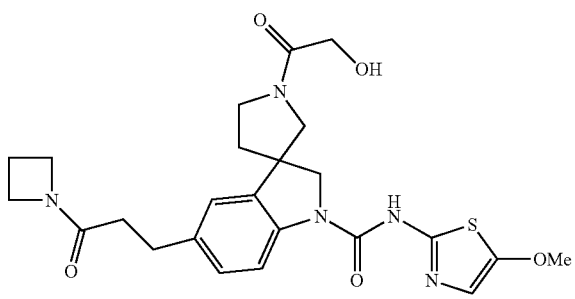 [SMILES: COc1cnc(NC(=O)N2CC3(CCN(C(=O)CO)C3)c3cc(CCC(=O)N4CCC4)ccc32)s1] |
| 415 | 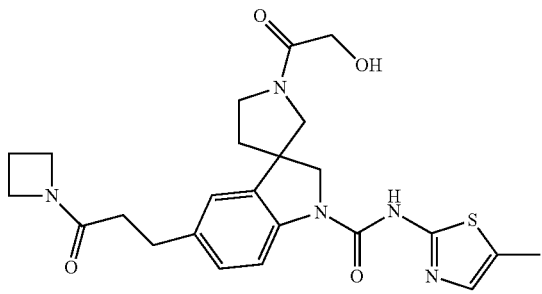 [SMILES: Cc1cnc(NC(=O)N2CC3(CCN(C(=O)CO)C3)c3cc(CCC(=O)N4CCC4)ccc32)s1] |
| 416 | 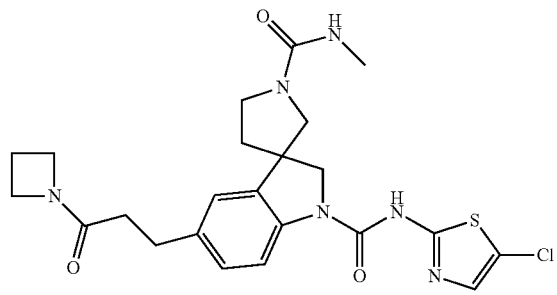 [SMILES: CNC(=O)N1CCC2(C1)CN(C(=O)Nc1ncc(Cl)s1)c1ccc(CCC(=O)N3CCC3)cc12] |

TABLE 1-27

| Example | Structural formula |
|---|---|
| 417 | |
| 418 | |
| 419 | |
| 420 | |
| 421 | |

TABLE 1-27-continued

| Example | Structural formula |
|---|---|
| 422 | |
| 423 | |
| 424 | |
| 425 | |
| 426 | |

TABLE 1-27-continued

| Example | Structural formula |
|---|---|
| 427 | |
| 428 | |
| 429 | |
| 430 | |
| 431 | |

TABLE 1-27-continued
| Example | Structural formula |
|---|---|
| 432 | 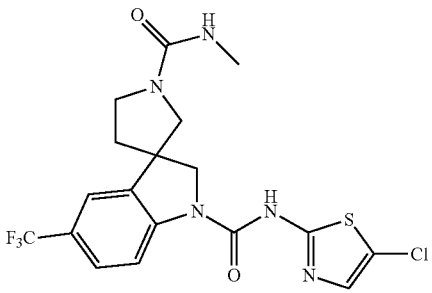 [SMILES: CNC(=O)N1CCC2(C1)CN(C(=O)Nc1ncc(Cl)s1)c1ccc(C(F)(F)F)cc12] |
TABLE 1-28
| Example | Structural formula |
|---|---|
| 433 | 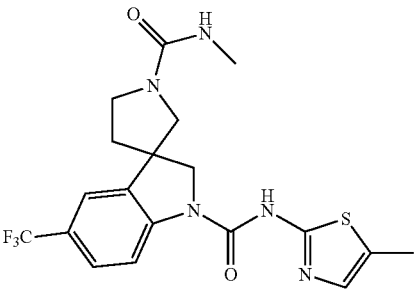 [SMILES: CNC(=O)N1CCC2(C1)CN(C(=O)Nc1ncc(C)s1)c1ccc(C(F)(F)F)cc12] |
| 434 | 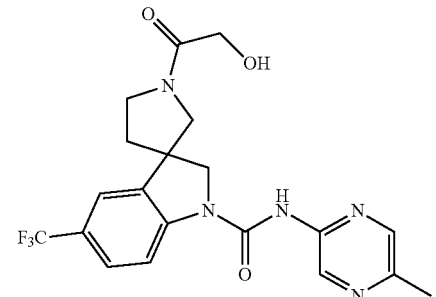 |
| 435 | 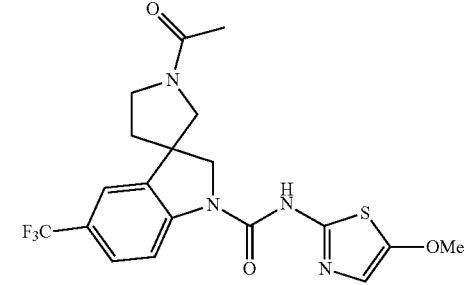 |
TABLE 1-28-continued
| Example | Structural formula |
|---|---|
| 436 | 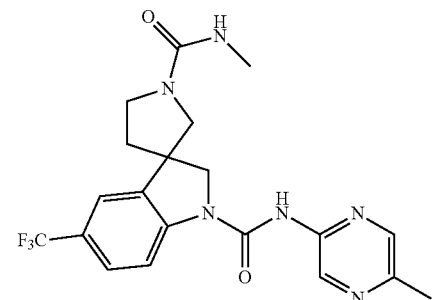 |
| 437 | 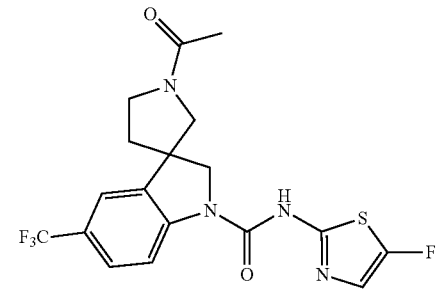 [SMILES: CC(=O)N1CCC2(C1)CN(C(=O)Nc1ncc(F)s1)c1ccc(C(F)(F)F)cc12] |
| 438 | 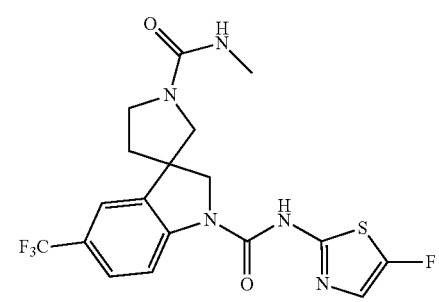 [SMILES: CNC(=O)N1CCC2(C1)CN(C(=O)Nc1ncc(F)s1)c1ccc(C(F)(F)F)cc12] |
| 439 | 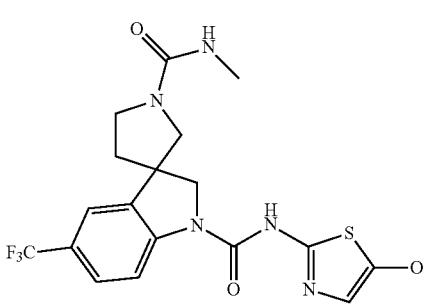 |

TABLE 1-28-continued

| Example | Structural formula |
|---|---|
| 440 | |
| 441 | |
| 442 | |
| 443 | |
| 444 | |

TABLE 1-28-continued

| Example | Structural formula |
|---|---|
| 445 | |
| 446 | |
| 447 | |
| 448 | |

TABLE 1-29
| Example | Structural formula |
|---|---|
| 449 | 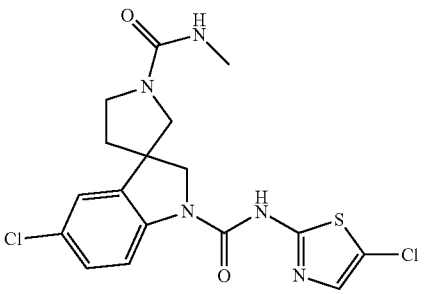 [SMILES: CNC(=O)N1CCC2(C1)CN(C(=O)Nc1ncc(Cl)s1)c1ccc(Cl)cc12] |
| 450 | 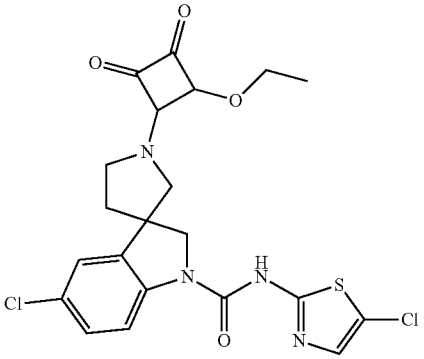 [SMILES: CCOC1C(=O)C(=O)C1N1CCC2(CN(C(=O)Nc3ncc(Cl)s3)c3ccc(Cl)cc32)C1] |
| 451 | 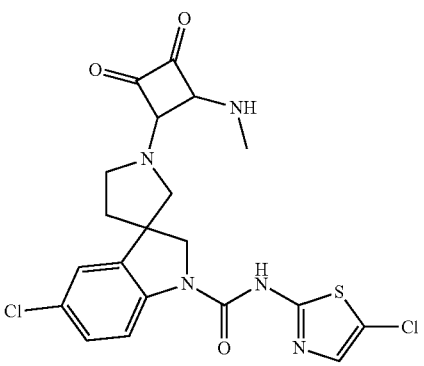 [SMILES: CNC1C(=O)C(=O)C1N1CCC2(CN(C(=O)Nc3ncc(Cl)s3)c3ccc(Cl)cc32)C1] |
| 452 | 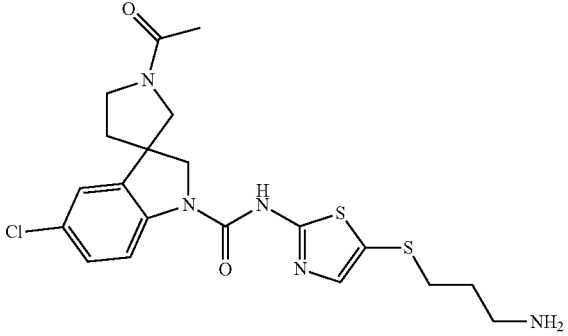 [SMILES: CC(=O)N1CCC2(C1)CN(C(=O)Nc1ncc(SCCCN)s1)c1ccc(Cl)cc12] |

TABLE 1-29-continued
| Example | Structural formula |
|---|---|
| 453 | 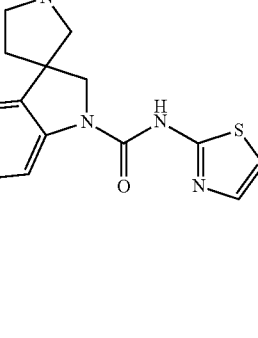 |
| 454 | 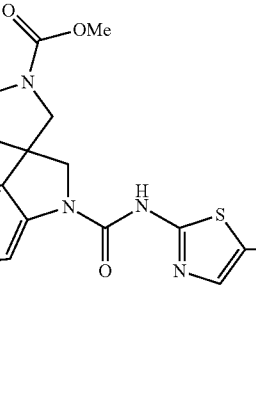 |
| 455 | 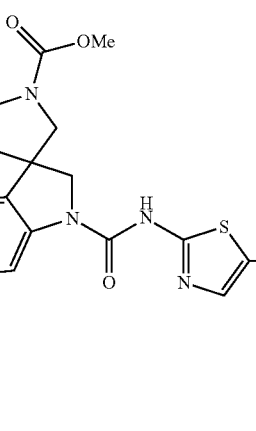 |
| 456 | 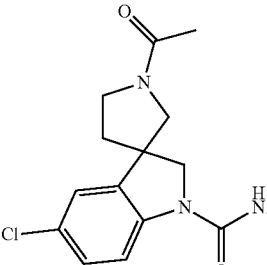 |

TABLE 1-29-continued

| Example | Structural formula |
|---------|-------------------|
| 457 | |
| 458 | |
| 459 | |
| 460 | |
| 461 | |

TABLE 1-29-continued
| Example | Structural formula |
|---|---|
| 462 | 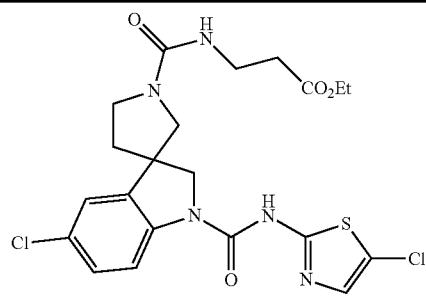 |
| 463 | 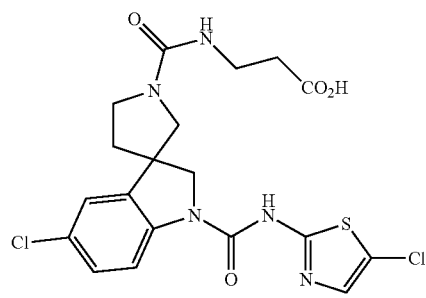 [SMILES: O=C(O)CCNC(=O)N1CCC2(C1)CN(C(=O)Nc1ncc(Cl)s1)c1ccc(Cl)cc12] |
| 464 | 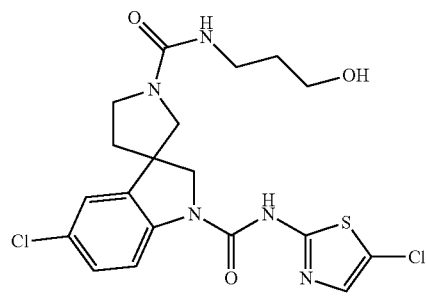 [SMILES: O=C(NCCCO)N1CCC2(C1)CN(C(=O)Nc1ncc(Cl)s1)c1ccc(Cl)cc12] |
TABLE 1-30
| Example | Structural formula |
|---|---|
| 465 | 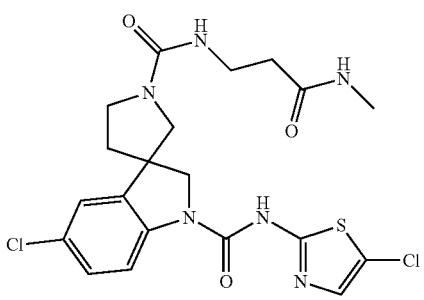 [SMILES: CNC(=O)CCNC(=O)N1CCC2(C1)CN(C(=O)Nc1ncc(Cl)s1)c1ccc(Cl)cc12] |
TABLE 1-30-continued
| Example | Structural formula |
|---|---|
| 466 | 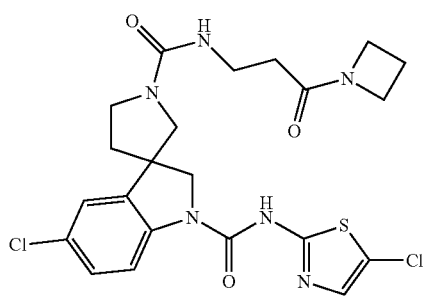 [SMILES: O=C(CCNC(=O)N1CCC2(C1)CN(C(=O)Nc1ncc(Cl)s1)c1ccc(Cl)cc12)N1CCC1] |

TABLE 1-30-continued
| Example | Structural formula |
|---|---|
| 467 | 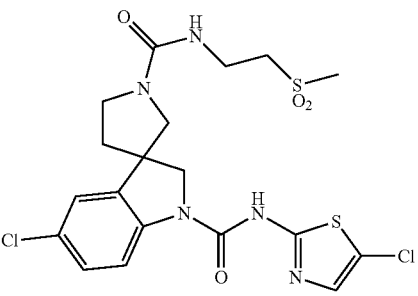 [SMILES: CS(=O)(=O)CCNC(=O)N1CCC2(C1)CN(C(=O)Nc1ncc(Cl)s1)c1ccc(Cl)cc12] |
| 468 | 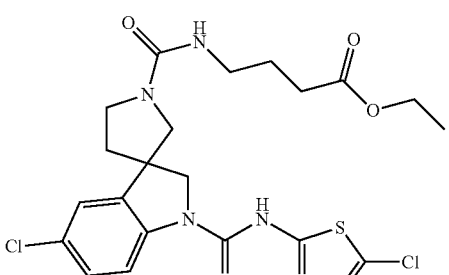 |
| 469 | 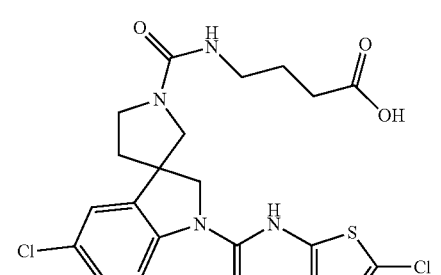 |
| 470 | 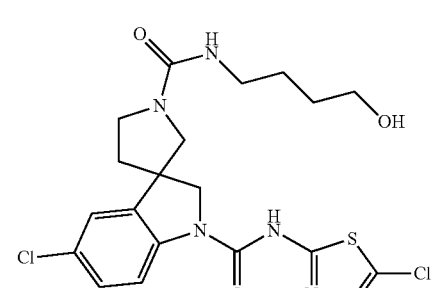 |
| 471 | 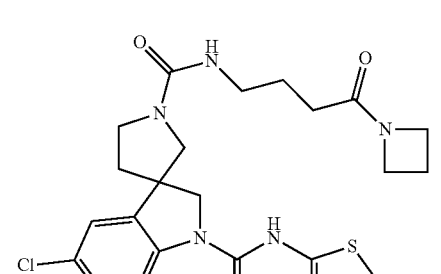 |
| 472 | 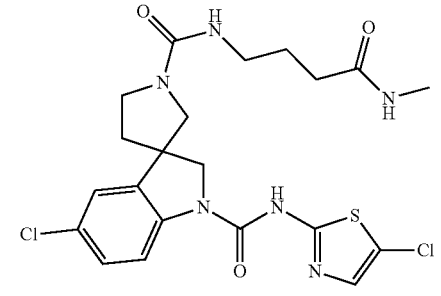 [SMILES: CNC(=O)CCCNC(=O)N1CCC2(C1)CN(C(=O)Nc1ncc(Cl)s1)c1ccc(Cl)cc12] |
| 473 | 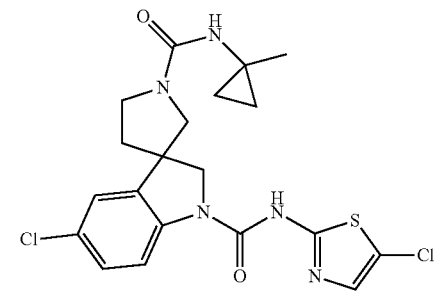 [SMILES: CC1(NC(=O)N2CCC3(C2)CN(C(=O)Nc2ncc(Cl)s2)c2ccc(Cl)cc23)CC1] |
| 474 | 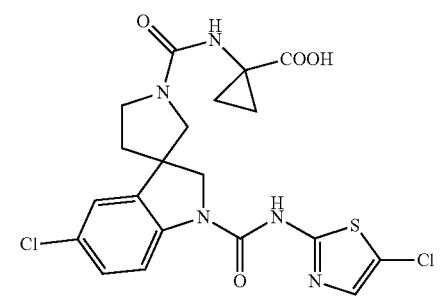 [SMILES: O=C(NC1(C(=O)O)CC1)N1CCC2(C1)CN(C(=O)Nc1ncc(Cl)s1)c1ccc(Cl)cc12] |
| 475 | 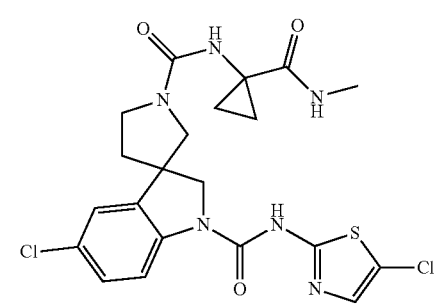 [SMILES: CNC(=O)C1(NC(=O)N2CCC3(C2)CN(C(=O)Nc2ncc(Cl)s2)c2ccc(Cl)cc23)CC1] |
| 476 | 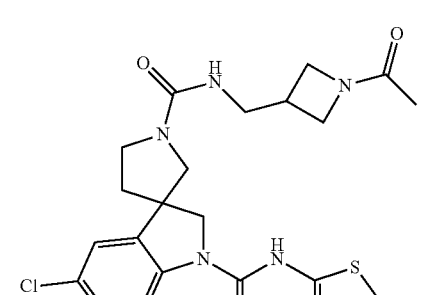 |

US 8,921,576 B2
TABLE 1-30-continued
| Example | Structural formula |
|---|---|
| 477 | 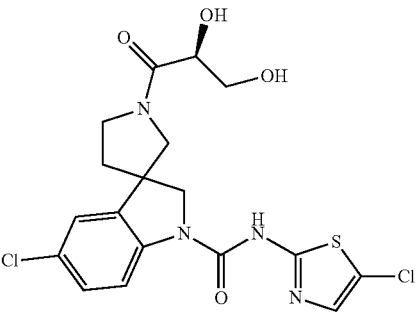 [SMILES: O=C([C@@H](O)CO)N1CCC2(C1)CN(C(=O)Nc1ncc(Cl)s1)c1ccc(Cl)cc12] |
| 478 | 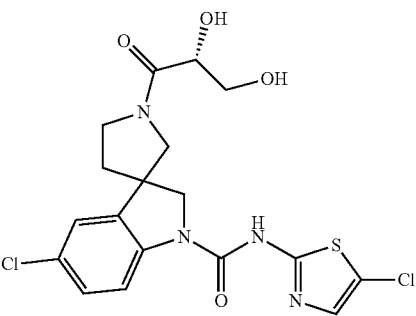 [SMILES: O=C([C@H](O)CO)N1CCC2(C1)CN(C(=O)Nc1ncc(Cl)s1)c1ccc(Cl)cc12] |
| 479 | 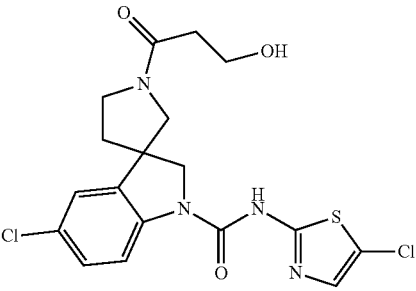 [SMILES: O=C(CCO)N1CCC2(C1)CN(C(=O)Nc1ncc(Cl)s1)c1ccc(Cl)cc12] |
| 480 | 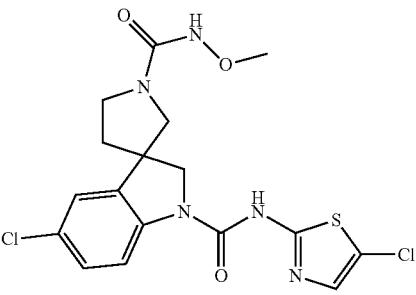 [SMILES: CONC(=O)N1CCC2(C1)CN(C(=O)Nc1ncc(Cl)s1)c1ccc(Cl)cc12] |
TABLE 1-31
| Example | Structural formula |
|---|---|
| 481 | 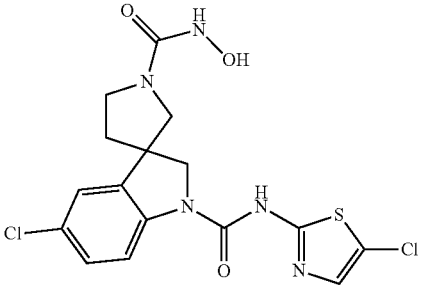 [SMILES: O=C(NO)N1CCC2(C1)CN(C(=O)Nc1ncc(Cl)s1)c1ccc(Cl)cc12] |
| 482 | 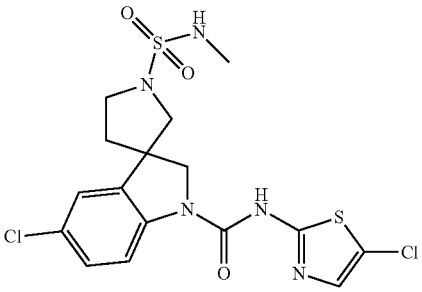 [SMILES: CNS(=O)(=O)N1CCC2(CN(C(=O)Nc3ncc(Cl)s3)c3ccc(Cl)cc32)C1] |
| 483 | 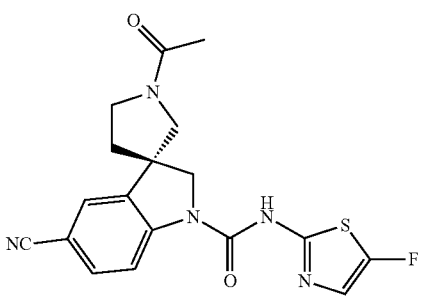 [SMILES: CC(=O)N1CC[C@@]2(C1)CN(C(=O)Nc1ncc(F)s1)c1ccc(C#N)cc12] |
| 484 | 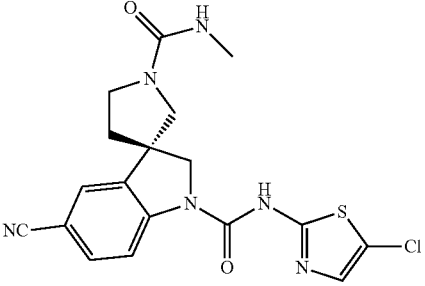 [SMILES: CNC(=O)N1CC[C@@]2(C1)CN(C(=O)Nc1ncc(Cl)s1)c1ccc(C#N)cc12] |
| 485 | 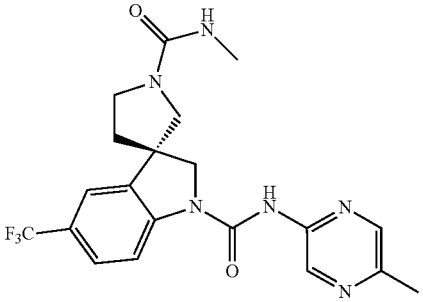 [SMILES: CNC(=O)N1CC[C@@]2(C1)CN(C(=O)Nc1cnc(C)cn1)c1ccc(C(F)(F)F)cc12] |

TABLE 1-31-continued

| Example | Structural formula |
|---------|-------------------|
| 486 | 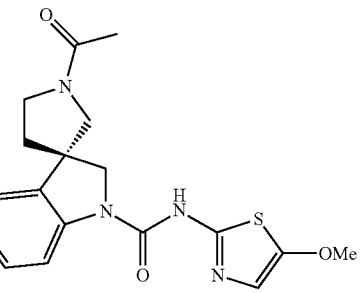 |
| 487 | 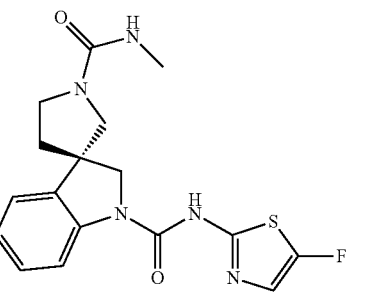 |
| 488 | 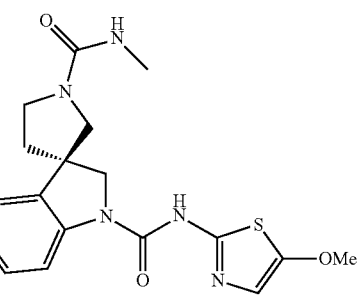 |
| 489 | 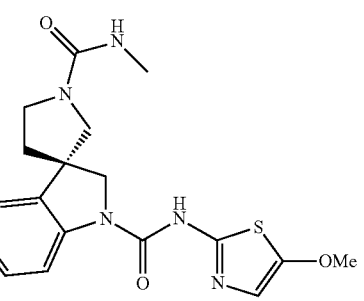 |

Test Example 1

In Vitro GK Activating Action (1) Preparation of GK Fusion Protein cDNA (GenBank Accession No. NM_033507, human glucokinase, variant 2) encoding human liver-type GK polypeptide was cloned by performing a polymerase chain reaction (hereinafter referred to as "PCR") using a human liver cDNA library (Human liver QUICK-Clone cDNA, TAKARA BIO INC.), and the thus cloned cDNA was then introduced into an expression vector (pGEX-3X, GE Healthcare Japan) for glutathione S transferase (hereinafter referred to as GST) fusion protein expression. The resulting vector was introduced into Escherichia coli (Competent high DH5α, Toyobo Co., Ltd.), and the transformed Escherichia coli was then cultured at 37° C. Thereafter, Isopropyl β-D-1-thiogalactopyranoside (final concentration: 1 mmol/L, Sigma Aldrich Japan) was added to the culture, and the obtained mixture was then cultured at 30° C. for 3 hours. Thereafter, a cell mass was recovered. The recovered cell mass was subjected to freezing-and-thawing, and the resulting cell mass was then suspended in phosphate buffer with final concentration of 1% Triton X-100, followed by disintegration with an ultrasonic disruptor. The homogenate was centrifuged at 33,200 rpm at 4° C. for 1 hour. Thereafter, the supernatant was recovered, and a GST-GK fusion protein was then purified using a glutathione column (GSTrap FF, GE Healthcare Japan). The obtained GST-GK fusion protein was divided into some portions each having a small volume, and the thus divided proteins were then preserved at −80° C.

(2) In Vitro GK Activity Measurement Test

A GK assay method was carried out at 25° C. at a final incubation volume of 100 μL in a flat-bottom 96-well assay plate. An assay buffer comprised 25 mmol/L Hepes buffer (pH 7.1), 25 mmol/L KCl, 2.5 mmol/L or 10 mmol/L D-glucose, 5 mmol/L ATP, 1 mmol/L nicotinamide adenine dinucleotide phosphate (abbreviated as NADP), 2 mmol/L $MgCl_2$, 1 mmol/L dithiothreitol (DTT), 2 units/mL glucose-6 phosphate dehydrogenase (G6PDH), and 1 μg/mL GST-GK derived from human liver GK. ATP, G6PDH, and NADP were purchased from Roche Diagnostics. Other reagents were purchased from Wako Pure Chemical Industries, Ltd. 10 μL of the test compound solution dissolved in dimethyl sulfoxide (DMSO) was added to the flat-bottom 96-well assay plate, and thereafter, 80 μL of assay buffer that did not contain GST-GK was added thereto. The thus mixed solution was preincubated in an incubator in which the temperature was controlled at 25° C. for 15 minutes. Subsequently, the reaction was initiated by adding 10 μL of the GST-GK solution to the reaction mixture, resulting in a final concentration of 0.1 μg/mL. After initiation of the reaction, an increase in the optical concentration at 340 nm (OD340) was monitored with a microplate spectrophotometer (Varsamax, Molecular Devices Japan K.K.) every 10 seconds over an incubation period of 10 minutes. An inclination of the OD340 increase was defined as raw data. The GK activating rate was indicated as a numerical value obtained from the expression: (Inclination of OD340 increase by addition of the test compound)/ (inclination of OD340 increase without addition of the test compound). The results of the GK activating rate obtained at a test compound concentration of 1 μmol/L under the condition of a glucose concentration of 2.5 mmol/L are shown in the following table.

TABLE 2

| Example No. | GK activation rate (%) |
|-------------|------------------------|
| 3 | 716 |
| 20 | 429 |
| 46 | 499 |
| 52 | 531 |
| 53 | 1010 |
| 131 | 411 |
| 141 | 574 |
| 151 | 656 |
| 154 | 473 |
| 161 | 514 |
| 162 | 484 |
| 164 | 567 |
| 168 | 462 |
| 169 | 532 |
| 170 | 506 |

TABLE 2-continued

| Example No. | GK activation rate (%) |
|---|---|
| 177 | 530 |
| 179 | 669 |
| 180 | 442 |
| 186 | 583 |
| 263 | 597 |
| 269 | 640 |
| 271 | 578 |
| 273 | 692 |
| 288 | 793 |
| 289 | 752 |
| 300 | 689 |
| 302 | 843 |
| 303 | 1118 |
| 307 | 887 |
| 308 | 504 |
| 13 | 678 |
| 320 | 818 |
| 334 | 705 |
| 336 | 451 |
| 340 | 1192 |
| 344 | 647 |
| 345 | 785 |
| 347 | 611 |
| 351 | 886 |
| 353 | 486 |
| 355 | 636 |
| 342 | 420 |

TABLE 3

| Example No. | GK activation rate (%) |
|---|---|
| 373 | 476 |
| 374 | 437 |
| 376 | 528 |
| 379 | 554 |
| 380 | 636 |
| 381 | 465 |
| 419 | 535 |
| 424 | 438 |
| 428 | 502 |
| 431 | 432 |
| 432 | 613 |
| 437 | 506 |
| 439 | 520 |
| 441 | 416 |
| 445 | 500 |
| 449 | 633 |
| 454 | 575 |
| 455 | 606 |
| 459 | 537 |
| 462 | 454 |
| 464 | 526 |
| 465 | 474 |
| 466 | 446 |
| 467 | 480 |
| 468 | 405 |
| 470 | 459 |
| 471 | 470 |
| 472 | 456 |
| 476 | 445 |
| 480 | 477 |
| 481 | 602 |
| 484 | 644 |
| 487 | 659 |
| 489 | 645 |

As given above, it was confirmed that the compound of the present invention has a strong glucokinase activating action.

Test Example 2

Oral Glucose Tolerance Test after Single Administration of Test Compound in Normal Mice The test compound (Example 68) (30 mg/kg) suspended in 10% (v/v) Gelucire44/14 (GATTEFOSSE) was orally administered to normal mice (C57BL/6j mice, CLEA Japan, Inc.). Thirty minutes later, 2 g/kg glucose was orally administered to the mice. The blood glucose level was measured using an automatic blood glucose level measurement apparatus (Medisafe, TERUMO), before administration of the test compound, 25 minutes after administration of the test compound, and 15, 30, 60, and 120 minutes after administration of glucose. Thus, the action of the test compound to lower blood glucose level was evaluated.

The results are shown in FIG. 1. As is clear from the FIGURE, the blood glucose level of the mice orally administered with the test compound was lower than that of the mice orally administered with the solvent alone.

INDUSTRIAL APPLICABILITY

Since the spiroindoline compound represented by the general formula (1) of the present invention, or a salt thereof, or a solvate of the compound or the salt has an excellent glucokinase-activating action and is useful for preventing and/or treating diabetes, it is industrially applicable.

The invention claimed is:

1. A spiroindoline compound represented by the following formula (1), a salt or solvate thereof:

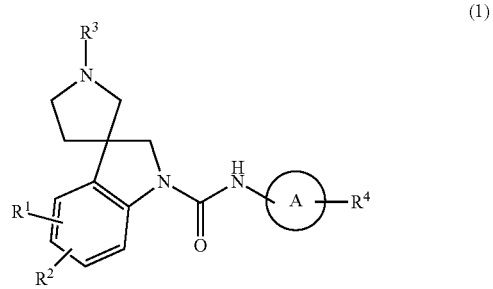

(1)

wherein ring A represents a nitrogen-containing 5-10 membered unsaturated heterocyclic group, $R^1$ and $R^2$, which are the same or different, each represent a hydrogen atom, a halogen atom, a halo $C_{1-6}$ alkyl group, a $C_{6-10}$ aryl group, a cyano group, a $C_{1-6}$ alkyl group optionally having a substituent, a $C_{2-6}$ alkenyl group optionally having a substituent, —O—$R^5$, —S(O)$_1$—$R^6$, or —CO—$R^{12}$, wherein $R^5$ represents a $C_{1-6}$ alkyl group optionally having a substituent, a halo $C_{1-6}$ alkyl group, or a $C_{6-10}$ aryl group optionally having a substituent, $R^6$ represents a $C_{1-6}$ alkyl group, a $C_{3-8}$ cycloalkyl group, a mono-$C_{1-6}$ alkylamino group optionally having a substituent, a di-$C_{1-6}$ alkylamino group optionally having a substituent, a mono-$C_{3-8}$ cycloalkylamino group, or a nitrogen-containing 3-7 membered saturated heterocyclic group optionally having a substituent, l represents an integer of 0 to 2, and $R^{12}$ represents a hydroxyl group, a $C_{1-6}$ alkyl group, a mono-$C_{1-6}$ alkylamino group optionally having a substituent, or a di-$C_{1-6}$ alkylamino group optionally having a substituent, $R^3$ represents a hydrogen atom, a $C_{1-6}$ alkyl group optionally having a substituent, $-CO-R^7$, $-S(O)_m-R^8$, $-CS-R^{13}$, or a group represented by the following formula (2):

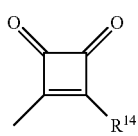

(2)

wherein $R^7$ represents a hydrogen atom, a $C_{1-6}$ alkyl group optionally having a substituent, a halo $C_{1-6}$ alkyl group, a $C_{3-8}$ cycloalkyl group, a $C_{1-6}$ alkoxy group, a $C_{6-10}$ aryl group, an amino group, a mono-$C_{1-6}$ alkylamino group optionally having a substituent, a di-$C_{1-6}$ alkylamino group, a carboxyl group, a $C_{1-6}$ alkoxycarbonyl group, a mono-$C_{1-6}$ alkylaminocarbonyl group, a di-$C_{1-6}$ alkylaminocarbonyl group, a carbamoyl group, a $C_{1-6}$ alkylcarbonyl group, a mono-$C_{3-8}$ cycloalkylamino group optionally having a substituent, a $C_{1-6}$ alkoxyamino group, or a hydroxyamino group, $R^8$ represents a $C_{1-6}$ alkyl group or a mono-$C_{1-6}$ alkylamino group, m represents an integer of 0 to 2, $R^{13}$ represents a mono-$C_{1-6}$ alkylamino group, and $R^{14}$ represents a $C_{1-6}$ alkoxy group or a mono-$C_{1-6}$ alkylamino group, and $R^4$ represents a hydrogen atom, a halogen atom, a cyano group, a $C_{1-6}$ alkyl group optionally having a substituent, $-O-R^9$, $-S(O)_n-R^{10}$, or $-CO-R^{11}$, wherein $R^9$ represents a $C_{1-6}$ alkyl group, a $C_{6-10}$ aryl group optionally having a substituent, or a nitrogen-containing 5-10 membered unsaturated heterocyclic group optionally having a substituent, $R^{10}$ represents a $C_{1-6}$ alkyl group optionally having a substituent, n represents an integer of 0 to 2, and $R^{11}$ represents a hydroxyl group, a $C_{1-6}$ alkoxy group, an amino group, a mono-$C_{1-6}$ alkylamino group, a di-$C_{1-6}$ alkylamino group, or a nitrogen-containing 3-7 membered saturated heterocyclic group.

2. The compound of claim 1, wherein the nitrogen-containing 5-10 membered unsaturated heterocyclic group as ring A is any one of the following formulae (3) to (12):

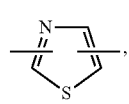

(3)

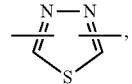

(4)

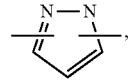

(5)

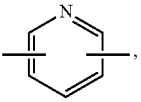

(6)

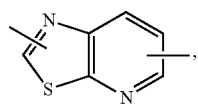

(7)

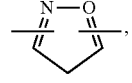

(8)

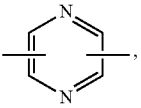

(9)

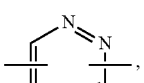

(10)

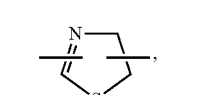

(11)

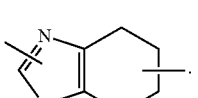

(12)

3. A pharmaceutical composition comprising the compound of claim 1, and a pharmaceutically acceptable carrier.

4. A method for activating glucokinase, comprising administering to a mammal in need thereof an effective amount of the compound of claim 1.

5. A method for lowering blood glucose level, comprising administering to a mammal in need thereof an effective amount of the compound of claim 1.

6. A method for treating diabetes, abnormal glucose tolerance, gestational diabetes, a chronic complication of diabetes, and metabolic syndrome, comprising administering to a mammal having diabetes, abnormal glucose tolerance, gestational diabetes, a chronic complication of diabetes, or metabolic syndrome an effective amount of the compound of claim 1, wherein the chronic complication of diabetes is diabetic peripheral neuropathy, diabetic nephropathy, diabetic retinopathy, or diabetic arteriosclerosis.

7. The method of claim 4, wherein the mammal is a human.

8. The method of claim 5, wherein the mammal is a human.

9. The method of claim 6, wherein the mammal is a human.

* * * * *